US011795225B2

(12) United States Patent
Kinneer et al.

(10) Patent No.: US 11,795,225 B2
(45) Date of Patent: Oct. 24, 2023

(54) THERAPEUTIC BINDING MOLECULES

(71) Applicant: MedImmune Limited, Cambridge (GB)

(72) Inventors: Krista Lynne Kinneer, Gaithersburg, MD (US); Gareth Charles Davies, Cambridge (GB); David Gareth Rees, Cambridge (GB); Jennifer Louise Percival-Alwyn, Cambridge (GB); John Edward Andrews, Cambridge (GB); Jon Chesebrough, Gaithersburg, MD (US)

(73) Assignee: MedImmune Limited, Cambridge (GB)

(*) Notice: Subject to any disclaimer, the term of this patent is extended or adjusted under 35 U.S.C. 154(b) by 0 days.

(21) Appl. No.: 17/471,723

(22) Filed: Sep. 10, 2021

(65) Prior Publication Data
US 2022/0098308 A1 Mar. 31, 2022

Related U.S. Application Data

(60) Provisional application No. 63/077,207, filed on Sep. 11, 2020.

(51) Int. Cl.
*C07K 16/28* (2006.01)
*A61K 47/68* (2017.01)
*A61P 35/00* (2006.01)
*C07K 16/30* (2006.01)

(52) U.S. Cl.
CPC ...... *C07K 16/2827* (2013.01); *A61K 47/6803* (2017.08); *A61K 47/6855* (2017.08); *A61P 35/00* (2018.01); *C07K 16/3015* (2013.01)

(58) Field of Classification Search
CPC ............ C07K 16/2827; C07K 16/3015; C07K 2317/21; C07K 2317/33; C07K 2317/73; C07K 2317/77; C07K 2317/732; C07K 2317/90; C07K 2317/92; A61K 47/6803; A61K 47/6855; A61K 47/6849; A61K 2039/505; A61P 35/00; G01N 33/574; G01N 33/68; G01N 33/57492
See application file for complete search history.

(56) References Cited

U.S. PATENT DOCUMENTS

2022/0017622 A1* 1/2022 Apgar .................. A61P 35/00

FOREIGN PATENT DOCUMENTS

WO 2016-040724 A1 3/2016
WO 2020-140070 A1 7/2020

OTHER PUBLICATIONS

Hakan Mellstedt, EJC Supplements II 2013, 3, pp. 1-11 (Year: 2013).*
Joshi SR. Biosimilar peptides: need for pharmacovigilance. J Assoc Physicians India. Apr. 2011;59 Suppl:44-7. (Year: 2011).*
Podojil JR, Miller SD. Potential targeting of B7-H4 for the treatment of cancer. Immunol Rev. Mar. 2017;276(1):40-51. (Year: 2017).*
Goli Var, Butreddy A. Biosimilar monoclonal antibodies: Challenges and approaches towards formulation. Chem Biol Interact. Oct. 1, 2022;366:110116. (Year: 2022).*
Murphy et al. Journal of Immunological Methods, vol. 463, p. 127-133, 2018 (Year: 2018).*
Ji, et al., Construction, expression and functional analysis of anti-B7—H4—scFv—CH3 recombinant antibody, J. of Biosciences, 2018, 43:4, pp. 661-671.
Smith et al., B7—H4 as a potential target for immunotherapy for gynecologic cancers: A closer look, Gynecol Oncol., 2014, 134, pp. 181-189.
Iizuka et al., A T-cell-engaging B7—H4/CD3-bispecific Fab—scFv Antibody Targets Human Breast Cancer, Clin. Cancer Res., 2019, 25:9, pp. 2925-2934.
International Search Report and Written Opinion for PCT/EP2021/075005 dated Dec. 1, 2021.

* cited by examiner

*Primary Examiner* — Julie Wu
*Assistant Examiner* — John J Skoko, III

(57) ABSTRACT

The present invention relates to binding molecules (e.g. antibodies) for the treatment of cancer, and related antibody-drug conjugates.

38 Claims, 98 Drawing Sheets
Specification includes a Sequence Listing.

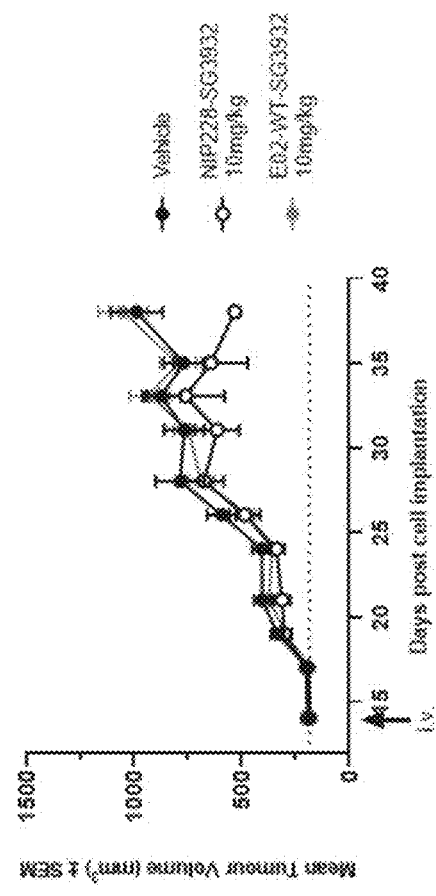
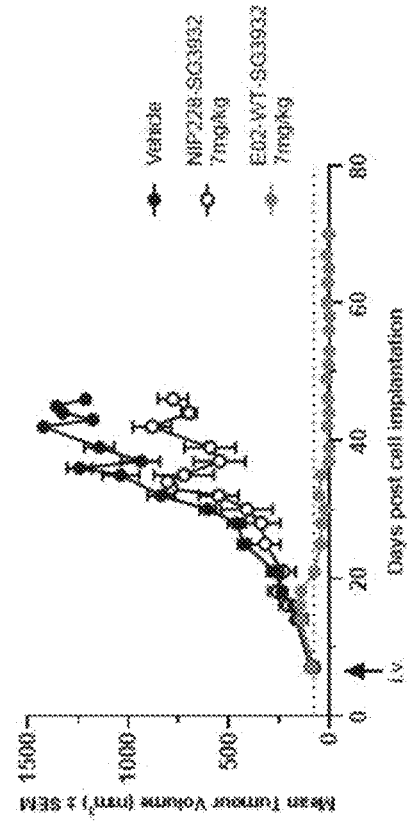
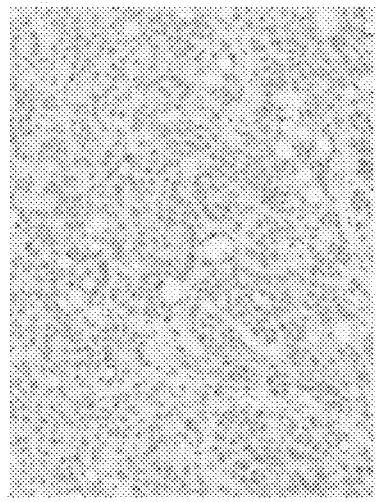
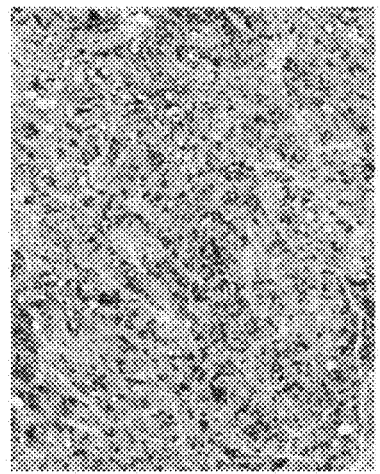
FIG. 11

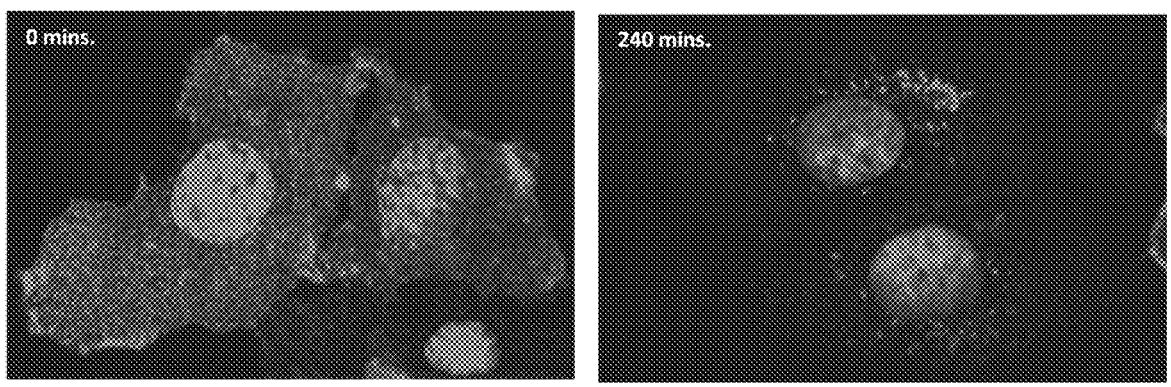
FIG. 16A
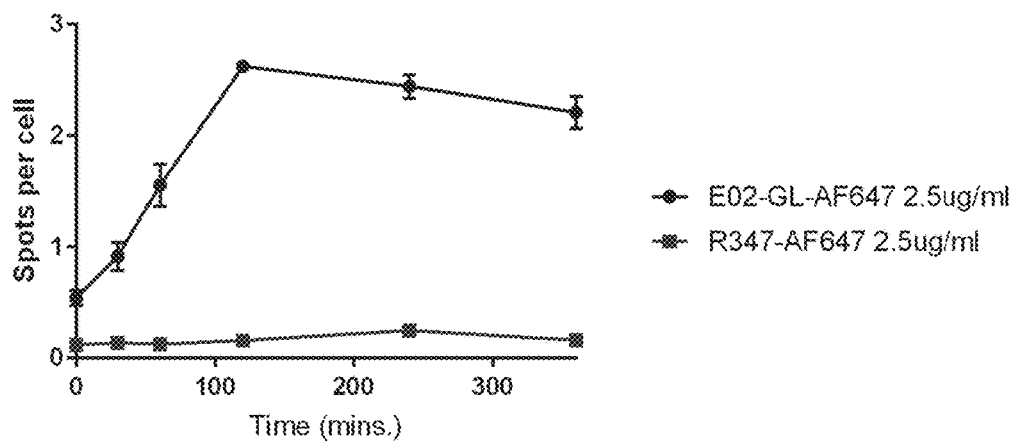
FIG. 16B
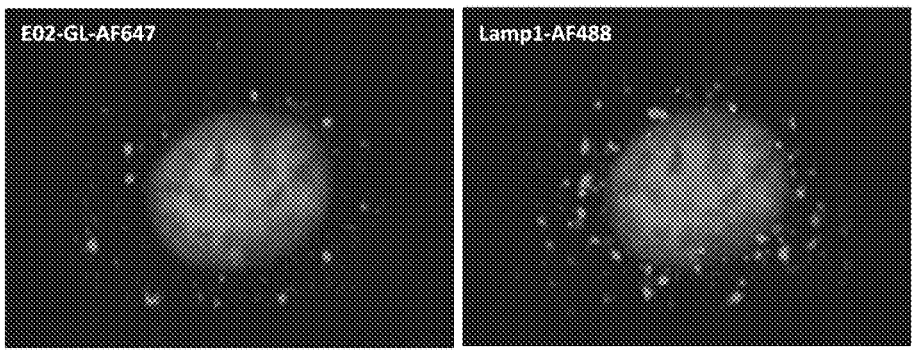
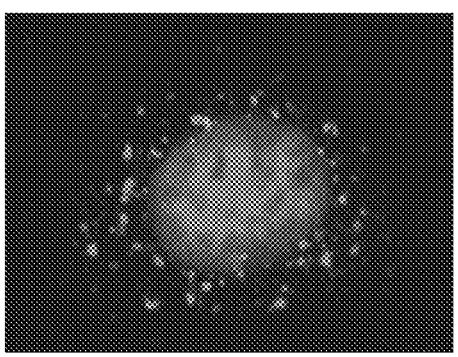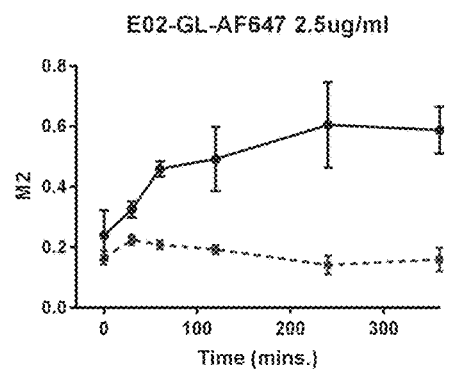
FIG. 16C

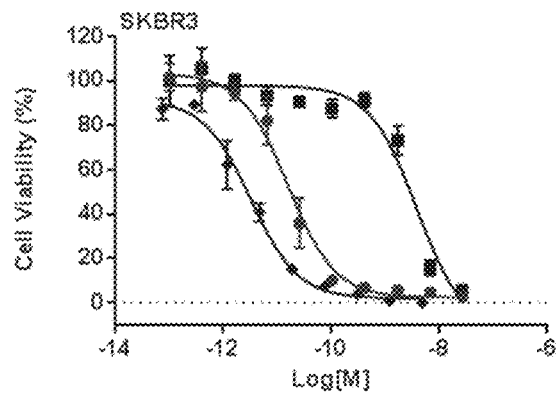
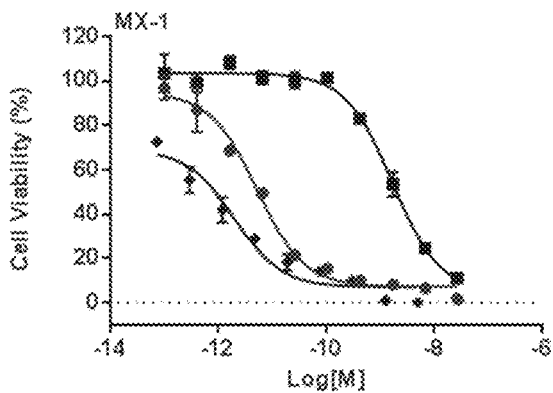
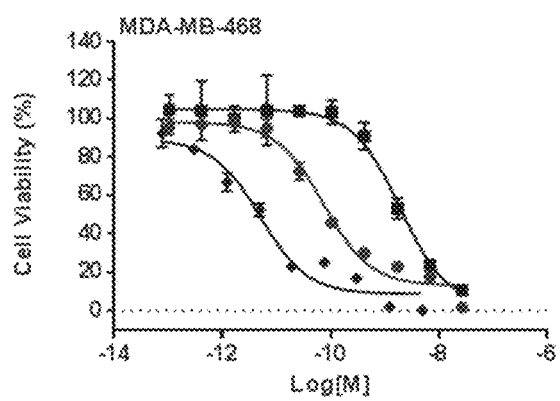
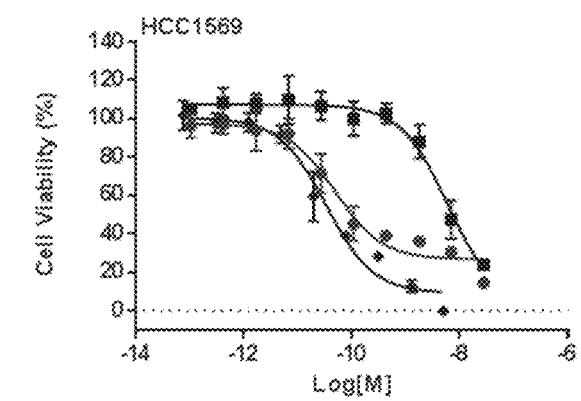
FIG. 19 (continued)

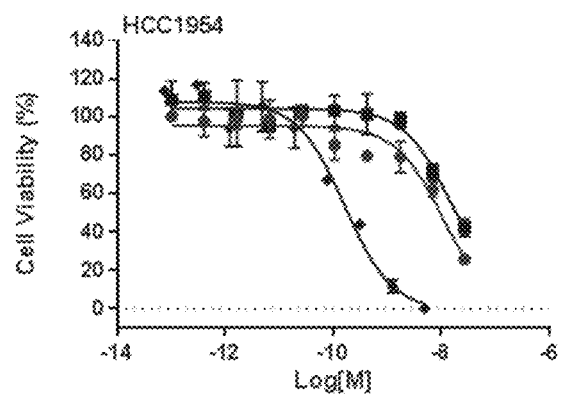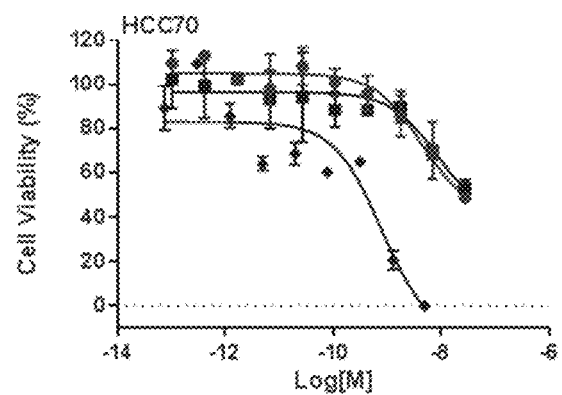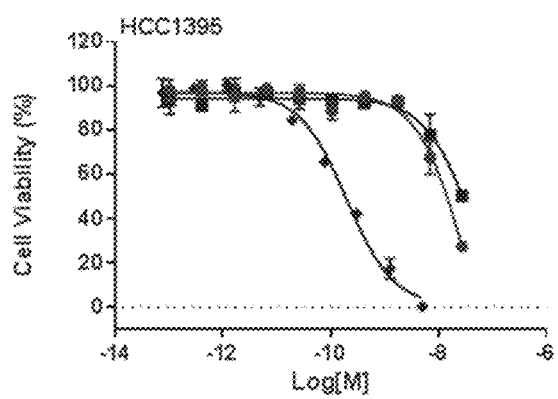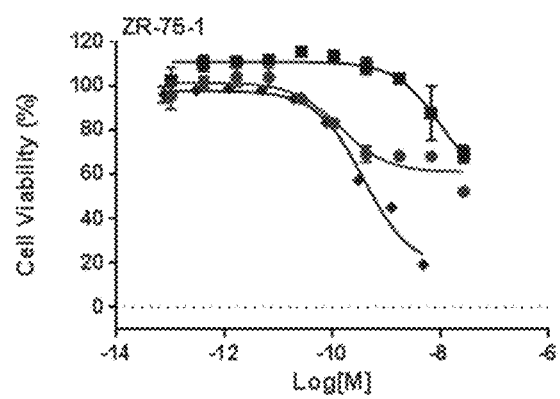
FIG. 19 (continued)

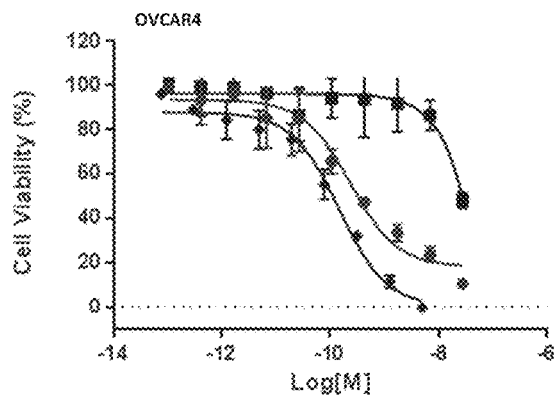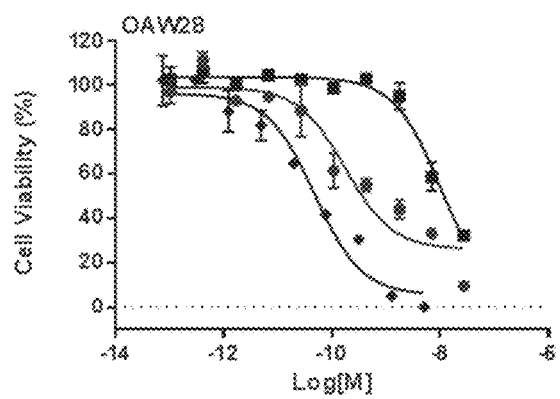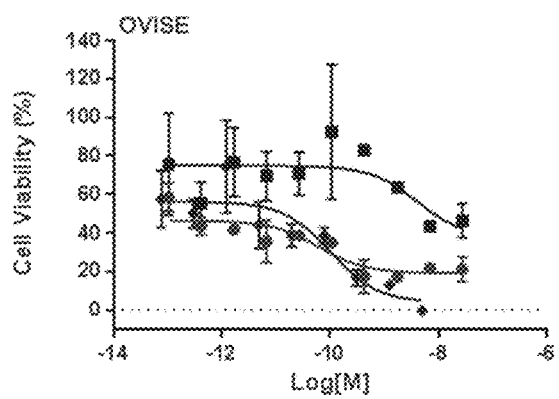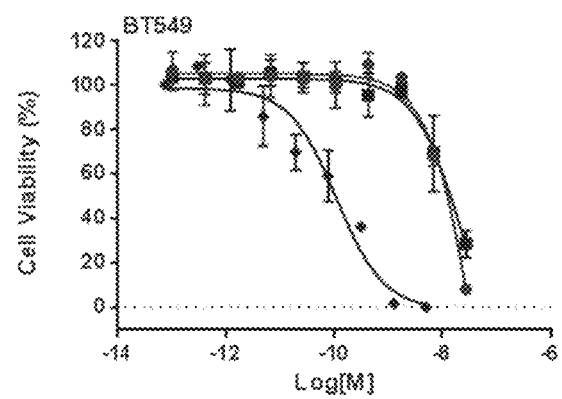
FIG. 19 (continued)

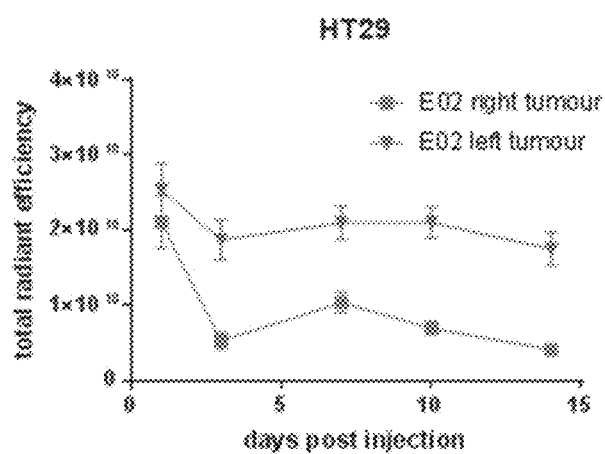
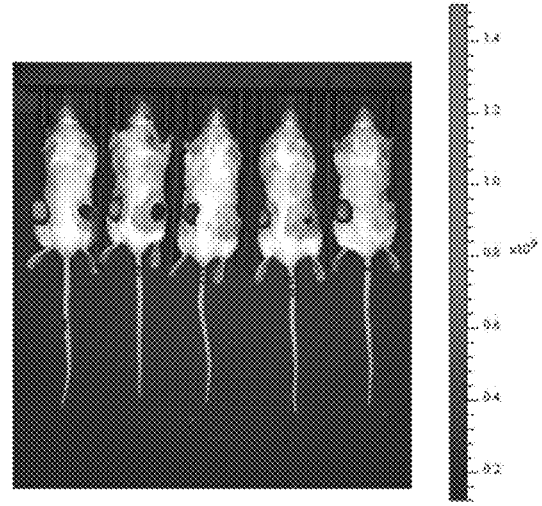
FIG. 26A  FIG. 26B
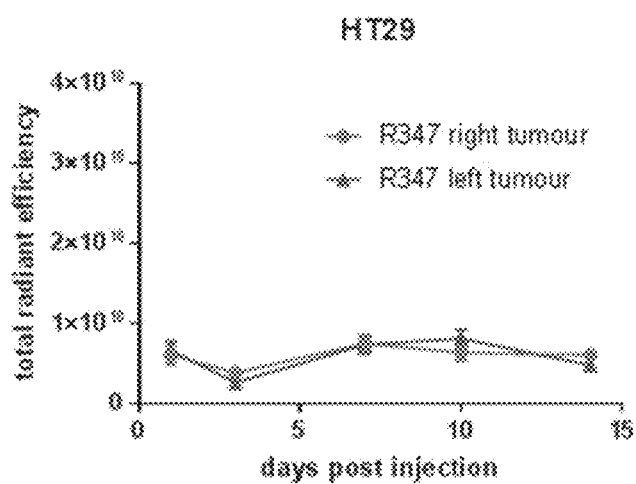
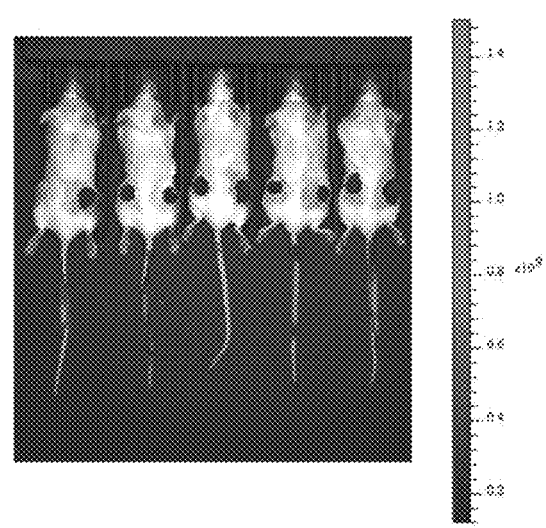
FIG. 26C  FIG. 26D

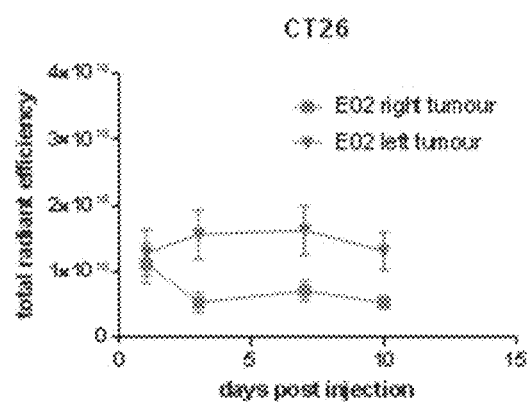
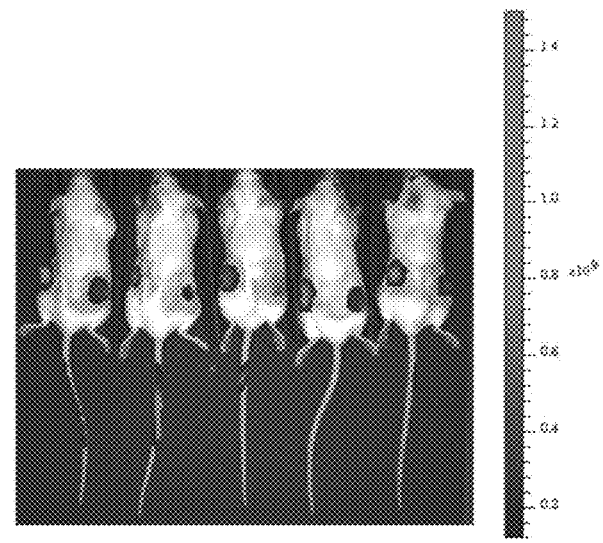
FIG. 27A  FIG. 27B
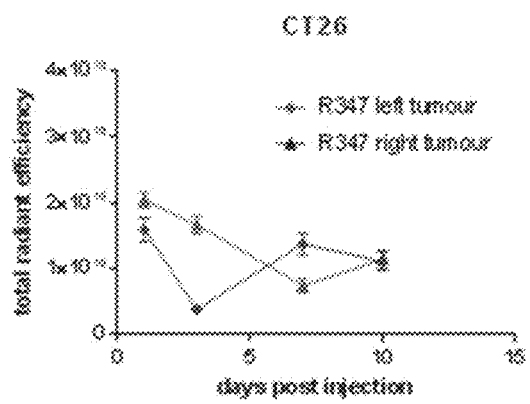
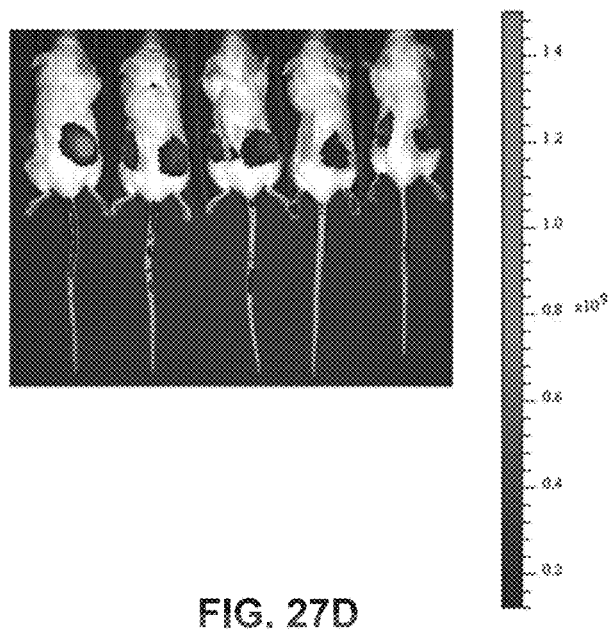
FIG. 27C  FIG. 27D

| Clone ID | Heavy FW1 | Heavy CDR1 | Heavy FW2 |
|---|---|---|---|
| ZY0EPQ-E02 | QVQLQQWGAGLLKPSETLSLTCAVYGGSFS | GYYWN | WIRQPPGKGLEWIG |
| ZY0EQD-E02 | QVQLQQWGAGLLKPSETLSLTCVYGGSFS | GYYWN | WIRQPPGRGLEWIG |
| ZY0EP0-C07 | QVQLVESGGVLVKPGGSLRLSCAASGFTLS | DYYMS | WIRQAPGMGLEWVS |
| ZY0E0B-F05 | QVQLQESGPGLVKPSQTLSLTCTVSDGSIS | SGGYYWS | WRQHPGKGLEWIG |
| ZY0E05-E07 | QVQLQESGPGLVKPSQTLSLTCTVSGGSIS | SGGYYWS | WIRQHPGKGLEWIG |

| Heavy CDR2 | Heavy FW3 | Heavy CDR3 | Heavy FW4 |
|---|---|---|---|
| EIN......HSGSTNYNPSLKS | RVTILVDTSKNQFSLKLSSV..TAADTAVYYCAR | NLYNWNL..........DS | WGQGTLVTVSS |
| EIN......HSGSTSYNPSLKS | RITISIDTSKNQFSLKLSSV..TAADTAVYYCAR | VLYNWNV..........DS | WGQGTLVTVSS |
| YISS.....SGSTIYYTDSVKG | RFTISRDSAKNSLYLQMNSL..RAEDTAVYYCAR | DGVGF.............DY | WGQGTLVTVSS |
| NIY......YGSTYYNPSLKS | RVTISVDTSKNQFSLKLNSV..TAADTAVYYCAT | EKALATVTPSGYENYYTV....DV | WGQGTTVTVSS |
| NIY......YGSTYYNPSLKS | RVTISVDTSKNQFSLKLSSV..TAADTAVYYCAR | EKALASVPSGYENYYV......DV | WGQGTTVTVSS |

FIG. 28A

| Clone ID | Light FW1 | Light CDR1 | Light FW2 |
|---|---|---|---|
| ZY0EQD-E02 | DIQMTQSPSSLSASVGDRVTITC | RASQ........DIRNDVG | WYQQKPGKAPKRLIY |
| ZY0EPQ-E02 | DIQMTQSPSSLSASVGDRVTITC | RASQ........GIRNDLG | WYQQKPGRAPKRLIY |
| ZY0EP0-C07 | EIVLTQSPGTLSLFPGERATLSC | RASQ........VSSSYLA | WYQQKPGQSPRLLIY |
| ZY0E05-E07 | DIQLTQSPSFLSASVGGRVTITC | WASQ........GIAGYLA | WYQQKPGKAPKLLIY |
| ZY0E0B-F05 | DIQLTQSPSFLSASVGDRVTITC | WASQ........GISSYLA | WYQQKPGKAPKLLIY |

| Light CDR2 | Light FW3 | Light CDR3 | Light FW4 |
|---|---|---|---|
| AA.....SRLQS | GVPSRFSGSGSG..TEFTLTISSLQPEDFATYYC | LQHNSYP......RT | FGQGTKVEL..K |
| VA.....SSLQS | GVPSRFSGSGSG..TEFTLTISSLQPEDFATYYC | LQHNSYP......RT | FGQGTKVEL..K |
| AA.....SSRAT | GIPDRFSGSGSG..TDFTLTISRLEPEDFAVYYC | QQYGSSPL.....YT | FGQGTKLEL..K |
| AA.....STLQS | GVPSRFSGSGSG..TEFTLTISSLQPEDFATYYC | QHLNSYP......LT | FGGGTKVEL..K |
| AA.....STLQS | GVPSRFSGSGSG..TEFTLTISSLQPEDFATYYC | QHLNSYP......LT | FGGGTKVEL..K |

FIG. 28B

ER: estrogen receptor; NSCLC-SCC: Non-small cell lung cancer, squamous cell carcinoma; TNBC: triple-negative breast cancer.

FIG. 32

ECD in boxes. h: human; cy: cynomolgus monkey; rh: rhesus monkey; m: mouse; r: rat.

FIG. 43A  FIG. 43B  FIG. 43C
Human IgG   γH2AX   Cleaved caspase 3
NIP228-SG3932
7 mg/kg
Mouse 2
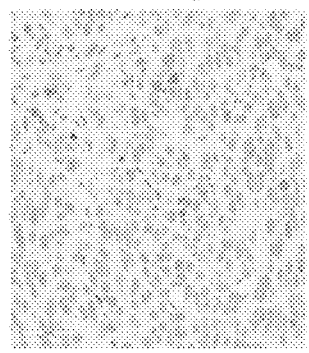
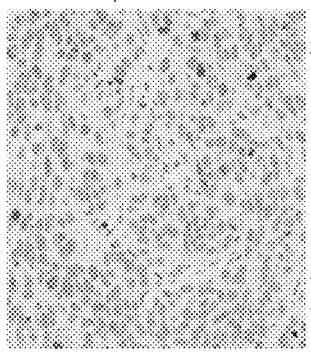
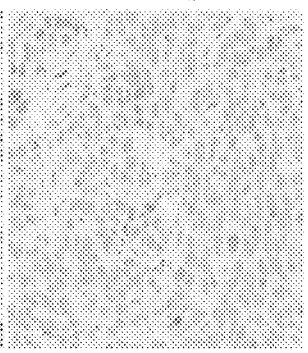
E02-GL-SG3932
7 mg/kg
Mouse 3
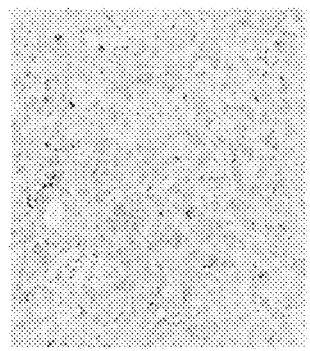
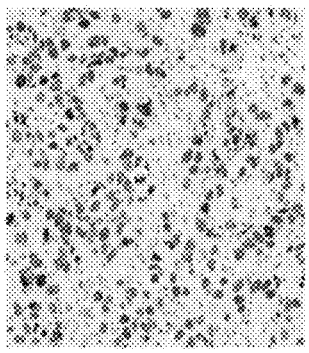
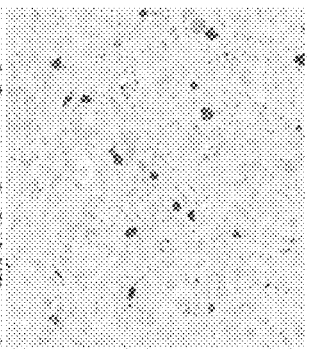
FIG. 43D  FIG. 43E  FIG. 43F

|   | ADC | Linker-warhead |
|---|---|---|
| 1 | E02-INT-cleavable mal-PEG8-val-ala linker-SG3932 | mp PEG8 Val-Ala SG3932 |
| 2 | E02-INT-SG4010 | mc Val-Ala SG3932 |
| 3 | E02-INT-SG4057 | mp PEG8 GGFG SG3932 |
| 4 | E02-INT-SG4052 | mc GGFG SG3932 |

** Cleavable mal-PEG8-val-ala linker-SG3932

| | ADC | Linker-warhead |
|---|---|---|
| 1 | E02-INT-cleavable mal-PEG8-val-ala linker-SG3932 | mp PEG8 Val-Ala SG3932 |
| 2 | E02-INT-SG4010 | mc Val-Ala SG3932 |
| 3 | E02-INT-SG4057 | mp PEG8 GGFG SG3932 |
| 4 | E02-INT-SG4052 | mc GGFG SG3932 |

THERAPEUTIC BINDING MOLECULES

CROSS-REFERENCE TO RELATED APPLICATIONS

This application claims priority benefit of U.S. Provisional Patent Application No. 63/077,207, filed Sep. 11, 2020, which is incorporated by reference herein in its entirety for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 50,723 Byte ASCII (Text) file named "B7H4-100-WO-PCT_seq-listing.txt" created on Sep. 8, 2021.

FIELD OF THE INVENTION

The present invention relates to binding molecules (e.g. antibodies) for the treatment of cancer, and related antibody-drug conjugates.

BACKGROUND

Despite years of research into and development of potential anti-cancer drugs, cancer remains one of the leading diseases globally, with one in three individuals developing some form of cancer in their lifetime. Two of the most common cancers types are breast cancer and lung cancer.

The principal therapies for cancer remain chemotherapy and radiotherapy. However, these therapies are associated with various undesirable side effects, from fatigue through to sickness and hair loss. These issues are exacerbated by the often lengthy courses of chemotherapy used.

Over the last couple of decades, a number of antibody therapies for cancer have been developed and marketed, leading to a reduction in the need for harsh forms of therapy (e.g. surgery and chemotherapy) for a number of cancer types. Although the availability of methodology for producing antibodies (e.g. monoclonal antibodies) has greatly improved over this time period, there are relatively few clinically available anti-cancer antibodies, and even fewer that may be used to target a broad spectrum of cancer types. Furthermore, there is a need to increase the potency of therapeutic antibodies, which is generally limited by the target antigen and subsequent effects on the cancer cell following antibody binding.

The present invention solves one or more of the above-mentioned problems.

SUMMARY OF THE INVENTION

The inventors have surprisingly found that the transmembrane polypeptide, B7-H4, is highly expressed in a multiple cell types (e.g. breast, lung, and pancreatic cancer), which is consistent with a role of a cancer antigen. The inventors have successfully generated antibodies which show high (e.g. better binding compared to commercially available antibodies) binding to B7-H4 expressing cells, both in vitro and in vivo. Advantageously, the antibodies can target multiple different cancer cell types expressing B7-H4, exemplifying the broad utility of the antibodies as anti-cancer therapies.

Furthermore, the antibodies can advantageously be linked/conjugated to suitable drugs/cytotoxins (e.g. to provide Antibody-drug conjugates (ADC)), thus increasing the potency of the antibodies as a therapy by allowing for targeted toxin delivery to cancer cells.

DETAILED DESCRIPTION

Thus, in one aspect the invention provides an antibody or antigen binding fragment thereof which binds to B7-H4 (e.g. a B7-H4 epitope), the antibody or antigen binding fragment thereof comprising:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
  v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

An antibody or antigen binding fragment thereof may suitably be comprised within a pharmaceutical composition, for example within a formulation suitable for administration to a patient.

In another aspect, there is provided a pharmaceutical composition comprising an antibody or antigen binding fragment thereof, the antibody or antigen binding fragment thereof comprising:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

The term "pharmaceutical composition" refers to a preparation that is in such form as to permit the biological activity of the active ingredient to be effective, and which contains no additional components which are unacceptably toxic to a subject to which the composition would be administered. Such composition can be sterile, and can comprise a pharmaceutically acceptable carrier, such as physiological saline. Suitable pharmaceutical compositions can comprise one or more of a buffer (e.g., acetate, phosphate or citrate buffer), a surfactant (e.g., polysorbate), a stabilizing agent (e.g., human albumin), a preservative (e.g., benzyl alcohol), and absorption promoter to enhance bioavailability, and/or other conventional solubilizing or dispersing agents.

Furthermore, the antibody or antigen binding fragment thereof of the invention has been demonstrated to target and suppress growth of B7-H4 positive tumours in vivo. Thus, the invention embraces the above defined antibody or antigen binding fragment thereof and the above defined pharmaceutical composition for use in a method of treating cancer. Preferably, said cancer comprises a cancer cell which expresses B7-H4.

In one aspect there is provided an antibody or antigen binding fragment thereof for use in treating a cancer (for example, wherein said cancer comprises a cancer cell that expresses B7-H4), wherein the antibody or antigen binding fragment comprises:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
  v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

In other words, one aspect of the invention provides a method of treating a cancer (for example, wherein said cancer comprises a cancer cell that expresses B7-H4), the method comprising administering to a subject an effective amount of an antibody or antigen binding fragment comprising:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
  v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

In yet other words, the invention embraces, in another aspect, use of an antibody or antigen binding fragment thereof in the manufacture of a medicament for the treatment of cancer (for example, wherein said cancer comprises a cancer cell that expresses B7-H4), said antibody or antigen binding fragment comprising:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
  v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

Certain definitions and preferred embodiments will now be outlined. It should be understood that the following definitions and embodiments may pertain to any aspect described herein, e.g. any method, composition, and/or composition for use in therapy described herein.

The term "epitope" refers to a target protein region (e.g. polypeptide) capable of binding to (e.g. being bound by) an antibody or antigen binding fragment of the invention.

B7-H4 (also known as V-set domain-containing T-cell activation inhibitor 1, encoded by the VTCN1 gene) is a transmembrane polypeptide of the B7 family of co-stimulatory proteins. B7-H4 is understood to be expressed on the surface of antigen-presenting cells for interactions with ligands of immune cells (e.g. T-lymphocytes, with CD28 being a potential ligand). Without wishing to be bound by theory, the present inventors' observation that B7-H4 is highly expressed on cells of various cancer types suggests that this molecule is a tumour-associated antigen. As such, the ability of the claimed antibody to target (and optionally deliver a cytotoxin to) a B7-H4 expressing renders said antibody particularly suitable for use in cancer therapy. Furthermore, B7-H4 expression is not limited to a particular cancer type, such that it represents a target antigen for treating a broad spectrum of cancer types.

The RNA, DNA, and amino acid sequences of B7-H4 are known to those skilled in the art and can be found in many databases, for example, in the databases of the National Center for Biotechnology Information (NCBI) and UniProt. Examples of these sequences found at UniProt are at Q7Z7D3 (VTCN1_HUMAN) for human B7-H4; and Q7TSP5 (VTCN1_MOUSE) for mouse B7-H4. The nucleotide sequence encoding for human B7-H4 may be SEQ ID NO: 53, more preferably SEQ ID NO: 54. The polypeptide sequence of human B7-H4 is preferably SEQ ID NO: 55.

In one embodiment, the antibody or antigen binding fragment thereof comprises a HCDR1, a HCDR2, a HCDR3, a LCDR1, LCDR2, and a LCDR3 comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof. An antibody or antigen binding fragment thereof comprising said sequences may be referred to as "ZY0EPQ-E02" or "EPQ-E02" herein.

In one embodiment, the antibody or antigen binding fragment thereof comprises a HCDR1, a HCDR2, a HCDR3, a LCDR1, LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof. An antibody or antigen binding fragment thereof comprising said sequences may be referred to as "ZY0EOB-F05" or "EOB-F05" herein.

In one embodiment, the antibody or antigen binding fragment thereof comprises a HCDR1, a HCDR2, a HCDR3, a LCDR1, LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof. An antibody or antigen binding fragment thereof comprising said sequences may be referred to as "ZY0EO5-E07" or "EO5-E07" herein.

In one embodiment, the antibody or antigen binding fragment thereof comprises a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof. An antibody or antigen binding fragment thereof comprising said sequences may be referred to as "ZY0EP0-007" or "EP0-007" herein.

In a particularly preferred embodiment, the antibody or antigen binding fragment thereof comprises a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof. An antibody or antigen binding fragment thereof comprising said sequences may be referred to as "ZY0EQD-E02" or "EQD-E02".

In other words, the antibody or antigen binding fragment thereof may preferably comprise:
- a HCDR1 comprising the amino acid sequence of SEQ ID NO: 7, or a functional variant thereof;
- a HCDR2 comprising the amino acid sequence of SEQ ID NO: 8, or a functional variant thereof;
- a HCDR3 comprising the amino acid sequence of SEQ ID NO: 9, or a functional variant thereof;
- a LCDR1 comprising the amino acid sequence of SEQ ID NO: 10, or a functional variant thereof;
- a LCDR2 comprising the amino acid sequence of SEQ ID NO: 11, or a functional variant thereof; and
- a LCDR3 comprising the amino acid sequence of SEQ ID NO: 12, or a functional variant thereof.

In one embodiment, the antibody or antigen binding fragment thereof comprises:
i. a HCDR1 comprising the amino acid sequence of SEQ ID NO: 1, or a functional variant thereof;
ii. a HCDR2 comprising the amino acid sequence of SEQ ID NO: 2, or a functional variant thereof;
iii. a HCDR3 comprising the amino acid sequence of SEQ ID NO: 3, or a functional variant thereof;
iv. a LCDR1 comprising the amino acid sequence of SEQ ID NO: 4, or a functional variant thereof;
v. a LCDR2 comprising the amino acid sequence of SEQ ID NO: 5, or a functional variant thereof; and
vi. a LCDR3 comprising the amino acid sequence of SEQ ID NO: 6, or a functional variant thereof.

In one embodiment, the antibody or antigen binding fragment thereof comprises:
i. a HCDR1 comprising the amino acid sequence of SEQ ID NO: 13, or a functional variant thereof;
ii. a HCDR2 comprising the amino acid sequence of SEQ ID NO: 14, or a functional variant thereof;
iii. a HCDR3 comprising the amino acid sequence of SEQ ID NO: 15, or a functional variant thereof;
iv. a LCDR1 comprising the amino acid sequence of SEQ ID NO: 16, or a functional variant thereof;
v. a LCDR2 comprising the amino acid sequence of SEQ ID NO: 17, or a functional variant thereof; and
vi. a LCDR3 comprising the amino acid sequence of SEQ ID NO: 18, or a functional variant thereof.

In one embodiment, the antibody or antigen binding fragment thereof comprises:
i. a HCDR1 comprising the amino acid sequence of SEQ ID NO: 19, or a functional variant thereof;
ii. a HCDR2 comprising the amino acid sequence of SEQ ID NO: 20, or a functional variant thereof;
iii. a HCDR3 comprising the amino acid sequence of SEQ ID NO: 21, or a functional variant thereof;
iv. a LCDR1 comprising the amino acid sequence of SEQ ID NO: 22, or a functional variant thereof;
v. a LCDR2 comprising the amino acid sequence of SEQ ID NO: 23, or a functional variant thereof; and
vi. a LCDR3 comprising the amino acid sequence of SEQ ID NO: 24, or a functional variant thereof.

In one embodiment, the antibody or antigen binding fragment thereof comprises:
i. a HCDR1 comprising the amino acid sequence of SEQ ID NO: 25, or a functional variant thereof;
ii. a HCDR2 comprising the amino acid sequence of SEQ ID NO: 26, or a functional variant thereof;
iii. a HCDR3 comprising the amino acid sequence of SEQ ID NO: 27, or a functional variant thereof;

iv. a LCDR1 comprising the amino acid sequence of SEQ ID NO: 28, or a functional variant thereof;
v. a LCDR2 comprising the amino acid sequence of SEQ ID NO: 29, or a functional variant thereof; and
vi. a LCDR3 comprising the amino acid sequence of SEQ ID NO: 30, or a functional variant thereof.

Additionally or alternatively, an antibody or antigen binding fragment thereof described herein may be described by means of a variable heavy (VH) chain and a variable light (VL) chain thereof.

Suitable a variable heavy (VH) chain sequences (which the antibody or antigen binding fragment thereof may comprise) are outlined in an individualised manner below:
SEQ ID NO: 31, or a functional variant thereof;
SEQ ID NO: 33, or a functional variant thereof
SEQ ID NO: 43, or a functional variant thereof
SEQ ID NO: 45, or a functional variant thereof
SEQ ID NO: 46, or a functional variant thereof
SEQ ID NO: 47, or a functional variant thereof
SEQ ID NO: 35, or a functional variant thereof
SEQ ID NO: 37, or a functional variant thereof
SEQ ID NO: 39, or a functional variant thereof Particularly suitable variable heavy (VH) chain sequences (which the antibody or antigen binding fragment thereof may comprise) are outlined in an individualised manner below:
SEQ ID NO: 45, or a functional variant thereof
SEQ ID NO: 33, or a functional variant thereof
SEQ ID NO: 43, or a functional variant thereof
SEQ ID NO: 46, or a functional variant thereof
SEQ ID NO: 47, or a functional variant thereof Suitable variable light (VL) chain sequences (which the antibody or antigen binding fragment thereof may comprise) are outlined in an individualised manner below:
SEQ ID NO: 32, or a functional variant thereof
SEQ ID NO: 34, or a functional variant thereof
SEQ ID NO: 36, or a functional variant thereof
SEQ ID NO: 38, or a functional variant thereof
SEQ ID NO: 40, or a functional variant thereof A preferred variable light (VL) chain sequence (which the antibody or antigen binding fragment thereof may comprise) may comprise an amino acid sequence of SEQ ID NO: 34 (or a functional variant thereof).

For example, in one embodiment, the antibody or antigen binding fragment thereof comprises:
i. a variable heavy chain comprising an amino acid sequence having at least 70%, 75%, 80%, 90%, 95% or 100% sequence identity to the amino acid sequence of SEQ ID NO: 31, 33, 35, 37, or 39, or a functional variant thereof; and
ii. a variable light chain comprising an amino acid sequence having at least 70%, 75%, 80%, 90%, 95% or 100% sequence identity to the amino acid sequence of SEQ ID NO: 32, 34, 36, 38, or 40, or a functional variant thereof.

For example, in one embodiment, the antibody or antigen binding fragment thereof comprises:
i. a variable heavy chain comprising an amino acid sequence having at least 70%, 75%, 80%, 90%, 95% or 100% sequence identity to the amino acid sequence of SEQ ID NO: 31, 33, 35, 37, 39, 43, 45, 46, or 47, or a functional variant thereof; and
ii. a variable light chain comprising an amino acid sequence having at least 70%, 75%, 80%, 90%, 95% or 100% sequence identity to the amino acid sequence of SEQ ID NO: 32, 34, 36, 38, or 40, or a functional variant thereof.

Suitably, the antibody or antigen binding fragment thereof may comprise:
i. a variable heavy chain comprising an amino acid sequence having at least 70%, 75%, 80%, 90%, 95% or 100% sequence identity to the amino acid sequence SEQ ID NO: 33, or a functional variant thereof; and
ii. a variable light chain comprising an amino acid sequence having at least 70%, 75%, 80%, 90%, 95% or 100% sequence identity to the amino acid sequence of SEQ ID NO: 34, or a functional variant thereof.

More suitably, the antibody or antigen binding fragment thereof may comprise:
i. a variable heavy chain comprising an amino acid sequence having at least 70%, 75%, 80%, 90%, 95% or 100% sequence identity to the amino acid sequence SEQ ID NO: 45, or a functional variant thereof; and
ii. a variable light chain comprising an amino acid sequence having at least 70%, 75%, 80%, 90%, 95% or 100% sequence identity to the amino acid sequence of SEQ ID NO: 34, or a functional variant thereof.

In one embodiment, the antibody or antigen binding fragment thereof comprises:
a variable heavy (VH) chain and a variable light (VL) chain comprising the amino acid sequence of SEQ ID NO: 31, and SEQ ID NO: 32, respectively, or a functional variant thereof;
a VH chain and a VL chain comprising the amino acid sequence of SEQ ID NO: 33 and SEQ ID NO: 34, respectively, or a functional variant thereof;
a VH chain and a VL chain comprising the amino acid sequence of SEQ ID NO: 43 and SEQ ID NO: 34, respectively, or a functional variant thereof;
a VH chain and a VL chain comprising the amino acid sequence of SEQ ID NO: 45 and SEQ ID NO: 34, respectively, or a functional variant thereof;
a VH chain and a VL chain comprising the amino acid sequence of SEQ ID NO: 46 and SEQ ID NO: 34, respectively, or a functional variant thereof;
a VH chain and a VL chain comprising the amino acid sequence of SEQ ID NO: 47 and SEQ ID NO: 34, respectively, or a functional variant thereof;
a VH chain and a VL chain comprising the amino acid sequence of SEQ ID NO: 35 and SEQ ID NO: 36, respectively, or a functional variant thereof;
a VH chain and a VL chain comprising the amino acid sequence of SEQ ID NO: 37 and SEQ ID NO: 38, respectively, or a functional variant thereof; or
a VH chain and a VL chain comprising the amino acid sequence of SEQ ID NO: 39 and SEQ ID NO: 40, respectively, or a functional variant thereof.

In a preferable embodiment the antibody or antigen binding fragment thereof comprises: a variable heavy (VH) chain comprising the amino acid sequence of SEQ ID NO: 45, 33, 43, 46 or 47 (or a functional variant thereof); and a variable light (VL) chain comprising the amino acid sequence of SEQ ID NO: 34 (or a functional variant thereof). For example, the VH of SEQ ID NOs: 33, 45, 46 and/47 may correspond to "germlined" versions of the VH of SEQ ID NO: 33 (e.g. all having same CDR sequences, but with framework variations). Advantageously, each variant retains equivalent binding properties.

In one embodiment, the antibody or antigen binding fragment thereof comprises: a variable heavy chain comprising the amino acid sequence of SEQ ID NO: 31, or a functional variant thereof; and a variable light chain comprising the amino acid sequence of SEQ ID NO: 32, or a functional variant thereof. An antibody or antigen binding fragment thereof comprising said sequences may be referred to as "ZY0EPD-E02" or "EPD-E02".

In one embodiment, the antibody or antigen binding fragment thereof comprises: a variable heavy chain comprising the amino acid sequence of SEQ ID NO: 35, or a functional variant thereof; and a variable light chain comprising the amino acid sequence of SEQ ID NO: 36, or a functional variant thereof. An antibody or antigen binding fragment thereof comprising said sequences may be referred to as "ZY0EOB-F05" or "EOB-F05".

In one embodiment, the antibody or antigen binding fragment thereof comprises: a variable heavy chain comprising the amino acid sequence of SEQ ID NO: 37, or a functional variant thereof; and a variable light chain comprising the amino acid sequence of SEQ ID NO: 38, or a functional variant thereof. An antibody or antigen binding fragment thereof comprising said sequences may be referred to as "ZY0EO5-E07" or "EO5-E07".

In one embodiment, the antibody or antigen binding fragment thereof comprises: a variable heavy chain comprising the amino acid sequence of SEQ ID NO: 39, or a functional variant thereof; and a variable light chain comprising the amino acid sequence of SEQ ID NO: 40, or a functional variant thereof. An antibody or antigen binding fragment thereof comprising said sequences may be referred to as "ZY0EP0-007" or "EP0-007".

In one embodiment, the antibody or antigen binding fragment thereof comprises: a variable heavy chain comprising the amino acid sequence of SEQ ID NO: 33, or a functional variant thereof; and a variable light chain comprising the amino acid sequence of SEQ ID NO: 34, or a functional variant thereof. An antibody or antigen binding fragment thereof comprising said sequences may be referred to as "ZY0EQD-E02" or "EQD-E02".

In one embodiment, the antibody or antigen binding fragment thereof comprises: a variable heavy chain comprising the amino acid sequence of SEQ ID NO: 43, or a functional variant thereof; and a variable light chain comprising the amino acid sequence of SEQ ID NO: 34, or a functional variant thereof.

In one embodiment, the antibody or antigen binding fragment thereof comprises: a variable heavy chain comprising the amino acid sequence of SEQ ID NO: 46, or a functional variant thereof; and a variable light chain comprising the amino acid sequence of SEQ ID NO: 34, or a functional variant thereof.

In one embodiment, the antibody or antigen binding fragment thereof comprises: a variable heavy chain comprising the amino acid sequence of SEQ ID NO: 47, or a functional variant thereof; and a variable light chain comprising the amino acid sequence of SEQ ID NO: 34, or a functional variant thereof.

In a preferable embodiment, the antibody or antigen binding fragment thereof comprises: a variable heavy chain comprising the amino acid sequence of SEQ ID NO: 45, or a functional variant thereof; and a variable light chain comprising the amino acid sequence of SEQ ID NO: 34, or a functional variant thereof. An antibody or antigen binding fragment thereof comprising said sequences may be referred to as "EQD-E02_GL".

In one embodiment, the antibody or antigen binding fragment thereof comprises a variable heavy chain comprising an amino acid sequence having at least 70%, 75%, 80%, 90%, 95% or 100% sequence identity to a reference amino acid sequence of SEQ ID NO: 43. In one embodiment, the antibody or antigen binding fragment thereof comprises a variable heavy chain comprising an amino acid sequence of SEQ ID NO: 43. For example, the antibody or antigen binding fragment thereof may comprise a variable heavy chain comprising an amino acid sequence of SEQ ID NO: 43, and a variable light chain comprising an amino acid sequence of SEQ ID NO: 34.

Additionally or alternatively, an antibody or antigen binding fragment thereof described herein may be described by means of a heavy chain and/or light chain thereof.

In one embodiment, the antibody or antigen binding fragment thereof comprises a light chain (e.g. comprising a VL and constant light chain) comprising an amino acid sequence having at least 70%, 75%, 80%, 90%, 95% or 100% sequence identity to the amino acid sequence of SEQ ID NO: 44. In a preferable embodiment, the antibody or antigen binding fragment thereof comprises a light chain (e.g. comprising a VL and constant light chain) comprising the amino acid sequence of SEQ ID NO: 44.

In one embodiment, the antibody or antigen binding fragment thereof comprises a heavy chain (e.g. comprising a VH and constant heavy chain) comprising an amino acid sequence having at least 70%, 75%, 80%, 90%, 95% or 100% sequence identity to a reference amino acid sequence of SEQ ID NO: 48. For example, the antibody or antigen binding fragment thereof may comprise a heavy chain (e.g. comprising a VH and constant heavy chain) comprising the amino acid sequence of SEQ ID NO: 48. Such heavy chain may be referred to as "E02-GL-Maia-heavy chain".

In one embodiment, the antibody or antigen binding fragment thereof comprises a heavy chain (e.g. comprising a VH and constant heavy chain) comprising an amino acid sequence having at least 70%, 75%, 80%, 90%, 95% or 100% sequence identity to a reference amino acid sequence of SEQ ID NO: 49. For example, the antibody or antigen binding fragment thereof may comprise a heavy chain (e.g. comprising a VH and constant heavy chain) comprising the amino acid sequence of SEQ ID NO: 49. Such heavy chain may be referred to as "E02-GLY-Maia-heavy chain".

In one embodiment, the antibody or antigen binding fragment thereof comprises a heavy chain (e.g. comprising a VH and constant heavy chain) comprising an amino acid sequence having at least 70%, 75%, 80%, 90%, 95% or 100% sequence identity to a reference amino acid sequence of SEQ ID NO: 50. For example, the antibody or antigen binding fragment thereof may comprise a heavy chain (e.g. comprising a VH and constant heavy chain) comprising the amino acid sequence of SEQ ID NO: 50. Such heavy chain may be referred to as "E02-GLQ-Maia-heavy chain".

In a preferred embodiment, the antibody or antigen binding fragment thereof comprises a heavy chain (e.g. comprising a VH and constant heavy chain) comprising an amino acid sequence having at least 70%, 75%, 80%, 90%, 95% or 100% sequence identity to a reference amino acid sequence of SEQ ID NO: 51. In a more preferable embodiment, the antibody or antigen binding fragment thereof comprises a heavy chain (e.g. comprising a VH and constant heavy chain) comprising the amino acid sequence of SEQ ID NO: 51. Such heavy chain may be referred to as "E02-GL-WT-heavy chain".

In one embodiment, the antibody or antigen binding fragment thereof comprises a light chain constant region comprising an amino acid sequence having at least 70%, 75%, 80%, 90%, 95% or 100% sequence identity to a reference amino acid sequence of SEQ ID NO: 42. In a preferable embodiment, the antibody or antigen binding fragment thereof comprises light chain constant region comprising an amino acid sequence of SEQ ID NO: 42.

In one embodiment, the antibody or antigen binding fragment thereof comprises a heavy chain constant region comprising the amino acid sequence of SEQ ID NO: 41. More preferably, the antibody or antigen binding fragment thereof comprises a heavy chain constant region comprising the amino acid sequence of SEQ ID NO: 52.

In a preferable embodiment, the antibody or antigen binding fragment thereof comprises a light chain (e.g. comprising a VL and constant light chain) comprising the amino acid sequence of SEQ ID NO: 44 and a heavy chain (e.g. comprising a VH and constant heavy chain) comprising the amino acid sequence of SEQ ID NO: 51.

Advantageously, the inventors have demonstrated that an antibody or antigen binding fragment of the claims may target a broader spectrum of B7-H4 expressing cells when compared with existing (commercially) available antibodies reported to target B7-H4. Thus, not only have the inventors provided an antibody (or antigen binding fragment) thereof having affinity and specificity for a clinically relevant target, but have demonstrated a unique advantage (e.g. unexpected technical effect) associated therewith.

For example, FIG. 4 demonstrates that an exemplary antibody of the claims binds to wide spectrum of cancer cell types with affinity not achievable with antibodies: Biosciences 14-5949 anti-Human B7H4 mouse IgG; US biological B0000-35B anti Human B7H4 mouse IgG; R and D systems AF2514 anti Mouse B7H4 goat IgG1; and Sigma SAB2500141 anti B7H4 Goat IgG1.

Preferably, antibody or antigen binding fragment thereof described herein is capable of binding to B7-H4 as an integral component of a cancer cell (for example, B7-H4 as an integral component of a cell membrane of a cancer cell).

An antibody or antigen binding fragment thereof described herein may bind to an OVCAR4 cell line and/or a CHO cell line (e.g. which may lack an exogenous nucleic acid encoding B7-H4). For example, the antibody or antigen binding fragment thereof binds to a B7-H4 (e.g. a B7-H4 epitope) of an OVCAR4 cell line and/or a CHO cell line (e.g. which may lack an exogenous nucleic acid encoding B7-H4). Suitably, the antibody or antigen binding fragment thereof described herein may bind to an OVCAR4 cell line and a CHO cell line (e.g. which may lack an exogenous nucleic acid encoding B7-H4).

In one embodiment, the antibody or antigen binding fragment thereof binds to an OVCAR4 cell line and/or CHO cell line (e.g. which may lack an exogenous nucleic acid encoding B7-H4) with higher affinity when compared to one or more antibody selected from E Biosciences 14-5949 anti-Human B7H4 mouse IgG, US biological B0000-35B anti Human B7H4 mouse IgG, R and D systems AF2514 anti-Mouse B7H4 goat IgG1, Sigma SAB2500141 anti B7H4 Goat IgG1, Isotype 1 CAT004 SP06-003, Isotype 2 R and D Normal goat IgG control (AB-108C), AdD serotec MCA2632, Epitomics 2516-1, eBiosciences, 145972-82, eBioscience 145970-85, or a combination thereof. For example, the antibody or antigen binding fragment thereof may bind to an OVCAR4 cell line and/or CHO cell line (e.g. which may lack an exogenous nucleic acid encoding B7-H4) with higher affinity when compared to one or more antibody selected from E Biosciences 14-5949 anti-Human B7H4 mouse IgG, US biological B0000-35B anti Human B7H4 mouse IgG, R and D systems AF2514 anti-Mouse B7H4 goat IgG1, and Sigma SAB2500141 anti B7H4 Goat IgG1, or a combination thereof.

In a preferable embodiment, the antibody or antigen binding fragment thereof binds to an OVCAR4 cell line with higher affinity when compared to E Biosciences 14-5949 anti-Human B7H4 mouse IgG.

Reference to "E Biosciences 14-5949 anti-Human B7H4 mouse IgG" may be used interchangeably with the term "B7-H4 Monoclonal Antibody (H74), eBioscience" herein. Said antibody is available from ThermoFisher Scientific (Catalog #14-5949-82).

In another preferable embodiment, the antibody or antigen binding fragment thereof binds to an OVCAR4 cell line with higher affinity when compared to US biological B0000-35B anti Human B7H4 mouse IgG.

Said affinity (e.g. binding affinity) can be measured by any suitable method of measuring binding affinity described herein.

The OVCAR4 cell line is a human ovary carcinoma cell line. The OVCAR4 cell line is obtainable from the National Cancer Institute for the transfer of cell lines from the Division of Cancer Treatment and Diagnosis Tumor Repository. The Chinese hamster ovary (CHO) cell line is an epithelial cell line derived from the ovary of the Chinese hamster, and is widely obtainable.

As described above, an antibody or antigen binding fragment thereof of the invention may be comprised within a pharmaceutical composition. The pharmaceutical composition may comprise one or more pharmaceutically acceptable excipient(s). In one embodiment, a pharmaceutical composition of the invention can comprise a pharmaceutically acceptable, non-toxic, sterile carrier such as physiological saline, non-toxic buffers, preservatives and the like. Suitable formulations for use in the therapeutic methods disclosed herein are described in Remington's Pharmaceutical Sciences, 22nd ed., Ed. Lloyd V. Allen, Jr. (2012).

In one embodiment, a pharmaceutical composition of the invention may be comprised within one or more formulation selected from a capsule, a tablet, an aqueous suspension, a solution, a nasal aerosol, or a combination thereof.

In one embodiment, the pharmaceutical composition comprises more than one type of antibody or antigen binding fragment of the invention. For example, a pharmaceutical composition may comprise two or more selected from an antibody, an antigen-binding fragment, an antibody or antigen binding fragment thereof conjugated to a cytotoxin, or a combination thereof.

The term "a pharmaceutically effective amount" of an antibody or antigen-binding fragment means an amount sufficient to achieve effective binding to a target and to achieve a benefit, e.g., to ameliorate symptoms of a disease or condition or to detect a substance or a cell.

In one embodiment, a pharmaceutical composition may comprise a buffer (e.g., acetate, phosphate or citrate buffer), a surfactant (e.g., polysorbate), optionally a stabilizer agent (e.g., human albumin), etc.

Suitably, the antibody or antigen binding fragment of the invention binds to B7-H4 molecule with sufficient affinity such that the antibody is useful as a therapeutic agent or a diagnostic reagent in targeting B7-H4.

In one embodiment, the antibody or antigen binding fragment thereof binds to a B7-H4 (preferably a human B7-H4) with a dissociation constant (KD) of $\leq 1$ µM, $\leq 100$ nM, $\leq 10$ nM, $\leq 1$ nM, $\leq 0.1$ nM, $\leq 10$ pM, $\leq 1$ pM, or $\leq 0.1$ pM. In one embodiment, the antibody or antigen binding fragment thereof binds to a B7-H4 (preferably a human B7-H4) with a KD of between about 0.1 nM to about 40 nM, between about 0.5 nM to about 30 nM, between about 1 nM to about 20 nM, or between about 1.5 nM to about 20 nM.

In a preferable embodiment, the antibody or antigen binding fragment thereof binds to a B7-H4 (preferably a human B7-H4) with a KD of between about 23 nM to about 27 nM. In a more preferable embodiment, the antibody or antigen binding fragment thereof binds to a B7-H4 (preferably a human B7-H4) with a KD of between about 1 nM to about 1.5 nM.

The KD measurements (binding affinity) may be carried out by any suitable assay known in the art. Suitable assays include an affinity assay performable via a KinExA system (e.g., KinExA 3100, KinExA 3200, or KinExA 4000) (Sapidyne Instruments, Idaho), or ForteBio Octet system.

In one embodiment, the extent of binding of an antibody or antigen binding fragment thereof of the invention to an unrelated, non-B7-H4 protein is less than about 10%, 5%, 2% or 1% (preferably less than about 10%) of the binding of the antibody (or antigen binding fragment thereof) to B7-H4 (preferably human B7-H4). Said binding may be measured, e.g., by a radioimmunoassay (RIA), BIACORE® (using recombinant B7-H4 as the analyte and antibody as the ligand, or vice versa), KINEXA®, ForteBio Octet system, or other binding assays known in the art.

In one embodiment, the antibody or antigen binding fragment thereof does not bind to one or more selected from a human B7-H1 molecule, a human B7-H2 molecule, a human B7-H3 molecule, a human BTN1A1 molecule, a human HHLA2 molecule, a human BTN3A2 molecule, or a combination thereof. In a preferable embodiment, the antibody or antigen binding fragment thereof does not bind to one or more selected from a human B7-H1 molecule, a human B7-H2 molecule, a human B7-H3 molecule, or a combination thereof.

The term "does not bind" means that the antibody or antigen binding fragment thereof described herein does not substantially bind to one of more of said molecules (e.g. human B7-H1 molecule, a human B7-H2 molecule, a human B7-H3 molecule, a human BTN1A1 molecule, a human HHLA2 molecule, a human BTN3A2 molecule, or a combination thereof). The term "substantially no" when used in the context of binding herein may mean less than 5%, 2%, 1%, 0.5% or 0.1% of cells expressing one or more of said molecules in a cell culture become bound by the antibody or antigen binding fragment thereof described herein (upon contact therewith). Suitably, the term "substantially no" when used in the context of binding herein may mean no such cells become bound.

In one embodiment, the antibody or antigen binding fragment thereof does not bind to a human B7-H1 molecule, a human B7-H2 molecule, a human B7-H3 molecule, a human BTN1A1 molecule, a human HHLA2 molecule, or a human BTN3A2 molecule. In a preferable embodiment, the antibody or antigen binding fragment thereof does not bind to a human B7-H1 molecule, a human B7-H2 molecule, or a human B7-H3 molecule.

In one embodiment, the B7-H4 polypeptide is comprised within a B7-H4 polypeptide sequence, or a fragment thereof.

A "B7-H4 polypeptide" may comprise the full length polypeptide sequence of B7-H4 (e.g. SEQ ID NO.: 55), or may comprise a fragment of B7-H4 of any length of the full length polypeptide sequence of B7-H4 (e.g. comprising a polypeptide sequence of 5%, 15%, 25%, 35%, 45%, 55%, 65%, 75%, 85% or 95% of the full length polypeptide sequence of B7-H4) which comprises an epitope which can bind (e.g. be bound by) an antibody or antigen binding fragment of the invention. The B7-H4 polypeptide may comprise a sequence having 75%, 80%, 85%, 90% or 90% sequence identity to the sequence of SEQ ID NO.: 55. Preferably, the B7-H4 polypeptide comprises the sequence of SEQ ID NO.: 55.

The antibody or antigen binding fragment has high affinity for B7-H4 both in vitro an in vivo, and thus may advantageously be used in methods for detecting a B7-H4 epitope, and associated methods of diagnosis.

To "treat" refers to therapeutic measures that cure, slow down, alleviate symptoms of, and/or halt progression of a diagnosed pathologic condition or disorder. Thus, those in need of treatment include those already with the disorder. In one embodiment, a subject is successfully "treated" for a disease or disorder (preferably cancer), according to the methods provided herein if the patient shows, e.g., total, partial, or transient alleviation or elimination of symptoms associated with the disease or disorder (preferably cancer).

In one embodiment, a method of the invention may be used to prevent the onset of a cancer comprising a cancer cell which expresses B7-H4. To "prevent" refers to prophylactic or preventative measures that prevent and/or slow the development of a targeted pathologic condition or disorder. Thus, those in need of prevention include those prone to have or susceptible to the disorder. In one embodiment, a disease or disorder (preferably cancer) is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

The terms "subject", "individual" and "patient" are used interchangeably herein to refer to a mammalian subject. In one embodiment the "subject" is a human, domestic animals, farm animals, sports animals, and zoo animals, e.g., humans, non-human primates, dogs, cats, guinea pigs, rabbits, rats, mice, horses, cattle, etc. In one embodiment, the subject is a cynomolgus monkey (*Macaca fascicularis*). In a preferable embodiment, the subject is a human. In methods of the invention, the subject may not have been previously diagnosed as having cancer. Alternatively, the subject may have been previously diagnosed as having cancer. The subject may also be one who exhibits disease risk factors, or one who is asymptomatic for cancer. The subject may also be one who is suffering from or is at risk of developing cancer. Thus, in one embodiment, a method of the invention may be used to confirm the presence of cancer in a subject. For example, the subject may previously have been diagnosed with cancer by alternative means. In one embodiment, the subject has been previously administered a cancer therapy.

In one embodiment, methods of treatment of the invention comprise one or more administration step selected from oral, intravenous, intraarterial, intraperitoneal, intramuscular, subcutaneous, rectal, or vaginal, inhalation, topical, or a combination thereof. In a preferable embodiment, the administration is intravenous or intraarterial (e.g. by injection or drip), or a combination thereof.

In one embodiment, the antibody or antigen binding fragment thereof is delivered directly to the site of the adverse cellular population (e.g. thereby increasing the exposure of the diseased tissue to the therapeutic agent). In one embodiment, the administration is directly to the airway, e.g., by inhalation or intranasal administration.

In a preferable embodiment, a cancer referred to herein is a cancer characterised by the expression (preferably overexpression) of a B7-H4 molecule. In other words, a cancer referred to herein may comprise a cancerous cell that expresses B7-H4. Said cancerous cell may be comprised within a tumor.

In one embodiment, the cancer is one or more selected from breast cancer, ovarian cancer, endometrial cancer, cholangiocarcinoma, NSCLC (squamous and adenocarcinoma), pancreatic cancer, and gastric cancer.

In one embodiment, the cancer is one or more selected from colorectal cancer, HNSCC, prostate cancer, lung cancer (e.g. NSCLC or SCLC), breast cancer, ovarian cancer pancreatic cancer, gastric cancer, cholangiocarcinoma, melanoma, endometrial cancer, hematological cancer (AML, MM, DLBCL), and cancers comprising CSCs.

In a preferable embodiment, the cancer is lung cancer, breast cancer, or a combination thereof. For example, the cancer may be lung cancer. The cancer may be breast cancer. The cancer may be ovarian cancer.

In one embodiment, the cancer is one or more breast cancer selected from hormone receptor (HR)-positive (HR+) breast cancer, human epidermal growth factor receptor 2 positive (HER2+) breast cancer, triple negative breast cancer (TNBC). A subject may be Herceptin eligible. A subject may have received treatment with Herceptin.

In one embodiment, the cancer is one or more non-small-cell lung carcinoma (NSCLC) preferably selected from squamous NSCLC, adenocarcinoma NSCLC, or a combination thereof.

An antibody or antigen binding fragment thereof also finds utility in detecting a cancer cell, for example as part of a diagnostic method.

In a further aspect, there is provided a method for detecting the presence or absence of a B7-H4 polypeptide (e.g. a B7-H4 polypeptide epitope) in a sample, comprising:
  a. contacting a sample with an antibody or antigen binding fragment thereof, or a pharmaceutical composition comprising an antibody or antigen binding fragment thereof, to provide an antibody-antigen complex; wherein said antibody or antigen binding fragment thereof comprises:
    i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
    ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
    iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
    iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
    v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.
  b. detecting the presence or absence of said antibody-antigen complex; and
  c. wherein the presence of the antibody-antigen complex confirms the presence of a B7-H4 polypeptide (e.g. B7-H4 polypeptide epitope); or
  d. wherein the absence of the antibody-antigen complex confirms the absence of B7-H4 polypeptide (e.g. B7-H4 polypeptide epitope).

In a related aspect, there is provided a method for detecting the presence or absence of a cancer cell expressing a B7-H4 polypeptide (e.g. B7-H4 polypeptide epitope) in a sample, comprising:
  a. contacting a sample with an antibody or antigen binding fragment thereof, or a pharmaceutical composition comprising an antibody or antigen binding fragment thereof, to provide an antibody-antigen complex; wherein said antibody or antigen binding fragment thereof comprises:
    i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
    ii. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
    iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
    iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
    v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof;
  b. detecting the presence or absence of said antibody-antigen complex; and
  c. wherein the presence of the antibody-antigen complex confirms the presence of a B7-H4 polypeptide (e.g. B7-H4 polypeptide epitope); or
  d. wherein the absence of the antibody-antigen complex confirms the absence of B7-H4 polypeptide (e.g. B7-H4 polypeptide epitope).

The invention embraces a corresponding use of the antibody or antigen binding fragment thereof of the invention for detecting a B7-H4 polypeptide (e.g. B7-H4 polypeptide epitope).

In one embodiment, the presence of antibody-antigen complex is indicative of the presence of a cancer cell, and the absence of the antibody-antigen complex is indicative of the absence of a cancer cell. For example, the method may comprise confirming the presence of cancer where an antibody-antigen complex is detected, or not confirming the presence of cancer where an antibody-antigen complex is not detected.

In a preferable embodiment, the cancer cell is a cancer cell expressing a B7-H4 polypeptide (e.g. B7-H4 polypeptide epitope).

Thus, the present invention embraces corresponding use of the method steps described herein in methods of diagnosing a subject with a cancer, preferably wherein said cancer comprises a B7-H4 expressing cancer cell.

In one embodiment, a method of detection or method of diagnosis may comprise measuring the expression level of B7-H4 on a cell (or tissue) obtainable from a subject, and comparing the measured expression level with a standard B7-H4 expression in a control cell (or tissue), wherein an increase in the expression level compared to the control is indicative of the presence of cancer. Preferably, said control sample comprises a non-cancer (e.g. normal) cell.

An "antibody-antigen complex" means a complex (e.g. macromolecular complex) comprising a B7-H4 antigen which has become bound to an antibody. The term "antibody-antigen complex" may be used synonymously with the terms "bound B7-H4-antibody complex" and "antibody bound to a B7-H4".

An antibody-antigen complex may be detected by any means known to the skilled person. In one embodiment, the antibody (or antigen binding fragment thereof) is labelled with a detectable label. Said label may be an epi-fluorescent label. In a preferable embodiment, the antibody is labelled with 800 CW.

In one embodiment, an antibody-antigen complex is detected by means of a secondary (e.g. detection) antibody which binds the antibody and/or antibody-antigen complex.

Suitably, said secondary antibody comprises a detection means, such as a tag/label to aid detection. Said detection means is preferably conjugated to the secondary antibody. Examples of suitable labels include detectable labels such as radiolabels or fluorescent or coloured molecules, enzymatic markers or chromogenic markers—e.g. dyes that provide a visible colour change upon binding of the detection antibody to an antigen. By way of example, the label may be fluorescein-isothiocyanate (FITC), R-phycoerythrin, Alexa 532, CY3 or digoxigenin. The label may be a reporter molecule, which is detected directly, such as by detecting its fluorescent signal, or by exposure of the label to photographic or X-ray film. Alternatively, the label is not directly detectable, but may be detected, for example, in a two-phase system. An example of indirect label detection is binding of an antibody to the label.

In a preferable embodiment, said secondary antibody comprises a fluorescent tag, and an antibody-antigen complex is detected by the florescence emitted from a, antibody-antigen-secondary antibody complex. An "antibody-antigen-secondary antibody complex" means a complex comprising an antigen (e.g. B7-H4) which has become bound to an antibody, wherein said complex has further become bound by a secondary antibody which binds said antibody and/or antibody-antigen complex.

Suitably, an antibody-antigen complex is detected when the signal (preferably fluorescence) emitted from the detection label is greater than the signal detected in a control comprising no antibody (e.g. no antibody which binds a B7-H4). Said control may alternatively comprise a B7-H4, but the sample is not applied to said control.

Suitably, a "sample" is a sample obtained from a subject (e.g. biopsy), cell line, tissue culture, or other source of cells potentially expressing B7-H4. In preferable embodiment, a sample is a biopsy from a subject. Said biopsy may be taken from a tumour, or a site at risk of developing a tumour.

In a preferable embodiment, the sample is an isolated sample obtainable (e.g. obtained) from a subject.

In a preferable embodiment, the B7-H4 polypeptide (e.g. B7-H4 polypeptide epitope) is an integral component of a cancer cell, more preferably an integral component of the cell membrane of a cancer cell.

The present invention encompasses the antibodies (e.g. the antibody or antigen binding fragment) defined herein having the recited CDR sequences or variable heavy and variable light chain sequences (reference antibodies), as well as functional variants thereof. A functional variant binds to the same target antigen as the reference antibody, and preferably exhibits the same antigen cross-reactivity as the reference antibody. The functional variants may have a different affinity for the target antigen when compared to the reference antibody, but substantially the same affinity is preferred.

The term "reference antibody" is used to conveniently refer, in comparison, to an antibody or antigen thereof of the invention. Thus, the term "reference antibody" refers to an antibody or antigen thereof of the invention. For example, the reference antibody may mean an antibody or antigen binding fragment thereof comprising a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively. More particularly, the reference antibody may mean an antibody or antigen binding fragment thereof comprising a variable heavy chain comprising the amino acid sequence of SEQ ID NO: 33; and a variable light chain comprising the amino acid sequence of SEQ ID NO: 34. Preferably, the reference antibody may mean an antibody or antigen binding fragment thereof comprising a variable heavy chain comprising the amino acid sequence of SEQ ID NO: 45; and a variable light chain comprising the amino acid sequence of SEQ ID NO: 34.

In one embodiment functional variants of a reference antibody show sequence variation at one or more CDRs when compared to corresponding reference CDR sequences. Thus, a functional antibody variant may comprise a functional variant of a CDR. Where the term "functional variant" is used in the context of a CDR sequence, this means that the CDR has at most 2, preferably at most 1 amino acid differences when compared to a corresponding reference CDR sequence, and when combined with the remaining 5 CDRs (or variants thereof) enables the variant antibody to bind to the same target antigen as the reference antibody, and preferably to exhibit the same antigen cross-reactivity as the reference antibody. A functional variant may be referred to as a "variant antibody".

In one embodiment a variant antibody (or antigen binding fragment thereof) comprises:
  a light chain CDR1 having at most 2 amino acid difference when compared to a corresponding reference CDR sequence;
  a light chain CDR2 having at most 2 amino acid difference when compared to a corresponding reference CDR sequence;
  a light chain CDR3 having at most 2 amino acid difference when compared to a corresponding reference CDR sequence;

a heavy chain CDR1 having at most 2 amino acid difference when compared to a corresponding reference CDR sequence;
a heavy chain CDR2 having at most 2 amino acid difference when compared to a corresponding reference CDR sequence; and
a heavy chain CDR3 having at most 2 amino acid difference when compared to a corresponding reference CDR sequence;
wherein the variant antibody binds to the same target antigen as the reference antibody, and preferably exhibits the same antigen cross-reactivity (or lack thereof) as the reference antibody.

Preferably a variant antibody (or antigen binding fragment thereof) comprises:
a light chain CDR1 having at most 1 amino acid difference when compared to a corresponding reference CDR sequence;
a light chain CDR2 having at most 1 amino acid difference when compared to a corresponding reference CDR sequence;
a light chain CDR3 having at most 1 amino acid difference when compared to a corresponding reference CDR sequence;
a heavy chain CDR1 having at most 1 amino acid difference when compared to a corresponding reference CDR sequence;
a heavy chain CDR2 having at most 1 amino acid difference when compared to a corresponding reference CDR sequence; and
a heavy chain CDR3 having at most 1 amino acid difference when compared to a corresponding reference CDR sequence;
wherein the variant antibody binds to the same target antigen as the reference antibody, and preferably exhibits the same antigen cross-reactivity (or lack thereof) as the reference antibody.

For example, a variant of the antibody or antigen binding fragment may comprise:
a heavy chain CDR1 having at most 2 amino acid difference when compared to SEQ ID NO: 7;
a heavy chain CDR2 having at most 2 amino acid difference when compared to SEQ ID NO: 8; and
a heavy chain CDR3 having at most 2 amino acid difference when compared to SEQ ID NO: 9;
a light chain CDR1 having at most 2 amino acid difference when compared to SEQ ID NO: 10;
a light chain CDR2 having at most 2 amino acid difference when compared to SEQ ID NO: 11;
a light chain CDR3 having at most 2 amino acid difference when compared to SEQ ID NO: 12;
wherein the variant antibody binds to a B7-H4 polypeptide (e.g. B7-H4 polypeptide epitope), and preferably exhibits the same antigen cross-reactivity (or lack thereof) as the reference antibody or antigen binding fragment.

For example, a variant of the antibody or antigen binding fragment may (preferably) comprise:
a heavy chain CDR1 having at most 1 amino acid difference when compared to SEQ ID NO: 7;
a heavy chain CDR2 having at most 1 amino acid difference when compared to SEQ ID NO: 8; and
a heavy chain CDR3 having at most 1 amino acid difference when compared to SEQ ID NO: 9;
a light chain CDR1 having at most 1 amino acid difference when compared to SEQ ID NO: 10;
a light chain CDR2 having at most 1 amino acid difference when compared to SEQ ID NO: 11;
a light chain CDR3 having at most 1 amino acid difference when compared to SEQ ID NO: 12;
wherein the variant antibody binds to a B7-H4 polypeptide (e.g. B7-H4 polypeptide epitope), and preferably exhibits the same antigen cross-reactivity (or lack thereof) as the reference antibody or antigen binding fragment.

The foregoing can be applied analogously to variants of the other antibodies described herein, wherein the amino acid differences are defined relative to the CDR sequences thereof, and wherein the variant antibody binds to the same target antigen as said antibodies, and preferably exhibits the same antigen cross-reactivity.

In one embodiment, a variant antibody may have at most 5, 4 or 3 amino acid differences total in the CDRs thereof when compared to a corresponding reference antibody, with the proviso that there is at most 2 (preferably at most 1) amino acid differences per CDR. Preferably a variant antibody has at most 2 (more preferably at most 1) amino acid differences total in the CDRs thereof when compared to a corresponding reference antibody, with the proviso that there is at most 2 amino acid differences per CDR. More preferably a variant antibody has at most 2 (more preferably at most 1) amino acid differences total in the CDRs thereof when compared to a corresponding reference antibody, with the proviso that there is at most 1 amino acid difference per CDR.

The amino acid difference may be an amino acid substitution, insertion or deletion. In one embodiment the amino acid difference is a conservative amino acid substitution as described herein.

In one embodiment a variant antibody has the same framework sequences as the exemplary antibodies described herein. In another embodiment the variant antibody may comprise a framework region having at most 2, preferably at most 1 amino acid difference (when compared to a corresponding reference framework sequence). Thus, each framework region may have at most 2, preferably at most 1 amino acid difference (when compared to a corresponding reference framework sequence).

In one embodiment a variant antibody may have at most 5, 4 or 3 amino acid differences total in the framework regions thereof when compared to a corresponding reference antibody, with the proviso that there is at most 2 (preferably at most 1) amino acid differences per framework region. Preferably a variant antibody has at most 2 (more preferably at most 1) amino acid differences total in the framework regions thereof when compared to a corresponding reference antibody, with the proviso that there is at most 2 amino acid differences per framework region. More preferably a variant antibody has at most 2 (more preferably at most 1) amino acid differences total in the framework regions thereof when compared to a corresponding reference antibody, with the proviso that there is at most 1 amino acid difference per framework region.

Thus, a variant antibody may comprise a variable heavy chain and a variable light chain as described herein, wherein:
the heavy chain has at most 14 amino acid differences (at most 2 amino acid differences in each CDR and at most 2 amino acid differences in each framework region) when compared to a heavy chain sequence herein; and
the light chain has at most 14 amino acid differences (at most 2 amino acid differences in each CDR and at most 2 amino acid differences in each framework region) when compared to a light chain sequence herein;

wherein the variant antibody binds to the same target antigen as the reference antibody, and preferably exhibits the same antigen cross-reactivity (or lack thereof) as the reference antibody.

Said variant heavy or light chains may be referred to as "functional equivalents" of the reference heavy or light chains.

In one embodiment a variant antibody may comprise a variable heavy chain and a variable light chain as described herein, wherein:
- the heavy chain has at most 7 amino acid differences (at most 1 amino acid difference in each CDR and at most 1 amino acid difference in each framework region) when compared to a heavy chain sequence herein; and
- the light chain has at most 7 amino acid differences (at most 1 amino acid difference in each CDR and at most 1 amino acid difference in each framework region) when compared to a light chain sequence herein;
- wherein the variant antibody binds to the same target antigen as the reference antibody, and preferably exhibits the same antigen cross-reactivity (or lack thereof) as the reference antibody.

Antibody-Drug Conjugates (ADCs)

Advantageously, an antibody or antigen binding fragment thereof of the invention may comprise a heterologous agent. In one embodiment, an antibody or antigen binding fragment of the invention is linked to a heterologous agent. In a preferable embodiment, the antibody or antigen binding fragment is conjugated to a heterologous agent. Suitably, "conjugated" means linked via a covalent or ionic bond. Preferably, said heterologous agent is a cytotoxin.

The heterologous agent may simply be referred to as an "agent" or "active agent". For example, in alternative language, an antibody or antigen binding fragment thereof of the invention may comprise an active agent. In one embodiment, an antibody or antigen binding fragment of the invention is linked to an active agent. In a preferable embodiment, the antibody or antigen binding fragment is conjugated to an active agent.

The heterologous/active agent can be a drug. Preferably, the heterologous/active is a cytotoxin.

It is particularly preferred that an antibody or antigen binding fragment thereof of the invention is linked (e.g. conjugated) to a heterologous/active agent in methods of treatment, as described below.

An agent and/or cytotoxin of the invention may be conjugated to the antibody or antigen binding fragment thereof by means of a spacer (e.g. at least one spacer). In one embodiment, the spacer is a peptide spacer. In one embodiment, the spacer is a non-peptide (e.g. chemical) spacer.

The cytotoxic agent or cytotoxin can be any molecule known in the art that inhibits or prevents the function of cells and/or causes destruction of cells (cell death), and/or exerts anti-neoplastic/anti-proliferative effects. A number of classes of cytotoxic agents are known to have potential utility in ADC molecules. These include, but are not limited to, topoisomerase I inhibitors, amanitins, auristatins, daunomycins, doxorubicins, duocarmycins, dolastatins, enediynes, lexitropsins, taxanes, puromycins, maytansinoids, vinca alkaloids, tubulysins and pyrrolobenzodiazepines (PBDs). Examples of such cytotoxic agents are AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretastatin, calicheamicin, maytansine, DM-1, vinblastine, methotrexate, and netropsin, and derivatives and analogs thereof. Additional disclosure regarding cytotoxins suitable for use in ADCs can be found, for example, in International Patent Application Publication Nos. WO 2015/155345 and WO 2015/157592, incorporated by reference herein in their entirety.

For example, the antibody or antigen binding fragment may be conjugated to such heterologous agent to provide an "antibody-drug conjugate" (ADC).

The agent is typically linked to, or "loaded onto" the antibody or antigen-binding fragment. The agent loading (p) is the average number of agent(s) per antibody or antigen-binding fragment (e.g. the Ligand unit).

The average number of agents per antibody (or antigen-binding fragment) in preparations of ADCs from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). In some instances, separation, purification, and characterization of homogeneous ADC, where p is a certain value from ADC with other drug loadings, may be achieved by means such as reverse phase HPLC or electrophoresis. Such techniques are also applicable to other types of conjugates.

Cysteine amino acids may be engineered at reactive sites in an antibody (or antigen-binding fragment thereof) and which preferably do not form intrachain or intermolecular disulfide linkages (Junutula, et al., 2008b Nature Biotech., 26(8):925-932; Dornan et al (2009) Blood 114(13):2721-2729; U.S. Pat. Nos. 7,521,541; 7,723,485; WO2009/052249). The engineered cysteine thiols may react with a linker within an agent (e.g. of formula I below) which may have thiol-reactive, electrophilic groups such as maleimide or alpha-halo amides to form ADC with cysteine engineered antibodies. The location of the drug unit can thus be designed, controlled, and known. The drug loading can be controlled since the engineered cysteine thiol groups typically react with drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody or antigen binding fragment thereof reacts with an agent, then the resulting product may be a mixture of ADC compounds with a distribution of agent units attached to an antibody, e.g. 1, 2, 3, etc. Liquid chromatography methods such as polymeric reverse phase (PLRP) and hydrophobic interaction (HIC) may separate compounds in the mixture by agent loading value. Preparations of ADC with a single agent loading value (p) may be isolated.

Thus, the antibody-drug conjugate compositions of the invention may include mixtures of antibody-drug conjugates where the antibody or antigen binding fragment thereof has one or more agent moieties and where the agent moieties may be attached to the antibody or antigen binding fragment thereof at various amino acid residues.

In one embodiment, the average number of agents per antibody (or antigen-binding fragment thereof) is in the range 1 to 20. In some embodiments the range is selected from 1 to 10, 2 to 10, 2 to 8, 2 to 6, and 4 to 10. In some embodiments, there is one agent per antibody (or antigen-binding fragment thereof). In some embodiments, the number of agents per antibody (or antigen-binding fragment thereof) can be expressed as a ratio of agent (i.e., drug) to antibody. This ratio is referred to as the Drug to Antibody Ratio (DAR)." The DAR is the average number of drugs (i.e., agents) linked to each antibody. In one embodiment of the present invention, the DAR is in the range 1 to 20. In some embodiments the range of DAR is selected from 1 to 10, 2 to 10, 2 to 8, 2 to 6, and 4 to 10. In a particular embodiment of the present invention, the DAR is about 8. In a particular embodiment of the present invention, the DAR is 8.

In one embodiment, the antibody or antigen-binding fragment is conjugated to one or more heterologous agent selected from the group consisting of a topoisomerase I inhibitor, a tubulysin derivative, a pyrrolobenzodiazepine, an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, or a combination thereof.

In one embodiment, the antibody antigen binding fragment is conjugated to one or more cytotoxin selected from a topoisomerase I inhibitor, tubulysin derivative, a pyrrolobenzodiazepine, or a combination thereof. For example, the antibody or antigen binding fragment thereof is conjugated to one or more cytotoxin selected from the group consisting of topoisomerase I inhibitor SG3932, SG4010, SG4057 or SG4052 (the structures of which are provided below); tubulysin AZ1508, pyrrolobenzodiazepine SG3315, pyrrolobenzodiazepine SG3249, or a combination thereof.

It is preferred that the antibody or antigen binding fragment thereof may be conjugated to a topoisomerase I inhibitor. Topoisomerase inhibitors are chemical compounds that block the action of topoisomerase (topoisomerase I and II), which is a type of enzyme that controls the changes in DNA structure by catalyzing the breaking and rejoining of the phosphodiester backbone of DNA strands during the normal cell cycle.

A general example of a suitable topoisomerase I inhibitor is represented by the following compound:

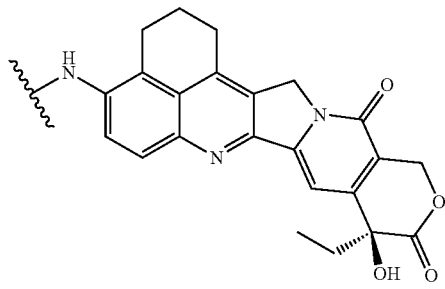

A*

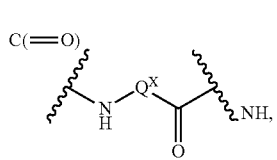

Said compound is denoted as A*, and may be referred to as a "Drug Unit" herein.

The compound (e.g. A*) is preferably provided with a linker for connecting (preferably conjugating) to an antibody or antigen binding fragment described herein (which may be referred to as a "Ligand Unit"). Suitably, the linker is attached (e.g. conjugated) in a cleavable manner to an amino residue, for example, an amino acid of an antibody or antigen binding fragment described herein.

More particularly, an example of a suitable topoisomerase I inhibitor is represented by the following compound, with the formula "I":

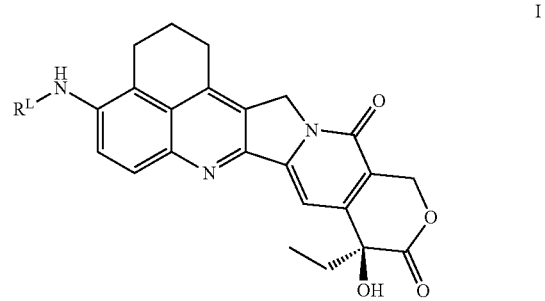

I and salts and solvates thereof, wherein $R^L$ is a linker for connection to an antibody or antigen binding fragment thereof described herein (e.g. the Ligand Unit), wherein said linker is preferably selected from:

(ia):

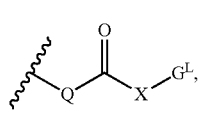

Ia wherein Q is:

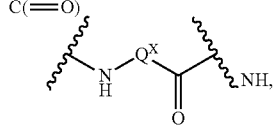

where $Q^X$ is such that Q is an amino-acid residue, a dipeptide residue, a tripeptide residue or a tetrapeptide residue;

X is:

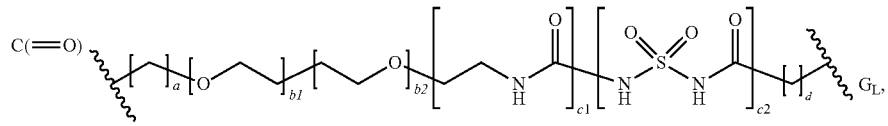

where a=0 to 5, b1=0 to 16, b2=0 to 16, c1=0 or 1, c2=0 or 1, d=0 to 5, wherein at least b1 or b2=0 (i.e. only one of b1 and b2 may not be 0) and at least c1 or c2=0 (i.e. only one of c1 and c2 may not be 0);

$G^L$ is a linker for connecting to an antibody or antigen binding fragment thereof described herein (e.g. the Ligand Unit); or (ib):

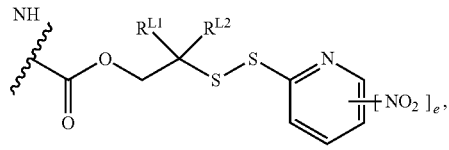
Ib where $R^{L1}$ and $R^{L2}$ are independently selected from H and methyl, or together with the carbon atom to which they are bound form a cyclopropylene or cyclobutylene group; and e is 0 or 1.

It will be understood by the person skilled in the art that more than one of said agent(s) (e.g. topoisomerase I inhibitor) may be conjugated to the antibody or antigen binding fragment thereof.

For example, a conjugate (e.g. antibody-drug conjugate) of the invention may be of the general formula IV:

(IV)

or a pharmaceutically acceptable salt or solvate thereof, wherein L is an antibody or antigen binding fragment thereof described herein (e.g. the Ligand Unit), $D^L$ is a topoisomerase I inhibitor having a linker (e.g. Drug Linker unit) that is of formula III:

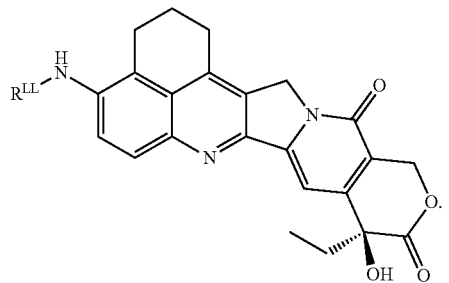
III $R^{LL}$ is a linker connected to an antibody or antigen binding fragment thereof described herein (e.g. the Ligand Unit), wherein the linker is preferably selected from (ia'):

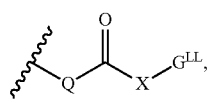
Ia' where Q and X are as defined above and $G^{LL}$ is a linker connected to an antibody or antigen binding fragment thereof described herein (e.g. the Ligand Unit); and (ib'):

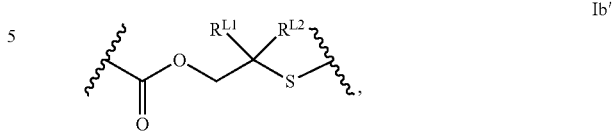
Ib' where $R^{L1}$ and $R^{L2}$ are as defined above; and p is an integer of from 1 to 20.

The drug loading is represented by p, the number of topoisomerase I inhibitor(s) (e.g. Drug units) per antibody or antigen binding fragment thereof (e.g. Ligand Unit). Drug loading may range from 1 to 20 Drug units (D) per Ligand unit. For compositions, p represents the average drug loading of the conjugates in the composition, and p ranges from 1 to 20.

Accordingly, the inventor embraces a conjugate comprising an antibody or antigen binding fragment thereof described herein (e.g. the Ligand Unit) covalently linked to at least one topoisomerase I inhibitor (e.g. Drug unit, such as A* illustrated above). Said inhibitor is preferably linked to the antibody or antigen binding fragment thereof by a linker (e.g. Linker unit), such as a linker described above as $R^L$ and/or $R^{LL}$. In other words, the invention embraces an antibody or antigen binding fragment thereof described herein (e.g. the Ligand Unit) with one or more topoisomerase I inhibitors attached, preferably via a linker (e.g. Drug-Linker units). The antibody or antigen binding fragment thereof (representing a Ligand unit), described more fully above, is a targeting agent that binds to a target moiety. More particularly, this Ligand unit can, for example, specifically bind to a B7-H4 on a target cell, to which the Drug unit is thus delivered. Accordingly, the present invention also provides methods for the treatment of, for example, various cancers and other disorders with an ADC (e.g. cancers/disorders which are associated with the presence of cells, preferably cancerous cells, which express B7-H4).

Further Preferences

Certain features of the topoisomerase I inhibitors described above are particularly preferred and may be defined in more detail as set out below. By way of example, a preferred embodiment of feature $Q^Y$ (e.g. within the linker of 1a described above) will be outlined.

The following preferences may apply to all aspects of the invention as described above, or may relate to a single aspect. The preferences may be combined together in any combination.

Various definitions which pertain to certain terms in this section are provided under the heading "Definitions" provided below.

$Q^Y$

In one embodiment, Q is an amino acid residue. The amino acid may be a natural amino acid or a non-natural amino acid. For example, Q may be selected from: Phe, Lys, Val, Ala, Cit, Leu, Ile, Arg, and Trp, where Cit is citrulline.

In one embodiment, Q comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, Q is selected from:

$^{NH}$-Phe-Lys-$^{C=O}$,
$^{NH}$-Val-Ala-$^{C=O}$,
$^{NH}$-Val-Lys-$^{C=O}$, $^{NH}$-Ala-Lys-$^{C=O}$,
$^{NH}$-Val-Cit-$^{C=O}$,
$^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$,
$^{NH}$-Trp-Cit-$^{C=O}$, and
$^{NH}$-Gly-Val-$^{C=O}$;
where Cit is citrulline.

Preferably, Q is selected from:
$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$, and
$^{NH}$-Val-Cit-$^{C=O}$.

More preferably, Q is selected from $^{NH}$-Phe-Lys-$^{C=O}$, $^{NH}$-Val-Cit-$^{C=O}$ or $^{NH}$-Val-Ala-$^{C=O}$.

Other suitable dipeptide combinations include:
$^{NH}$-Gly-Gly-$^{C=O}$,
$^{NH}$-Gly-Val-$^{C=}$
$^{NH}$-Pro-Pro-$^{C=O}$, and
$^{NH}$-Val-Glu-$^{C=O}$.

Other dipeptide combinations may be used, including those described by Dubowchik et al., *Bioconjugate Chemistry*, 2002, 13,855-869, which is incorporated herein by reference.

In some embodiments, Q is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin. Tripeptide linkers of particular interest are:

$^{NH}$-Glu-Val-Ala-$^{C=O}$
$^{NH}$-Glu-Val-Cit-$^{C=O}$
$^{NH}$-αGlu-Val-Ala-$^{C=O}$
$^{NH}$-αGlu-Val-Cit-$^{C=O}$

In some embodiments, Q is a tetrapeptide residue. The amino acids in the tetrapeptide may be any combination of natural amino acids and non-natural amino acids. In some embodiments, the tetrapeptide comprises natural amino acids. Where the linker is a cathepsin labile linker, the tetrapeptide is the site of action for cathepsin-mediated cleavage. The tetrapeptide then is a recognition site for cathepsin. Tetrapeptide linkers of particular interest are:

$^{NH}$-Gly-Gly-Phe-Gly$^{C=O}$; and
$^{NH}$-Gly-Phe-Gly-Gly$^{C=O}$.

In some embodiments, the tetrapeptide is:
$^{NH}$-Gly-Gly-Phe-Gly$^{C=O}$.

In the above representations of peptide residues, $^{NH}$— represents the N-terminus, and -$^{C=O}$ represents the C-terminus of the residue. The C-terminus binds to the NH of A*.

Glu represents the residue of glutamic acid, i.e.:

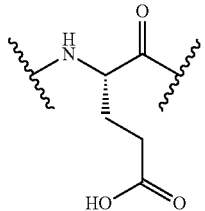 [SMILES: *N[C@@H](CCC(=O)O)C(*)=O]

αGlu represents the residue of glutamic acid when bound via the α-chain, i.e.:

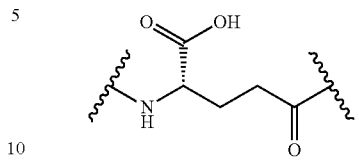

In one embodiment, the amino acid side chain is chemically protected, where appropriate. The side chain protecting group may be a group as discussed above. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

$G^L$ $G^L$ may be selected from:

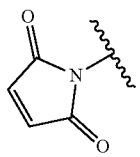 [SMILES: *N1C(=O)C=CC1=O] (G$^{L1-1}$)

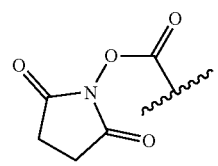 [SMILES: *C(=O)ON1C(=O)CCC1=O] (G$^{L6}$)

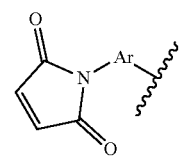 (G$^{L1-2}$)

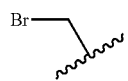 (G$^{L7}$)

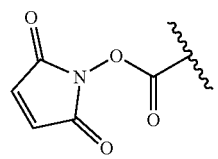 [SMILES: *C(=O)ON1C(=O)C=CC1=O] (G$^{L2}$)

 (G$^{L8}$)

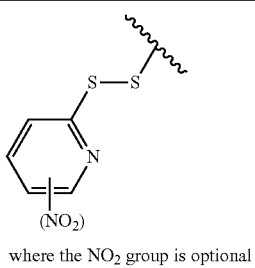

(G<sup>L3-1</sup>)

where the NO₂ group is optional

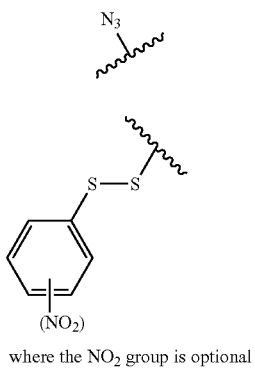

(G<sup>L9</sup>) / (G<sup>L3-2</sup>)

where the NO₂ group is optional

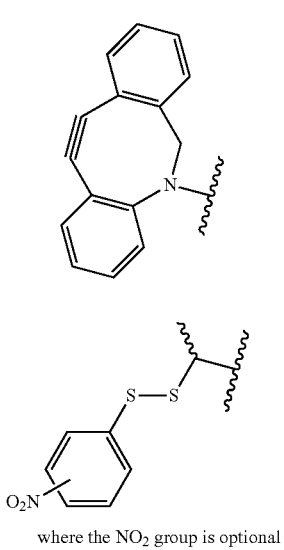

(G<sup>L10</sup>) / (G<sup>L3-3</sup>) / (G<sup>L11</sup>) / (G<sup>L3-4</sup>)

where the NO₂ group is optional

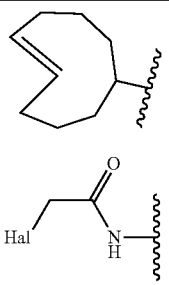

(G<sup>L12</sup>)

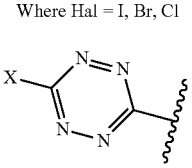

(G<sup>L4</sup>)

Where Hal = I, Br, Cl

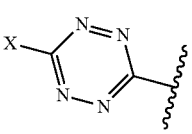

(G<sup>L13</sup>)

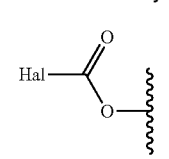

(G<sup>L5</sup>)

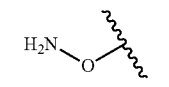

(G<sup>L14</sup>)

where Ar represents a $C_{5-6}$ arylene group, e.g. phenylene, and X represents $C_{1-4}$ alkyl.

In some embodiments, $G^L$ is selected from $G^{L1-1}$ and $G^{L1-2}$. In some of these embodiments, $G^L$ is $G^{L1-1}$.

$G^{LL}$ $G_{LL}$ may be selected from:

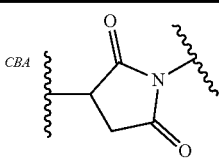

($G^{LL1-1}$)

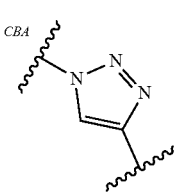 [SMILES: *c1cn(*)nn1]

($G^{LL8-1}$)

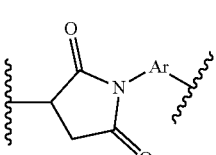

($G^{LL1-2}$)

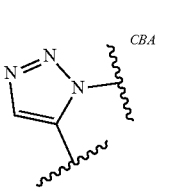 [SMILES: *c1cnnn1*]

($G^{LL8-2}$)

-continued
(G^{LL2})
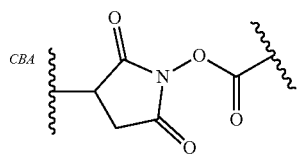 [SMILES: *C(=O)ON1C(=O)CC(*)C1=O]
(G^{LL9-1})
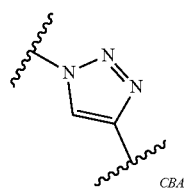 [SMILES: *c1cn(*)nn1]
(G^{LL3-1})
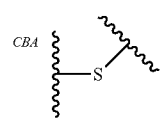
(G^{LL9-2})
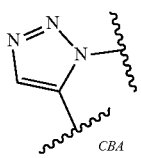 [SMILES: *c1cnnn1*]
(G^{LL3-2})
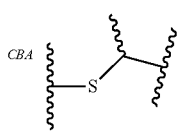 [SMILES: *SC(*)C]
(G^{LL10})
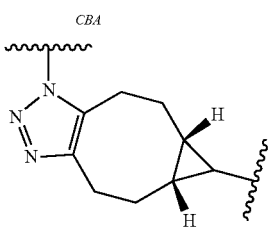 [SMILES: *C1[C@H]2CCc3c(nnn3*)CC[C@@H]12]
(G^{LL-4})
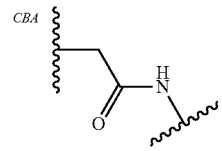 [SMILES: *CC(=O)N*]
-continued
(G^{LL11})
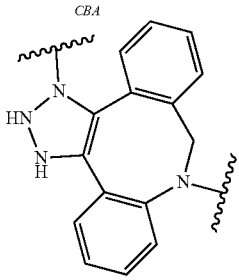 [SMILES: *N1NNC2=C1c1ccccc1CN(*)c1ccccc12]
(G^{LL5})
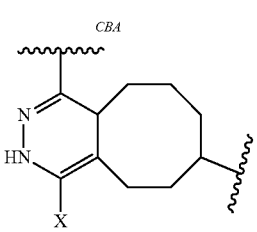
(G^{LL12})
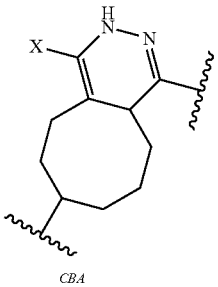
(G^{LL6})
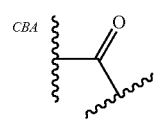 [SMILES: *C(*)=O]
(G^{LL13})
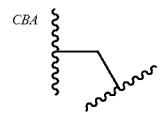
(G^{LL7})
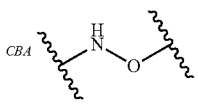
(G^{LL14})
where Ar represents a $C_{5-6}$ arylene group, e.g. phenylene and X represents $C_{1-4}$ alkyl.
In some embodiments, $G^{LL}$ is selected from $G^{LL1-1}$ and $G^{LL1-2}$. In some of these embodiments, $G^{LL}$ is $G_{LL1-1}$.

X

X is preferably:

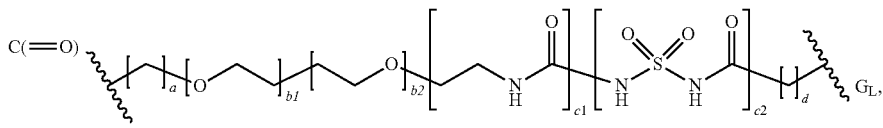

where a=0 to 5, b1=0 to 16, b2=0 to 16, c=0 or 1, d=0 to 5, wherein at least b1 or b2=0 and at least c1 or c2=0.

a may be 0, 1, 2, 3, 4 or 5. In some embodiments, a is 0 to 3. In some of these embodiments, a is 0 or 1. In further embodiments, a is 0.

b1 may be 0, 1, 2, 3, 4, 5, 6, 7, 8, 9, 10, 11, 12, 13, 14, 15 or 16. In some embodiments, b1 is 0 to 12. In some of these embodiments, b1 is 0 to 8, and may be 0, 2, 3, 4, 5 or 8.

b2 may be 0, 1, 2, 3, 4, 5, 6, 7, 8, 9, 10, 11, 12, 13, 14, 15 or 16. In some embodiments, b2 is 0 to 12. In some of these embodiments, b2 is 0 to 8, and may be 0, 2, 3, 4, 5 or 8. Preferably, only one of b1 and b2 may not be 0.

c1 may be 0 or 1. c2 may be 0 or 1. Preferably, only one of c1 and c2 may not be 0.

d may be 0, 1, 2, 3, 4 or 5. In some embodiments, d is 0 to 3. In some of these embodiments, d is 1 or 2. In further embodiments, d is 2. In further embodiments, d is 5.

In some embodiments of X, a is 0, b1 is 0, c1 is 1, c2 is 0 and d is 2, and b2 may be from 0 to 8. In some of these embodiments, b2 is 0, 2, 3, 4, 5 or 8. In some embodiments of X, a is 1, b2 is 0, c1 is 0, c2 is 0 and d is 0, and b1 may be from 0 to 8. In some of these embodiments, b1 is 0, 2, 3, 4, 5 or 8. In some embodiments of X, a is 0, b1 is 0, c1 is 0, c2 is 0 and d is 1, and b2 may be from 0 to 8. In some of these embodiments, b2 is 0, 2, 3, 4, 5 or 8. In some embodiments of X, b1 is 0, b2 is 0, c1 is 0, c2 is 0 and one of a and d is 0. The other of a and d is from 1 to 5. In some of these embodiments, the other of a and d is 1. In other of these embodiments, the other of a and d is 5. In some embodiments of X, a is 1, b2 is 0, c1 is 0, c2 is 1, d is 2, and b1 may be from 0 to 8. In some of these embodiments, b2 is 0, 2, 3, 4, 5 or 8.

In some embodiments, $R^L$ is of formula Ib. In some embodiments, $R^{LL}$ is formula Ib'.

$R^{L1}$ and $R^{L2}$ may be independently selected from H and methyl, or together with the carbon atom to which they are bound form a cyclopropylene or cyclobutylene group.

In some embodiments, both $R^{L1}$ and $R^{L2}$ are H. In some embodiments, $R^{L1}$ is H and $R^{L2}$ is methyl. In some embodiments, both $R^{L1}$ and $R^{L2}$ are methyl.

In some embodiments, $R^{L1}$ and $R^{L2}$ together with the carbon atom to which they are bound form a cyclopropylene group. In some embodiments, $R^{L1}$ and $R^{L2}$ together with the carbon atom to which they are bound form a cyclobutylene group.

In the group Ib, in some embodiments, e is 0. In other embodiments, e is 1 and the nitro group may be in any available position of the ring. In some of these embodiments, it is in the ortho position. In others of these embodiments, it is in the para position.

In some embodiments where compounds described herein are provided in a single enantiomer or in an enantiomerically enriched form, the enantiomerically enriched form has an enantiomeric ratio greater than 60:40, 70:30; 80:20 or 90:10. In further embodiments, the enantiomeric ratio is greater than 95:5, 97:3 or 99:1.

In some embodiments, $R^L$ is selected from:

(i)

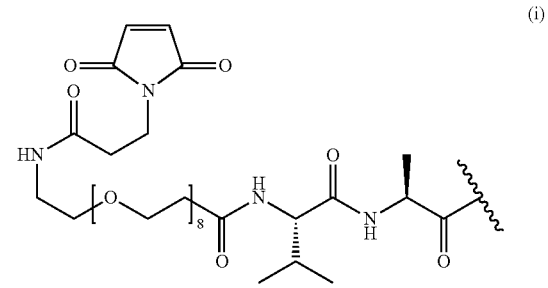

(ii)

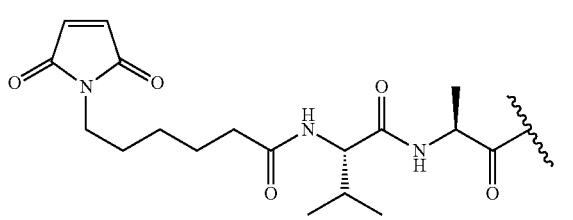

(iii)

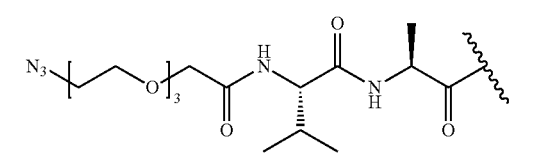

(iv)

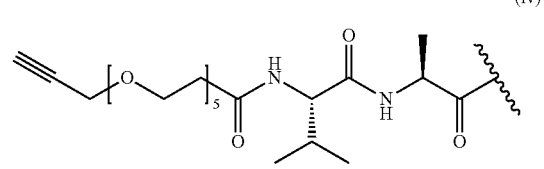

(v)

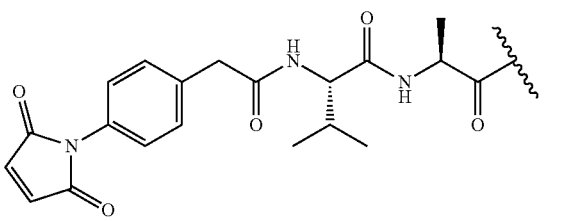

(vi)

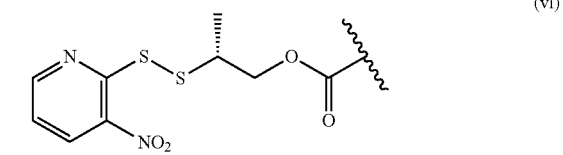

-continued (vii)

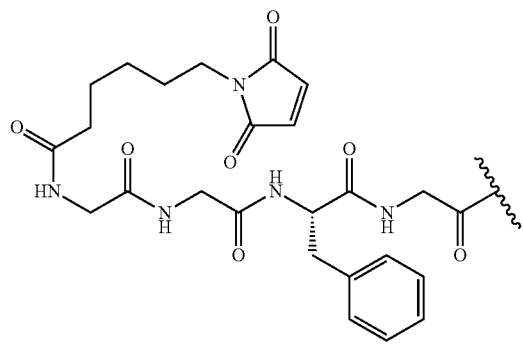

(viii)

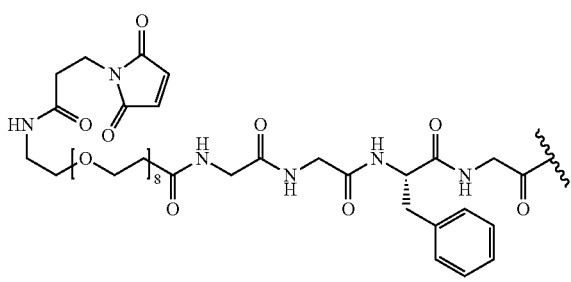

(ix)

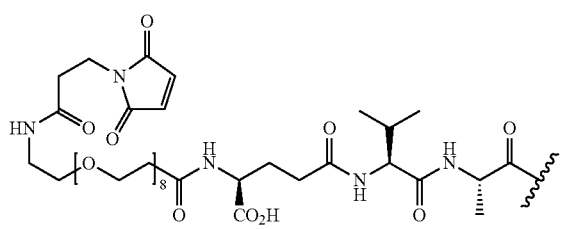

In some embodiments, $R^{LL}$ is a group derived from the $R^L$ groups above.

Having outlined said preferences above, certain preferred topoisomerase I-linker (e.g. Drug Linker unit) formulas are now described.

In some embodiments, the compound of formula I is of the formula $I^P$:

$I^P$

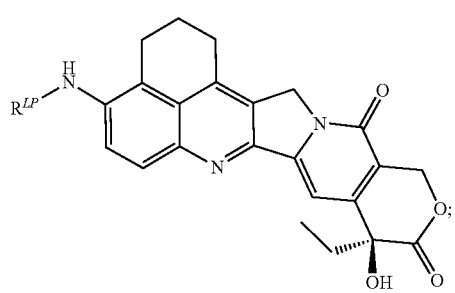

and salts and solvates thereof, wherein $R^{LP}$ is a linker for connection to an antibody or antigen binding fragment thereof described herein, wherein said linker is selected from:

(ia):

$Ia^P$

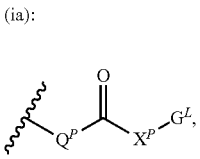

wherein
$Q^P$ is:

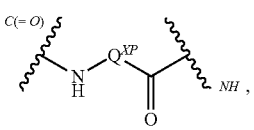

where $Q^{XP}$ is such that $Q^P$ is an amino-acid residue, a dipeptide residue or a tripeptide residue;
$X^P$ is:

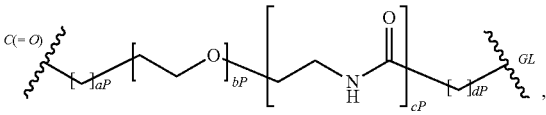

where aP=0 to 5, bP=0 to 16, cP=0 or 1, dP=0 to 5;
$G^L$ is a linker for connecting to an antibody or antigen binding fragment thereof described herein (e.g. Ligand Unit);
(ib):

Ib

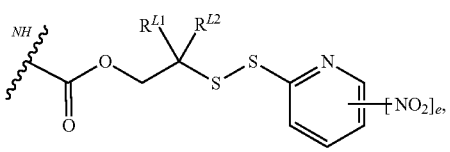

where $R^{L1}$ and $R^{L2}$ are independently selected from H and methyl, or together with the carbon atom to which they are bound form a cyclopropylene or cyclobutylene group; and
e is 0 or 1.
aP may be 0, 1, 2, 3, 4 or 5. In some embodiments, aP is 0 to 3. In some of these embodiments, aP is 0 or 1. In further embodiments, aP is 0.
bP may be 0, 1, 2, 3, 4, 5, 6, 7, 8, 9, 10, 11, 12, 13, 14, 15 or 16. In some embodiments, b is 0 to 12. In some of these embodiments, bP is 0 to 8, and may be 0, 2, 4 or 8.
cP may be 0 or 1.
dP may be 0, 1, 2, 3, 4 or 5. In some embodiments, dP is 0 to 3. In some of these embodiments, dP is 1 or 2. In further embodiments, dP is 2.
In some embodiments of $X^P$, aP is 0, cP is 1 and dP is 2, and bP may be from 0 to 8. In some of these embodiments, bP is 0, 4 or 8.
The preferences for $Q^X$ above for compounds of Formula I may apply to Q (for example, where appropriate).
The preferences for $G^L$, $R^{L1}$, $R^{L2}$ and e above for compounds of Formula I may apply to compounds of Formula $I^P$.

In some embodiments, the conjugate of formula IV is of the formula $IV^P$:

$$L\text{-}(D^{LP})_p \quad (IV^P)$$

or a pharmaceutically acceptable salt or solvate thereof, wherein L is an antibody or antigen binding fragment thereof described herein (e.g. Ligand Unit), $D^{LP}$ is a topoisomerase I inhibitor (e.g. Drug Linker unit) that is of formula $III^P$:

$III^P$

[Chemical structure showing $R^{LLP}$-NH linked to a camptothecin-like pentacyclic core with OH and carbonyl groups]

$R^{LLP}$ is a linker connected to the antibody or antigen binding fragment thereof (e.g. Ligand unit), wherein said linker is selected from (ia'):

[Chemical structure: $Q^P$—C(=O)—$X^P$—$G^{LL}$]

where $Q^P$ and $X^P$ are as defined above and $G^{LL}$ is a linker connected to an antibody or antigen binding fragment thereof described herein (e.g. Ligand Unit); and (ib'):

[Chemical structure: NH—C(=O)—O—C($R^{L1}$)($R^{L2}$)—S—]

where $R^{L1}$ and $R^{L2}$ are as defined above; and
p is an integer of from 1 to 20.

In some embodiments, the compound of formula I is of the formula $I^{P2}$:

$I^{P2}$

[Chemical structure showing $R^{LP2}$-NH linked to a camptothecin-like pentacyclic core with OH and carbonyl groups]

and salts and solvates thereof, wherein $R^{LP2}$ is a linker for connection to an antibody or antigen binding fragment thereof described herein, wherein said linker is selected from:

(ia):

$Ia^{P2}$

[Chemical structure: Q—C(=O)—$X^{P2}$—$G^L$]

wherein
Q is:

[Chemical structure: C(=O)—NH—$Q^X$—C(=O)—NH]

where $Q^X$ is such that Q is an amino-acid residue, a dipeptide residue, a tripeptide residue or a tetrapeptide residue;
$X^{P2}$ is:

[Chemical structure: C(=O)—[CH$_2$]$_{aP2}$—[O—CH$_2$CH$_2$]$_{b1P2}$—[O—CH$_2$CH$_2$]$_{b2P2}$—[CH$_2$]$_{cP2}$—NH—C(=O)—[CH$_2$]$_{dP2}$—$G^L$]

where aP2=0 to 5, b1P2=0 to 16, b2P2=0 to 16, cP2=0 or 1, dP2=0 to 5, wherein at least b1P2 or b2P2=0 (i.e. only one of b1 and b2 may not be 0);
$G^L$ is a linker for connecting to an antibody or antigen binding fragment thereof described herein (e.g. Ligand Unit);

(ib):

Ib

[Chemical structure: NH—C(=O)—O—C($R^{L1}$)($R^{L2}$)—S—S—pyridine—$[NO_2]_e$]

where $R^{L1}$ and $R^{L2}$ are independently selected from H and methyl, or together with the carbon atom to which they are bound form a cyclopropylene or cyclobutylene group; and
e is 0 or 1.

aP2 may be 0, 1, 2, 3, 4 or 5. In some embodiments, aP2 is 0 to 3. In some of these embodiments, aP2 is 0 or 1. In further embodiments, aP2 is 0.

b1P2 may be 0, 1, 2, 3, 4, 5, 6, 7, 8, 9, 10, 11, 12, 13, 14, 15 or 16. In some embodiments, b1P2 is 0 to 12. In some of these embodiments, b1P2 is 0 to 8, and may be 0, 2, 3, 4, 5 or 8.

b2P2 may be 0, 1, 2, 3, 4, 5, 6, 7, 8, 9, 10, 11, 12, 13, 14, 15 or 16. In some embodiments, b2P2 is 0 to 12. In some of these embodiments, b2P2 is 0 to 8, and may be 0, 2, 3, 4, 5 or 8.

Preferably, only one of b1P2 and b2P2 may not be 0.

cP2 may be 0 or 1.

dP2 may be 0, 1, 2, 3, 4 or 5. In some embodiments, dP2 is 0 to 3. In some of these embodiments, dP2 is 1 or 2. In further embodiments, dP2 is 2. In further embodiments, dP2 is 5.

In some embodiments of $X^{P2}$, aP2 is 0, b1P2 is 0, cP2 is 1 and dP2 is 2, and b2P2 may be from 0 to 8. In some of these embodiments, b2P2 is 0, 2, 3, 4, 5 or 8. In some embodiments of $X^{P2}$, aP2 is 1, b2P2 is 0, cP2 is 0 and dP2 is 0, and b1P2 may be from 0 to 8. In some of these embodiments, b1P2 is 0, 2, 3, 4, 5 or 8. In some embodiments of $X^{P2}$, aP2 is 0, b1P2 is 0, cP2 is 0 and dP2 is 1, and b2P2 may be from 0 to 8. In some of these embodiments, b2P2 is 0, 2, 3, 4, 5 or 8. In some embodiments of $X^{P2}$, b1P2 is 0, b2P2 is 0, cP2 is 0 and one of aP2 and dP2 is 0. The other of aP2 and d is from 1 to 5. In some of these embodiments, the other of aP2 and d is 1. In other of these embodiments, the other of aP2 and dP2 is 5.

The preferences for $Q^X$ above for compounds of Formula I may apply to $Q^X$ in Formula $Ia^{P2}$ (e.g. where appropriate).

The preferences for GL, $R^{L1}$, $R^{L2}$ and e above for compounds of Formula I may apply to compounds of Formula $I^{P2}$.

In some embodiments, the conjugate of formula IV is of the formula $IV^{P2}$:

$$L\text{-}(D^{LP2})_p \qquad (IV^{P2})$$

or a pharmaceutically acceptable salt or solvate thereof, wherein L is an antibody or antigen binding fragment thereof described herein (e.g. Ligand unit), $D^{LP2}$ is a topoisomerase I inhibitor (e.g. Drug Linker unit) that is of formula $III^{P2}$:

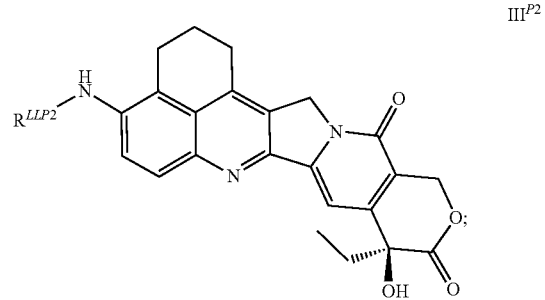

$R^{LLP2}$ is a linker connected to the antibody or antigen binding fragment thereof (e.g. Ligand unit), wherein said linker is selected from (ia'):

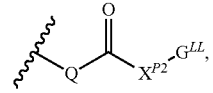

where Q and $X^{P2}$ are as defined above and $G^{LL}$ is a linker connected to the antibody or antigen binding fragment thereof; and (ib'):

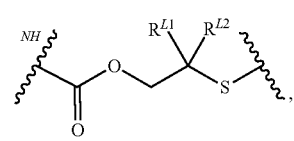

where $R^{L1}$ and $R^{L2}$ are as defined above; and p is an integer of from 1 to 20.

Particularly suitable topoisomerase I inhibitors include those having the following formulas:

(SG3932)

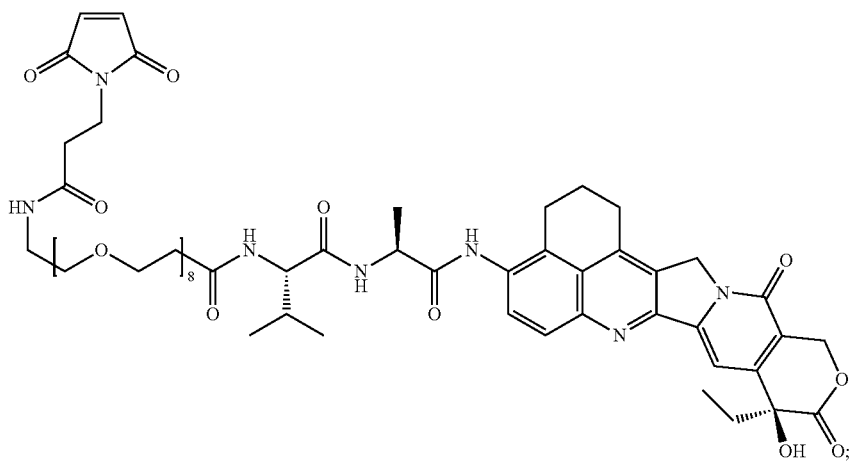

(SG4010)
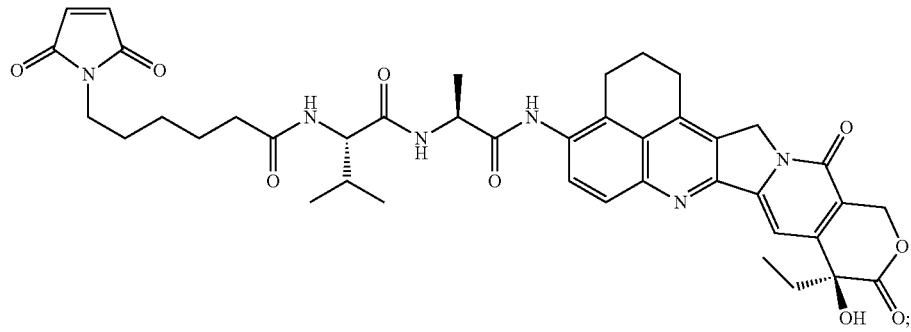
(SG4057)
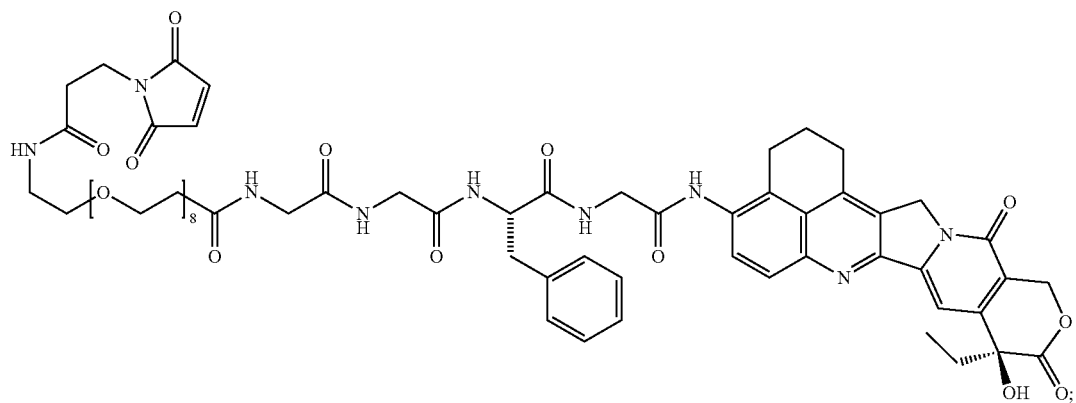
(SG4052)
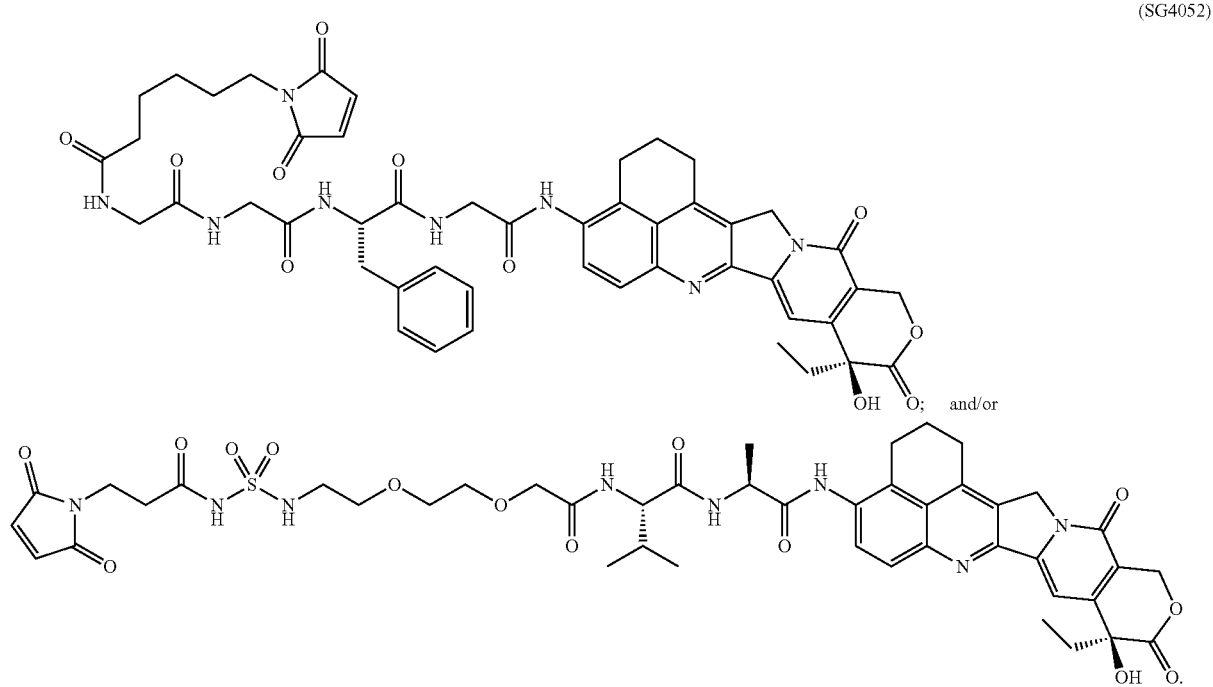
and/or

SG3932 is particularly preferred. Thus, in preferable embodiment, an antibody or antigen binding fragment thereof described herein is conjugated to a topoisomerase I inhibitor having the following formula (e.g. SG3932):

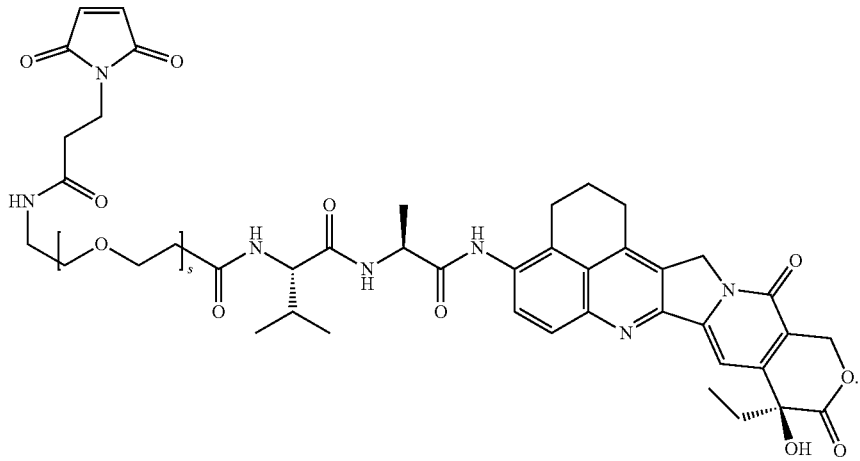
(SG3932)

For the avoidance of doubt, the numeral '8' specifies that the structure within boxed parentheses is repeated eight times. Thus, another representation of SG3932 is:

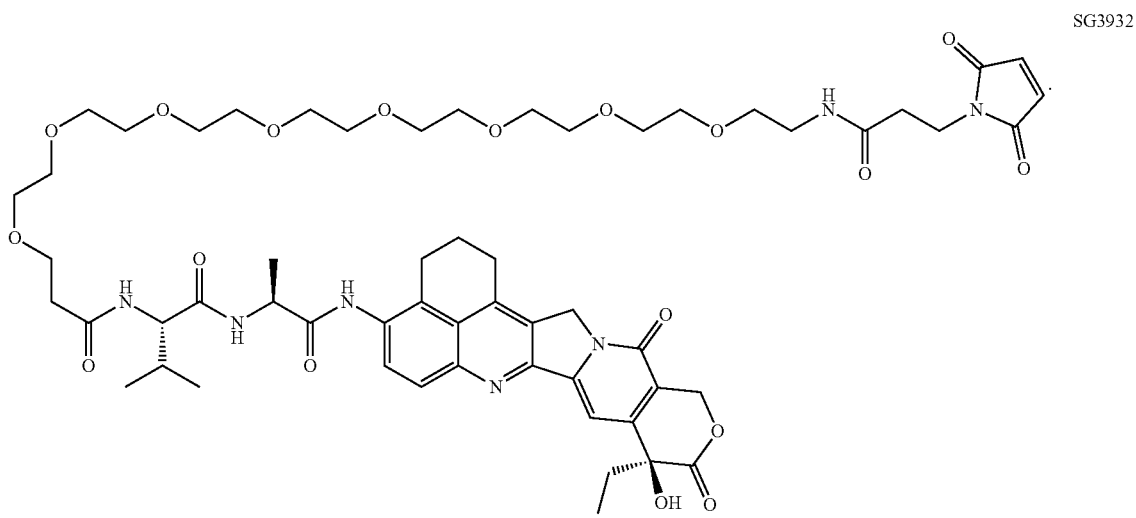 [SMILES: CC[C@@]1(O)C(=O)OCc2c1cc1n(c2=O)Cc2c-1nc1ccc(NC(=O)[C@H](C)NC(=O)[C@@H](NC(=O)CCOCCOCCOCCOCCOCCOCCOCCOCCNC(=O)CCN3C(=O)C=CC3=O)C(C)C)c3c1c2CCC3]
SG3932

Another representation of SG4010 is:

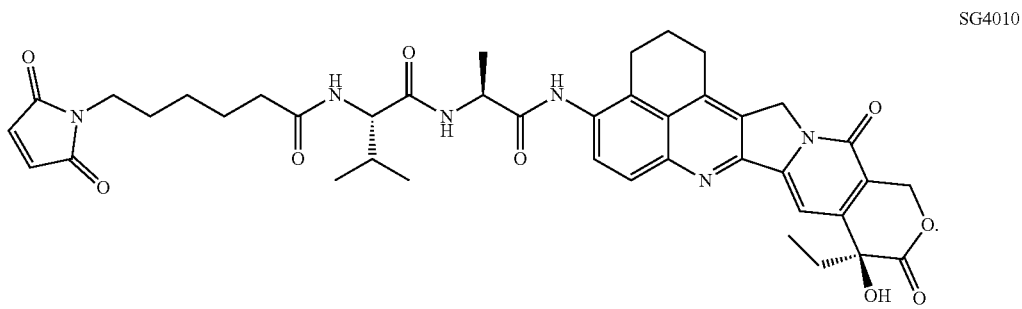 [SMILES: CC[C@@]1(O)C(=O)OCc2c1cc1n(c2=O)Cc2c-1nc1ccc(NC(=O)[C@H](C)NC(=O)[C@@H](NC(=O)CCCCCN3C(=O)C=CC3=O)C(C)C)c3c1c2CCC3]
SG4010

Another representation of SG4057 is:

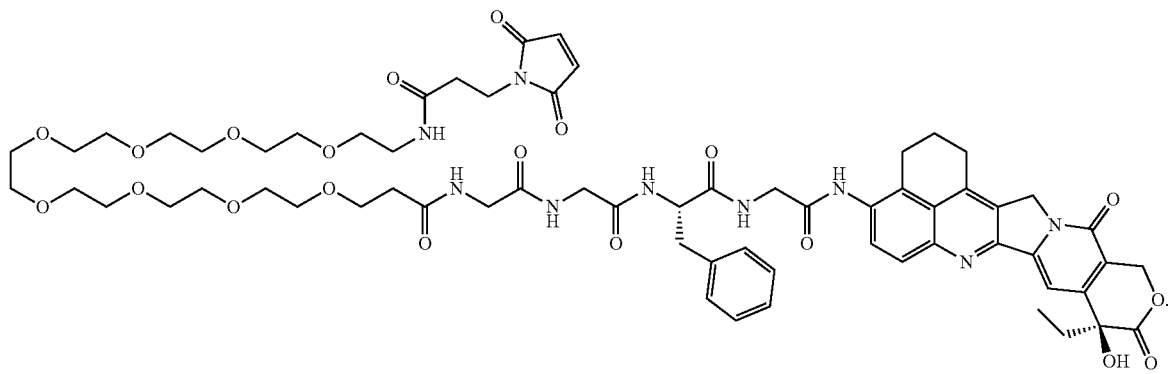

SG4057

Another representation of SG4052 is:

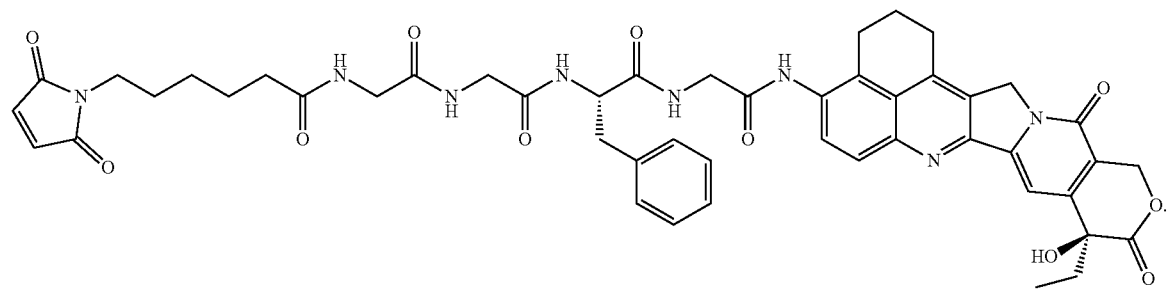

SG4052

Any antibody or antigen binding fragment thereof described herein may be conjugated to one or more of said topoisomerase I inhibitor(s).

In a preferred aspect, there is provided an antibody or antigen binding fragment thereof which binds to a B7-H4 polypeptide (e.g. B7-H4 polypeptide epitope), comprising:
i. a HCDR1 comprising the amino acid sequence of SEQ ID NO: 7, or a functional variant thereof;
ii. a HCDR2 comprising the amino acid sequence of SEQ ID NO: 8, or a functional variant thereof;
iii. a HCDR3 comprising the amino acid sequence of SEQ ID NO: 9, or a functional variant thereof;
iv. a LCDR1 comprising the amino acid sequence of SEQ ID NO: 10, or a functional variant thereof;
v. a LCDR2 comprising the amino acid sequence of SEQ ID NO: 11, or a functional variant thereof; and
vi. a LCDR3 comprising the amino acid sequence of SEQ ID NO: 12, or a functional variant thereof;
wherein the antibody or antigen binding fragment thereof is conjugated to a SG3932:

(SG3932)

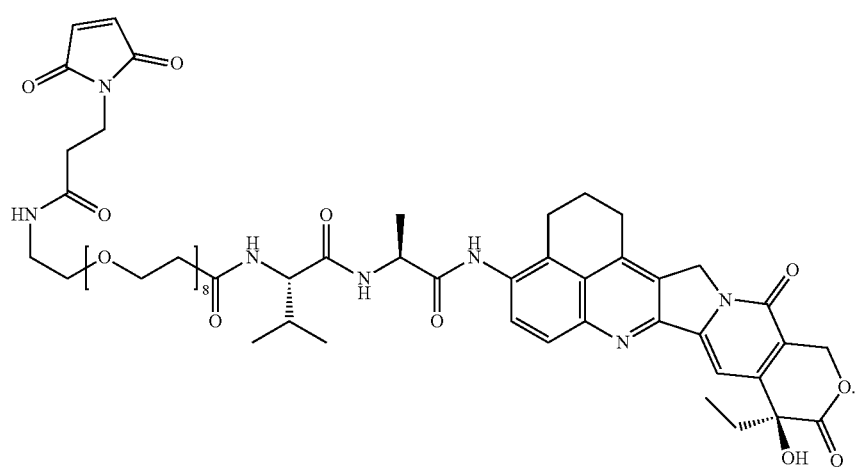

Another preferred aspect provides an antibody or antigen binding fragment thereof comprising: a variable heavy chain comprising the amino acid sequence of SEQ ID NO: 33, or a functional variant thereof; and a variable light chain comprising the amino acid sequence of SEQ ID NO: 34, or a functional variant thereof;

wherein the antibody or antigen binding fragment thereof is conjugated to a SG3932:

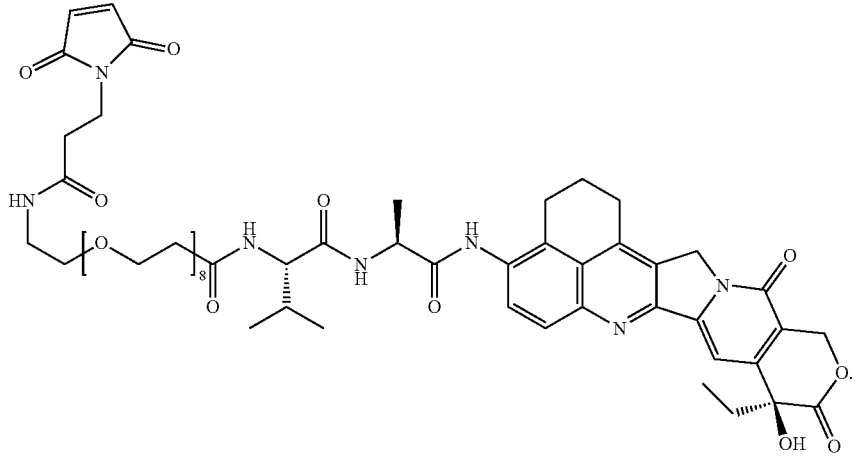

(SG3932)

A particularly preferred aspect provides an antibody or antigen binding fragment thereof comprising: a variable heavy chain comprising the amino acid sequence of SEQ ID NO: 45, or a functional variant thereof; and a variable light chain comprising the amino acid sequence of SEQ ID NO: 34, or a functional variant thereof;

wherein the antibody or antigen binding fragment thereof is conjugated to a SG3932:

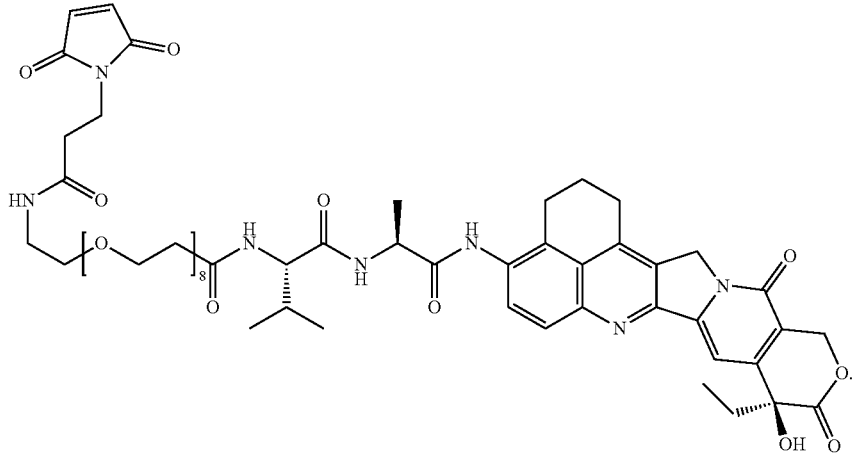

(SG3932)

Another preferred aspect provides and antibody or antigen binding fragment thereof comprising: a heavy chain comprising the amino acid sequence of SEQ ID NO: 51, or a functional variant thereof; and a light chain comprising the amino acid sequence of SEQ ID NO: 44, or a functional variant thereof;

wherein the antibody or antigen binding fragment thereof is conjugated to a SG3932:

(SG3932)

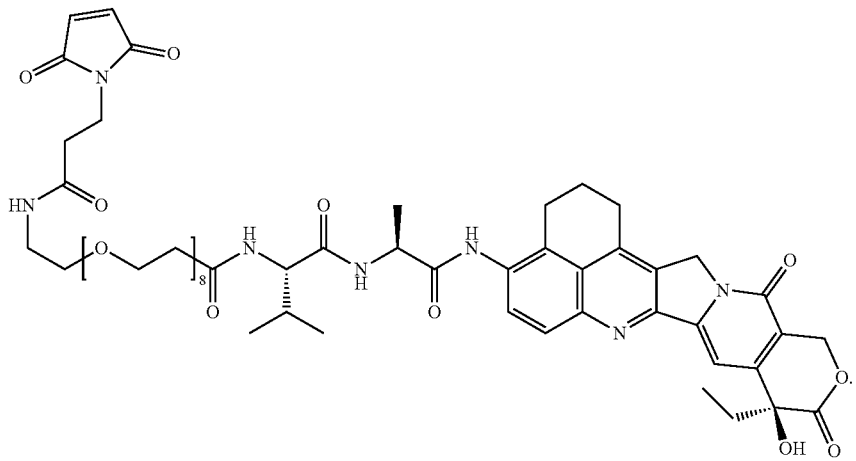

Synthesis of Topoisomerase I Inhibitors

For completion, certain general synthetic routes for the preparation of preferred topoisomerase I inhibitor(s) will now be described. Further details may be found in the Examples section.

Compounds of formula I where $R^L$ is of formula Ia may be synthesised from a compound of Formula 2:

Formula 2

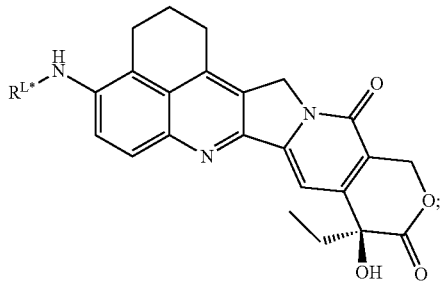

where $R^{L*}$ is -QH by linking a compound of Formula 3:

Formula 3

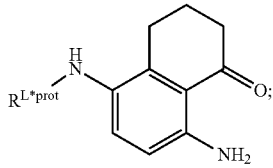

or an activated version thereof.

Such a reaction may be carried out under amide coupling conditions.

Compounds of Formula 2 may be synthesised by the deprotection of a compound of Formula 4:

Formula 4

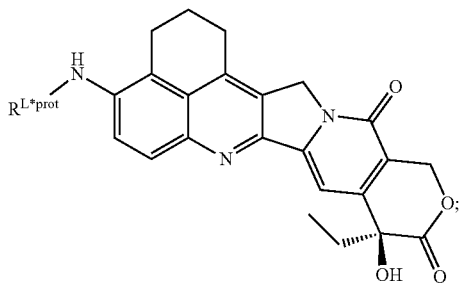

where $R^{L*prot}$ is -Q-Prot$^N$, where Prot$^N$ is an amine protecting group.

Compounds of Formula 4 may be synthesised by the coupling of a compound of Formula 5:

Formula 5

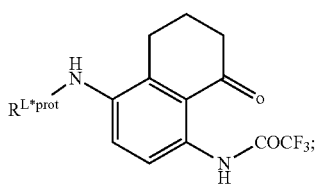

with the compound A3 using the Friedlander reaction.

Compounds of Formula 5 may be synthesised from compounds of Formula 6:

Formula 6 by removal of the trifluoroacetamide protecting group.

Compounds of Formula 6 may be synthesised by coupling: $R^{L*prot}$—OH to the compound 17.

Compounds of formula I where $R^L$ is of formula Ia or Ib may be synthesised from the compound I11 by coupling of the compound $R^L$—OH, or an activated form thereof.

Amine Protecting Groups:

Amine protecting groups are well-known to those skilled in the art. Particular reference is made to the disclosure of suitable protecting groups in Greene's Protecting Groups in Organic Synthesis, Fourth Edition, John Wiley & Sons, 2007 (ISBN 978-0-471-69754-1), pages 696-871.

Further ADCs

Although topoisomerase I inhibitors are preferred as outlined above, it should be noted that any suitable agent (e.g. drug/cytotoxin) may be linked to an antibody or antigen binding fragment thereof of the invention. Examples of other suitable agents are outlined below.

In one embodiment, the cytotoxin is a tubulysin or tubulysin derivative. In one embodiment, the cytotoxin is Tubulysin A, having the following chemical structure:

WO2004005326A2, WO2012019123A1, WO2009134279A1, WO2009055562A1, WO2004005327A1, U.S. Pat. Nos. 7,776,841, 7,754,885, US20100240701, U.S. Pat. No. 7,816,377, US20110021568, and US20110263650, incorporated herein by reference. It is to be understood that such derivatives include, for example, tubulysin prodrugs or tubulysins that include one or more protection or protecting groups, one or more linking moieties.

In one embodiment, the cytotoxin is tubulysin 1508, also referred to herein as "AZ1508" and described in more detail in WO 2015157594, incorporated herein by reference, having the following structure:

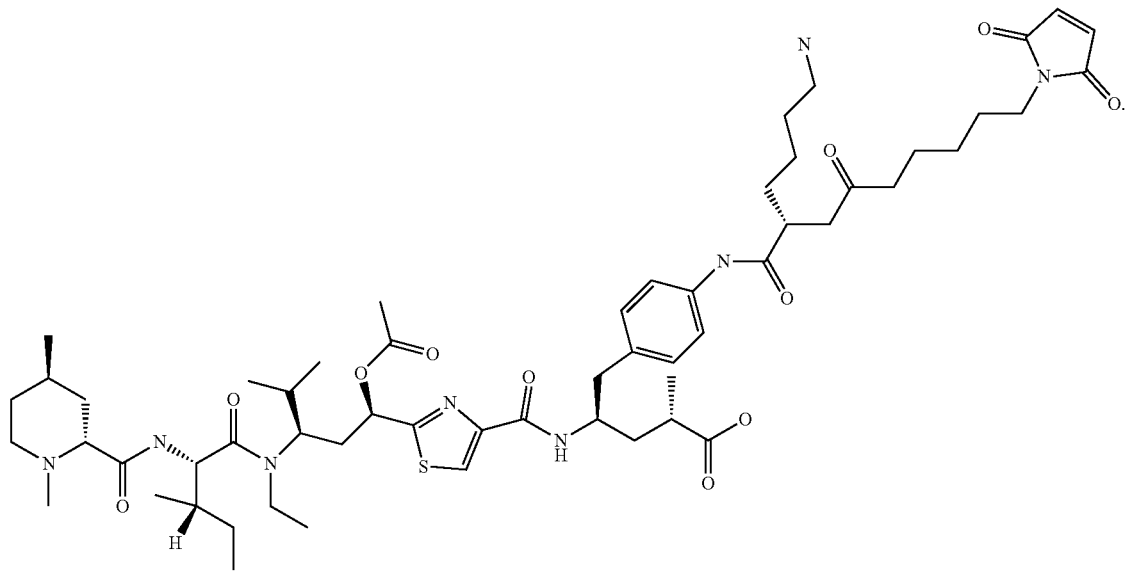 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)CC(=O)CCCCCN3C(=O)C=CC3=O)cc2)C[C@H](C)C(=O)O)cs1)C(C)C]

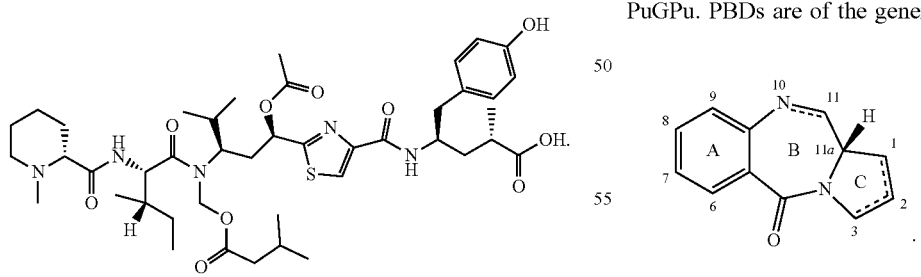

Tubulysins are members of a class of natural products isolated from myobacterial species. As cytoskeleton-interacting agents, tubulysins are mitotic poisons that inhibit tubulin polymerization and lead to cell cycle arrest and apoptosis. As used herein, the term "tubulysin" refers both collectively and individually to the naturally occurring tubulysins and analogs and derivatives of tubulysins. Illustrative examples of tubulysins are disclosed, for example, in In another embodiment, the cytotoxin may be a pyrrolobenzodiazepine (PBD) or a PBD derivative. PBD translocates to the nucleus where it crosslinks DNA, preventing replication during mitosis, damaging DNA by inducing single strand breaks, and subsequently leading to apoptosis. Some PBDs have the ability to recognize and bond to specific sequences of DNA; the preferred sequence is PuGPu. PBDs are of the general structure:

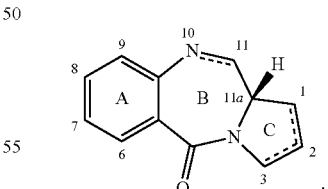

PBDs differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (5)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. Their ability to form an adduct in the minor groove enables them to interfere with DNA processing, hence their use as anti-tumour agents.

The first PBD anti-tumor antibiotic, anthramycin, was discovered in 1965. Since then, a number of naturally occurring PBDs have been reported, and over 10 synthetic routes have been developed to a variety of analogues. Family members include abbeymycin, chicamycin, DC-81, mazethramycin, neothramycins A and B, porothramycin, prothracarcin, sibanomicin (DC-102), sibiromycin and tomamycin. PBDs and ADCs comprising them are also described in WO 2015/155345 and WO 2015/157592, incorporated in their entirety herein by reference.

In one embodiment, the cytotoxin is PBD 3249, also referred to herein as "SG3249" and described in more detail in WO 2014/057074, incorporated herein by reference, having the following structure:

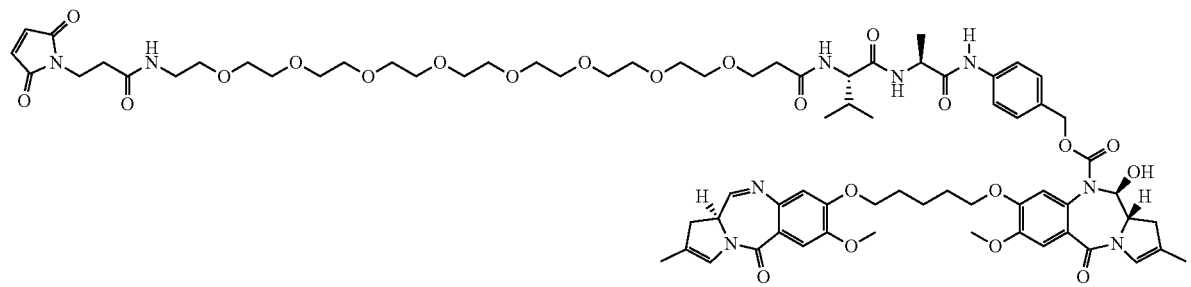

Thus, the antibody or antigen binding fragment thereof is conjugated to a pyrrolobenzodiazepine SG3249 cytotoxin.

For example, in one aspect, there is provided an antibody or antigen binding fragment thereof which binds to a B7-H4 polypeptide (e.g. B7-H4 polypeptide epitope), comprising:

i. a HCDR1 comprising the amino acid sequence of SEQ ID NO: 7, or a functional variant thereof;
ii. a HCDR2 comprising the amino acid sequence of SEQ ID NO: 8, or a functional variant thereof;
iii. a HCDR3 comprising the amino acid sequence of SEQ ID NO: 9, or a functional variant thereof;
iv. a LCDR1 comprising the amino acid sequence of SEQ ID NO: 10, or a functional variant thereof;
v. a LCDR2 comprising the amino acid sequence of SEQ ID NO: 11, or a functional variant thereof; and
vi. a LCDR3 comprising the amino acid sequence of SEQ ID NO: 12, or a functional variant thereof;

wherein the antibody or antigen binding fragment thereof is conjugated to a pyrrolobenzodiazepine SG3249 cytotoxin:

(SG3249)

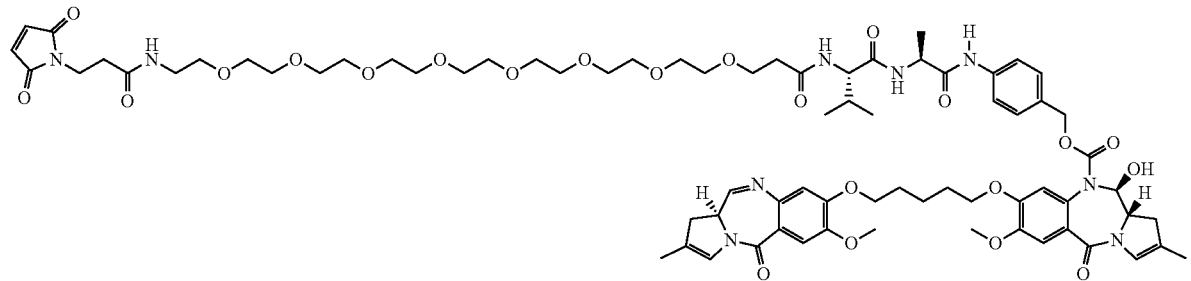

In another aspect, there is provided an antibody or antigen binding fragment thereof which binds to a B7-H4 polypeptide (e.g. B7-H4 polypeptide epitope), comprising: antibody or antigen binding fragment thereof comprising a variable heavy chain comprising the amino acid sequence of SEQ ID NO: 33, or a functional variant thereof; and a variable light chain comprising the amino acid sequence of SEQ ID NO: 34, or a functional variant thereof; wherein the antibody or antigen binding fragment thereof is conjugated to a pyrrolobenzodiazepine SG3249 cytotoxin:

(SG3249)

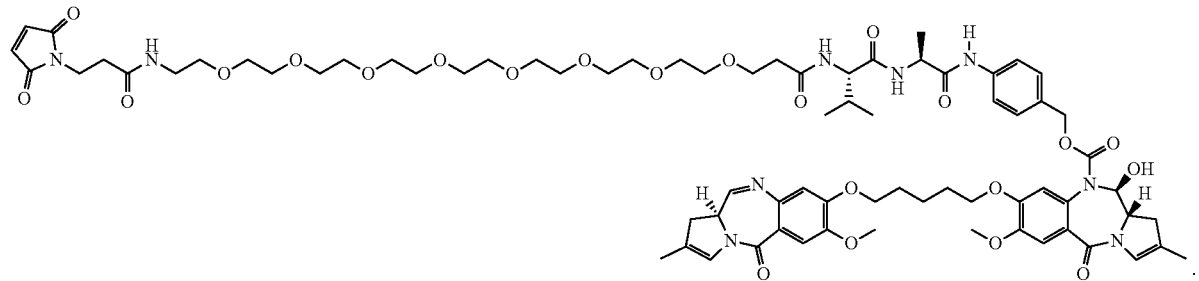

In another aspect, there is provided an antibody or antigen binding fragment thereof which binds to a B7-H4 polypeptide (e.g. B7-H4 polypeptide epitope), comprising: antibody or antigen binding fragment thereof comprising a variable heavy chain comprising the amino acid sequence of SEQ ID NO: 45, or a functional variant thereof; and a variable light chain comprising the amino acid sequence of SEQ ID NO: 34, or a functional variant thereof; wherein the antibody or antigen binding fragment thereof is conjugated to a pyrrolobenzodiazepine SG3249 cytotoxin:

cytotoxin) using site-specific or non-site specific methods of conjugation. In one embodiment, the antibodies and antigen fragment thereof comprise one, two, three, four or more therapeutic moieties. In one embodiment, all therapeutic moieties are the same.

Conventional conjugation strategies for antibodies or antigen-binding fragments thereof rely on randomly conjugating the payload to the antibody or fragment through lysines or cysteines. In one embodiment, the antibody or antigen-binding fragment thereof is randomly conjugated to (SG3249)

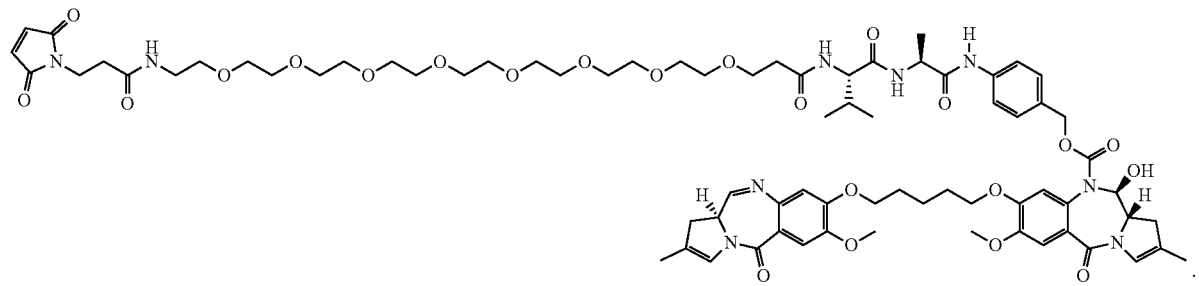 [SMILES: COc1cc2c(cc1OCCCCCOc1cc3c(cc1OC)C(=O)N1C=C(C)C[C@H]1[C@H](O)N3C(=O)OCc1ccc(NC(=O)[C@H](C)NC(=O)[C@@H](NC(=O)CCOCCOCCOCCOCCOCCOCCOCCOCCNC(=O)CCN3C(=O)C=CC3=O)C(C)C)cc1)N=C[C@@H]1CC(C)=CN1C2=O]

In one embodiment, the cytotoxin is PBD 3315, also referred to herein as "SG3315" and described in more detail in WO 2015/052322, incorporated herein by reference, having the following structure:

a heterologous agent (preferably a cytotoxin), for example, by partial reduction of the antibody or fragment, followed by reaction with a desired agent, with or without a linker moiety attached. The antibody or fragment may be reduced using

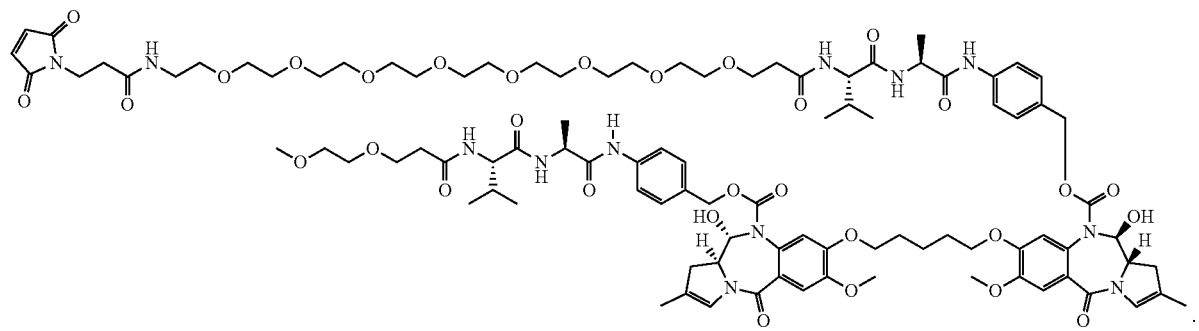 [SMILES: COCCOCCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4[C@H](O)N5C(=O)OCc4ccc(NC(=O)[C@H](C)NC(=O)[C@@H](NC(=O)CCOCCOCCOCCOCCOCCOCCOCCOCCNC(=O)CCN5C(=O)C=CC5=O)C(C)C)cc4)c(OC)cc3C(=O)N3C=C(C)C[C@H]3[C@@H]2O)cc1)C(C)C]

The antibody or antigen binding fragment thereof is preferably conjugated to a pyrrolobenzodiazepine SG3249 cytotoxin through a cysteine residue.

The antibody or antigen fragment thereof of the invention may be conjugated to heterologous agents (preferably a DTT or similar reducing agent. The agent with or without a linker moiety attached can then be added at a molar excess to the reduced antibody or fragment in the presence of DMSO. After conjugation, excess free cysteine may be added to quench unreacted agent. The reaction mixture may then be purified and buffer-exchanged into PBS.

In one embodiment, an agent (e.g. cytotoxin) is conjugated to an antibody or antigen binding fragment thereof by site-specific conjugation. In one embodiment, site-specific conjugation of therapeutic moieties to antibodies using reactive amino acid residues at specific positions yields homogeneous ADC preparations with uniform stoichiometry.

The site specific conjugation can be through a cysteine, residue or a non-natural amino acid. In a preferable embodiment, the heterologous agent (preferably cytotoxin) is conjugated to the antibody or antigen binding fragment thereof through at least one cysteine residue.

In one embodiment, the heterologous agent (preferably cytotoxin) is chemically conjugated to the side chain of an amino acid (preferably at a specific Kabat position in the Fc region). In one embodiment, the agent (e.g. the cytotoxic or imaging agent) is conjugated to the antibody or antigen binding fragment thereof through a cysteine substitution of at least one of positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446, wherein the numbering corresponds to the EU index in Kabat. In one embodiment, the specific Kabat positions are 239, 442, or both. In one embodiment, the specific positions are Kabat position 442, an amino acid insertion between Kabat positions 239 and 240, or both. In one embodiment, the heterologous agent (preferably cytotoxin) is conjugated to the antibody or antigen binding fragment thereof through a thiol-maleimide linkage. In some aspects, the amino acid side chain is a sulfhydryl side chain.

In one embodiment, the antibody or antigen binding fragment thereof comprises a light chain (e.g. preferably comprising a VL and constant light chain) comprising the amino acid sequence of SEQ ID NO: 44 and a heavy chain (e.g. comprising a VH and constant heavy chain) comprising the amino acid sequence of SEQ ID NO: 48; wherein the antibody or antigen binding fragment thereof is conjugated to a pyrrolobenzodiazepine SG3249 cytotoxin; preferably wherein the pyrrolobenzodiazepine SG3249 cytotoxin is conjugated to the cysteine residue at amino acid position 240 of said heavy chain.

In one embodiment, the antibody or antigen binding fragment thereof comprises a light chain (e.g. preferably comprising a VL and constant light chain) comprising the amino acid sequence of SEQ ID NO: 44 and a heavy chain (e.g. comprising a VH and constant heavy chain) comprising the amino acid sequence of SEQ ID NO: 51; wherein the antibody or antigen binding fragment thereof is conjugated to a pyrrolobenzodiazepine SG3249 cytotoxin.

Reference herein to an antibody or antigen-binding fragment conjugated to a cytotoxin is synonymous with the term "antibody drug conjugate (ADC)", or "anti-B7-H4 ADC".

In one embodiment, the antibody or antigen binding fragment thereof (e.g., anti-B7-H4 ADC) delivers a cytotoxic payload to a cell (preferably a B7-H4-expressing cell) and inhibits or suppresses proliferation (e.g. of a tumour) by at least 10%, or at least 20%, or at least 30%, or at least 40%, or at least 50%, or at least 60%, or at least 70%, or at least 80%, or at least 90% or about 100% (preferably at least 40%) relative to a level of inhibition or suppression in the absence of the antibody or antigen binding fragment thereof (e.g., anti-B7-H4 ADC). Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

In one embodiment, the antibody or antigen fragment thereof (e.g., anti-B7-H4 ADC) of the invention binds to B7-H4 on the surface of a cell, and is internalised into the cell. In one embodiment, the antigen or antibody fragment thereof is internalised into a cell (preferably a B7-H4-expressing cell) with an IC50 at 10 minutes of about 100 ng/ml to about 1 µg/ml, about 100 ng/ml to about 500 ng/ml, about 100 ng/ml to about 250 ng/ml, about 250 ng/ml to about 500 ng/ml, about 350 ng/ml to about 450 ng/ml, about 500 ng/ml to about 1 µg/ml, about 500 ng/ml to about 750 ng/ml, about 750 ng/ml to about 850 ng/ml, or about 900 ng/ml to about 1 µg/ml.

In one embodiment, the antibody or antigen fragment thereof (e.g., anti-B7-H4 ADC) is internalised into a cell (preferably a B7-H4-expressing cell) with an IC50 at 30 minutes of about 100 ng/ml to about 1 µg/ml, about 100 ng/ml to about 500 ng/ml, about 100 ng/ml to about 250 ng/ml, about 250 ng/ml to about 500 ng/ml, about 250 ng/ml to about 350 ng/ml, about 350 ng/ml to about 450 ng/ml, about 500 ng/ml to about 1 µg/ml, about 500 ng/ml to about 750 ng/ml, about 750 ng/ml to about 850 ng/ml, or about 900 ng/ml to about 1 µg/ml.

In one embodiment, the antibody or antigen fragment thereof (e.g., anti-B7-H4 ADC) is internalised into a cell (preferably a B7-H4-expressing cell) with an IC50 at 120 minutes of about 50 ng/ml to about 500 ng/ml, about 50 ng/ml to about 100 ng/ml, about 100 ng/ml to about 200 ng/ml, about 200 ng/ml to about 300 ng/ml, about 300 ng/ml to about 400 ng/ml, or about 400 ng/ml to about 500 ng/ml.

In one embodiment, the antibody or antigen fragment thereof (e.g., anti-B7-H4 ADC) is internalised into a cell (preferably a B7-H4-expressing cell) with an IC50 at 8 hours of about 5 ng/ml to about 250 ng/ml, about 10 ng/ml to about 25 ng/ml, about 25 ng/ml to about 50 ng/ml, about 50 ng/ml to about 100 ng/ml, about 100 ng/ml to about 150 ng/ml, about 150 ng/ml to about 200 ng/ml, or about 200 ng/ml to about 250 ng/ml.

For the avoidance of doubt, reference to a "conjugate" herein means an antibody or antigen binding fragment conjugated to a heterologous agent (preferably a cytotoxin) including any such agent described above.

In addition to the therapeutic applications of an antibody or antigen binding fragment of the invention described above, the "conjugates" of the present invention may be also used in a method of therapy. Thus, also provided is a method of treatment, comprising administering to a subject in need of treatment a therapeutically-effective amount of a conjugate described herein (e.g. conjugate of formula IV). The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs); surgery; and radiation therapy.

Pharmaceutical compositions according to the present invention, and for use in accordance with the present invention, may comprise, in addition to the active ingredient, i.e.

a conjugate/ADC of the invention (e.g. formula IV), a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Preferably, the conjugates can be used to treat proliferative disease. The term "proliferative disease" pertains to an unwanted or uncontrolled cellular proliferation of excessive or abnormal cells which is undesired, such as, neoplastic or hyperplastic growth, whether in vitro or in vivo. The term "proliferative disease" may alternatively be referred to as "cancer".

A suitable proliferative disease (e.g. cancer) will preferably be characterised by the presence cancerous cells that express B7-H4.

Examples of proliferative conditions include, but are not limited to, benign, pre-malignant, and malignant cellular proliferation, including but not limited to, neoplasms and tumours (e.g., histocytoma, glioma, astrocytoma, osteoma), cancers (e.g. lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin. Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

The antibody-drug conjugate may be labelled, for example to aid detection of cell binding (in vitro or in vivo). The label may be a biotin label. In another embodiment, the label may be a radioisotope.

In another aspect, there is provided a polynucleotide comprising a nucleic acid sequence encoding an antibody or antigen binding fragment thereof of the invention.

In one embodiment, the polynucleotide may be an isolated polynucleotide.

The sequence(s) (e.g. polynucleotide sequence(s)) of the present invention include sequences that have been removed from their naturally occurring environment, recombinant or cloned (e.g. DNA) isolates, and chemically synthesized analogues or analogues biologically synthesized by heterologous systems.

The sequence(s) (e.g. polynucleotide sequence(s)) of the present invention may be prepared by any means known in the art. For example, large amounts of the sequence(s) may be produced by replication and/or expression in a suitable host cell. The natural or synthetic DNA fragments coding for a desired fragment will typically be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured bacterial, insect, mammalian, plant or other eukaryotic cell lines.

The sequence(s) (e.g. polynucleotide sequence(s)) of the present invention may also be produced by chemical synthesis, e.g. a polynucleotide by the phosphoramidite method or the tri-ester method and may be performed on commercial automated oligonucleotide synthesizers. A double-stranded (e.g. DNA) fragment may be obtained from the single stranded product of chemical synthesis either by synthesizing the complementary strand and annealing the strand together under appropriate conditions or by adding the complementary strand using DNA polymerase with an appropriate primer sequence.

When applied to a sequence (e.g. polynucleotide sequence) of the invention, the term "isolated" preferably denotes that the sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

Another aspect provided herein is a host cell comprising a polynucleotide, said polynucleotide comprising a nucleic acid sequence encoding an antibody or antigen binding fragment thereof of the invention.

In one embodiment, the polynucleotide encodes a VH chain of an antibody or antigen binding fragment thereof. In one embodiment, a polynucleotide of the invention may encode a VL chain of an antibody or antigen binding fragment thereof. In one embodiment, the polynucleotide may encode a VH and a VL chain of an antibody or antigen binding fragment thereof. In one embodiment, the polynucleotide may further encode a leader sequence (e.g. which functions as a secretory sequence for controlling transport of a polypeptide from the cell).

In another aspect there is provided a vector (e.g. plasmid) comprising the polynucleotide of the invention.

Variants of a polynucleotide described above are embraced by the invention. Polynucleotide variants can contain alterations in the coding regions, non-coding regions, or both. In one embodiment, a polynucleotide variant comprises an alteration that produces silent substitutions, additions, or deletions, but do not alter the properties or activities of the encoded polypeptide. In one embodiment, a polynucleotide variant is produced by a silent substitution due to the degeneracy of the genetic code. A polynucleotide variant can be produced for a variety of reasons, e.g., to optimize codon expression for a particular host (change codons in the human mRNA to those preferred by a bacterial host such as *E. coli*). Vectors and cells comprising said polynucleotide variant are also provided.

The present invention embraces methods for producing an antibody or antigen binding fragment thereof that binds to a B7-H4 polypeptide (e.g. B7-H4 polypeptide epitope), comprising expressing a polynucleotide in a host cell, said polynucleotide comprising a nucleic acid sequence encoding an antibody or antigen binding fragment thereof of the invention.

The present invention further embraces an antibody or antigen binding fragment thereof obtainable by said methods for producing an antibody or antigen binding fragment thereof that binds to a B7-H4 polypeptide (e.g. B7-H4 polypeptide epitope).

In a preferable embodiment, the method for producing an antibody or antigen binding fragment thereof comprises (a) culturing the host cell and (b) isolating the antibody or antigen binding fragment thereof expressed from the cell.

Suitable host cells for expression of an antibody or antigen binding fragment thereof of the invention include a prokaryote, yeast, insect, or higher eukaryotic cells (preferably wherein the polynucleotide is under the control of appropriate promoters). Prokaryotes include gram negative or gram-positive organisms, for example *E. coli* or *bacilli*. Higher eukaryotic cells include established cell lines of mammalian origin as described herein. Cell-free translation systems can also be employed.

In one aspect, there is provided a kit comprising an antigen or antibody binding fragment described herein. There is further embraced use of said kit in the methods of the present invention.

In one embodiment, a kit comprises an isolated (e.g. purified) antigen or antibody binding fragment of the invention. In one embodiment, a kit comprises an isolated (e.g. purified) antigen or antibody binding fragment of the invention, wherein the antigen or antibody binding fragment comprises an agent (e.g. conjugated cytotoxin) described herein. In one embodiment, the kit comprises one or more container. The kit may provide the antigen or antibody binding fragment and the agent individually (e.g. the agent is not conjugated to the antigen or antibody binding fragment, but is in a form suitable for conjugation thereto); optionally wherein the kit is further provided with instructions and/or reagents for conjugating the agent to the antigen or antibody binding fragment. In one embodiment, the kit comprises all of the components necessary and/or sufficient to perform a detection assay, including all controls, directions for performing assays, and any necessary software for analysis and presentation of results.

An antibody or antigen binding fragment thereof of the invention can be used in assays for immunospecific binding by any method known in the art. The immunoassays that can be used include, but are not limited to, competitive and non-competitive assay systems using techniques such as Western blot, RIA, ELISA, ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays.

An antibody or antigen binding fragment thereof of the invention can be employed histologically, as in immunofluorescence, immunoelectron microscopy, or non-immunological assays, for example, for in situ detection of B7-H4 or conserved variants or peptide fragments thereof. In situ detection can be accomplished by removing a histological specimen from a patient, and applying thereto a labelled an antibody or antigen binding fragment thereof of the invention, e.g., applied by overlaying the labelled antibody or antigen binding fragment thereof onto a biological sample. Through the use of such a procedure, it is possible to determine not only the presence of B7-H4, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Antibodies

The term "antibody" covers monoclonal antibodies and fragments thereof (e.g. exhibiting the desired biological activity). In a preferable embodiment, an antibody of the present invention is a monoclonal antibody. In a more preferable embodiment, the antibody is a fully human monoclonal antibody. In one embodiment, methods of the invention may employ polyclonal antibodies.

In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987). Preferably, each VHC and VLC is composed of three CDRs and four FRs, arranged from amino-terminus to carboxy-terminus in the following order: FR1, CDR1, FR2, DR2, FR3, CDR3, FR4. The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, $CH_1$, $CH_2$ and $CH_3$. The light chain constant region is comprised of one domain, CL. The variable region of the heavy and light chains contains a binding domain that interacts with an antigen. The term "antibody" includes intact immunoglobulins of types IgA, IgG, IgE, IgD, IgM (as well as subtypes thereof), wherein the light chains of the immunoglobulin may be of types kappa or lambda. The term antibody, as used herein, also refers to a portion of an antibody that binds to one of the above-mentioned markers, e.g., a molecule in which one or more immunoglobulin chains is not full length, but which binds to a marker. Examples of binding portions encompassed within the term antibody include (i) a Fab fragment, a monovalent fragment consisting of the VLC, VHC, CL and $CH_1$ domains; (ii) a F(ab')2 fragment, a bivalent fragment comprising two Fab fragments linked by a disulfide bridge at the hinge region; (iii) a Fc fragment consisting of the VHC and $CH_1$ domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 1A1-ATi-A1β; and Huston et al. (1988) Proc. Natl. Acad. Sci. USA 85:5879-5883). Such single chain antibodies are also encompassed within the term antibody. These may be obtained using conventional techniques known to those skilled in the art, and the portions are screened for utility in the same manner as are intact antibodies.

In one embodiment, the antibody or antigen binding fragment is one or more selected from a murine antibody, a humanized antibody, a chimeric antibody, a monoclonal antibody, a polyclonal antibody, a recombinant antibody, a multispecific antibody, or a combination thereof.

In one embodiment, the antigen-binding fragment is one or more selected from a Fv fragment, an Fab fragment, an F(ab')2 fragment, an Fab' fragment, a dsFv fragment, an scFv fragment, an sc(Fv)2 fragment, or a combination thereof.

In a preferable embodiment, the antibody or antigen binding fragment thereof is a monoclonal antibody (mAb).

In one embodiment, the antibody or antigen binding fragment thereof (e.g. mAb) of the invention is a scFV.

In one embodiment, the antibody or antigen binding fragment thereof can bind to B7-H4 molecules across species, e.g., the antibody or fragment can bind to mouse B7-H4, rat B7-H4, rabbit, human B7-H4 and/or cynomolgus monkey B7-H4. In one embodiment, the antibody or fragment can bind to human B7-H4 and cynomolgus monkey B7-H4. In one embodiment, the antibody or antigen binding fragment can also bind to mouse B7-H4.

In one embodiment, the antibody or antigen binding fragment thereof can specifically bind to B7-H4, e.g., human B7-H4 and cynomolgus monkey B7-H4, but does not specifically bind to human B7-H1, B7-H2, and/or B7-H3.

In one embodiment, the antibody or antigen-binding fragment thereof can include, in addition to a VH and a VL, a heavy chain constant region or fragment thereof. In one embodiment, the heavy chain constant region is a human heavy chain constant region, e.g., a human IgG constant region, e.g., a human IgG1 constant region. In one embodiment (preferably where the antibody or antigen-binding fragment thereof is conjugated to an agent, such as a cytotoxic agent), a cysteine residue is inserted between amino acid 5239 and V240 in the $CH_2$ region of IgG1. This cysteine is referred to as "a 239 insertion" or "239i."

In one embodiment, the antibody or antigen binding fragment thereof may comprise a heavy chain constant region comprising the amino acid sequence of SEQ ID NO: 41. Preferably, the antibody or antigen binding fragment thereof may comprise a heavy chain constant region comprising the amino acid sequence of SEQ ID NO: 52.

In one embodiment, a heavy chain constant region or fragment thereof, e.g., a human IgG constant region or fragment thereof, can include one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In one embodiment the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. In a preferable embodiment, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E). In one embodiment, the antibody or antigen-binding fragment thereof comprises a heavy chain, wherein the heavy chain is a human IgG1 YTE mutant.

In one embodiment, the antibody or antigen-binding fragment thereof can include, in addition to a VH and a VL, and optionally a heavy chain constant region or fragment thereof, a light chain constant region or fragment thereof. In one embodiment, the light chain constant region is a kappa lambda light chain constant region, e.g., a human kappa constant region or a human lambda constant region.

In one embodiment, the antibody or antigen binding fragment thereof comprises a light chain constant region comprising the amino acid sequence of SEQ ID NO: 42.

In one embodiment, a VH and/or VL amino acid sequence can have 85%, 90%, 95%, 96%, 97%, 98% or 99% similarity to a sequence set forth herein. In one embodiment, a VH and/or VL amino acid sequence may comprise 1, 2, 3, 4, 5 or more substitutions, e.g., conservative substitutions relative to a sequence set forth herein. A B7-H4 antibody having VH and VL regions having a certain percent similarity to a VH region or VL region, or having one or more substitutions, e.g., conservative substitutions can be obtained by mutagenesis (e.g., site-directed or PCR-mediated mutagenesis) of nucleic acid molecules encoding VH and/or VL regions described herein, followed by testing of the encoded altered antibody for binding to B7-H4 and optionally testing for retained function using the functional assays described herein.

The affinity or avidity of an antibody or antigen binding fragment thereof for an antigen can be determined experimentally using any suitable method well known in the art, e.g., flow cytometry, enzyme-linked immunosorbent assay (ELISA), or radioimmunoassay (RIA), or kinetics (e.g., KINEXA® or BIACORE™ analysis). Direct binding assays as well as competitive binding assay formats can be readily employed. (See, e.g., Berzofsky et al., Antibody-Antigen Interactions, In Fundamental Immunology, Paul, W. E., Ed., Raven Press: New York, N.Y. (1984); Kuby, Immunology, W. H. Freeman and Company: New York, N.Y. (1992); and methods described herein.) The measured affinity of a particular antibody-antigen interaction can vary if measured under different conditions (e.g., salt concentration, pH, temperature). Thus, measurements of affinity and other antigen-binding parameters (e.g., KD or Kd, Kon, Koff) are made with standardized solutions of antibody and antigen, and a standardized buffer, as known in the art.

In one embodiment, the antibody or antigen-binding fragment thereof, can bind to B7-H4-expressing cells with an IC50 lower than about 500 nM, lower than about 350 nM, lower than about 250 nM, lower than about 150 nM, lower than about 100 nM, lower than about 75 nM, lower than about 60 nM, lower than about 50 nM, lower than about 40 nM, lower than about 30 nM, lower than about 20 nM, lower than about 15 nM, lower than about 10 nM, lower than about 5 nM, lower than about 1 nM, lower than about 500 pM, lower than about 350 pM, lower than about 250 pM, lower than about 150 pM, lower than about 100 pM, lower than about 75 pM, lower than about 60 pM, lower than about 50 pM, lower than about 40 pM, lower than about 30 pM, lower than about 20 pM, lower than about 15 pM, lower than about 10 pM, or lower than about 5 pM. Preferably, said IC50 is measured by flow cytometry.

A "monoclonal antibody" (mAb) refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

In a preferable embodiment, the antibody or antigen binding fragment thereof (e.g. mAb) of the invention is a humanised antibody or antigen binding fragment thereof. Suitably, said humanised the antibody or antigen binding fragment thereof is an IgG.

The term "humanised antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FW) residues of a human immunoglobulin are replaced with the corresponding residues in an antibody from a non-human species that has the desired specificity, affinity, and capability.

Humanised antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs), also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The "Kabat numbering system" is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop, when numbered using the Kabat numbering convention, varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The table below lists the positions of the amino acids comprising the variable regions of the antibodies in each system.

| Region | Kabat | AbM | Chothia |
|---|---|---|---|
| LCDR1 | L24-L34 | L24-L34 | L24-L34 |
| LCDR2 | L50-L56 | L50-L56 | L50-L56 |
| LCDR3 | L89-L97 | L89-L97 | L89-L97 |
| HCDR1[1] | H31-H35B | H26-H35B | H26-H32 . . . 34 |

| Region | Kabat | AbM | Chothia |
|---|---|---|---|
| HCDR1[2] | H31-H35 | H26-H35 | H26-H32 |
| HCDR2 | H50-H65 | H50-H58 | H52-H56 |
| HCDR3 | H95-H102 | H95-H102 | H95-H102 |

[1]Kabat Numbering
[2]Chothia Numbering

ImMunoGeneTics (IMGT) also provides a numbering system for the immunoglobulin variable regions, including the CDRs. See, e.g., Lefranc, M. P. et al., Dev. Comp. Immunol. 27: 55-77(2003). The IMGT numbering system is based on an alignment of more than 5,000 sequences, structural data, and characterization of hypervariable loops and allows for easy comparison of the variable and CDR regions for all species. According to the IMGT numbering schema, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

In one embodiment, an antibody of the invention a human antibody.

The term "human antibody" means an antibody produced in a human or an antibody having an amino acid sequence corresponding to an antibody produced in a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

In one embodiment, an antibody of the invention a chimeric antibody.

The term "chimeric antibodies" refers to antibodies in which the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., J. Biol. Chem. 281:23514-24 (2006); Robbie et al., (2013) Antimicrob. Agents Chemother. 57, 6147-6153). See also U.S. Pat. No. 7,083,784, which is hereby incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Potency of the antibody or antigen binding fragment thereof is normally expressed as an IC50 value, in ng/ml unless otherwise stated. IC50 is the median inhibitory concentration of an antibody molecule. In functional assays, IC50 is the concentration that reduces a biological response by 50% of its maximum. In ligand-binding studies, IC50 is the concentration that reduces receptor binding by 50% of maximal specific binding level. IC50 can be calculated by any number of means known in the art.

The fold improvement in potency for the antibody or antigen binding fragment thereof of the invention as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

Binding potency of an antibody is normally expressed as an EC50 value, in nM or pM unless otherwise stated. EC50 is the concentration of a drug that induces a median response between baseline and maximum after a specified exposure time. EC50 can be calculated by any number of means known in the art.

Antibody Preparation

The antibodies of the present invention can be obtained using conventional techniques known to persons skilled in the art and their utility confirmed by conventional binding studies—an exemplary method is described in Example 2. By way of example, a simple binding assay is to incubate the cell expressing an antigen with the antibody. If the antibody is tagged with a fluorophore, the binding of the antibody to the antigen can be detected by FACS analysis.

Antibodies of the present invention can be raised in various animals including mice, rats, rabbits, goats, sheep, monkeys or horses. Antibodies may be raised following immunisation with individual capsular polysaccharides, or with a plurality of capsular polysaccharides. Blood isolated from these animals contains polyclonal antibodies—multiple antibodies that bind to the same antigen. Antigens may also be injected into chickens for generation of polyclonal antibodies in egg yolk. To obtain a monoclonal antibody that is specific for a single epitope of an antigen, antibody-secreting lymphocytes are isolated from an animal and immortalized by fusing them with a cancer cell line. The fused cells are called hybridomas, and will continually grow and secrete antibody in culture. Single hybridoma cells are isolated by dilution cloning to generate cell clones that all produce the same antibody; these antibodies are called monoclonal antibodies. Methods for producing monoclonal antibodies are conventional techniques known to those skilled in the art (see e.g. Making and Using Antibodies: A Practical Handbook. GC Howard. CRC Books. 2006. ISBN 0849335280). Polyclonal and monoclonal antibodies are often purified using Protein A/G or antigen-affinity chromatography.

The antibody or antigen binding fragment thereof of the invention may be prepared as a monoclonal anti-B7-H4 antibody, which can be prepared using hybridoma methods, such as those described by Kohler and Milstein, Nature 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or an in vitro binding assay, e.g., radioimmunoassay (RIA) or enzyme-linked immunosorbent assay (ELISA), can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid using known methods.

Alternatively, the antibody or antigen binding fragment thereof (e.g. as monoclonal antibodies) can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or antigen-binding fragments thereof of the desired species can be isolated from phage display libraries expressing CDRs of the desired species as described in McCafferty et al., Nature 348:552-554 (1990); Clackson et al., Nature, 352:624-628 (1991); and Marks et al., J. Mol. Biol. 222:581-597 (1991).

The polynucleotide(s) encoding an antibody or an antigen-binding fragment thereof of the invention can further be modified in a number of different manners using recombinant DNA technology to generate alternative antibodies. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In one embodiment, the antibody or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated. See, e.g., Cole et al., Monoclonal Antibodies and Cancer Therapy, Alan R. Liss, p. 77 (1985); Boemer et al., J. Immunol. 147 (1):86-95 (1991); U.S. Pat. No. 5,750,373.

In one embodiment, the antibody or antigen-binding fragment thereof can be selected from a phage library, where that phage library expresses human antibodies, as described, for example, in Vaughan et al., Nat. Biotech. 14:309-314 (1996); Sheets et al., Proc. Natl. Acad. Sci. USA, 95:6157-6162 (1998); Hoogenboom and Winter, J. Mol. Biol. 227: 381 (1991); and Marks et al., J. Mol. Biol. 222:581 (1991). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., J. Molec. Biol. 376:1182-1200 (2008), each of which is incorporated by reference in its entirety.

Affinity maturation strategies and chain shuffling strategies are known in the art and can be employed to generate high affinity human antibodies or antigen-binding fragments thereof. See Marks et al., BioTechnology 10:779-783 (1992), incorporated by reference in its entirety.

In one embodiment, the antibody or antigen binding fragment thereof (e.g. an monoclonal antibody) can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate, or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. Suitably, the CDR residues may be directly and most substantially involved in influencing B7-H4 binding. Accordingly, part or all of the non-human or human CDR sequences are preferably maintained while the non-human sequences of the variable and constant regions can be replaced with human or other amino acids.

Antibodies can also optionally be humanized, resurfaced, engineered or human antibodies engineered with retention of high affinity for the antigen B7-H4 and other favourable biological properties. To achieve this goal, humanized (or human) or engineered anti-B7-H4 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as B7-H4. In this way, FW residues can be selected and combined from the consensus and import sequences so that the desired antibody characteristic, such as increased affinity for the target antigen(s), is achieved.

Humanization, resurfacing or engineering of anti-B7-H4 antibodies or antigen-binding fragments thereof of the present invention can be performed using any known method, such as but not limited to those described in, Jones et al., Nature 321:522 (1986); Riechmann et al., Nature 332:323 (1988); Verhoeyen et al., Science 239:1534 (1988); Sims et al., J. Immunol. 151: 2296 (1993); Chothia and Lesk, J. Mol. Biol. 196:901 (1987); Carter et al., Proc. Natl. Acad. Sci. USA 89:4285 (1992); Presta et al., J. Immunol. 151:2623 (1993); U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-B7-H4 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In one embodiment, a fragment (e.g. antibody fragment) of the antibody (e.g. anti-B7-H4 antibody) is provided. Various techniques are known for the production of antibody fragments. Traditionally, these fragments are derived via proteolytic digestion of intact antibodies, as described, for example, by Morimoto et al., J. Biochem. Biophys. Meth. 24:107-117 (1993) and Brennan et al., Science 229:81 (1985). In one embodiment, anti-B7-H4 antibody fragments are produced recombinantly. Fab, Fv, and scFv antibody fragments can all be expressed in and secreted from E. coli or other host cells, thus allowing the production of large amounts of these fragments. Such anti-B7-H4 antibody fragments can also be isolated from the antibody phage libraries discussed above. The anti-B7-H4 antibody fragments can also be linear antibodies as described in U.S. Pat. No. 5,641,870. Other techniques for the production of antibody fragments will be apparent to the skilled practitioner.

According to the present invention, techniques can be adapted for the production of single-chain antibodies specific to B7-H4. See, e.g., U.S. Pat. No. 4,946,778). In addition, methods can be adapted for the construction of Fab expression libraries to allow rapid and effective identification of monoclonal Fab fragments with the desired specificity for B7-H4, or derivatives, fragments, analogs or homologs thereof. See, e.g., Huse et al., Science 246:1275-1281 (1989). Antibody fragments can be produced by techniques known in the art including, but not limited to: F(ab')2 fragment produced by pepsin digestion of an antibody molecule; Fab fragment generated by reducing the disulfide bridges of an F(ab')2 fragment; Fab fragment generated by the treatment of the antibody molecule with papain and a reducing agent; or Fv fragments.

In one embodiment, an antibody or antigen-binding fragment thereof of the invention can be modified in order to increase its serum half-life. This can be achieved, for example, by incorporation of a salvage receptor binding epitope into the antibody or antibody fragment, by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule, such as PEG, are known in the art.

A modified antibody or antigen-binding fragment thereof as provided herein can comprise any type of variable region that provides for the association of the antibody or polypeptide with B7-H4. In this regard, the variable region can comprise or be derived from any type of mammal that can be induced to mount a humoral response and generate immunoglobulins against the desired antigen. As such, the variable region of an anti-B7-H4 antibody or antigen-binding fragment thereof can be, for example, of human, murine, non-human primate (e.g., cynomolgus monkeys, macaques, etc.) or lupine origin. In one embodiment, both the variable and constant regions of the modified antibody or antigen-binding fragment thereof are human. In one embodiment, the variable regions of a compatible antibody (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In one embodiment, the variable domains in both the heavy and light chains of an antibody or antigen-binding fragment thereof are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art to carry out routine experimentation to obtain a functional antibody with reduced immunogenicity.

Alterations to the variable region notwithstanding, those skilled in the art will appreciate that a modified antibody or antigen-binding fragment thereof of this invention will comprise an antibody (e.g., full-length antibody or antigen-binding fragment thereof) in which at least a fraction of one or more of the constant region domains has been deleted or otherwise altered so as to provide desired biochemical characteristics such as increased tumour localization or reduced serum half-life when compared with an antibody of approximately the same immunogenicity comprising a native or unaltered constant region. In one embodiment, the constant region of the modified antibody will comprise a human constant region. Modifications to the constant region compatible with this invention comprise additions, deletions or substitutions of one or more amino acids in one or more domains. That is, the modified antibody disclosed herein can comprise alterations or modifications to one or more of the three heavy chain constant domains ($CH_1$, $CH_2$ or $CH_3$) and/or to the light chain constant domain (CL). In one embodiment, a modified constant region wherein one or more domains are partially or entirely deleted are contemplated. In one embodiment, a modified antibody will comprise domain deleted constructs or variants wherein the entire $CH_2$ domain has been removed ($\Delta CH_2$ constructs). In one embodiment, the omitted constant region domain can be replaced by a short amino acid spacer (e.g., 10 residues) that provides some of the molecular flexibility typically imparted by the absent constant region.

Besides their configuration, it is known in the art that the constant region mediates several effector functions. For example, antibodies bind to cells via the Fc region, with an Fc receptor site on the antibody Fc region binding to an Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, an antibody or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody. In other cases it can be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well-known biochemical or molecular engineering techniques well within the purview of the skilled artisan.

In one embodiment, the antibody or antigen-binding fragment thereof does not have one or more effector functions. For instance, in one embodiment, the antibody or antigen-binding fragment thereof has no antibody-dependent cellular cytotoxicity (ADCC) activity and/or no complement-dependent cytotoxicity (CDC) activity. In one embodiment, the antibody or antigen-binding fragment thereof does not bind to an Fc receptor and/or complement factors. In one embodiment, the antibody or antigen-binding fragment thereof has no effector function.

In one embodiment, the antibody or antigen-binding fragment thereof can be engineered to fuse the $CH_3$ domain directly to the hinge region of the respective modified antibodies or fragments thereof. In other constructs a peptide spacer can be inserted between the hinge region and the modified $CH_2$ and/or $CH_3$ domains. For example, compatible constructs can be expressed in which the $CH_2$ domain has been deleted and the remaining $CH_3$ domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. In one embodiment, any spacer added to the construct can be relatively non-immunogenic, or even omitted altogether, so as to maintain the desired biochemical qualities of the modified antibodies.

Besides the deletion of whole constant region domains, an antibody or antigen-binding fragment thereof provided herein can be modified by the partial deletion or substitution of a few or even a single amino acid in a constant region. For example, the mutation of a single amino acid in selected areas of the $CH_2$ domain can be enough to substantially reduce Fc binding and thereby increase tumor localization. Similarly one or more constant region domains that control the effector function (e.g., complement C1Q binding) can be fully or partially deleted. Such partial deletions of the constant regions can improve selected characteristics of the antibody or antigen-binding fragment thereof (e.g., serum half-life) while leaving other desirable functions associated with the subject constant region domain intact. Moreover, the constant regions of the antibody and antigen-binding fragment thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. In one embodiment, there may be an addition of one or more amino acids to the constant region to enhance desirable characteristics such as decreasing or increasing effector function or provide for more cytotoxin or carbohydrate attachment. In one embodiment, it can be desirable to insert or replicate specific sequences derived from selected constant region domains.

The present invention further embraces variants and equivalents that are substantially homologous an antibody or antigen binding fragment of the invention (e.g. murine, chimeric, humanized or human antibody, or antigen-binding fragments thereof). These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

In one embodiment, the antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 22nd ed., Ed. Lloyd V. Allen, Jr. (2012).

Definitions

The following definitions pertain, in particular, to the description of topoisomerase I inhibitors above, and may even more particularly pertain to the section entitled "further preferences".

$C_{5-6}$ arylene: The term "$C_{5-6}$ arylene", as used herein, pertains to a divalent moiety obtained by removing two hydrogen atoms from an aromatic ring atom of an aromatic compound.

In this context, the prefixes (e.g. $C_{5-6}$) denote the number of ring atoms, or range of number of ring atoms, whether carbon atoms or heteroatoms.

The ring atoms may be all carbon atoms, as in "carboarylene groups", in which case the group is phenylene ($C_6$).

Alternatively, the ring atoms may include one or more heteroatoms, as in "heteroarylene groups". Examples of heteroarylene groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); and
$N_3$: triazole ($C_5$), triazine ($C_6$).

$C_{1-4}$ alkyl: The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). The term "$C_{1-n}$ alkyl" as used herein, pertains to a monovalent moiety obtained by removing a hydrogen atom from a carbon atom of a hydrocarbon compound having from 1 to n carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$) and butyl ($C_4$).

Examples of saturated linear alkyl groups include, but are not limited to, methyl ($C_1$), ethyl ($C_2$), n-propyl ($C_3$) and n-butyl ($C_4$).

Examples of saturated branched alkyl groups include iso-propyl ($C_3$), iso-butyl ($C_4$), sec-butyl ($C_4$) and tert-butyl ($C_4$).

$C_{2-4}$ Alkenyl: The term "$C_{2-4}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$) and butenyl ($C_4$).

$C_{2-4}$ alkynyl: The term "$C_{2-4}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-4}$ cycloalkyl: The term "$C_{3-4}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane ($C_3$) and cyclobutane ($C_4$); and
unsaturated monocyclic hydrocarbon compounds:
cyclopropene ($C_3$) and cyclobutene ($C_4$).
Connection labels: In the formula

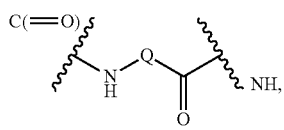

the superscripted labels $^{C(=O)}$ and $^{NH}$ indicate the group to which the atoms are bound. For example, the NH group is shown as being bound to a carbonyl (which is not part of the moiety illustrated), and the carbonyl is shown as being bound to a NH group (which is not part of the moiety illustrated).

Salts

It may be convenient or desirable to prepare, purify, and/or handle a corresponding salt of the active compound/agent, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds/agents of the invention may exist in one or more particular geometric, optical, enantiomeric, diasteriomeric, epimeric, atrophic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Enantiomerically enriched form" refers to a sample of a chiral substance whose enantiomeric ratio is greater than 50:50 but less than 100:0.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/enediamine, nitroso/oxime, thioketone/enethiol, N-nitroso/hyroxyazo, and nitro/aci-nitro.

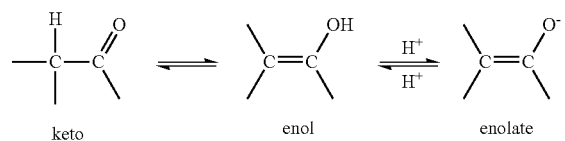

keto          enol          enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, chlorine and iodine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

ALIGNMENT SCORES FOR DETERMINING SEQUENCE IDENTITY

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of indentical matches}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine; lysine; histidine
Acidic: glutamic acid; aspartic acid
Polar: glutamine; asparagine
Hydrophobic: leucine; isoleucine; valine
Aromatic: phenylalanine; tryptophan; tyrosine
Small: glycine; alanine; serine; threonine; methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and amino-acylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically amino-acylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-aza-phenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an agent" includes a plurality of such agents and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

FIG. 11 shows bystander killing of tumor cells in vivo (E02-GL-SG3932).

FIG. 16A-16C shows results of internalisation experiments, demonstrating internalization of bound E02-GL-antigen complex in live cells.

FIG. 26A-26D shows retention of B7-H4 Ab in the B7H4 expressing tumour (HT29 cells). Intensity scale shows Epifluorescence intensity. Radiant efficiency=(p/sec/cm$^2$/sr)/(μW/cm$^2$); Intensity scale, Min=1.20 e8, Max=1.50 e9.

FIG. 27A-27D shows retention of B7-H4 Ab in the B7H4 expressing tumour (CT26 cells). Intensity scale shows Epifluorescence intensity. Radiant efficiency=(p/sec/cm$^2$/sr)/(μW/cm$^2$); Intensity scale, Min=1.20 e8, Max=1.50 e9.

FIG. 28A-28B shows sequence alignment of the five exemplary antibody clones.

FIG. 32 is a B7-H4 ortholog alignment.

FIGS. 43A-43F are images of immunohistochemical (IHC) staining of human IgG, γH2AX and cleaved Caspase 3 in HT29-huB7-H4 clone 26 xenograft tumors after treatment with E02-GL-SG3932. The images are representative of IHC staining for human IgG, γH2AX, and cleaved caspase-3 in the HT29-huB7-H4 Clone 26 tumor xenograft model, 168 hours after a single IV administration of 7 mg/kg E02-GL-SG3932 (43D-43F) or isotype-matched control ADC NIP228-SG3932 (43A-43C).

In FIGS. 53B-53E, the triangle "Δ" symbol marks models deficient in homologous recombination (as determined by BRCA mutations or RAD51 foci assay). The circle "●" symbol marks models without defects in homologous recombination.

FIG. 57A is the key to FIG. 57B.

FIG. 59A is the key to FIG. 59B.

EXAMPLES

Materials and Methods

Protein Reagents

Figure 1A:
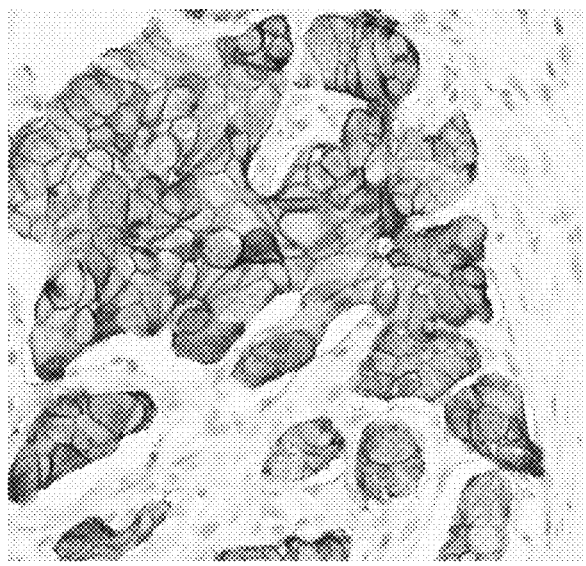
FIG. 1A-1D shows B7-H4 overexpression in breast cancer. (A) TNBC (re-treatment); (B) HR+(pre-treatment); (C) HER2+(pre-treatment, eligible for Herceptin); (D) HER2+ve (Herceptin treated).
Figure 1B:
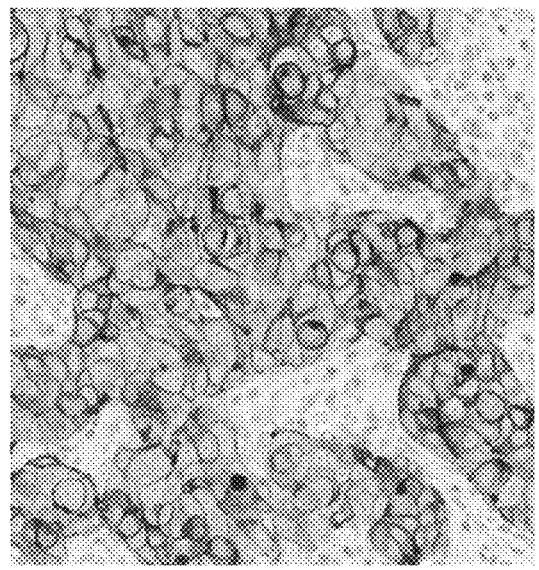
Figure 1C:
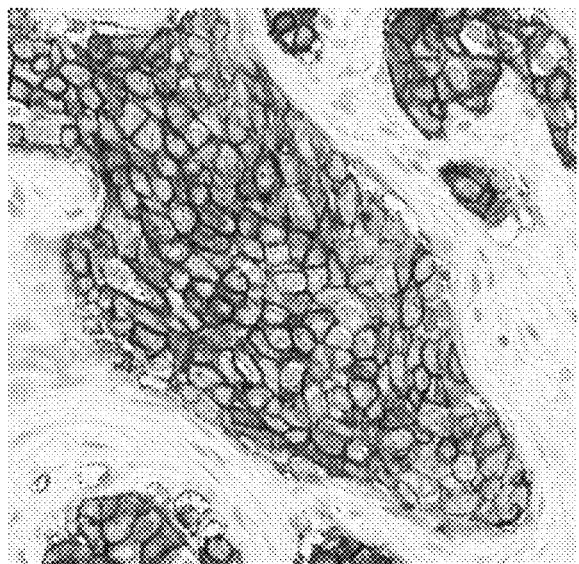
Figure 1D:
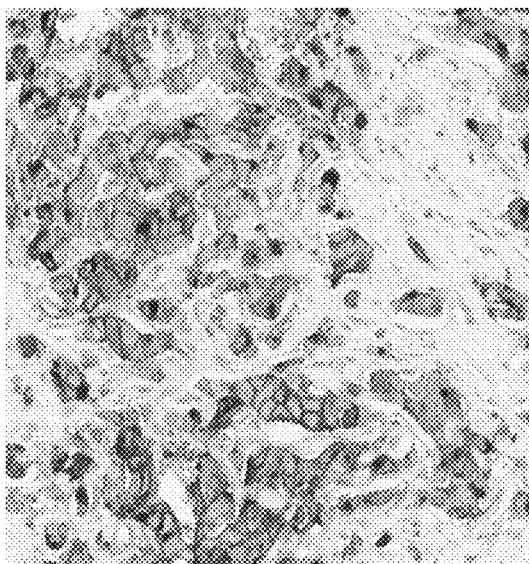

Protein reagents (e.g. constructs) produced are shown in Table 1. The table indicates what species the protein is from (human, mouse or cynomolgus), the vector used to clone the construct and whether the leader sequence used was either native or the Human CD33 leader sequence.

TABLE 1

Protein constructs made for B7H4 project

| Cloned insert | Vector | Comments |
| --- | --- | --- |
| Human B7H4 ECD | pDest12.2 oriP_Fc_6His | Native Leader |
| Mouse B7H4 ECD | pDest12.2 oriP_Fc_6His | Native Leader |
| Human B7H4 ECD | pDest12.2 oriP_Flag_10His | Native Leader |
| Mouse B7H4 ECD | pDest12.2 oriP_Flag_10His | Native Leader |
| Cyno B7H4 ECD | pDest12.2 oriP_Flag_10His | Native Leader |
| Human B7H4 ECD | pDest12.2 oriP_FcTM_6His | Native Leader Triple mutant Fc |
| Mouse B7H4 ECD | pDest12.2 oriP_FcTM_6His | Native Leader Triple mutant Fc |
| Cyno B7H4 ECD | pDest12.2 oriP_FcTM_6His | Native Leader Triple mutant Fc |
| Human B7H4 ECD | pDest12.2 oriP_N_CD33_10His_FLAG | Human CD33 leader |
| Human B7H4 ECD | pDest12.2 oriP_N_CD33_C_mIgG2a_Fc_10His | Human CD33 leader |
| Human B7H4 ECD (SV) | pDest12.2 oriP_N_CD33_10His_FLAG | Human CD33 leader Splice variant |

A "triple mutant Fc" (TM) comprises the mutations triple mutation L234F/L235E/P331S within the Fc region, as previously described in Acta Crystallogr D Biol Crystallogr. 2008 Jun. 1; 64 (Pt 6): 700-704 (incorporated herein by reference). For the avoidance of any doubt, the inventors have the antibodies hereinafter described retain their advantageous binding properties/profiles also in the absence of such TM (e.g. where there is a WT Fc).

All the proteins in the Table were purified using standard conditions. In brief, expression was carried out in HEK EBNAs, concentrated using a TFF concentration setup, purified using a His trap column or a Protein G column (depending on whether a 10 His Flag tag was present or an Fc tag was present), followed by final polish step of a SEC S200 column.

ELISA

The binding of the anti-B7-H4 antibodies (e.g. intermediate ZY0EQD-E02-GL and anti-B7-H4 mAB D11) to B7-H4 (e.g. human and mouse B7-H4) was measured by ELISA. Recombinant B7-H4-Fc (e.g. Human B7-H4-Fc and mouse B7-H4-Fc) proteins were diluted into DPBS to give 5 ug/ml solution. 50 µL of the diluted stocks was then added Nunc Maxisorp 96 well plates. 50 µL/well DPBS was added to control wells. The antigens were allowed to adsorb to the plates overnight at 4° C., washed once with DPBS and incubated with blocking buffer (3% w/v Marvel in DPBS) at room temperature for 1 hour. The plates were then washed once with PBS and incubated for 1 hour with 6.4 pM-100 nM anti-B7-H4 antibody (e.g. intermediate ZY0EQD-E02-GL or anti-B7-H4 mAb D11) diluted in DPBS containing 1% BSA, 0.3% Triton X-100. The plates were then washed three times with PBS containing 0.1% Tween and incubated with peroxidase-conjugated goat anti-human light chain antibody (Sigma Aldrich, Poole, UK) for 1 hour at room temperature. The plates were then washed five times with PBS containing 0.1% Tween. Following a 5-minute incubation with TMB peroxidase substrate, the reaction was stopped by the addition of 0.5 M $H_2SO_4$. Absorbance at 450 nm (A450) was measured using an Envision multilabel plate reader (Perkin Elmer, Seer Green, UK).

Flow Cytometry (for Detecting Antibody Binding to B7-H4 Positive Cells)

Cells were detached from tissue culture flasks by accutase (Gibco, Paisley, UK), pelleted by centrifugation, and resuspended in ice cold DPBS (Gibco, Paisley, UK). Viable cells were counted by trypan blue exclusion using a haemocytometer. Cell densities were adjusted to $5 \times 10^6$ cells/mL in DPBS. 100 µL of the cell suspension ($5 \times 10^5$ cells) was added to 96-well V-bottomed plates and placed on ice. Then, the cells were incubated with Live/Dead fixable violet stain (ThermoFisher Scientific, Loughborough, UK) for 20 minutes on ice. Following a wash with flow cytometry buffer (eBiosciences, Hatfield, UK), the cells were incubated on ice for 30 minutes in 100 µL flow cytometry buffer alone (unstained control cells) or supplemented with AF647-labelled anti-B7H4 antibodies (e.g. E02-GL or 1D11) or isotype R347 at a concentration ranging from 10 µg/ml to 78 ng/ml. The cells were then washed three times with 200 µL ice cold flow cytometry buffer, fixed with 200 µL of 4% paraformaldehyde (Sigma Aldrich, Poole, UK) for 20 minutes, and suspended in DPBS on ice for flow cytometry analysis on a FACSCanto II instrument (BD Biosciences, San Jose, CA, USA). FlowJo cytometry analysis software (Treestar, Ashland, OR, USA) was used to quantify antibody binding to cells as follows. Live, single cells were gated based on forwards scatter, side scatter, and Live/Dead violet fluorescence intensity and the AF647 geometric mean fluorescence intensity (MFI) was determined.

Cytotoxicity Assay

Cell lines were detached from tissue culture flasks by accutase (Gibco, Paisley, UK), pelleted by centrifugation, and resuspended in growth media (McCoy's 5A, 10% FBS, 400 µg/mL G418 for HT29-hB7H4 clone 44, McCoys'5A, 10% FBS for SKBR3 and RPMI-1640, 10% FBS for HCC1569). Viable cells were counted by trypan blue exclusion using a haemocytometer. Cell densities were adjusted to $2.7 \times 10^4$ cells/mL in growth media. 75 µL/well of the cell suspension ($2 \times 10^3$ cells) was added to 96-well white walled clear bottom tissue culture treated plates and cultured overnight in a humidified tissue culture incubator at 37° C. in 5% $CO_2$.

ADCs (e.g. 1D11-MMAE, E02-GL-MMAE and E02-GL-SG3249) were diluted into DPBS to give 400 µg/mL or 16 µg/mL stocks respectively. Four-fold serial dilutions of the stocks were prepared in DPBS. 25 µL of the diluted stocks was then added to duplicate wells of the cultured cells, with a ten-point, four-fold serial dilution of antibody (e.g. 1D11-MMAE or E02-GL-MMAE or E02-GL-SG3249). 25 µL/well DPBS was added to mock-treated control cells.

Cells were cultured in the presence of ADCs or DPBS (mock-treated control cells) for six days. Cell viability was assessed using CellTiter-Glo® assay: 100 µL of CellTiter-Glo® (Promega, Southampton, UK) was added to each well. Plates were agitated on a benchtop shaker for 2 minutes and were then incubated at room temperature for an additional 10 minutes. Luminescence was measured using an Envision multilabel plate reader (Perkin Elmer, Seer Green, UK). The potency for test article antibodies (e.g. 1D11-MMAE or E02-GL-MMAE or E02-GL-SG3249) was determined by generating half-maximal inhibitory concentration (IC50) values using a nonlinear regression model [log agonist vs. response—variable slope (three parameters)] in GraphPad Prism, version 7 (GraphPad Software, La Jolla, CA) and presented as percent cell viability relative to Mock-treated control cells—

([(Treated cells−Background)/(Mock-treated control cells−Background)]×100).

On-Cell Western

The on-cell western method was developed and used to run 5 exemplary antibody clones with the following cells: SKBR3, A549, OVCAR4 (all minus transfections with B7-H4 vector), CHO and HEK cells (plus and minus transfection with full length B7-H4 vector).

In addition to the exemplary antibody clones, the following antibodies (for comparative purposes) were also used:
E Biosciences 14-5949 anti-Human B7H4 mouse IgG
US biological B0000-35B anti Human B7H4 mouse IgG
R and D systems AF2514 anti Mouse B7H4 goat IgG1
Sigma SAB2500141 anti B7H4 Goat IgG1
Isotype 1 CAT004 SP06-003
Isotype 2 R and D Normal goat IgG control (AB-108C)
Affinity Analysis KinExA 3200
E02_GL Fab: E02_GL Fab SEC fraction (33.4-34.5 min, 07031802.D),
B7H4: hB7H4-ECD-Flag-His10 (4.34 mg mL-1, J Watson, 31/10/17).
KinExA Buffers:
D-PBS with added 0.02% sodium azide (VWR/Merck 103692K, lot: K35580906), 1 Litre, 0.20 µm sterile filtered.
D-PBS with added 0.02% sodium azide (VWR/Merck 103692K, lot: K35580906) and 1 mg mL$^{-1}$ bovine serum albumin (Sigma A-2058, lot: 108H0573). 1.0 Litre, 0.20 µm sterile filtered.
Secondary Detection Reagent:
DyLight649 labelled Mouse anti-human H+L chain secondary detection reagent (Jackson Immunoresearch, 209-495-088, lot 91003) was used for detection of whole IgGs or Fab. Vial (~1 mg) reconstituted with 800 µL Milli-Q water.
Minimal Amine Biotinylation of r Human B7H4 ECD:
Protein: r human B7H4 ECD-FlagHis10 (4.34 mg mL$^{-1}$, batch 1, 31 Oct. 2017)
Source: JWPur006
Volume/buffer: 0.100 mL/PBS
Mass of protein (Da): 29,053.57 Da
Mass of protein to be biotinylated=0.434 mg
Amount protein to be biotinylated (pmoles) 0.000434 g/29,054 Da=1.494 E-8 moles (14,938 pmoles)
Biotinylation:
10 µL saturated NaHCO$_3$ in D-PBS added.
Reagent: EZ link Sulfo-NHS-LC-Biotin (Perbio/Pierce, product no. 21335) in (1.0 mg mL$^{-1}$ in DMF).
First pulse protein:biotin ratio: 1:0.5 14,938×0.5=14,938 7,468/1,797 pmol µL$^{-1}$=4.16 µL
Start: 16:07 p.m.; sampled: 16:35 p.m.
All applied to a Dulbecco's PBS equilibrated PD-10 column.
Imaging Studies In Vivo
Antibody clones (e.g. E02_GL) were labelled with 800 CW (LI-COR Biosciences). 800 CW labelled R347 was used in control experiments.

B7-H4 expressing CT26/4TI/HT29 cancer cells were grafted (e.g. inoculated subcutaneously) to the left flank 3-5 day old nude mice (Charles River Laboratories, Wilmington, MA), and non-B7-H4 expressing CT26/4TI/HT29 cancer cells were grafted to the right flank to provide an internal control. Mice were kept for a week to develop tumours, 800 CW-labelled E02_GL was injected. 800 CW-labelled R347 was injected into control mice. In vivo imaging of tumours was performed at days 1, 3, 7 and 9 following injection of labelled antibodies, by imaging radiance from the label.

Example 1

B7-H4 is Over-Expressed in Multiple Cell Types

Immunohistochemistry was carried out on sections from a number of sections of tumours taken from human subjects, representing a number of tumour types (as outlined in Table 2). Expression of B7-H4 was found to be particularly pronounced in breast cancer (e.g. hormone-receptor-positive (HR+)) breast cancer, as well as non-small-cell lung carcinoma (NSCLC) (see FIGS. 1A-1D). Interestingly, the majority of tumours showed heterogeneous expression.

Expression was maintained in a proportion of patients following treatment (where HER2+ breast cancer patients were treated with Herceptin; and ovarian cancer patients were treated with platinum-based chemotherapy).

TABLE 2

| Tumor Type | | % Pos[1] | % High Pos[2] | % Low Pos[3] | N Evaluated |
|---|---|---|---|---|---|
| Breast | HR+ | 85 | 23 | 51 | 39 |
| | TNBC | 70 | 32 | 23 | 230 |
| | HER2+ | 87 | 42 | 28 | 98 |
| | Herceptin eligible | 83 | 43 | 20 | 30 |
| | Herceptin treated | 88 | 41 | 31 | 68 |
| Ovarian (Serous) | | 72 | 24 | 33 | 71 |
| Endometrial | | 84 | 35 | 48 | 39 |
| NSCLC | Squamous | 63 | 15 | 48 | 160 |
| | Adenocarcinoma | 19 | 2 | 15 | 143 |
| Pancreatic | | 31 | 1 | 18 | 90 |
| Gastric | | 10 | 0 | 10 | 21 |
| Cholangiocarcinoma | | 13 | 38 | 38 | 13 |

[1]Positive: Tumors with staining at any intensity and frequency
[2]High Positive: Tumors with membrane staining with intensity of >2+ in >50% of tumor cells
[3]Low Positive: Tumors with membrane staining with intensity of ≤2+ in <50% of tumor cells
Data based on Tissue MicroArray analysis Example 2

Generation of Anti-B7-H4 Antibodies

A repetitive immunisation multiple site (RIMS) strategy was taken, in which VelocImmune II mice (Regeneron, Tarrytown, NY) were immunised as follows:
Minus 4 days: pre-bleed
0 days: prime immunisation
7 days: second boost
13 days: first bleed
15 days: third boost
20 days: second bleed
22 days: fourth boost
24 days: fifth boost
28 days: terminal bleed and sp1. and LN fusions For immunisation, sixteen V2 mice were split into 4 groups, each group containing 4 animals. Animals were immunised with human and mouse recombinant B7-H4, as well as SkBr3 cells (e.g. which express B7-H4). Details of immunogen can be found in Table 3 below (TT=tetanus toxin; DTA=diphtheria toxin; KLH=Keyhole limpet haemocyanin).

TABLE 3

| Group N = 4 | Prime | 2 | 3 | 4 | 5 |
|---|---|---|---|---|---|
| G1 | KLH-mB7H4 | KLH-mB7H4 | KLH-mB7H4 | KLH-hB7H4 | KLH-hB7H4 |
| G2 | KLH-mB7H4 | SkBr3 | KLH-mB7H4 | SkBr3 | SkBr3 |
| G3 | mB7H4-TT | KLH-hB7H4 | mB7H4-TT | KLH-hB7H4 | mB7H4-TT |
| G4 | mB7H4-DTA | KLH-hB7H4 | mB7H4-DTA | KLH-hB7H4 | mB7H4-DTA |

Hybridoma Generation

Lymphoid cells were harvested from 10 mice, cells from mice 3 and 9 were enriched for B cells, no selection was performed on cells from the other 8 mice. Lymphoid cells and Sp2/0 Ag14 myeloma cells were mixed at 5:1 ratio, washed in serum-free medium, and fusions were performed using PEG either manually or by the tecan robot. Following fusion, the cells were resuspended in 200 ml of complete HM20 medium and 100 µl added to columns 1-11 of 20 plates. After 3 days, a further 100 µl of medium was added to each well. Fusion details for each mouse are shown in Table 4.

TABLE 4

| Mouse | Group | Spleen cells × 10^6 | LN cells × 10^6 | Total × 10^6 | % LNC | Fusion Type | Selection |
|---|---|---|---|---|---|---|---|
| 1 | 1 | 57.72 | 13.78 | 71.50 | 19.27 | Tecan | None |
| 3 | 1 | 73.42 | 10.35 | 83.77 | 12.36 | Manual | B cell |
| 4 | 1 | 27.78 | 11.47 | 39.25 | 29.21 | Tecan | None |
| 5 | 2 | 67.92 | 23.45 | 91.37 | 25.66 | Tecan | None |
| 7 | 2 | 78.20 | 25.70 | 103.90 | 24.74 | Tecan | None |
| 9 | 3 | 62.47 | 11.98 | 74.45 | 16.09 | Manual | B cell |
| 10 | 3 | 53.43 | 5.25 | 58.68 | 8.95 | Manual | None |
| 11 | 3 | 50.80 | 9.25 | 60.05 | 15.40 | Tecan | None |
| 13 | 4 | 41.33 | 11.98 | 53.30 | 22.47 | Manual | None |
| 14 | 4 | 38.20 | 34.30 | 72.50 | 47.31 | Tecan | None |

Hybridoma Screening and Cloning

Supernatants harvested 13 days following fusion were screened in a bead based IgG/IgM screen by the hybridoma group and in human, cynomolgus and mouse B7H4 HTRF biochemical binding assays, and in a SkBr3 FMAT assay by HTS.

Following screening positive hits were picked of which 58 were cloned out into semi-solid media. IgG positive clones were picked from each well line using the ClonePix-FL, which were subsequently screened in the primary assays. A maximum of 4 clones were then picked from each well line, which were grown up and small scale IgG purifications performed (Phytip—protein A).

Following biological screens of the Phytip material, 5 exemplary antibodies were chosen for further characterisation (details of which can be found in Table 5).

TABLE 5

| Clone ID | Mouse ID | Immunogen |
|---|---|---|
| ZY0EPQ-E02 | 5 | Group 2 (SkBr3 cells/mB7H4-KLH) |
| ZY0EQD-E02 | 7 | Group 2 (SkBr3 cells/mB7H4-KLH) |
| ZY0EP0-C07 | 4 | Group 1 (mB7H4-KLH/h-B7H4-KLH) |
| ZY0EOB-F05 | 1 | Group 1 (mB7H4-KLH/h-B7H4-KLH) |
| ZY0EO5-E07 | 1 | Group 1 (mB7H4-KLH/h-B7H4-KLH) |

ZY0EPQ-E02 (and germlined versions thereof, e.g. connotated by the abbreviation "GL") comprises a CHDR1-3 of SEQ ID NO: 1-3 (respectively), and a CLDR1-3 of SEQ ID NO: 4-6 (respectively). ZY0EPQ-E02 comprises a VH chain of SEQ ID NO: 31, and a VL of SEQ ID NO: 32.

ZY0EQD-E02 comprises a CHDR1-3 of SEQ ID NO: 7-9 (respectively), and a CLDR1-3 of SEQ ID NO: 10-12 (respectively). ZY0EQD-E02 comprises a VH chain of SEQ ID NO: 33, and a VL of SEQ ID NO: 34. A germlined version of ZY0EQD-E02 is referred to later e.g. by inclusion of the abbreviation "GL", and referred to e.g. as EQD-E02_GL (having a VH chain of SEQ ID NO: 45, and a VL of SEQ ID NO: 34).

ZY0EOB-F05 comprises a CHDR1-3 of SEQ ID NO: 13-15 (respectively), and a CLDR1-3 of SEQ ID NO: 16-18 (respectively). ZY0EOB-F05 comprises a VH chain of SEQ ID NO: 35, and a VL of SEQ ID NO: 36.

ZY0EO5-E07 comprises a CHDR1-3 of SEQ ID NO: 19-21 (respectively), and a CLDR1-3 of SEQ ID NO: 22-24 (respectively). ZY0EO5-E07 comprises a VH chain of SEQ ID NO: 37, and a VL of SEQ ID NO: 38.

ZY0EP0-007 comprises a CHDR1-3 of SEQ ID NO: 25-27 (respectively), and a CLDR1-3 of SEQ ID NO: 28-30 (respectively). ZY0EP0-007 comprises a VH chain of SEQ ID NO: 39, and a VL of SEQ ID NO: 40.

These 5 exemplary antibodies were reformatted onto human IgG1, human IgG1-TM (triple mutation) and murine IgG1 backbones.

Sequence analysis of the 5 reformatted exemplary antibodies shows identity between ZY0EPQ-E02 and ZY0EQD-E02 as well as clones ZY0EOB-F05 and ZY0EO5-E07 (see FIG. 28).

Example 3

Antigen Binding Assays with Selected Clones

Concentration-effect binding of the 5 exemplary antibodies as murine IgG1, human IgG1 and human IgG1-TM were performed using human, cynomolgus and murine B7-H4-Fc via HTRF assay. For the murine IgG1 antibodies, anti-murine IgG conjugated with Dylight-649 was used for detection. A similar assay format was used with the human IgG1 and IgG1-TM antibodies; however anti-human kappa conjugated with Dylight-649 was used for detection.

Antibodies ZY0EPQ-E02 and ZY0EQD-E02 have a higher EC50 and a lower max binding to murine B7-H4-Fc than to human or cynomolgus B7-H4-Fc, indicating a lower affinity to the murine B7-H4. All the other antibodies have a similar EC50 and max binding to the human, cynomolgus and murine B7-H4-Fc (see Tables 6-8).

TABLE 6

HTRF Data using human B7-H4-Fc

| | Human B7-H4-Fc | | | | | |
|---|---|---|---|---|---|---|
| | Murine IgG1 | | Human IgG1 | | Human IgG1-TM | |
| Antibody | EC50 (nM) | Max | EC50 (nM) | Max | EC50 (nM) | Max |
| ZY0EPQ-E02 | 0.38 | 2741 | 0.38 | 1127 | 0.41 | 1092 |
| ZY0EQD-E02 | 0.22 | 3166 | 0.35 | 1237 | 0.33 | 1272 |
| ZY0EOB-F05 | 0.30 | 3025 | 0.15 | 1816 | 0.15 | 1873 |
| ZY0E05-E07 | 0.68 | 2150 | 0.19 | 1708 | NT | NT |
| ZY0EP0-C07 | 0.95 | 1736 | 0.30 | 1221 | 0.31 | 1207 |

TABLE 7

HTRF Data using cynomolgus B7-H4-Fc

| | Cyno B7-H4-Fc | | | | | |
|---|---|---|---|---|---|---|
| | Murine IgG1 | | Human IgG1 | | Human IgG1-TM | |
| Antibody | EC50 (nM) | Max | EC50 (nM) | Max | EC50 (nM) | Max |
| ZY0EPQ-E02 | 0.38 | 2236 | 0.33 | 987 | 0.35 | 934 |
| ZY0EQD-E02 | 0.22 | 2494 | 0.28 | 1127 | 0.28 | 1100 |
| ZY0EOB-F05 | 0.32 | 2398 | 0.14 | 1483 | 0.15 | 1483 |
| ZY0E05-E07 | 0.71 | 1698 | 0.18 | 1359 | NT | NT |
| ZY0EP0-C07 | 1.28 | 1247 | 0.33 | 946 | 0.39 | 890 |

TABLE 8

HTRF Data using murine B7-H4-Fc

| | Murine B7-H4-Fc | | | | | |
|---|---|---|---|---|---|---|
| | Murine IgG1 | | Human IgG1 | | Human IgG1-TM | |
| Antibody | EC50 (nM) | Max | EC50 (nM) | Max | EC50 (nM) | Max |
| ZY0EPQ-E02 | 2.03 | 790 | 1.49 | 279 | 1.76 | 256 |
| ZY0EQD-E02 | 3.64 | 447 | 1.40 | 167 | 1.44 | 224 |
| ZY0EOB-F05 | 0.38 | 2190 | 0.19 | 1319 | 0.19 | 1342 |
| ZY0E05-E07 | 0.73 | 1697 | 0.21 | 1300 | NT | NT |
| ZY0EP0-C07 | 0.49 | 1910 | 0.18 | 1321 | 0.20 | 1252 |

Binding Affinity Measurements

Antibody affinity to the human, murine and splice variant B7-H4 ECD's was measured with the ForteBio Octet system. Human IgG1-TM antibodies were captured by Protein G and the monomeric species B7-H4-FLAG ECD were measured binding to the antibody. Affinity to human B7-H4 was in the 10-25 nM range, whereas the murine affinity was between 10-600 nM. All antibodies except ZY0EP0-007 could bind the splice variant, with affinities between 200-1600 nM. Kinetic binding parameters are summarised in Table 9 below.

TABLE 9

Octet Affinity Summary

| | | hIgG1-TM (n = 4 – 7) | | | hIgG1 (n = 1) | | |
|---|---|---|---|---|---|---|---|
| Antibody | Protein | KD (nM) | kon(1/Ms) | kdis(1/s) | KD (nM) | kon(1/Ms) | kdis(1/s) |
| ZY0EPQ-E02 | HumanB7-H4 | 25.7 | 7.09E+04 | 1.82E-03 | 24 | 8.59E+04 | 2.08E-03 |
| | MurineB7-H4 | 396 | 7.67E+04 | 3.04E-02 | 498 | 1.00E+05 | 4.98E-02 |
| | B7-H4-SV | 1660 | 1.38E+03 | 2.29E-03 | 1030 | 2.46E+03 | 2.52E-03 |
| ZY0EQD-E02 | HumanB7-H4 | 14.4 | 1.93E+05 | 2.78E-03 | 14.9 | 2.16E+05 | 3.21E-03 |
| | MurineB7-H4 | 621 | 2.03E+05 | 1.26E-01 | 625 | 3.41E+05 | 2.13E-01 |
| | B7-H4-SV | 801 | 3.36E+03 | 2.69E-03 | 834 | 4.19E+03 | 3.49E-03 |
| ZY0EOB-F05 | HumanB7-H4 | 13.4 | 2.65E+04 | 3.55E-04 | 11.7 | 3.10E+04 | 3.62E-04 |
| | MurineB7-H4 | 25 | 1.87E+04 | 4.76E-04 | 19.8 | 2.49E+04 | 4.93E-04 |
| | B7-H4-SV | 174 | 3.35E+03 | 5.84E-04 | 127 | 4.71E+03 | 5.98E-04 |
| ZY0E05-E07 | HumanB7-H4 | 19.8 | 1.71E+04 | 3.38E-04 | 14.6 | 2.17E+04 | 3.18E-04 |
| | MurineB7-H4 | 30 | 1.21E+04 | 3.61E-04 | 23.2 | 1.79E+04 | 4.15E-04 |
| | B7-H4-SV | 264 | 1.89E+03 | 4.99E-04 | 182 | 2.91E+03 | 5.28E-04 |
| ZY0EP0-C07 | HumanB7-H4 | 9.4 | 4.16E+04 | 3.97E-04 | 7 | 4.88E+04 | 3.63E-04 |
| | MurineB7-H4 | 11 | 4.30E+04 | 5.24E-04 | 9 | 6.02E+04 | 5.51E-04 |
| | B7-H4-SV | No Binding | | | No Binding | | |

Epitope Binning

Epitope binning was performed in an HTRF assay format using the exemplary antibodies (IgG1-TM) conjugated with DyLight-649 binding to the monomeric B7-H4-FLAG ECD with detection with europium conjugated anti-FLAG antibody.

Bin 1 was defined with the ZY0EPQ-E02, ZY0EQD-E02 and ZY0EO5-E07 antibodies fully inhibiting each other, and only partial inhibiting ZY0EP0-007. Bin 2 was defined with the ZY0EOB-F05 antibody fully competing with all antibodies and all antibodies fully competing with it. Bin 3 was defined with ZY0EP0-007 partially competing with antibodies ZY0EPQ-E02, ZY0EQD-E02 and ZY0EO5-E07 (Bin 1).

TABLE 10

HTRF Epitope Summary Table

| Competing Antibody | Dy649 conjugated antibody ||||| 
|---|---|---|---|---|---|
| | ZY0EPQ-E02 | ZY0EQD-E02 | ZY0EOB-F05 | ZY0EO5-E07 | ZY0EP0-C07 |
| ZY0EPQ-E02 | Full | Full | Full | Not Tested | Partial |
| ZY0EQD-E02 | Full | Full | Full | | Partial |
| ZY0EOB-F05 | Full | Full | Full | | Full |
| ZY0EO5-E07 | Full | Full | Full | | Partial |
| ZY0EP0-C07 | Partial | Partial | Full | | Full |

Species Cross-Reactivity ELISA

Each of the above-mentioned 5 VelocImmune derived anti-B7-H4 exemplary antibodies were tested for binding to in house derived murine B7-H4 (ECD). All exemplary antibodies were tested as human IgG1-TMs, alongside 4/5 murine IgG1 s (ZY0EP0-007 was not available as a murine IgG1 at this time). Binding to monomeric and dimeric murine and human B7-H4 variants were compared (FlagHis10 or FcHis6 tagged, respectively).

All IgGs, irrespective of isotype, retained cross-reactivity to both murine and human B7-H4 antigens. The dimeric nature of the FcHis6-tagged B7-H4 antigens produced binding curves that were uniformly shifted to the left of those curves provided by the corresponding monomeric FlagHis10 B7-H4 antigens. This effect was more marked for murine B7-H4.

No significant binding to irrelevant antigen controls was observed with any of the VelocImmune exemplary antibodies. Isotype control IgGs did not bind non-specifically to the B7-H4 antigens (NIP228—human IgG1-TM and MOPC-21-murine IgG1)—see FIGS. 2A-2K.

Commercial Anti-B7-H4 Polyclonal and Monoclonal Specificity ELISA

A panel of commercial monoclonal and polyclonal antisera were tested for binding to human and murine B7-H4 antigens by ELISA. Each antiserum was also tested for binding to a truncated human B7-H4 splice variant (essentially missing its extracellular IgV domain). Equivalent data was obtained irrespective of whether FlagHis10 or FcHis6 B7-H4 antigens were used. The different cross reactivity profiles are summarised within Tables 11 and 12.

TABLE 11

| | Monoclonals | | | | | |
|---|---|---|---|---|---|---|
| | | | | B7-H4 | | |
| Company | Cat # | Lot # | Human | Murine | Splice Variant |
| AdD serotec | MCA2632 | 707 | Y | N | N |
| eBioscience | 14-5949 | E021763 | Y | Y | Y |
| Epitomics | 2516-1 | YD-08-23-02 | N | N | n/a |
| US Biologicals | B0000-35B | L10061519 | Y | N | N |
| eBioscience | 145972-82 | E010563 | Y | Y | Y |
| eBioscience | 145970-85 | E010556 | N | N | n/a |
| R & D | MAB2154 | WVP0107101 | Y | Y | Y |

TABLE 12

| | Polyclonals | | | | | |
|---|---|---|---|---|---|---|
| | | | | B7-H4 | | |
| Company | Cat # | Lot # | Human | Murine | Splice Variant |
| Santa Cruz | sc68872 (H108) | L1008 | Y | Y | n/a |
| Santa Cruz | sc68254 (G-18) | C1910 | N | N | n/a |
| R & D | AF2154 | WVP016011 | Y | Y | Y |
| Abbiotec | 250473 | 10051104 | N | N | n/a |
| Sigma Aldrich | SAB2500141 | 7942P1 | Y | Y | N |

B7-H4 Homolog Specificity ELISA

Each of the five selected clones (VelocImmune IgGs) were tested for non-specific binding to B7-H4 family members and homologs (murine IgG1 ZY0EP0-007 was available to test). The choice of which antigens to test was guided by undertaking a BLASTP search using the ECD of human B7-H4 as test sequence. Advantageous hits from this list were then aligned using CLUSTALW analysis and those antigens displaying the highest percentage identity at the primary amino acid level were sourced (see Table 13).

TABLE 13

| | Percent Identity | | | | | | | | | | |
|---|---|---|---|---|---|---|---|---|---|---|---|
| Divergence | 1 | 2 | 3 | 4 | 5 | 6 | 7 | 8 | 9 | 10 | |
| 1 | — | 13.2 | 21.5 | 21.4 | 25.9 | 21.6 | 20.7 | 25.4 | 25.2 | 25.8 | 1 Human B7-H4 ECD.pro |
| 2 | 377.0 | — | 11.7 | 12.1 | 13.1 | 10.3 | 11.0 | 13.7 | 9.7 | 8.4 | 2 Human MOG1.pro |
| 3 | 229.0 | 426.0 | — | 19.2 | 27.8 | 21.5 | 20.1 | 18.2 | 18.1 | 13.8 | 3 Human B7-H1.pro |
| 4 | 229.0 | 414.0 | 255.0 | — | 21.2 | 20.8 | 17.7 | 21.4 | 18.2 | 13.4 | 4 Human B7-H2.pro |
| 5 | 190.5 | 377.0 | 174.9 | 231.0 | — | 25.6 | 19.5 | 23.4 | 24.1 | 20.1 | 5 Human B7-H3.pro |
| 6 | 228.0 | 498.0 | 229.0 | 236.0 | 192.5 | — | 42.3 | 45.8 | 34.8 | 15.0 | 6 Human BTN1A1.pro |
| 7 | 238.0 | 461.0 | 244.0 | 279.0 | 253.0 | 103.0 | — | 41.0 | 33.6 | 15.8 | 7 Human BTN2A1.pro |
| 8 | 194.4 | 362.0 | 270.0 | 229.0 | 209.0 | 91.9 | 107.6 | — | 32.5 | 17.5 | 8 Human BTN3A2.pro |

TABLE 13-continued

| | Percent Identity | | | | | | | | | | | |
|---|---|---|---|---|---|---|---|---|---|---|---|---|
| Divergence | 1 | 2 | 3 | 4 | 5 | 6 | 7 | 8 | 9 | 10 | | |
| 9 | 196.4 | 538.0 | 271.0 | 270.0 | 203.0 | 133.7 | 139.3 | 145.3 | — | 11.8 | 9 | Human BTNL3.pro |
| 10 | 191.3 | 661.0 | 360.0 | 368.0 | 245.0 | 330.0 | 311.0 | 282.0 | 426.0 | — | 10 | Human HHLA2.pro |
| | 1 | 2 | 3 | 4 | 5 | 6 | 7 | 8 | 9 | 10 | | |

The five exemplary antibodies do not bind measurably to homologues huB7-H1, huB7-H2, huB7-H3, huBTN1A1, huHHLA2 or huBTN3A2, irrespective of antibody isotype. Note that binding was not seen when testing huMOG1, huBTN2A1 or huBTNL3 antigens either (see FIG. 3).

On-Cell Western Binding Analysis

Cells were detached from T175 flasks using Accutase and counted. Transfection method used was essentially that stated in the Invitrogen Lipofectamine LTX protocol (high throughput protocol using the reverse transfection method). 1000 of cells ($4.5 \times 10^4$ per 1000) was added to 96 well plates containing the DNA-lipofectamine mix. Plates incubated at 37° C. for 18 hours and fixed using 10% buffered formalin overnight. Plates were blocked with Odyssey blocking buffer, incubated with appropriate primary antibodies overnight followed by washing and detection with the appropriate Odyssey secondary antibody.

Plates were air dried and scanned using the Odyssey Imager using the recommended scan levels provided by the manufacturer.

Figure 4A:
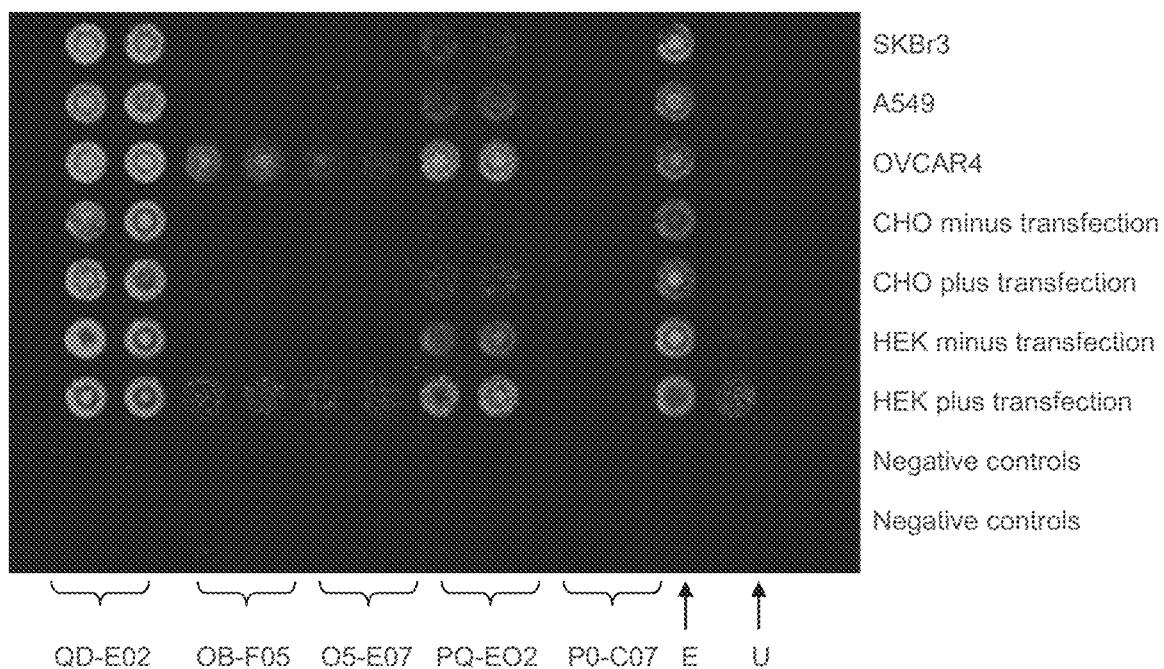
FIG. 4A-4B shows results of on cell western analysis for binding of the selected clones (and commercial antibodies) to various cell types. E=E Biosciences 14-5949 anti-Human B7H4 mouse IgG; U=US biological B0000-35B anti Human B7H4 mouse IgG; R=R and D systems AF2514 anti Mouse B7H4 goat IgG1; S=Sigma SAB2500141 anti B7H4 Goat IgG1
Figure 4B:
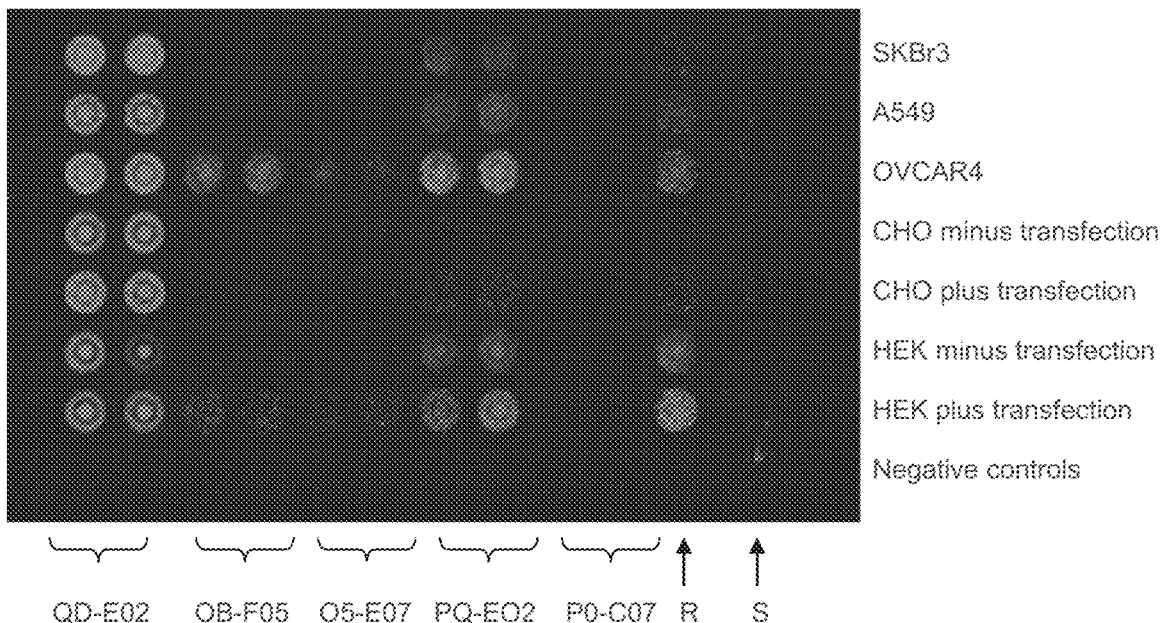
Figure 5A:
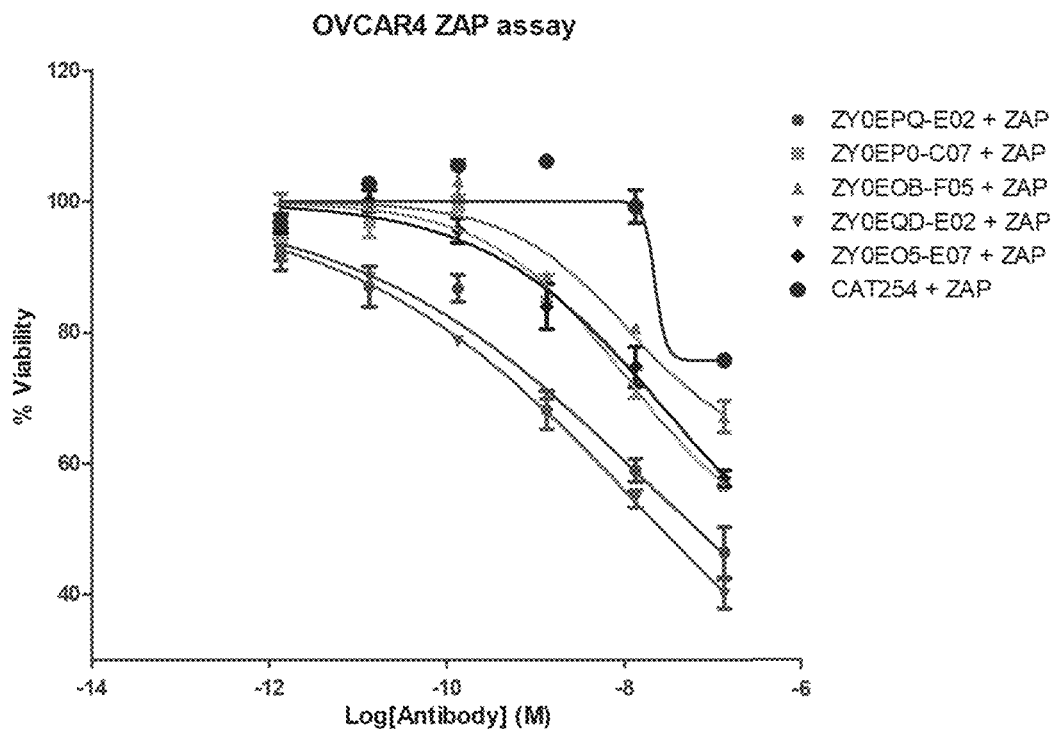
FIG. 5A-5F shows results from in vitro cytotoxicity assay with the selected clones.
Figure 5B:
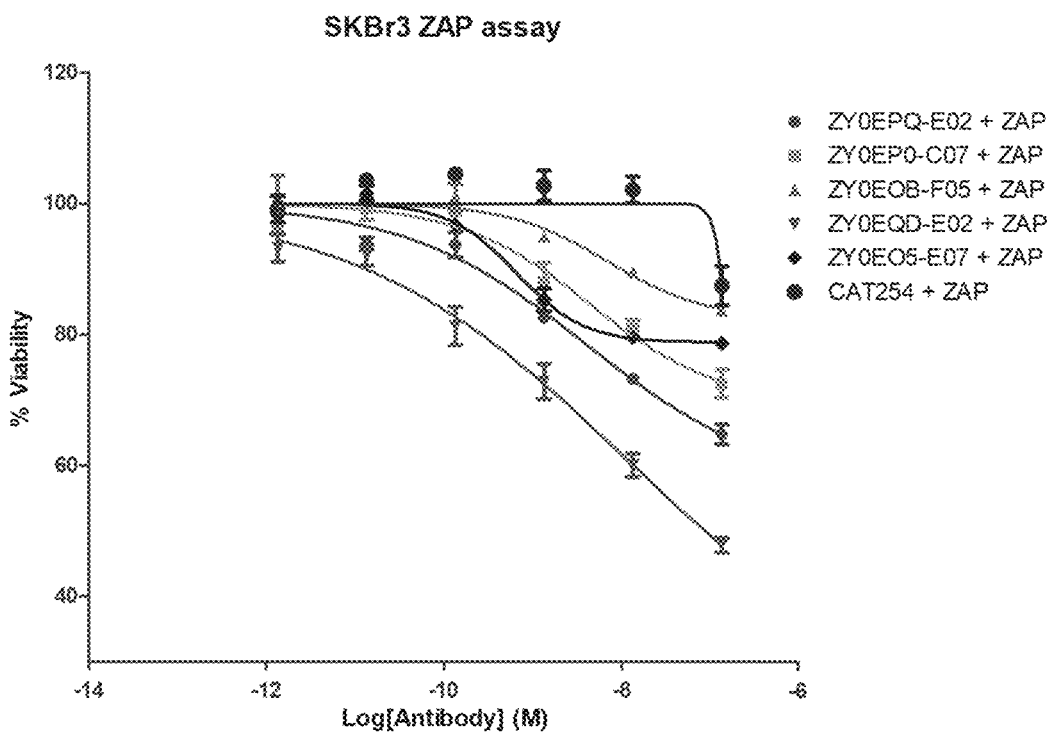
Figure 5C:
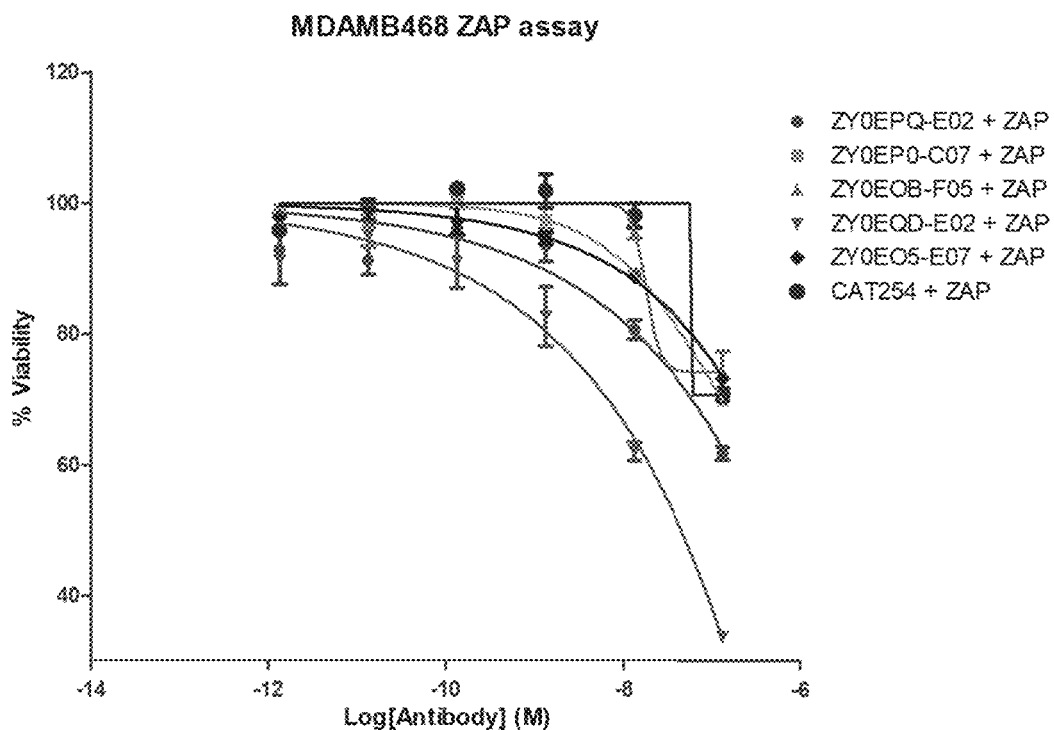
Figure 5D:
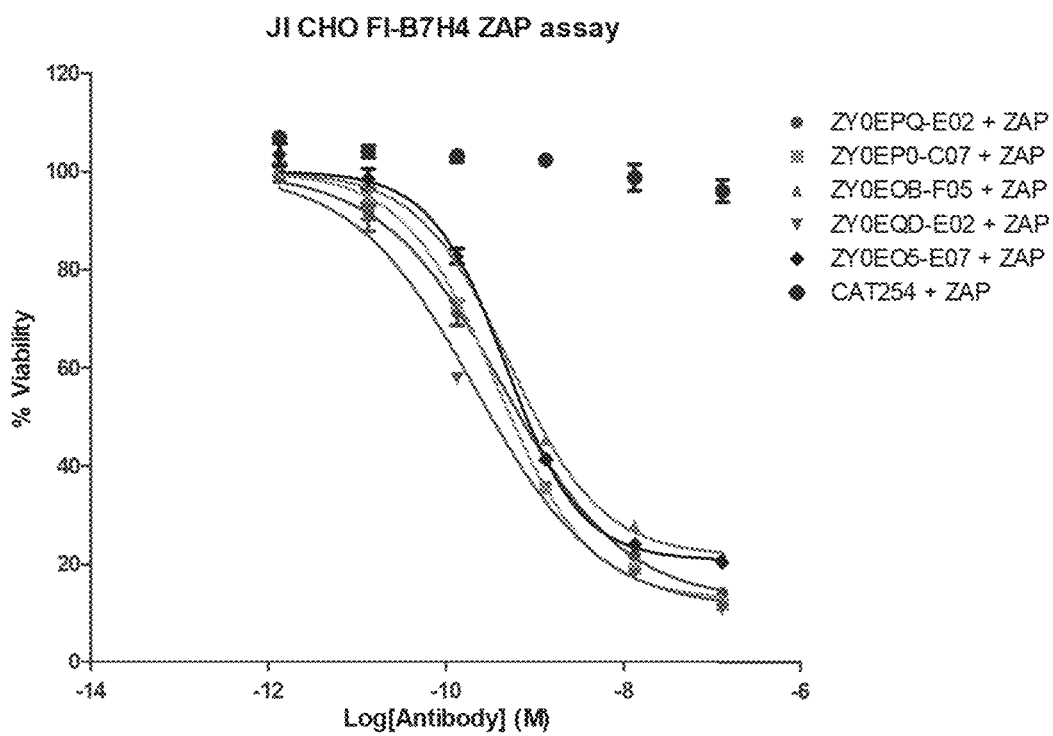
Figure 5E:
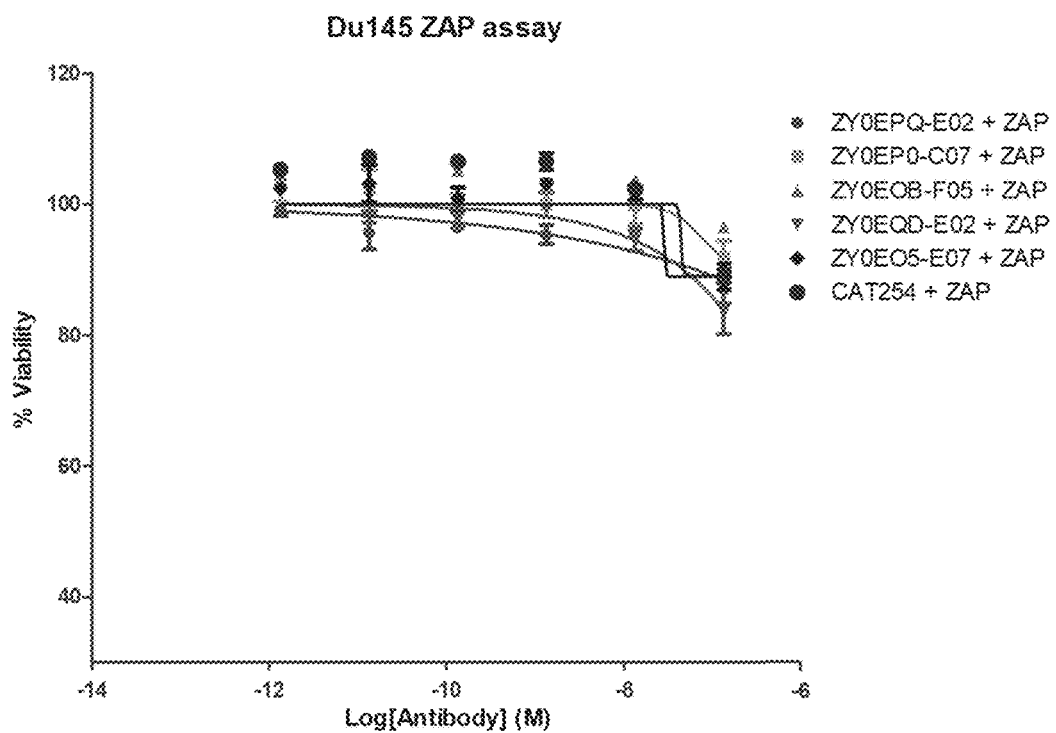
Figure 5F:
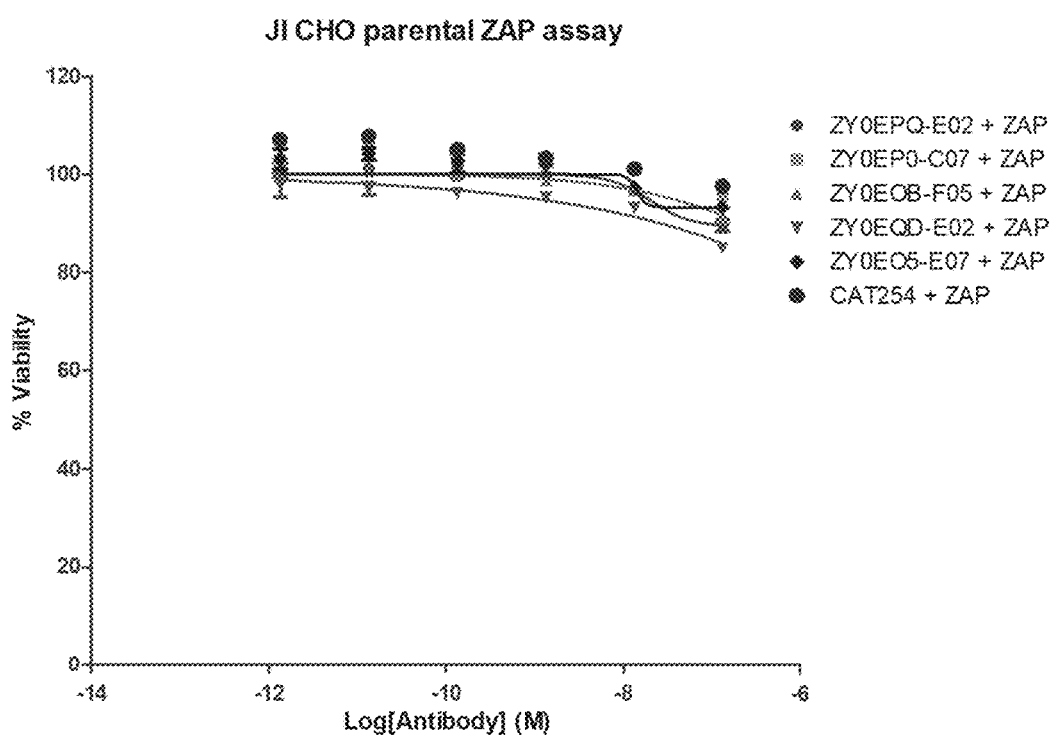

QD-E02 and PQ-E02 high levels of non-specific binding, such that the antibodies surprisingly bind a wide spectrum of cell types in a manner which goes beyond that seen for the control antibodies (lanes E, U, R, S)—see FIG. 4. OB-F05 and 05-E07 give good results with transfected HEKs and also bind to transfected CHOs. Exemplary antibodies QD-E02, OB-F05 and 05-E07 and PQ-E02 bind to the OVCAR4 cells.

Summary

Table 14 shows a summary of properties of the five exemplary antibodies.

Example 4

Screening Cell Lines for B7-H4 Surface Expression by Flow Cytometry

The following human cell lines have been tested positive for B7-H4 expression using exemplary antibodies and/or commercial anti-B7-H4 antibodies (relative B7-H4 expression levels indicated by '+'):

SK-BR-3 (+++)
T47D (+)
MDA-MB-468 (++)
OVCAR4 (+++)
NIH:OVCAR3 (+)
Calu-3 (+)

The following human cell lines have been tested negative: NCI-H322, Raji (+/− IFNg activation), Ramos (+/− IFNg activation) and Du145.

Example 5

In Vitro Cytotoxicity Assay

Internalisation of the five human IgG1-TM exemplary antibodies by B7-H4 expressing cell lines have been confirmed experimentally (SK-BR-3, MDA-MB-468, OVCAR4 and JumpIn CHO Fl-B7H4). ADC cytotoxicity was demonstrated for the five IgG1-TM exemplary antibodies using saporin-conjugated anti-human IgG secondary antibody (see FIG. 5). Cell viability at 20 μg/ml 'antibody-alone' control was around 100%.

TABLE 14

| Antibody | Protein | Octet KD (nM) | Epitope Bin | | ZAP | |
|---|---|---|---|---|---|---|
| ZY0EPQ-E02 | HumanB7-H4 | 26 | 1 | Cell | IC50 (M) | % Viability |
| | MurineB7-H4 | 396 | | SKBR3 | 4.E−09 | 65 |
| | B7-H4-SV | 1660 | | OVCAR4 | 2.E−08 | 46 |
| ZY0EQD-E02 | HumanB7-H4 | 14 | 1 | Cell | IC50 (M) | % Viability |
| | MurineB7-H4 | 621 | | SKBR3 | 1.E−08 | 48 |
| | B7-H4-SV | 801 | | OVCAR4 | 2.E−08 | 40 |
| ZY0EOB-F05 | HumanB7-H4 | 13 | 2 | Cell | IC50 (M) | % Viability |
| | MurineB7-H4 | 25 | | SKBR3 | 4.E−18 | 84 |
| | B7-H4-SV | 174 | | OVCAR4 | 3.E−17 | 67 |
| ZY0E05-E07 | HumanB7-H4 | 20 | 1 | Cell | IC50 (M) | % Viability |
| | MurineB7-H4 | 30 | | SKBR3 | 2.E−16 | 79 |
| | B7-H4-SV | 264 | | OVCAR4 | 7.E−17 | 58 |
| ZY0EP0-C07 | HumanB7-H4 | 9 | 3 | Cell | IC50 (M) | % Viability |
| | MurineB7-H4 | 11 | | SKBR3 | 4.E−09 | 72 |
| | B7-H4-SV | No Binding | | OVCAR4 | 1.E−08 | 57 |

Example 6

Clone ZY0EQD_E02 Specificity ELISA

Due to the superior performance of clone ZY0EQD_E02, this clone was chosen for more detailed analysis. The ZY0EQD_E02 comprises a CHDR1 of SEQ ID NO: 7; a CHDR2 of SEQ ID NO: 8; a CHDR3 of SEQ ID NO: 9; a CLDR1 of SEQ ID NO: 10; a CLDR1 of SEQ ID NO: 11; a CLDR1 of SEQ ID NO: 12. Said clone comprises a VH chain of SEQ ID NO: 33, and a VL chain of SEQ ID NO: 34. Said clone comprises a heavy chain of SEQ ID NO: 48, and light chain of SEQ ID NO: 44. A germlined version (E02-GL) comprises a VH chain of SEQ ID NO: 45, and a VL chain of SEQ ID NO: 34; e.g. a heavy chain of SEQ ID NO: 51, and light chain of SEQ ID NO: 44.

ELISA analysis was performed to determine binding to B7-H4 from human (including a splice variant), cynomolgus macaque (cyno), mouse and rat. Percentage sequence identity of human B7-H4 in said species is: Domain FL—cynomolgus macaque (98.6%); rabbit (91.6%); mouse (87.9%); rat (86.9%); Domain ECD—cynomolgus macaque (99.6%); rabbit (94.3%); mouse (90%); rat (89.6%).

Figure 6:
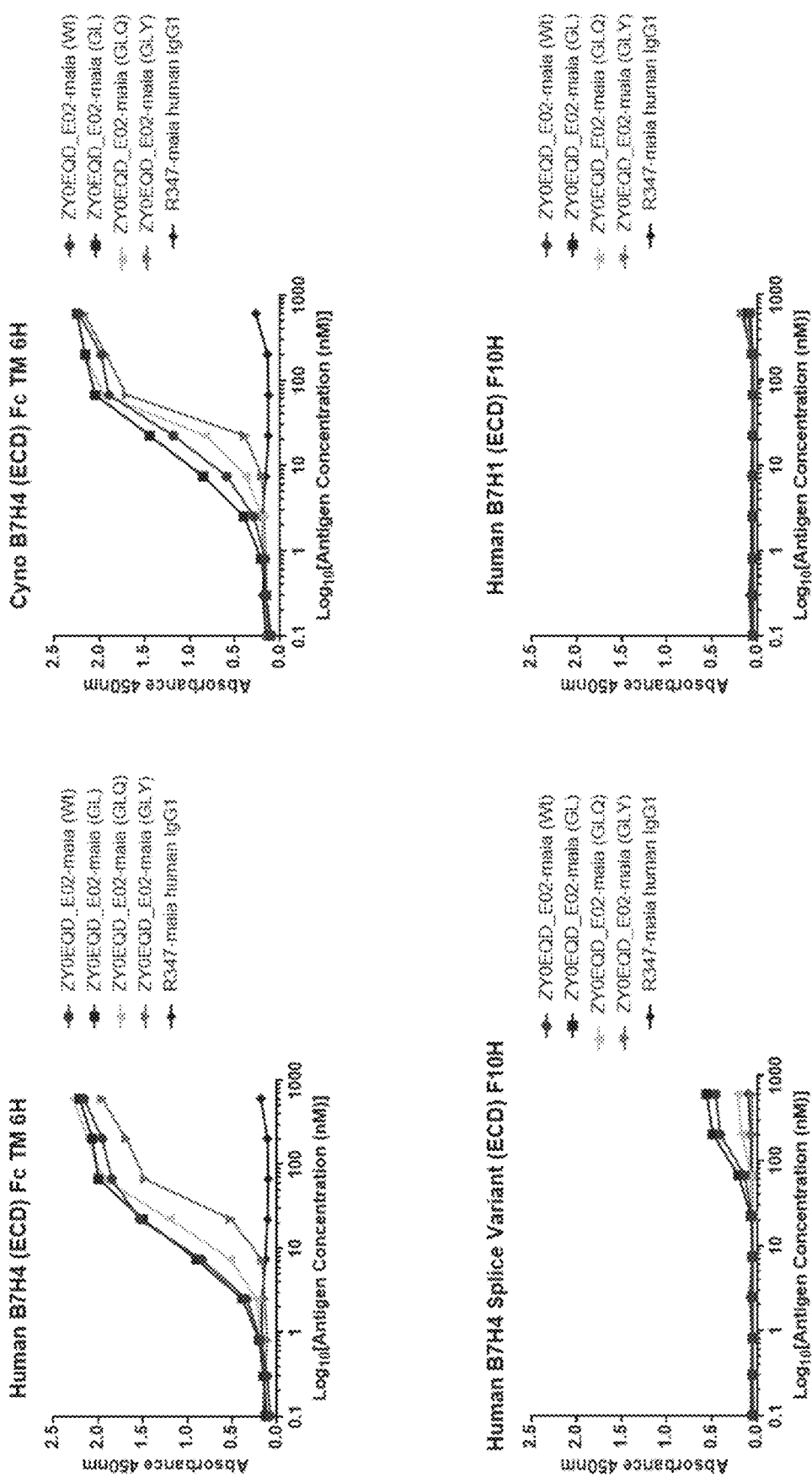
FIG. 6 shows results of ELISA analysis performed for the clone ZY0EQD_E02 (as well as a number of variants thereof), demonstrating binding to human, cynomolgus, mouse and rat B7-H4.
Figure 6:
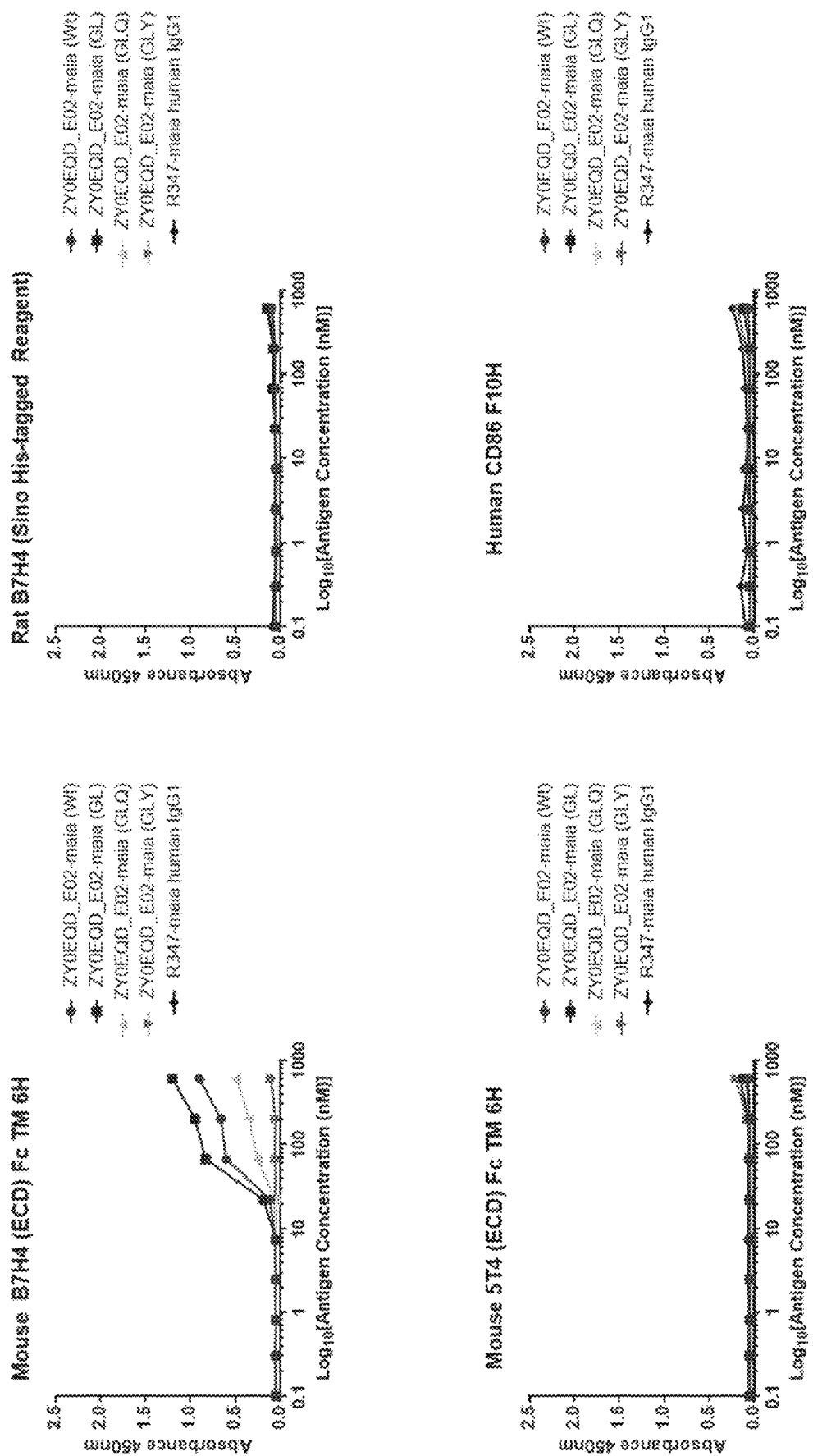

Maia format mAbs (e.g. comprising a C insertion, as shown, for example, in SEQ ID NO.: 41) of the clone were tested for binding. Wildtype, as well as a number of variants (germlined (GL), GLQ, GLY) were assayed, together with R347-maia human IgG1 as a control (see FIG. 6).

R347-maia isotype control shows no binding to any antigen tested. E02-maia binding profile is similar to previous experiments. E02-maia and E02-GL-maia have similar binding profiles. Advantageously, this demonstrates that both germlined (GL) and non-germlined (e.g. WT) versions of the antibody retain the advantageous binding properties/profiles of the antibody.

Example 7

Comparison of E02-GL Binding to the mAb "1D11"

Clone ZY0EQD_E02, germlined (referred to here as E02-GL) binding affinity was directly compared to that of the known anti-B7-H4 antibody "1D11" (Genentech; described in WO2016040724, which is incorporated herein by reference) by ELISA (see Materials & Methods, above).

"E02-GL" antibody has the CDR sequences (e.g. corresponds to) of ZY0EQD-E02 ("GL" means the antibody has been germlined). For example, E02-GL in these examples comprises a VH chain sequence of SEQ ID NO: 45, e.g. a germlined version of SEQ ID NO: 43.

Figure 7:
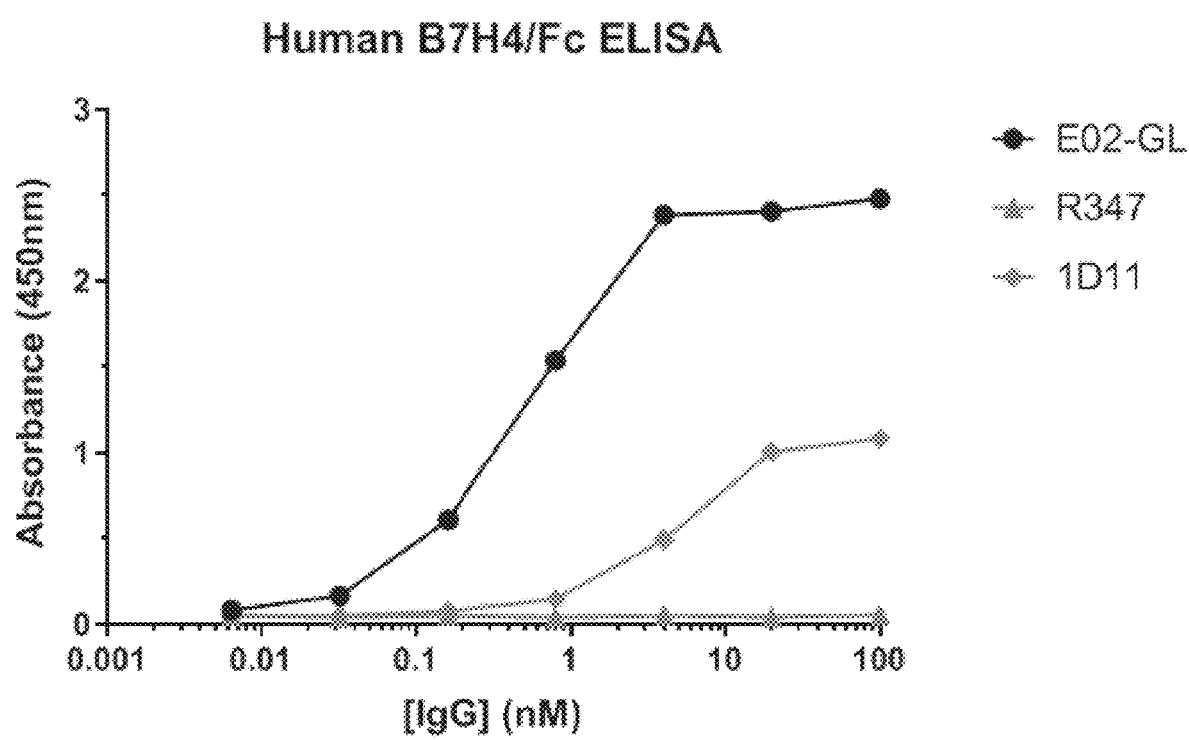
FIG. 7 shows results of ELISA analysis performed for the clone E02_GL compared with 1D11, demonstrating improved binding of E02_GL to human B7-H4.

Direct comparison demonstrates that clone E02-GL demonstrates significantly better binding (affinity) that 1D11 (see FIG. 7). Consistent with Example 7, R347-mala isotype control shows no binding to any antigen tested.

Figure 8A:
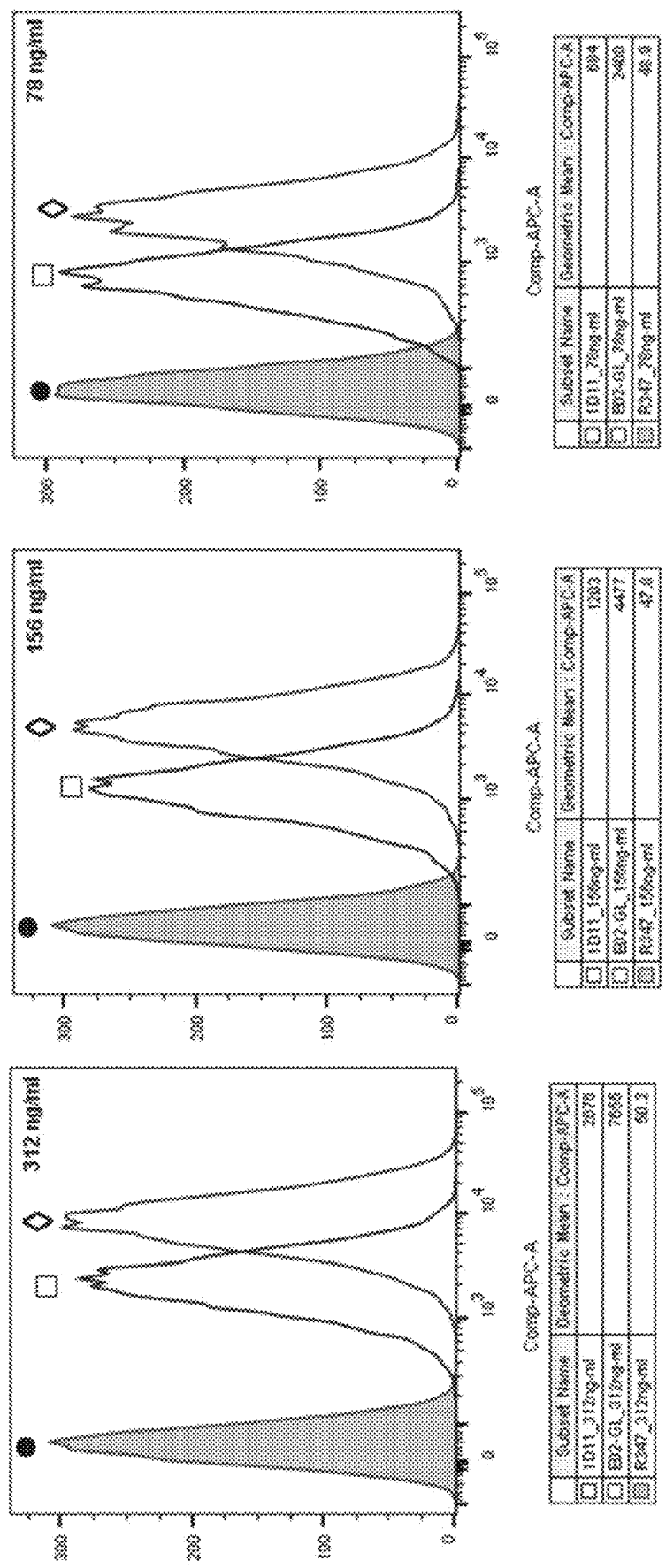
FIG. 8A-8B shows results of Flow Cytometry analysis performed for the clone E02_GL compared with 1D11, demonstrating improved binding of E02_GL to human B7-H4 when present on cells. Results for HT29 cells are shown in (A), and results for SKBR-3 cells are shown in (B). The sign ◇ marks the 'E02-GL fraction', and the sign □ marks the '1D11 fraction'. The sign "●" marks a (negative) control 'R347 fraction'.
Figure 8B:
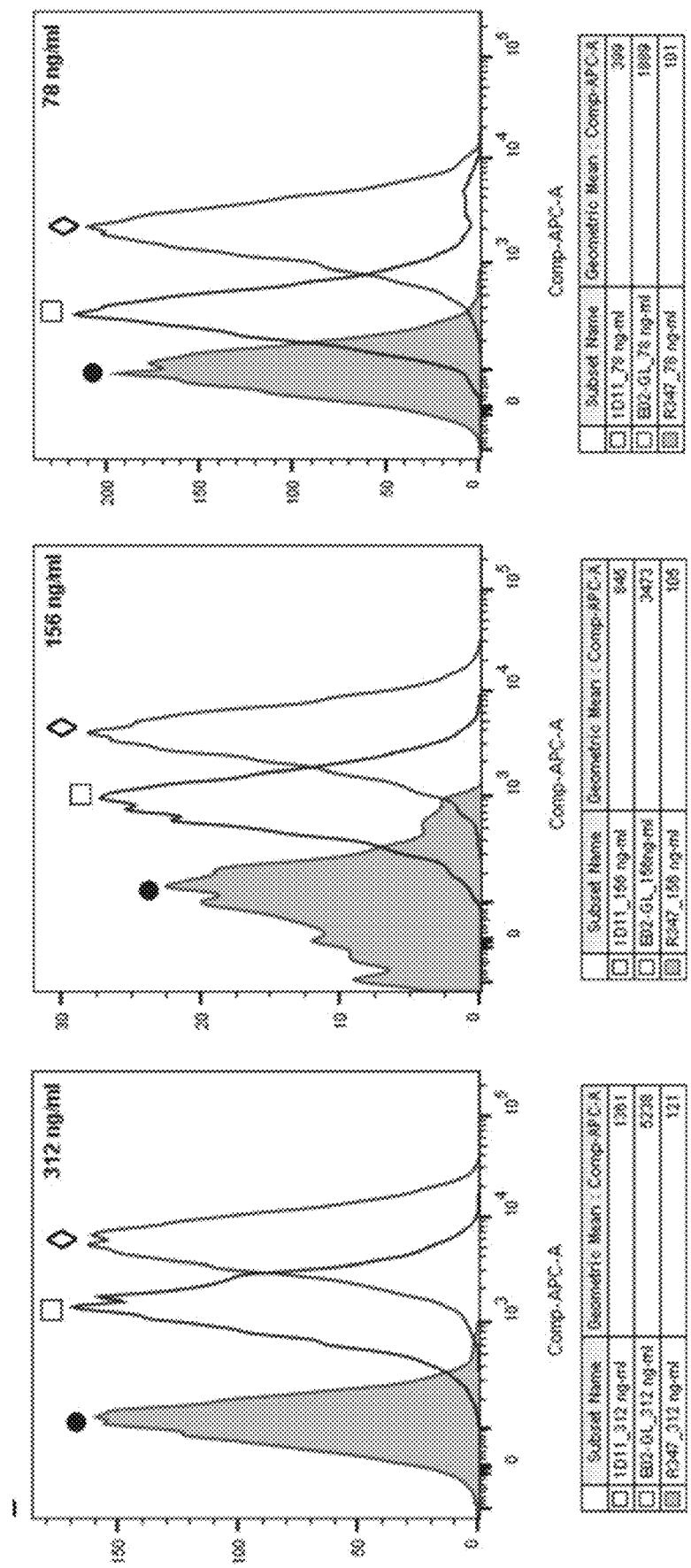

Furthermore, E02-GL was shown (via flow cytometry experiments, see Materials and Methods above) to have superior binding to the B7-H4 expressed on cancer cells, when compared with 1D11. Thus, not only does E02-GL show superior binding, but superior targeting of cancer cells. Binding to both hB7-H4 expressing HT29 cells and SK-BR-3 cells (which express B7-H4) was tested. Antibody binding at concentrations of 31 ng/ml, 156 ng/ml and 78 ng/ml were tested. Results for HT29 cells is shown in FIG. 8A, and results for SK-BR-3 cells is shown in FIG. 8B. The sign ◊ marks the 'E02-GL fraction', and the sign □ marks the '1D11 fraction'. The sign "●" marks a (negative) control '12347 fraction'.

As can be seen in FIGS. 8A-8B, the number of cells stained cells in the 'E02-GL fraction' was significantly higher than the number of stained cells in the '1D11 fraction'.

Example 8

In Vitro Cytotoxicity of Ad293 Cells, with and without B7-H4 Transfection (E02-GL-SG3932)

Figure 9A:
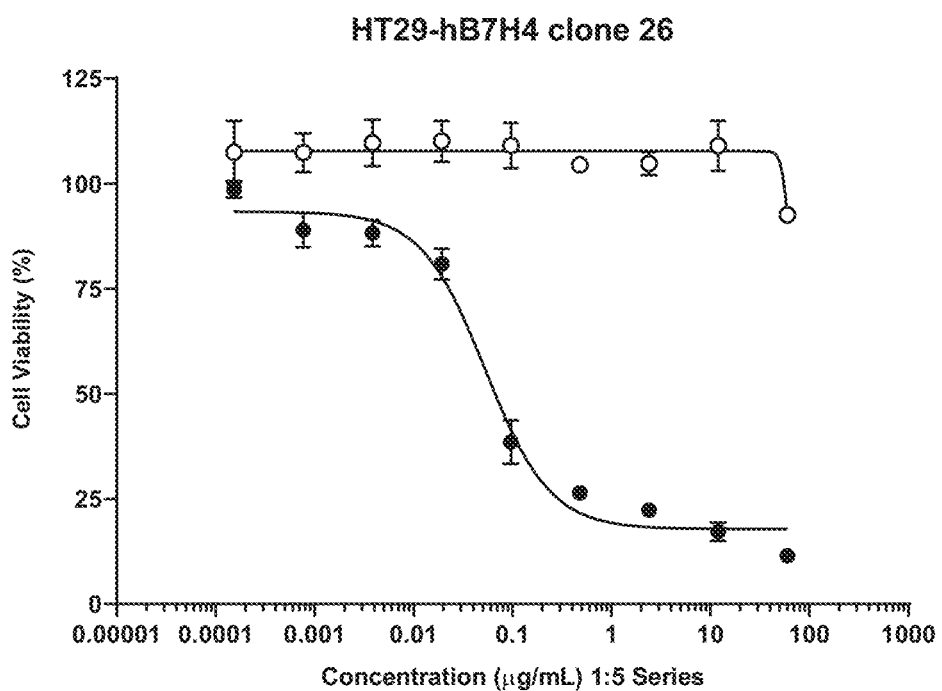
FIG. 9A-9B shows cytotoxicity of human B7-H4 transfected (and non-transfected control) Ad293 cells following treatment with E02-GL-SG3932 conjugate. Open circles=isotype control ADC (e.g. NIP228-SG3932); filled circles=E02-GL-SG3932.
Figure 9B:
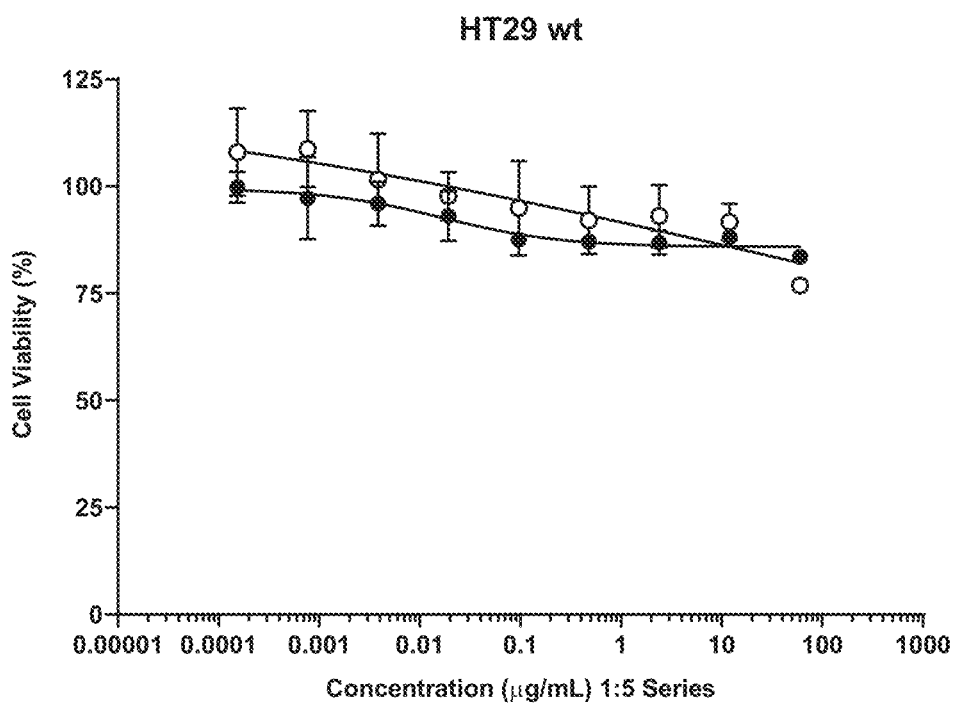

The clone E02-GL was conjugated to the topoisomerase I payload SG3932 at an average Drug Antibody Ratio (DAR) of 8 (providing E02-GL-SG3932) and tested for the ability to target and kill both human B7-H4 transfected and non-transfected Ad293 cells (e.g. the latter representing a negative control). The antibody NIP228 conjugated to SG3932 was used as a control. The transfected cells were readily targeted and killed by the E02-GL-SG3932 conjugate, which had an IC50 of 53.3 ng/ml (see FIG. 9A). No significant killing following addition of the E02-GL-SG3932 conjugate was observed in the non-transfected cells (see FIG. 9B). In all experiments described herein involving E02-GL conjugated to a topoisomerase inhibitor, the E02-GL clones used typically had a heavy chain sequence of SEQ ID NO.: 51.

Method:

Cell lines were detached from tissue culture flasks by TrypLE Express (Gibco, Paisley, UK), pelleted by centrifugation, and resuspended in growth media (RPMI-1640, 10% FBS). Viable cells were counted by trypan blue exclusion using a Vi-CELL XR Cell Viability Analyzer (Beckman Coulter Life Sciences, Indianapolis, Indiana). Cell densities were adjusted to $3.33 \times 10^4$ cells/mL in growth media. 75 μL/well of the cell suspension ($2.5 \times 10^3$ cells) was added to 96-well white walled clear bottom tissue culture treated plates and cultured overnight in a humidified tissue culture incubator at 37° C. in 5% $CO_2$.

ADCs (e.g. NIP228-SG3932 and E02-GL-SG3932) were diluted into growth media (RPMI-1640, 10% FBS) at a concentration of 240 μg/mL. Five-fold serial dilutions were prepared in growth media (RPMI-1640, 10% FBS), and 25 μL was then added to triplicate wells of the cultured cells, with a nine-point, five-fold serial dilution of antibody (e.g. NIP228-SG3932 or E02-GL-SG3932). 25 μL/well of growth media (RPMI-1640, 10% FBS) was added to mock-treated control cells. Cells were cultured in a humidified tissue culture incubator at 37° C. in 5% $CO_2$ for six days at which time cell viability was assessed using CellTiter-Glo® assay (Promega, Southampton, UK) according to the manufacturer's protocol. Luminescence was measured using an Envision multilabel plate reader (Perkin Elmer, Seer Green, UK). The potency for test article antibodies (e.g. NIP228-SG3932 or E02-GL-SG3932) was determined by generating half-maximal inhibitory concentration (IC50) values using a nonlinear regression model [log agonist vs. response—variable slope (four parameters)] in GraphPad Prism, version 8 (GraphPad Software, La Jolla, CA) and presented as percent cell viability relative to Mock-treated control cells–([(Treated cells–Background)/(Mock-treated control cells–Background)]×100).

Example 9

E02-GL-SG3932 Causes Bystander Killing of Tumor Cells In Vitro

Figure 10A:
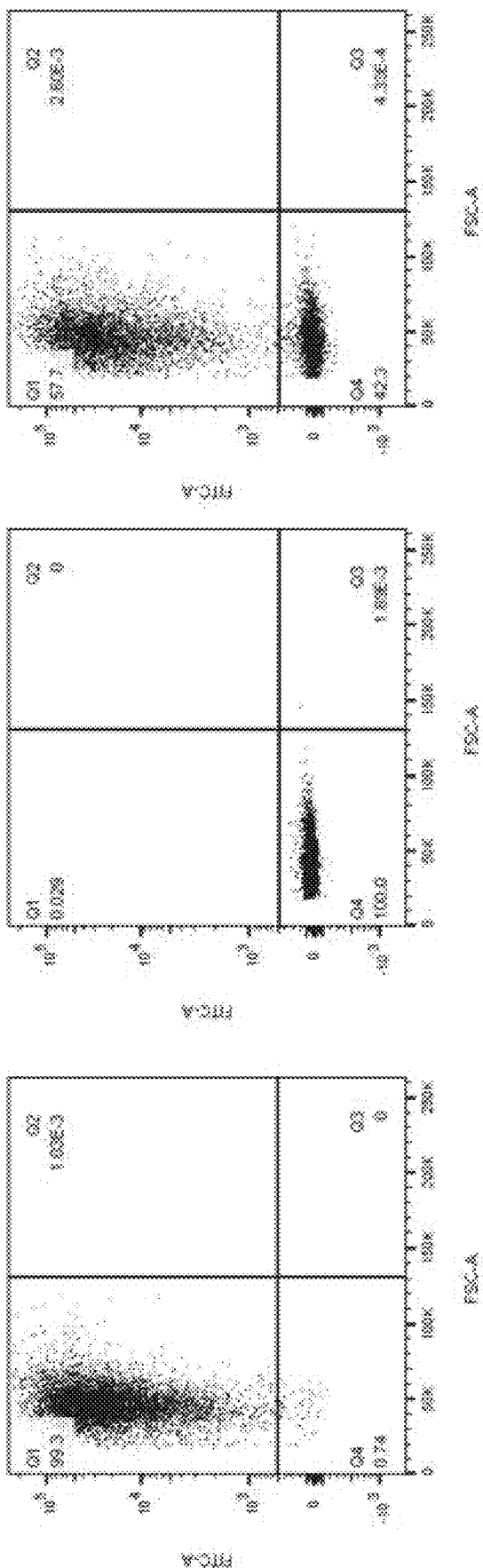
FIG. 10A-10B shows bystander killing of tumor cells in vitro (E02-GL-SG3932).
Figure 10B:
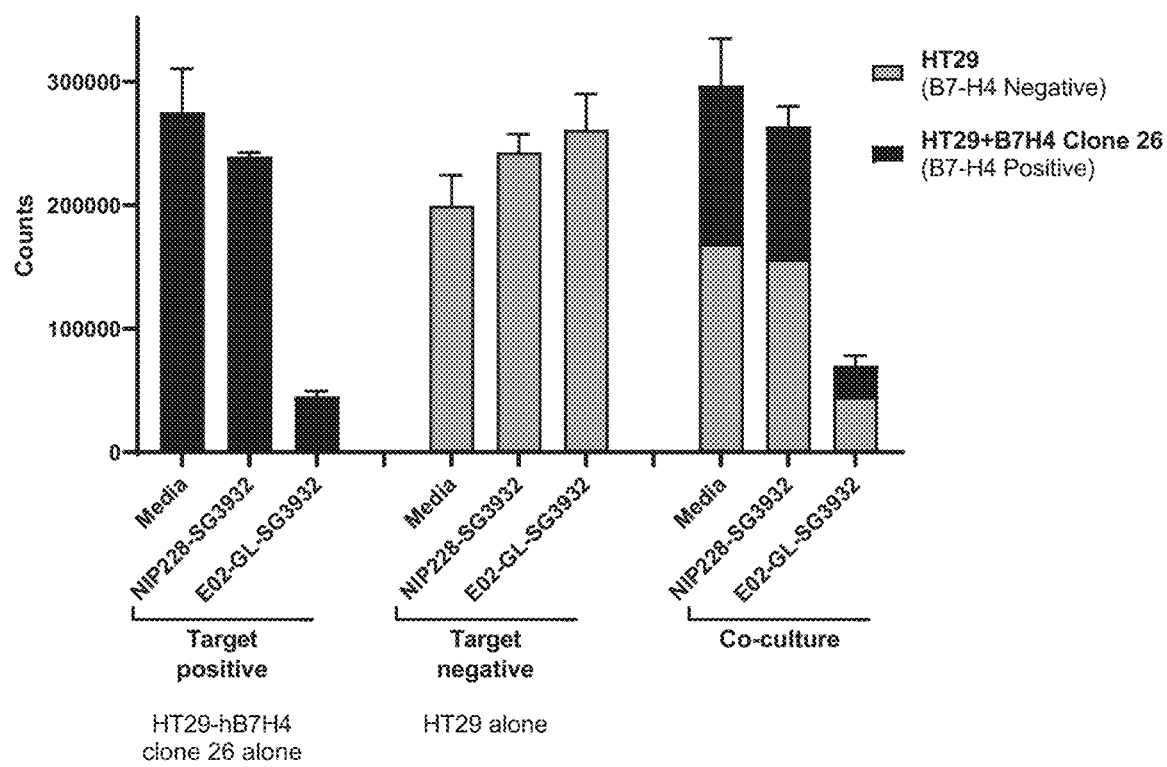

HT29-huB7-H4 clone 26 target positive and GFP-labelled HT29 target negative cells, plated either individually or mixed at a ratio of 1:1 and cultured for 1 day, were treated with 200 ng/mL E02-GL-SG3932 or NIP228-SG3932 isotype control ADC for 6 days. At the end of treatment, the number of live GFP-negative HT29-huB7-H4 clone 26 cells or GFP-positive HT29 cells was determined using flow cytometry. Results are shown in FIG. 10: A) Dot plots show representative images from flow cytometry analyses at the end of treatment for media treated samples of HT29-GFP and HT29+huB7-H4 clone 26 cells cultured alone or together. Numbers shown in the upper-left and lower-left quadrants reflect the percentage of HT29-GFP and HT29+ huB7-H4 clone 26 cells, respectively. B) When plated individually, a decrease in cell count was observed following treatment with E02-GL-SG3932 in HT29+huB7H4 clone 26 cells which was not observed in the target negative HT29- GFP cells. When cells were plated in co-culture, cell counts for both the target negative HT29-GFP and target positive HT29+huB7H4 clone 26 cells were reduced, demonstrating a bystander killing effect.

Method:

A lentiviral expression system was used to prepare the HT29-GFP cell line, which stably expresses green fluorescent protein (GFP). Cells were plated at a total cell density of 15,000 cells per well in 24-well plates, cultured individually or mixed at a ratio of 1:1 and cultured for 1 day. Media was then removed and replaced with fresh media alone or media containing 200 ng/mL of NIP228-SG3932 or E02-GL-SG3932 ADCs, and cells were incubated for an additional 6 days. At the end of treatment, the number of live GFP-negative HT29+huB7-H4 clone 26 cells or GFP-positive HT29 cells was determined using flow cytometry and FlowJo software.

Example 10

E02-GL-SG3932 Causes Bystander Killing of Tumor Cells In Vivo

Tumor cells were implanted subcutaneously into female SCID mice between 8 to 10 weeks of age. When tumors reached the appropriate tumor volume range (typically 150-250 mm$^3$), animals were randomized into treatment and control groups and dosing was initiated. Tumor-bearing mice were administered a single dose of test articles via intravenous injection. Animals were observed daily and tumor dimensions and body weight were measured and recorded two to three times weekly. Results are shown in FIG. 11. Tumor volumes were measured by caliper and the volumes of tumors were calculated using the following formula: tumor volume=length (mm)×width (mm)$^2$/2, where the length and width are the longest and shortest diameters of the tumor, respectively.

Example 11

Figure 12:
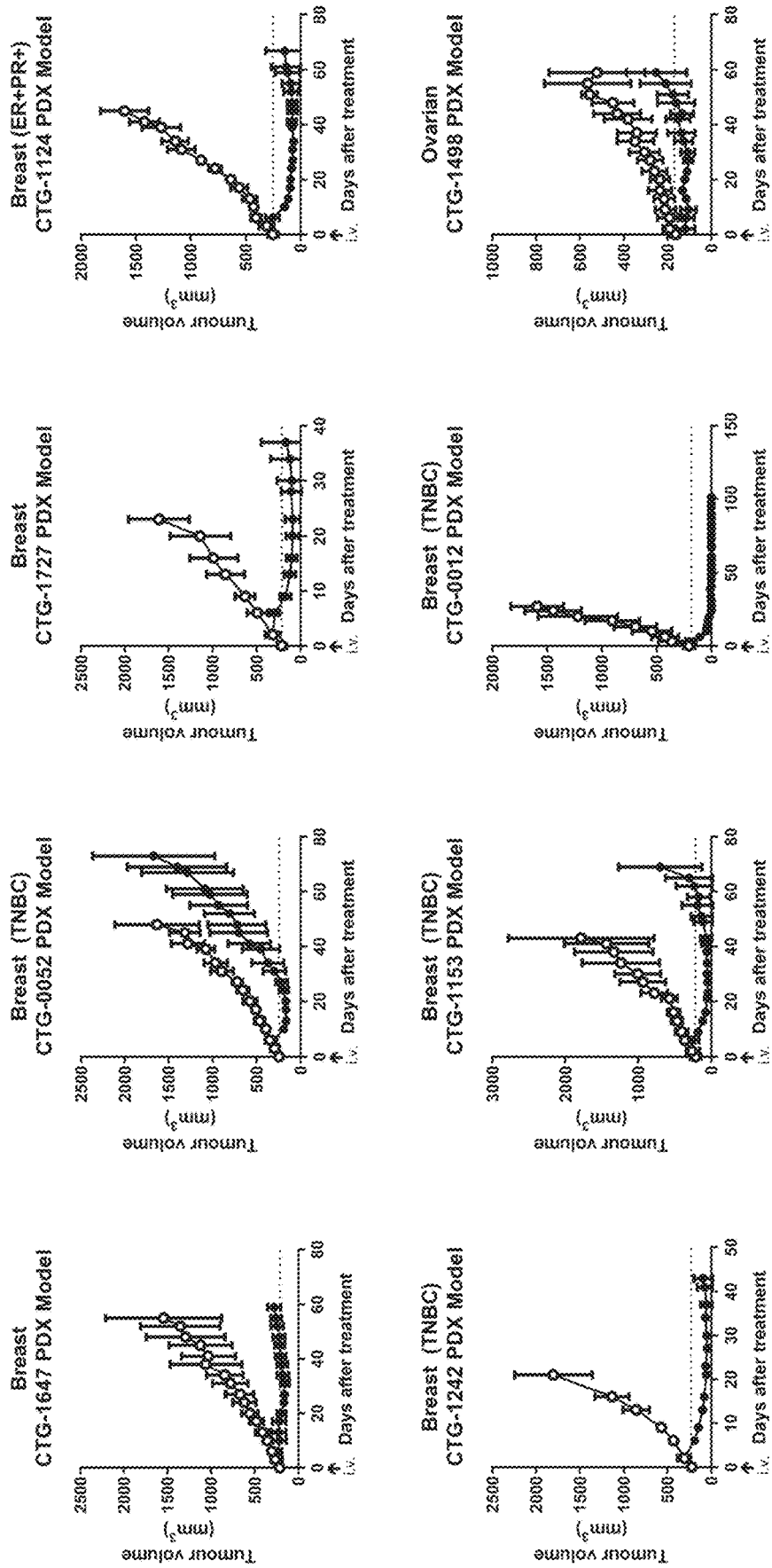
FIG. 12 shows that E02-GL-SG3932 has potent in vivo activity in patient derived xenograft (PDX) models. Open circles=vehicle only control; Filled circles=E02-GL-SG3932 (7 mg/kg).
Figure 12:
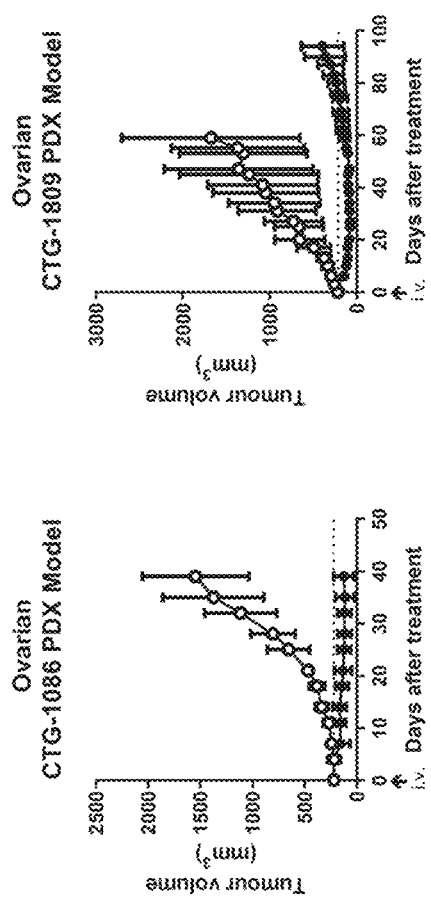

E02-GL-SG3932 has Potent In Vivo Activity in Patient Derived Xenograft (PDX) Models Tumor tissue fragments were implanted subcutaneously into female athymic nude mice between 6 to 8 weeks of age. When tumors reached the appropriate tumor volume range (typically 150-300 mm$^3$), animals were randomized into treatment and control groups and dosing was initiated. Tumor-bearing mice were administered a single dose of test articles via intravenous injection. Animals were observed daily and tumor dimensions and body weight were measured and recorded twice weekly. Results are shown in FIG. 12, and demonstrate that E02-GL-SG3932 has potent in vivo activity in patient derived xenograft (PDX) models. Tumor volumes were measured by digital caliper and the volumes of tumors were calculated using the following formula: tumor volume=[length (mm)×width (mm)$^2$×0.52, where the length and width are the longest and shortest diameters of the tumor, respectively.

Figure 13:
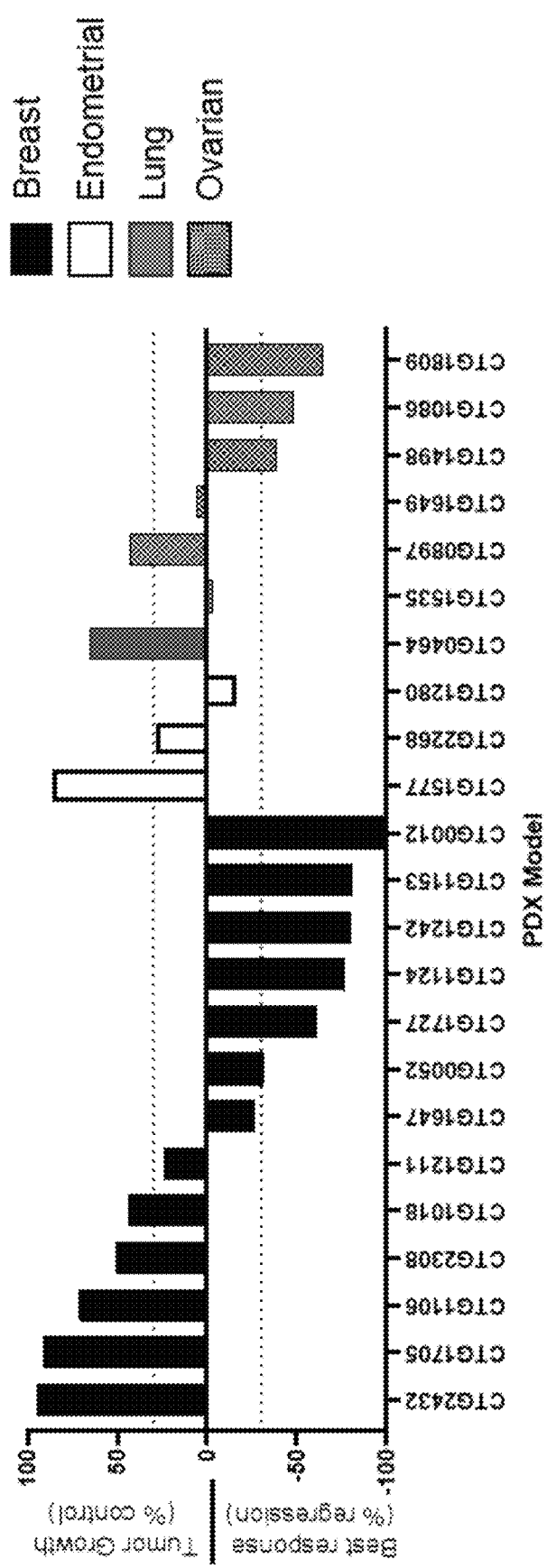
FIG. 13 shows the anti-tumor activity of E02-GL-SG3932 in PDX models after a single i.v. injection at 7 mg/kg.

FIG. 13 shows the results of further assessment of the in vivo anti-tumor response to E02-GL-SG3932 by determining the tumor volume changes following treatment, again demonstrating anti-tumor activity of E02-GL-SG3932 in PDX models after a single i.v. injection. Tumor volume at the beginning of treatment is referred as the initial tumor volume (ITV); tumor volume at the time showing maximal response to the ADC treatment is referred to as the end tumor volume (ETV). If ETV is less than ITV, the anti-tumor response is calculated as follows: [(ETV−ITV)/ITV]×100. Otherwise, the anti-tumor response is expressed as percent tumor volume change in the treatment arm relative to the vehicle control arm: 100−[1−((ETV−ITV)treatment/(ETV−ITV)vehicle)×100].

Example 12

Figure 14A:
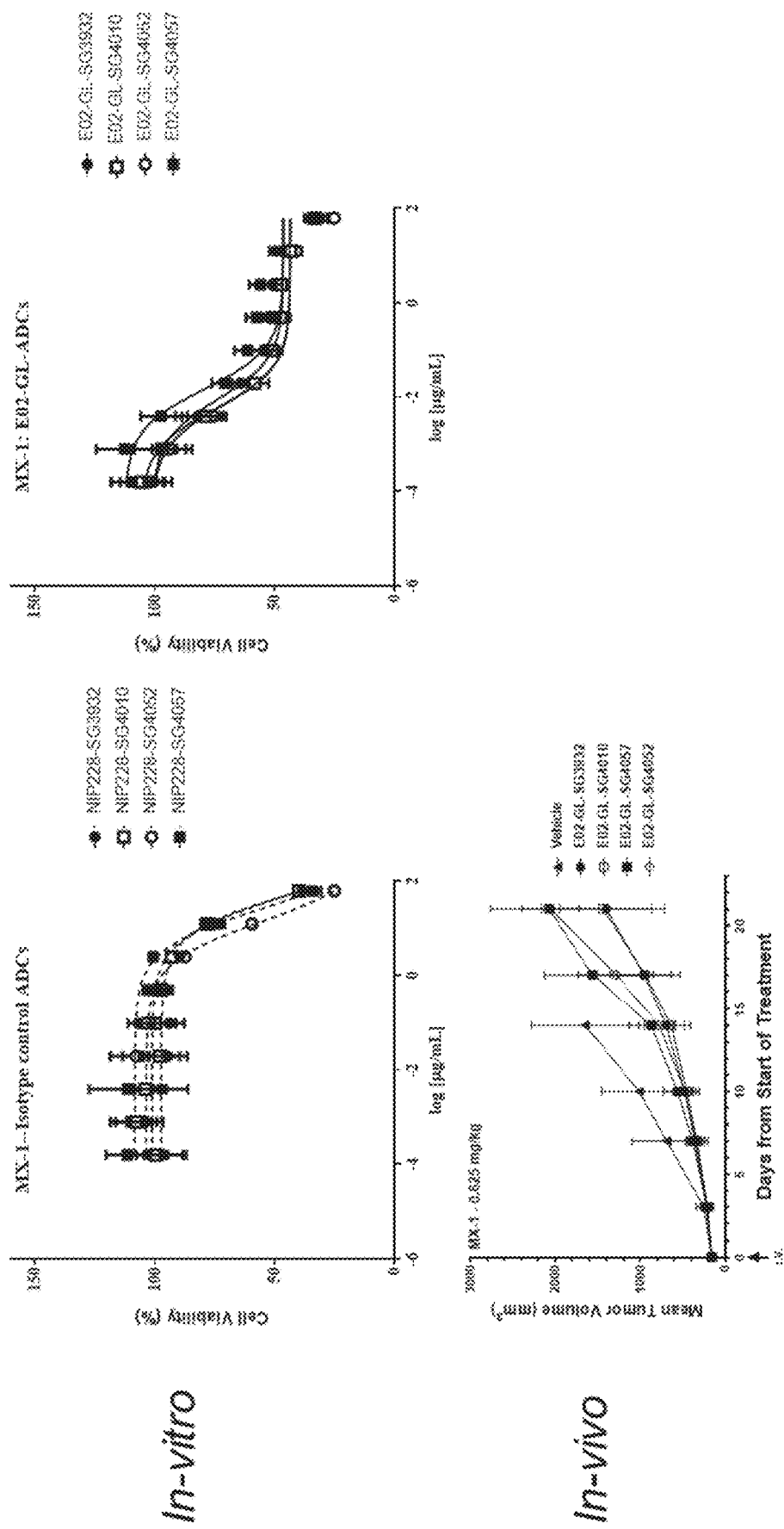
FIG. 14A-14B shows that E02-GL-topo I inhibitor ADCs have similar potency in MX-1 cells in vitro and in vivo (A); and in HT29-derived models in vitro and in vivo (B).
Figure 14B:
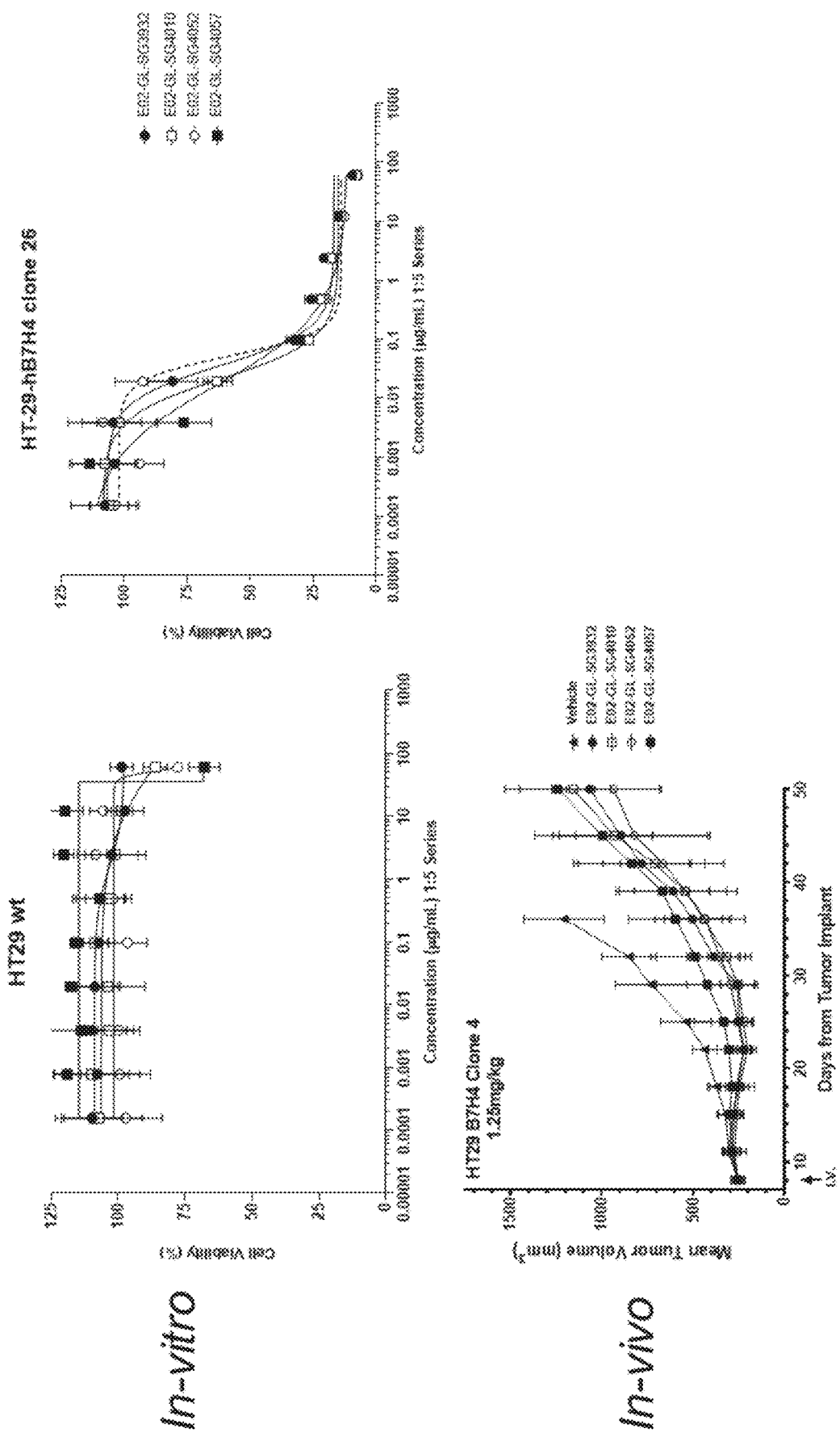

E02-GL-Topo I Inhibitor ADCs have Similar Potency in MX-1 Cells and HT29-Derived Models In Vitro and In Vivo MX-1 Model The MX-1 xenograft model was performed at Crown Biosciences, (Taicang, China). The study was conducted in accordance with both the CRO and AstraZeneca IACUC guidelines. The MX-1 tumor cells were maintained in vitro in RPMI-1640 medium supplemented with 10% fetal bovine serum at 37° C. in an atmosphere of 5% $CO_2$ in air. Exponentially growing cells were harvested and 5×10$^6$ cells (in 0.1 ml volume of PBS:matrigel=1:1) were implanted in the right flank of female BALB/c nude mice. Immediately prior to start of treatment, mice were randomized into treatment groups (mean tumor volume=153 mm$^3$) using the "Matched distribution" randomization method (Study Director™ software). All antibody-drug conjugates were diluted in buffer (25 mM Histidine, 7% Sucrose, 0.02% PS80, pH 6.0), immediately prior to administration. The ADC's were administered as a single i.v. dose. Tumor and body weight measurements were recorded twice a week and tumor volume calculated using the equation length (mm)×width (mm)$^2$/2. Animals were monitored daily for morbidity and mortality. Results are shown in FIG. 14A.

HT29+huB7-H4 (Clone 4)

The HT29+huB7-H4 clone 4 cell line was maintained in vitro in McCoy's Modified 5A medium supplemented with 10% fetal bovine serum at 37° C. in an atmosphere of 5% $CO^2$ in air. Exponentially growing HT29+B7-H4 Clone 4 cells were harvested and 5×10$^6$ cells (in 0.2 ml volume of PBS:Cultrex=1:1) implanted into the right flank of female CB-17 SCID mice. Mice were randomized into treatment groups immediately prior to treatment (mean tumor volume=250 mm$^3$) using the "Deterministic" randomization method (Study Director™ software). All antibody-drug conjugates were diluted in buffer (25 mM Histidine, 7% Sucrose, 0.02% PS80, pH 6.0), immediately prior to administration. The ADC's were administered i.v. as a single dose. Tumor and body weight measurements were recorded twice a week and tumor volume calculated using the equation

Example 13

In Vitro Cytotoxicity of Cyno B7-H4 Transfected Cells (E02-GL-SG3249)

The clone E02-GL was conjugated to the cytotoxin SG3249 (providing E02-GL-SG3249), and tested for the ability to target and kill both cynomolgus B7-H4 transfected and non-transfected B7-H4 cells. For convenience, the antibody tested in this example comprised the Maia heavy chain backbone (e.g. having a cysteine insertion providing an additional site to which SG3249 can conjugate, see SEQ ID NO: 48) was used. No loss of efficacy occurs where other heavy chain backbones (e.g. lacking such cysteine insertion, for example see SEQ ID NO: 52) is used. The antibody R347 conjugated to SG3249 was used as a control.

"E02-GL" antibody has the CDR sequences (e.g. corresponds to) of ZY0EQD-E02 ("GL" means the antibody has been germlined). For example, E02-GL in these examples comprises a VH chain sequence of SEQ ID NO: 45, e.g. a germlined version of SEQ ID NO: 43.

Figure 15A:
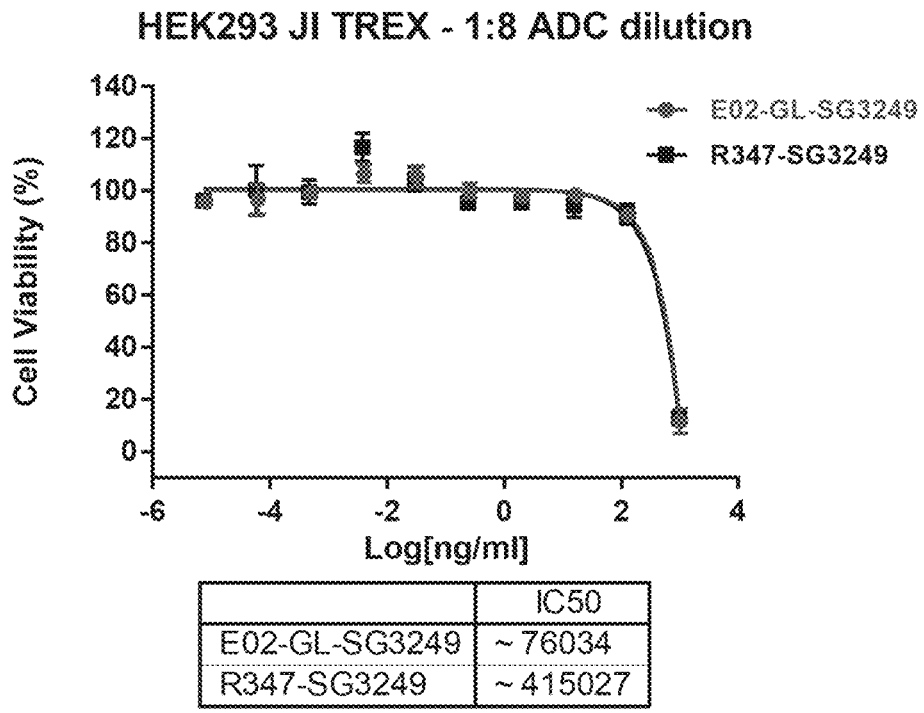
FIG. 15A-15B shows cytotoxicity of cynomolgus B7-H4 transfected (and non-transfected control) HEK293 cells following treatment with E02-GL-SG3249 conjugate.
Figure 15B:
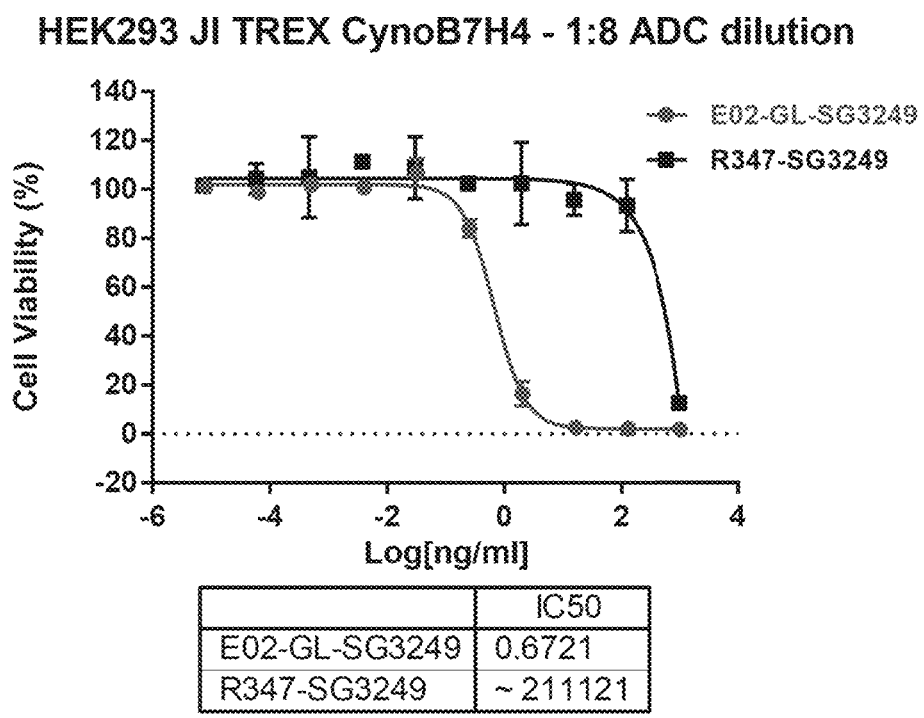

The transfected cells were readily targeted and killed by the E02-GL-SG3249 conjugate, which had an IC50 of 0.6721 ng/ml. No significant killing following addition of the E02-GL-SG3249 conjugate was observed in the non-transfected cells (see FIG. 15).

Example 14

E02-GL Mode of Action

Monitoring Internalisation Kinetics of E02-GL in Live Cells

E02-GL conjugated to fluorescence marker AF647 was used to treat live cells. At 0 mins following treatment, clusters of fluorescence were noted on the cell membranes (indicative of binding to B7-H4 present on the membrane). Time course analysis showed that the number of fluorescent spots within the cells increased steadily over time, indicating internalisation of the antibody together with the receptor antigen. Co-visualisation with Lamp1-AF488 (a marker of lysosomes) showed significant overlap, indicating that the bound antibody is internalised by endocytosis (see FIG. 16A-16C).

The observed internalisation of the antibody upon binding with the target antigen is highly advantageous, as such internalisation is generally considered a prerequisite to achieving the desired ADC effect.

"E02-GL" antibody has the CDR sequences (e.g. corresponds to) of ZY0EQD-E02 ("GL" means the antibody has been germlined). For example, E02-GL in these examples comprises a VH chain sequence of SEQ ID NO: 45, e.g. a germlined version of SEQ ID NO: 43.

E02-GL-SG3932 ADC: Mechanism of Action

Figure 17A:
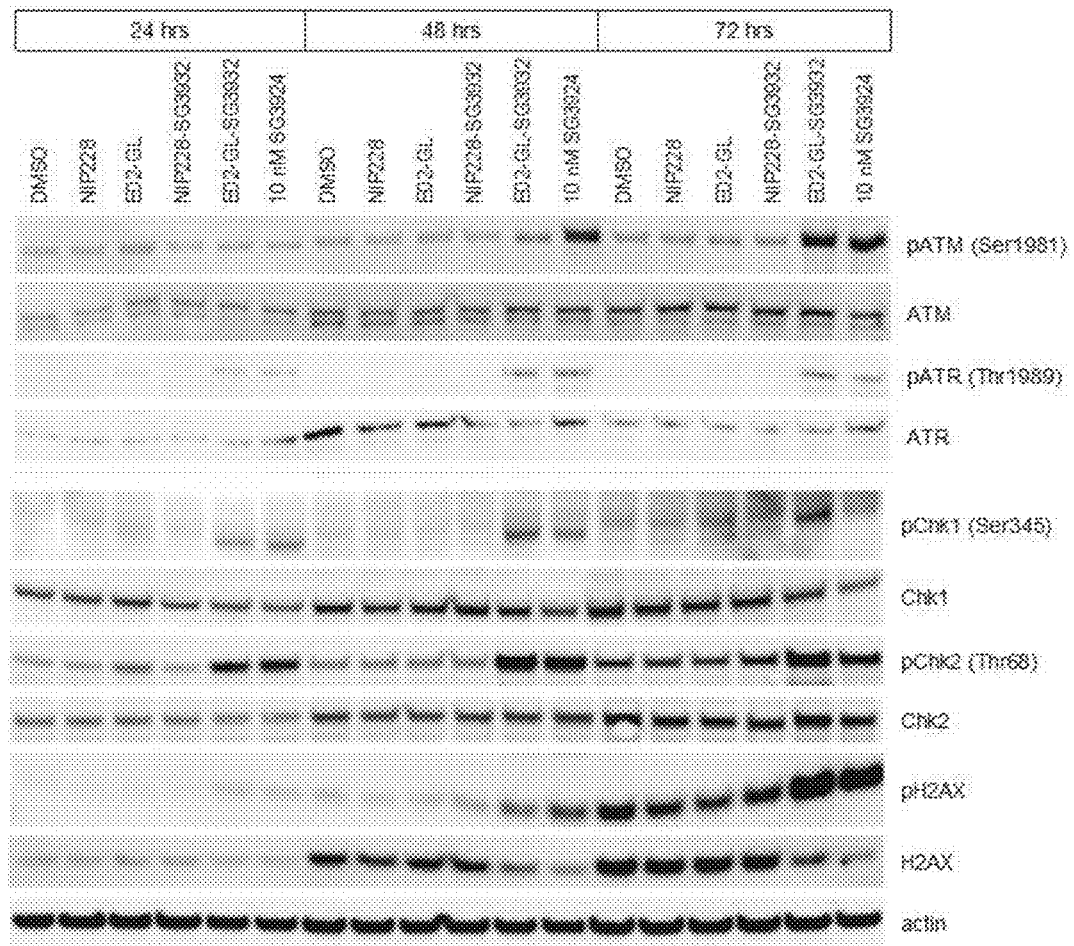
FIG. 17A-17B shows western blot analysis demonstrating that E02-GL-SG3932 treatment leads to double strand DNA breaks in vitro.

Following treatment of HT29+huB7-H4 clone26 cells with NIP228, E02-GL, NIP228-SG3932, E02-GL-SG3932, or the warhead SG3924 as a control (10 ug/ml for the mAbs or ADCs and 10 nM for the warhead), lysate was prepared and subjected to western blot analysis with antibodies to pATR, ATR, pChk1, Chk1, pATM, ATM, pChk2, ChK2, pH2AX, H2AX and actin (loading control)—see FIG. 17A. Results demonstrate that the Topoisomerase I poison warhead (SG3924) of E02-GL-SG3932 activates ATM and ATR signalling, indicating E02-GL-SG3932 treatment leads to double strand DNA breaks in vitro.

Figure 17B:
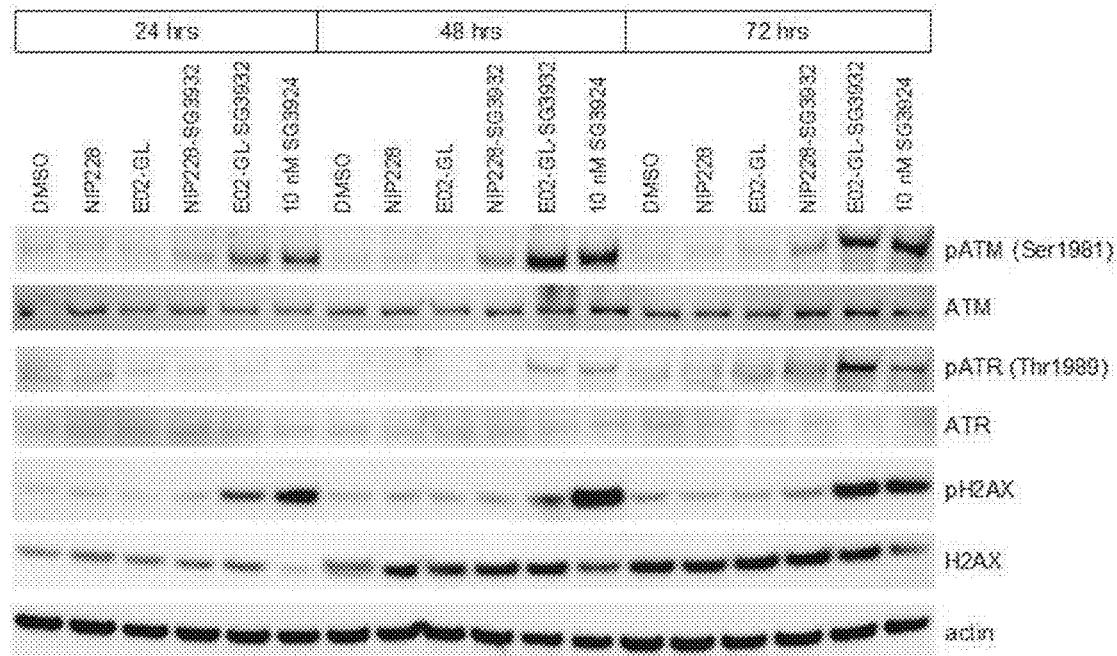

Following treatment of MX-1 cells with NIP228, E02-GL, NIP228-SG3932, E02-GL-SG3932, or the warhead SG3924 as a control (10 ug/ml for the mAbs or ADCs and 10 nM for the warhead), lysate was prepared and subjected to western blot analysis with antibodies to pATR, ATR, pATM, ATM, pH2AX, H2AX and actin (loading control)—see FIG. 17B. Results demonstrate that the Topoisomerase I poison warhead (SG3924) of E02-GL-SG3932 activates ATM and ATR signalling, indicating E02-GL-SG3932 treatment leads to double strand DNA breaks in vitro.

Method:

HT29+huB7-H4 clone 26 and MX-1 cells were plated in 6-well plates at a density of 500,000 and 1,500,000 cells per well respectively in medium containing 10% heat-inactivated FBS. The next day, the plating medium was removed and cells were subjected to incubation with HT29+huB7-H4 clone26 cells with NIP228, E02-GL, NIP228-SG3932, and E02-GL-SG3932 in complete medium at a concentration of 10 μg/mL. The warhead SG3924 was used at 10 nM as a control. After 72 hours, cells were washed once with phosphate-buffered saline (PBS) and then lysed by adding Laemmil Reducing buffer (loading buffer Boston BioProducts). After a brief incubation, cell lysates were collected, equal amounts were loaded onto Bis NuPAGE Novex Bis-Tris gels (Invitrogen) and proteins transferred to polyvinylidene fluoride (PVDF) membranes (Invitrogen). Membranes were blocked with 5% nonfat dry milk and 0.1% Tween 20 (Sigma) in Tris-buffered saline pH 7.4 (TBST) and incubated overnight at 4° C. with antibodies from Cell Signaling to pATM-Ser1981 (#4526), ATM (#2873), pATR-Thr1989 (#58014), ATR (#13934), pChk1-Ser345 (#2348), Chk1 (#2360), pChk2-Thr68 (#2197), Chk2 (#3440), pH2AX-Ser139 (#2577) and H$_2$AX (#2595). An antibody to actin (A1978, Sigma) was used to ensure equal amount of protein was loaded across all wells. Membranes were washed in 0.1% Tween 20 in TBS and then incubated for 1 hour with horseradish peroxidase (HRP)-conjugated streptavidin secondary antibodies (GE Healthcare). After washing, protein bands were detected by using SuperSignal West Femto Chemiluminescent substrate and SuperSignal West Pico Chemiluminescent substrate (Pierce/Thermo Scientific). The ImageQuant LAS4000 instrument (GE Healthcare) was used to capture and analyze images.

E02-GL-SG3249 ADC: Mechanism of Action

Following treatment of HCC1569 cells with E02-GL-SG3249, and SG3199 as a control (at 100 ng/ml and 100 pM, respectively), lysate was prepared and subjected to western blot analysis with antibodies to pATR, ATR, pChk1, Chk1, pRPA32, RPA32, pATM, ATM (all involved in ATR signalling), pChk2, ChK2, pKAP1, KAP1 (all involved in ATM signalling), pDNA-PK, DNA-PK, pH2AX, H2AX, pBRCA1, BRCA1 (all involved in DNA double strand break), pFANCD2 and GAPDH (load control). Negative controls were PBS treatment alone.

Figure 17C:
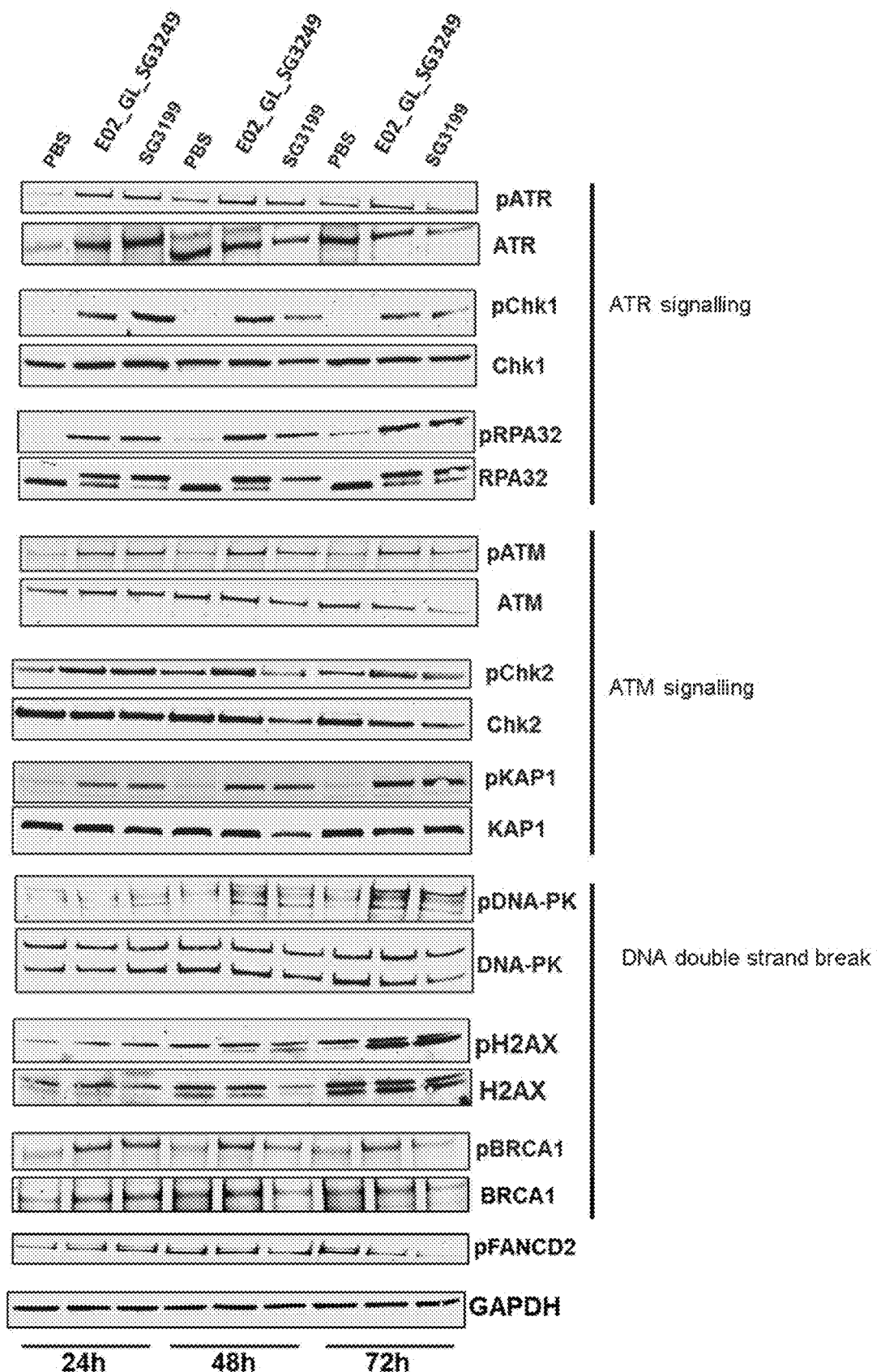
(FIG. 17C) shows western blot analysis of key double strand break markers following treatment of HCC1569 cells with anti-B7-H4 antibody conjugated to SG3249, more specifically E02-GL-SG3249.

Results demonstrate that the PBD dimer warhead (SG3199) of E02-GL-SG3249 activates ATM and ATR signalling, indicating E02-GL-SG3249 treatment leads to double strand DNA breaks in vitro (see FIG. 17C).

Caspase 3/7 Activity

Figure 18:
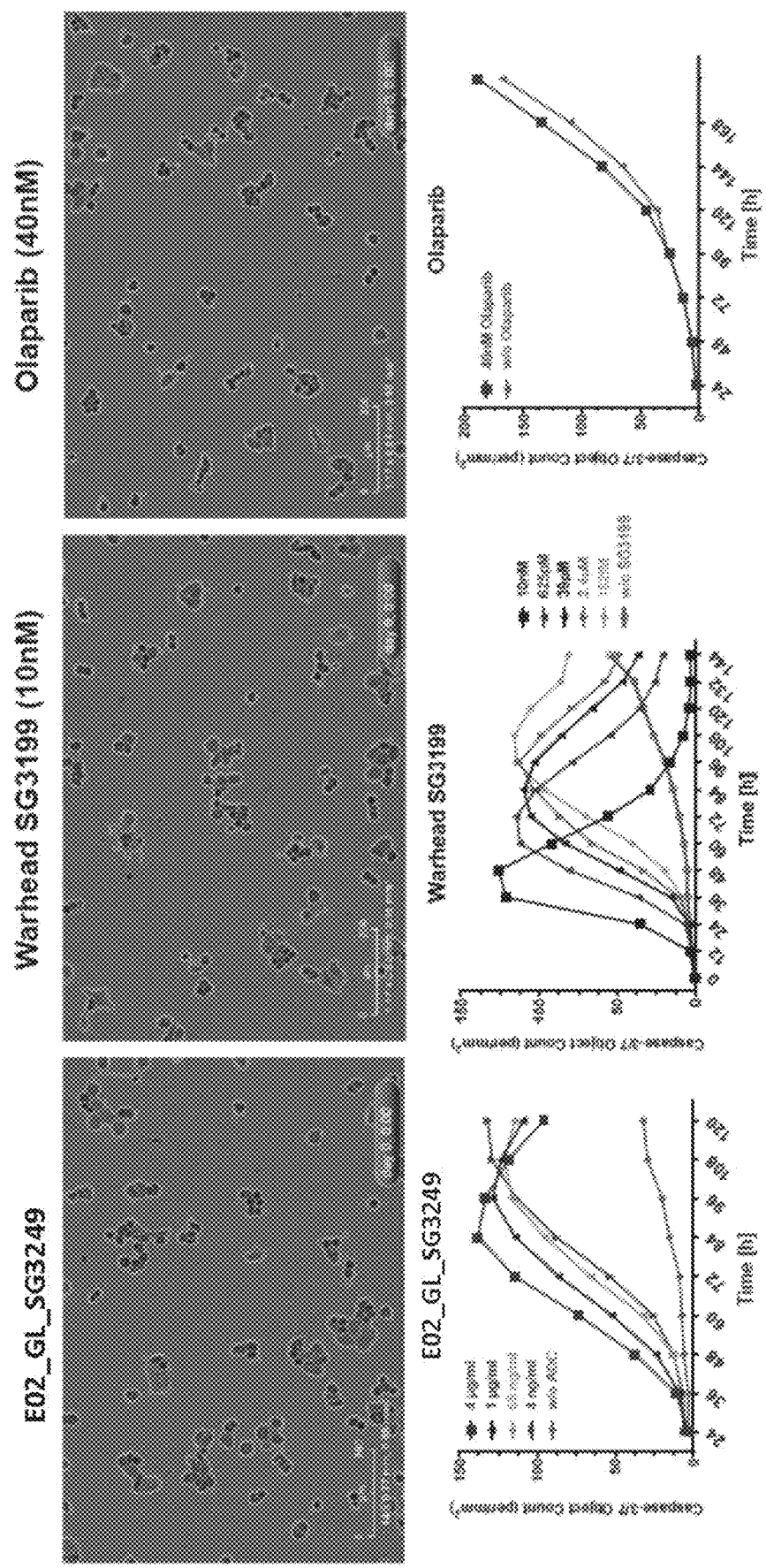
FIG. 18 shows caspase 3/7 activity in SKBR3 cells following treatment with E02-GL-SG3249.

SKBR-3 cells were treated with E02-GL-SG3249, SG3199 and Olaparib (control) and monitored for caspase 3/7 activity (e.g. apoptosis) by IncuCyte. A dose dependent increase in the level of caspase 3/7 activity was observed (see FIG. 18).

Example 15

In Vitro Activity of E02-GL-SG3249 and Warhead SG3199 on Tumour Cells

Figure 19:
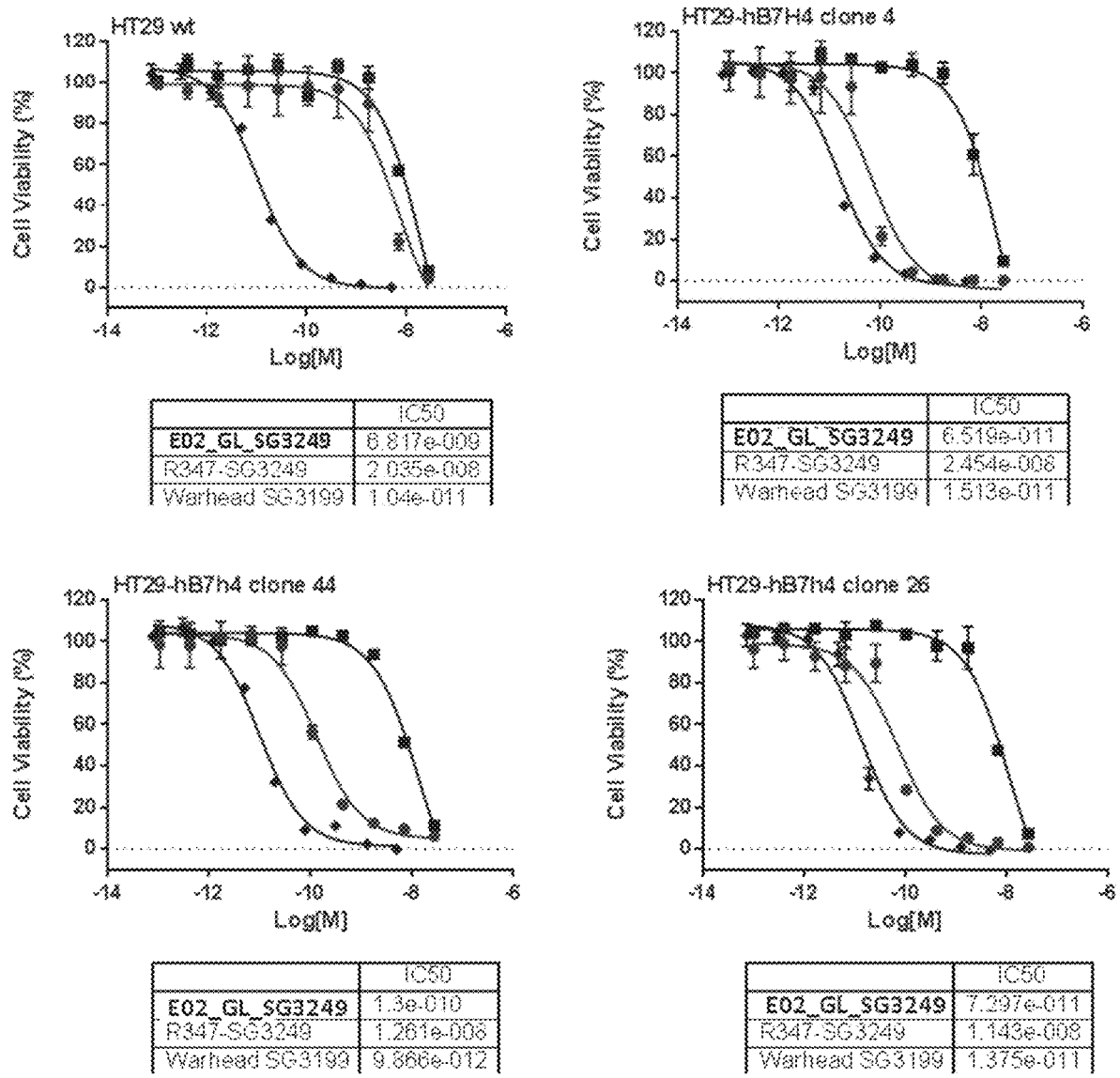
FIG. 19 shows in vitro activity of E02-GL-SG3249 and Warhead SG3199 on tumour cells.
Figure 20A:
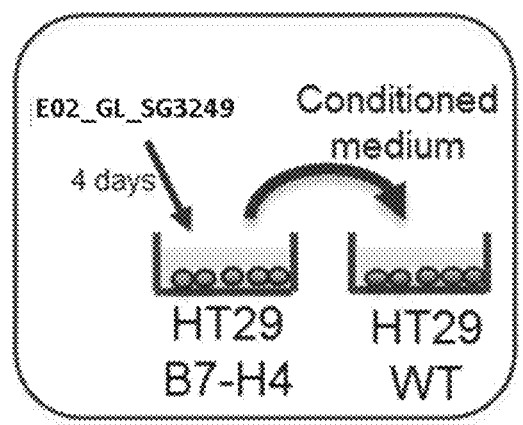
FIG. 20A-20D shows bystander killing of tumor cells in vitro (E02-GL-SG3249).
Figure 20B:
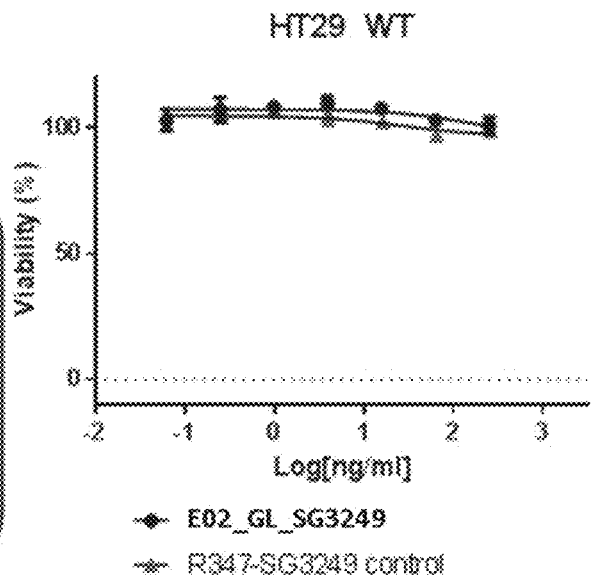
Figure 20C:
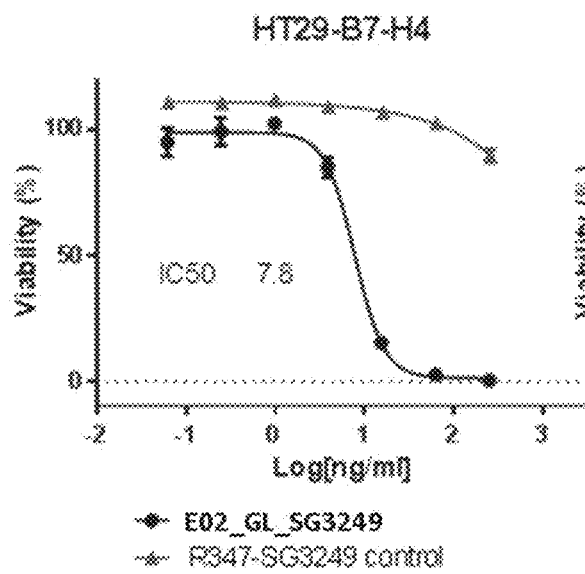
Figure 20D:
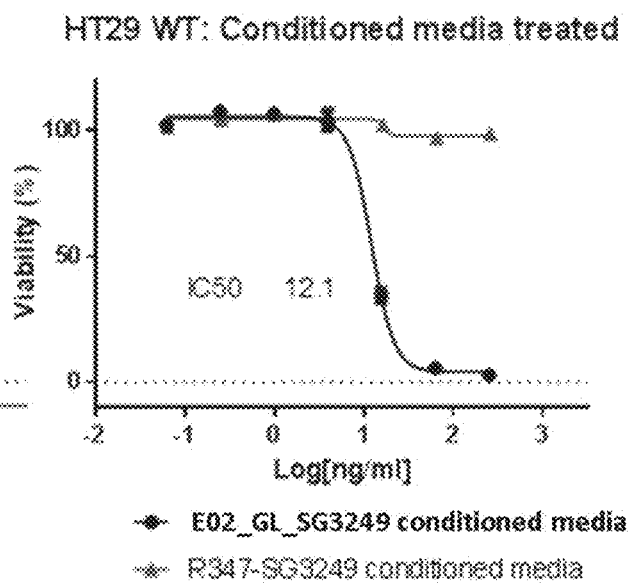

A number of cancer cell lines were treated with clone E02-GL-SG3249 (e.g. conjugated to a cytotoxin), as outlined in Table 15. Results are shown in FIG. 19.

TABLE 15

| Cell line | COMMENTS | E02-GL MESF |
|---|---|---|
| HT29 | B7-H4 negative | 2,101 |
| HT29 hB7H4 clone 4 | | 71,928 |
| HT29 hB7H4 clone 44 | | 147,125 |
| HT29 hB7H4 clone 26 | | 429,398 |
| HEK293 JI parental | B7-H4 negative | 3,266 |
| HEK 293 JI hB7H4 pool | Has some negative cells in pool | 2,481,266 |
| HCC1954 | | 47,173 |
| SKBr3 | | 78,343 |
| Zr75-1 | | 80,699 |
| HCC1569 | | 112,608 |
| MDA-MB-468 | | 92,157 |
| OVCAR4 | | 261,997 |

Example 16

E02-GL-SG3249 Causes Bystander Killing of Tumor Cells In Vitro

HT29 B7-H4 expressing cells were treated with E02-GL-SG3249 for 4 days, after which the conditioned medium was removed and added to HT29 WT (i.e. not expressing B7-H4). A rapid decrease in cell viability was observed following addition of the conditioned medium, which was not observed in the non-treated control (see FIG. 20).

"E02-GL" antibody has the CDR/VH sequences (e.g. corresponds to) of ZY0EQD-E02 ("GL" means the antibody has been germlined).

Example 17

E02-GL-SG3249 Suppresses Growth of Tumour Xenografts

Tumour xenografts were prepared on mice using the following cancer cell lines:
- OVCAR4 (Cisplatin refractory ovarian cancer; high B7-H4 expression)
- HCC1569 (HER2 positive breast cancer; heterogeneous B7-H4 expression)
- MDA-MB-468 (Triple negative breast cancer; low B7-H4 expression)

"E02-GL" antibody has the CDR/VH sequences (e.g. corresponds to) of ZY0EQD-E02 ("GL" means the antibody has been germlined).

Figure 22A:
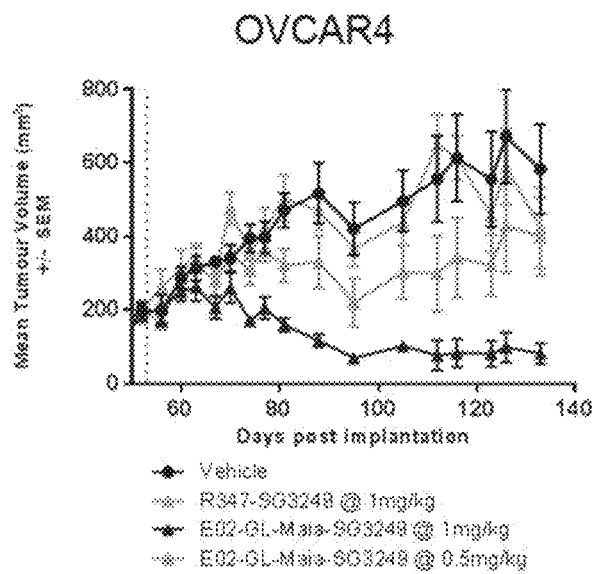
FIG. 22A-22C shows in vivo activity of E02-GL-SG3249 against tumour grafts of (A) OVCAR4 cells (cisplatin refractory ovarian cancer, high B7-H4), (B) HCC1569 cells (HER2+ breast cancer, heterogeneous expression of B7-H4), and (C) MDA-MB-468 cells (triple negative breast cancer, low B7-H4 expression).
Figure 22B:
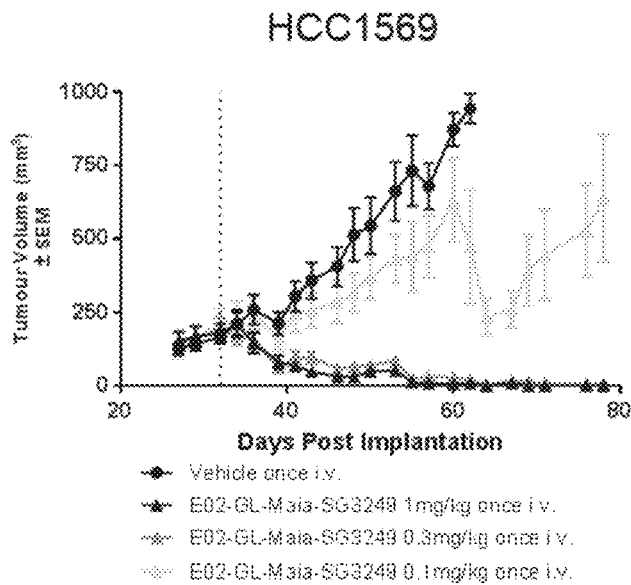
Figure 22C:
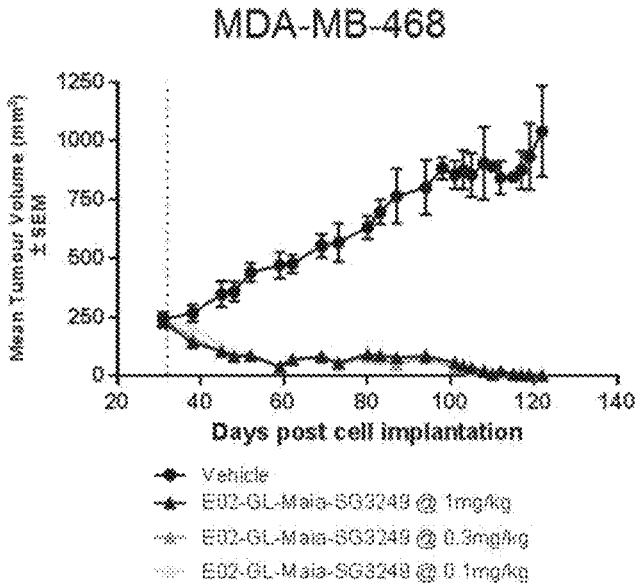

A significant decrease in tumour volume was observed compared to the control (vehicle only), which was surprisingly also the case for low-level B7-H4 expressing TNBC tumours (see FIG. 22), indicating high potency of E02-GL-SG3249 at suppressing tumour growth.

Example 18

E02-GL-SG3249 Causes Bystander Killing of Tumour Cells In Vivo

Figure 23:
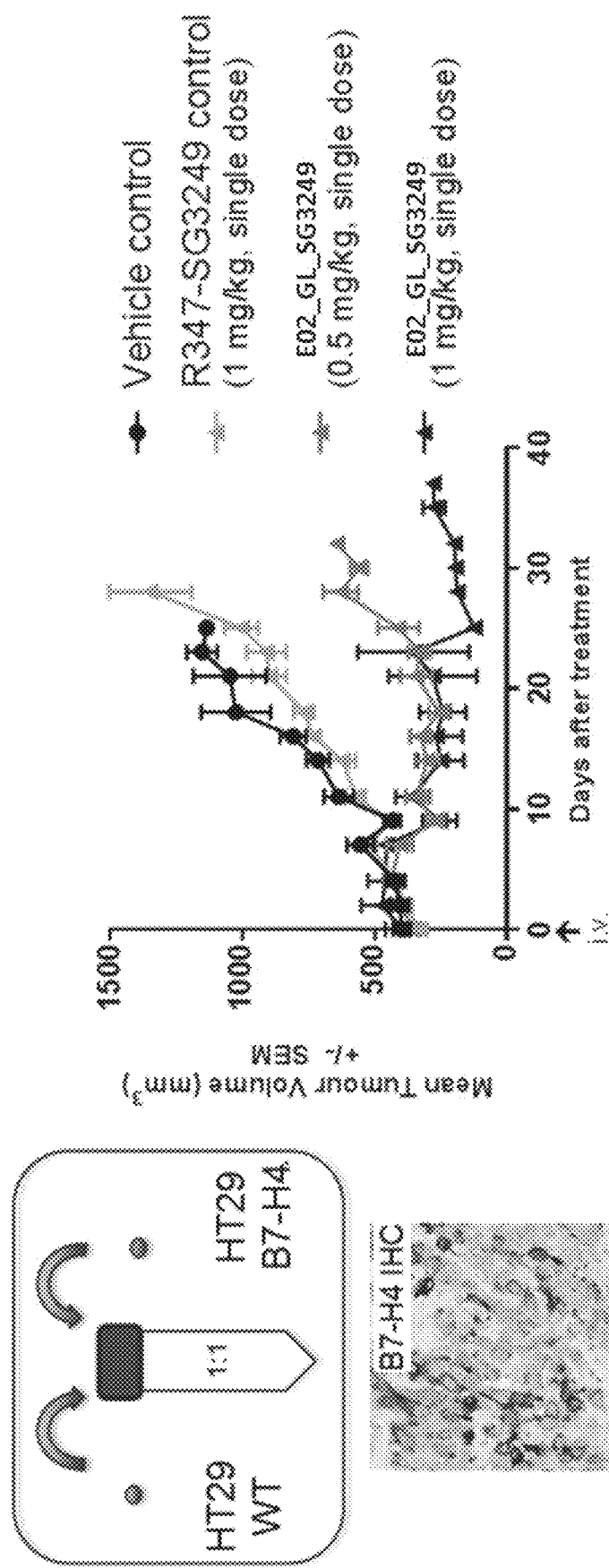
FIG. 23 shows bystander killing of tumour cells in vivo.
Figure 24A:
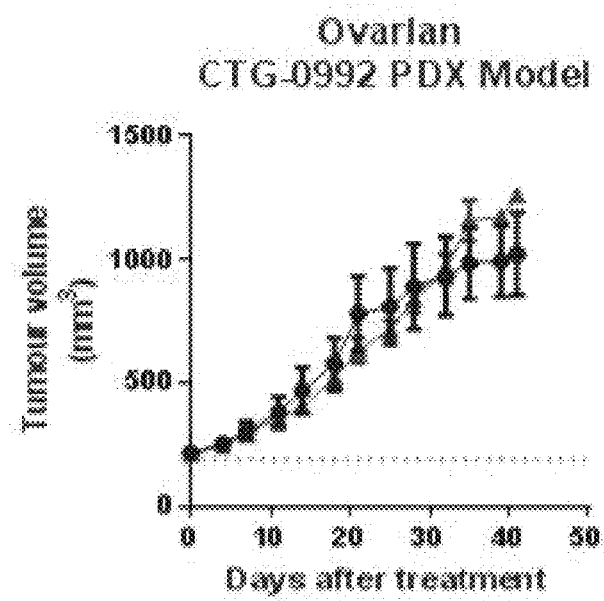
FIG. 24A-24O shows that E02-GL-SG3249 has potent in vivo activity in patient derived xenograft (PDX) models. Circles=vehicle only control; Squares=E02-GL-SG3249 (0.3 mg/kg); Triangles=E02-GL-SG3249 (1.0 mg/kg).
Figure 24B:
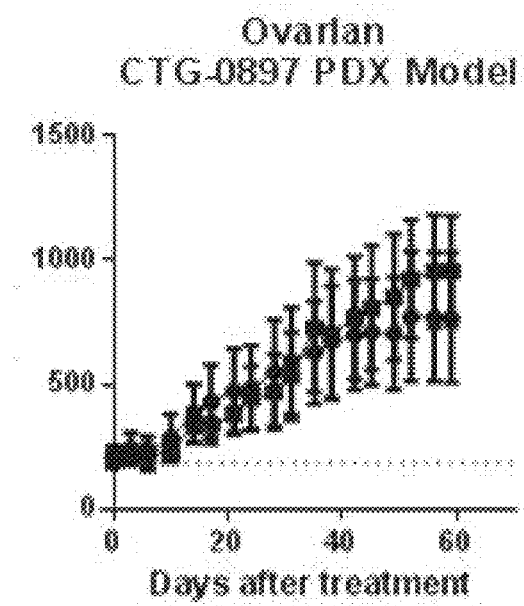
Figure 24C:
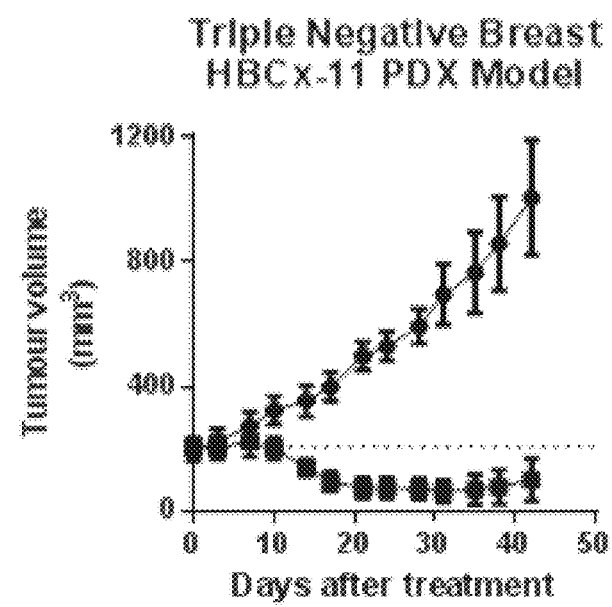
Figure 24D:
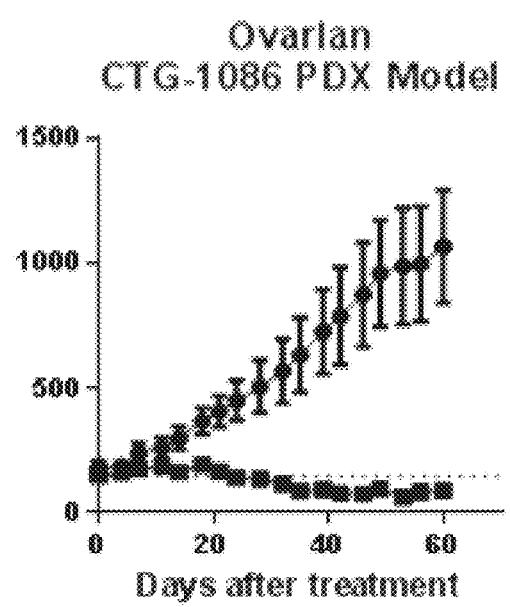
Figure 24E:
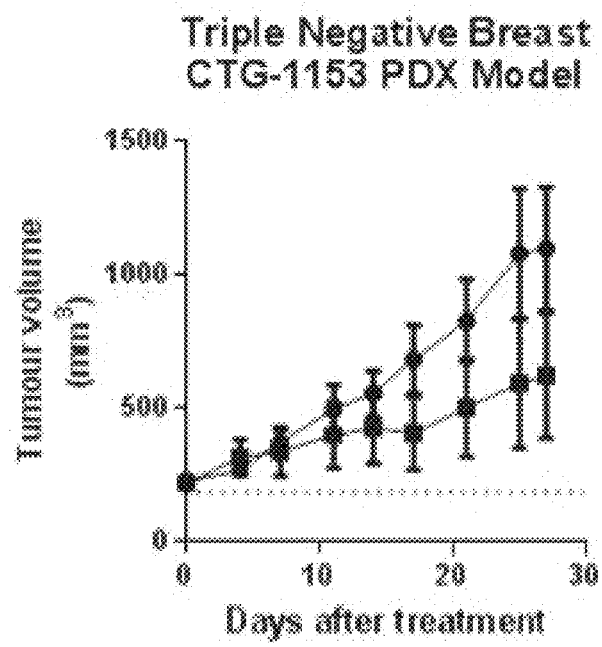
Figure 24F:
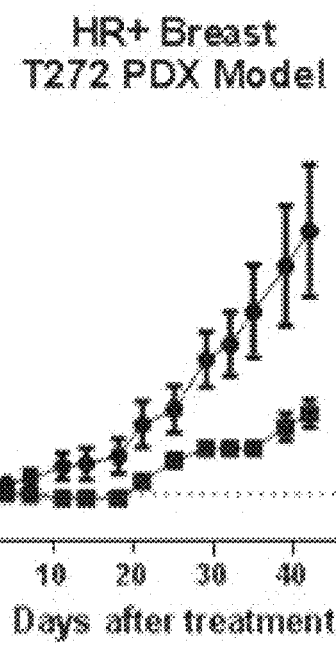
Figure 24G:
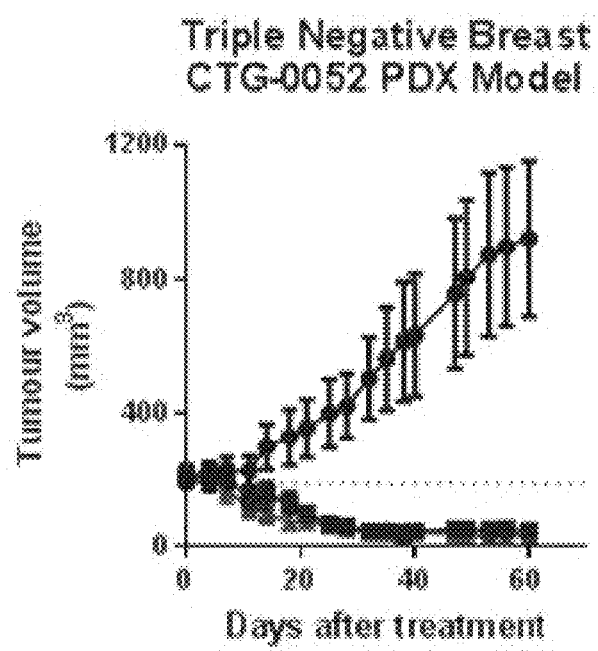
Figure 24H:
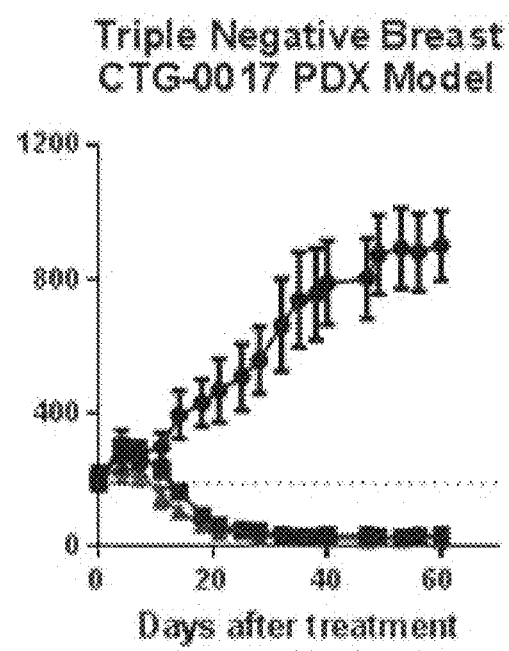
Figure 24I:
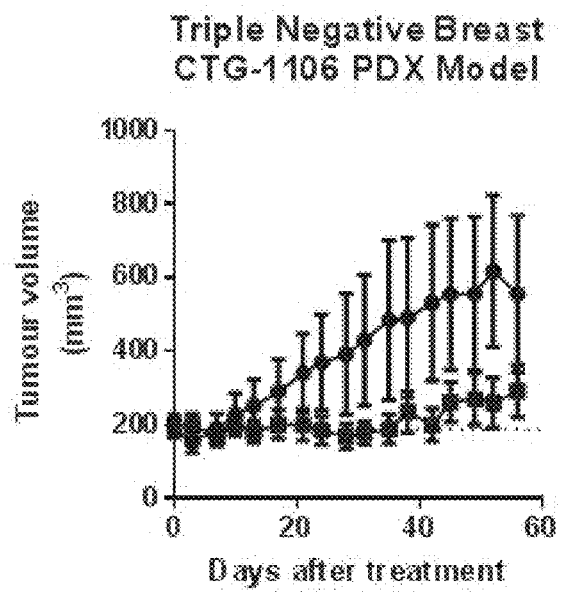
Figure 24J:
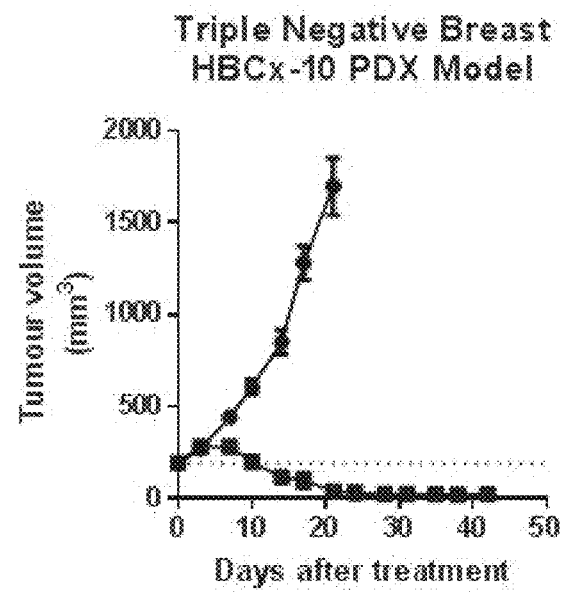
Figure 24K:
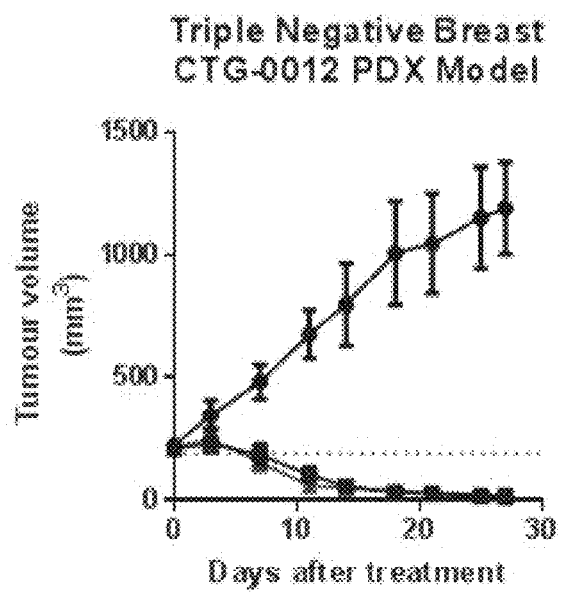
Figure 24L:
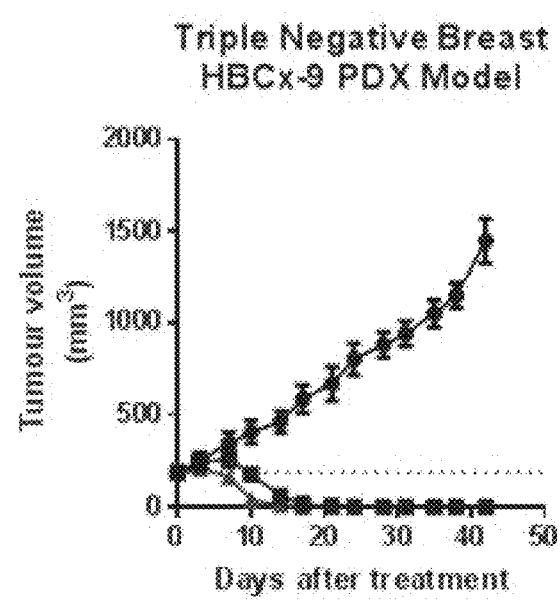
Figure 24M:
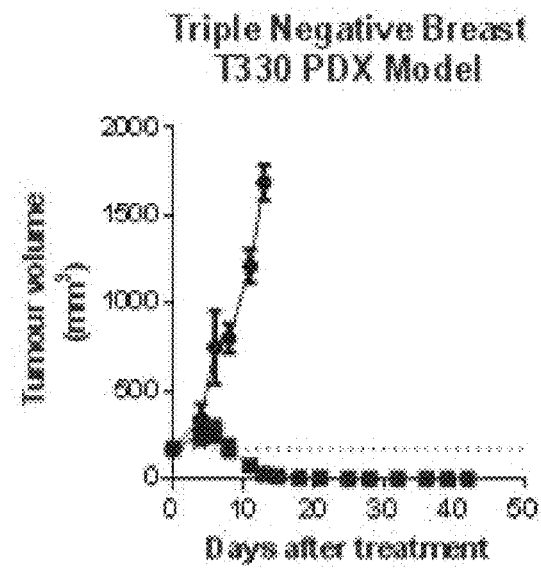
Figure 24N:
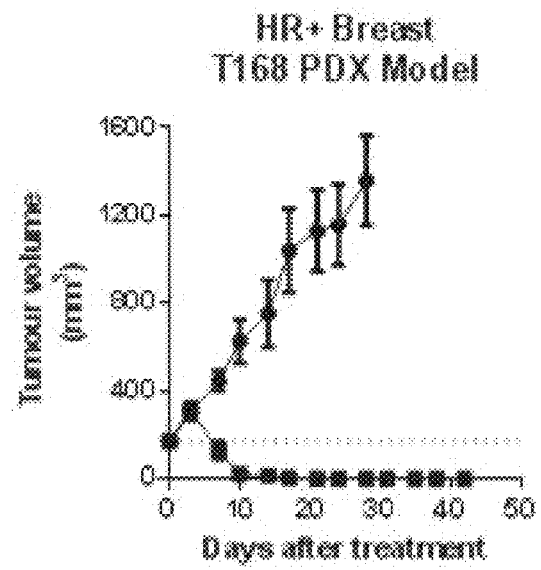
Figure 24O:
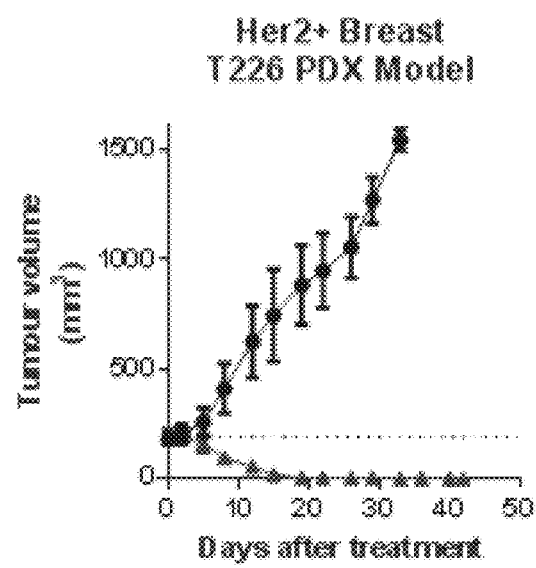

B7-H4 heterogeneous tumours were generated by co-implantation of B7-H4 expressing HT29 cell lines with non-expressing HT29 cells (1:1 ratio). The heterogeneous nature of these xenografts did not prevent their growth suppression by E02-GL-SG3249, which was pronounced (see FIG. 23). This is highly advantageous, as the inventors have found B7-H4 to be heterogeneously expressed within tumours.

Example 19

E02-GL ADCs have Superior In Vitro Cytotoxicity of B7-H4 Expressing Cells Compared with "1D11"

The clone E02-GL (ZY0EQD_E02-germlined (GL)) was conjugated to the cytotoxin SG3249 (providing an E02-GL-SG3249 ADC), or to AZ1508 (providing E02-GL-AZ1508) and compared with a Genentech "1D11" ADC (1D11 conjugated to (A114C-) MMAE) for the ability to target and kill B7-H4 expressing cells.

"E02-GL" antibody has the CDR/VH sequences (e.g. corresponds to) of ZY0EQD-E02 ("GL" means the antibody has been germlined).

Figure 21A:
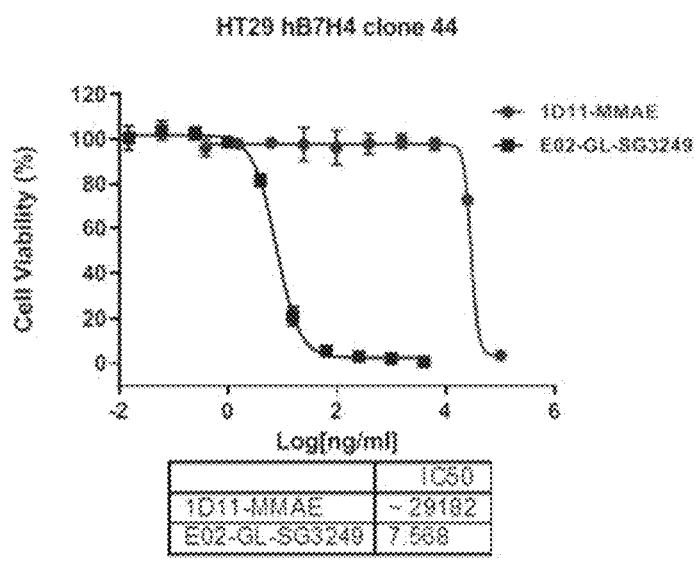
FIG. 21A-21C show E02_GL ADCs have improved cytotoxicity/potency compared with 1D11 ADCs. Comparative cytotoxicity is shown against a HT29 cell line expressing human B7-H4 (A), an SKBR3 cell line (B), and an HCC1569 cell line (C).
Figure 21B:
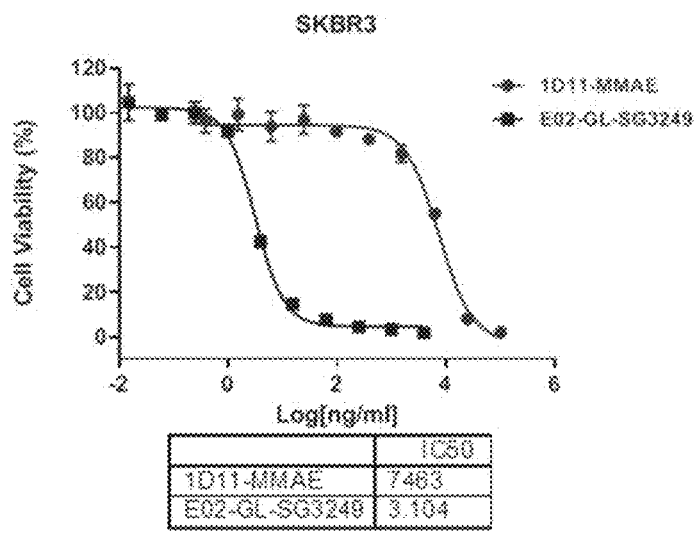
Figure 21C:
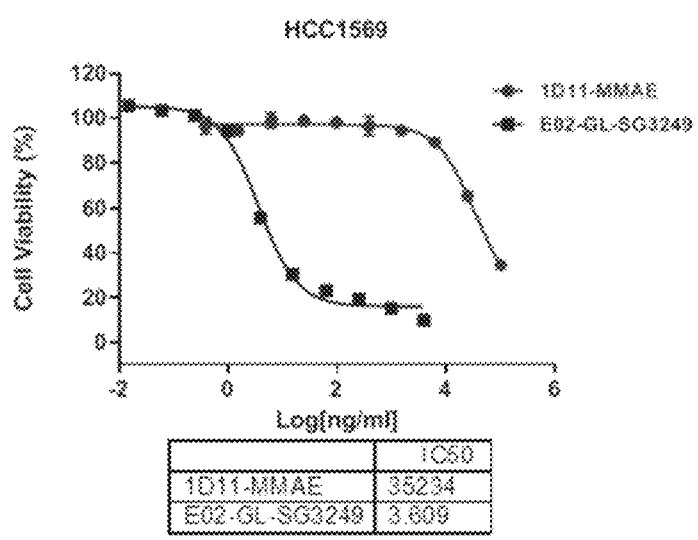

Cytotoxicity assays (see Materials and Methods, above) demonstrated that E02-GL ADCs (E02-GL-SG3249) had superior cytotoxicity potency when compared with 1D11 ADCs (1D11 conjugated to (A114C-) MMAE)—see FIG. 21.

ADC titrations were as follows:

| | | | | | | | | | | |
|---|---|---|---|---|---|---|---|---|---|---|
| 1D11-A114C-MMAE | 100 µg/ml | 25 µg/ml | 6.25 µg/ml | 1.56 µg/ml | 390 ng/ml | 98 ng/ml | 24.5 ng/ml | 6.12 ng/ml | 1.53 ng/ml | 382 pg/ml |
| E02-maia-GL-SG3249 | 4 µg/ml | 1 µg/ml | 250 ng/ml | 65 ng/ml | 16 ng/ml | 4 ng/ml | 1 ng/ml | 250 pg/ml | 62.5 pg/ml | 16 pg/ml |

Example 20

E02-GL-SG3249 has Potent In Vivo Activity in Patient Derived Xenograft (PDX) Models Patient derived xenograft models were generated using cancer cell lines with varying levels of B7-H4 expression, as outlined in Table 16. Suppressed tumour growth was observed in all models (see FIG. 24). "E02-GL" antibody has the CDR/VH sequences (e.g. corresponds to) of ZY0EQD-E02 ("GL" means the antibody has been germlined).

TABLE 16

| Model | Cancer type | % Tumour Growth Inhibition (TGI) * |
|---|---|---|
| HBCx-10 | Breast (Triple negative) | 90 |
| CTG-012 | Breast (Triple negative) | 90 |
| HBCx-11 | Breast (Triple negative) | 80 |
| T330 | Breast (Triple negative) | 70 |
| HBCx-9 | Breast (Triple negative) | 70 |
| T168 | Breast (HR+) | 60 |
| T272 | Breast (HR+) | 30 |
| CTG-1106 | Breast (Triple negative) | 30 |
| CTG-052 | Breast (Triple negative) | 30 |
| CTG-1086 | Ovarian | 20 |
| CTG-1153 | Breast (Triple negative) | <10 |
| CTG-0897 | Ovarian | <10 |
| CTG-017 | Breast (Triple negative) | <10 |

TABLE 16-continued

| Model | Cancer type | % Tumour Growth Inhibition (TGI) * |
| --- | --- | --- |
| T226 | Breast (Her2+) | <10 |
| CTG-0992 | Ovarian | 0 |

* % Tumour Growth Inhibition (TGI) 0.3 mg/kg E02-GL-SG3249 vs vehicle; Least square mean (LSM) & TGI = 100*(LSM vehicle − LSM 'E02-GL-SG3249')/LSM Vehicle
+++ = high positive expression;
++ & + = low positive expression

Example 21

E02-GL-SG3249 Causes Double Strand Breaks in Tumor Xenografts

Tumour xenograft models were generated (using HCC1954 cells), and treated with E02-GL-SG3249. "E02-GL" antibody has the CDR/VH sequences (e.g. corresponds to) of ZY0EQD-E02 ("GL" means the antibody has been germlined).

Figure 25A:
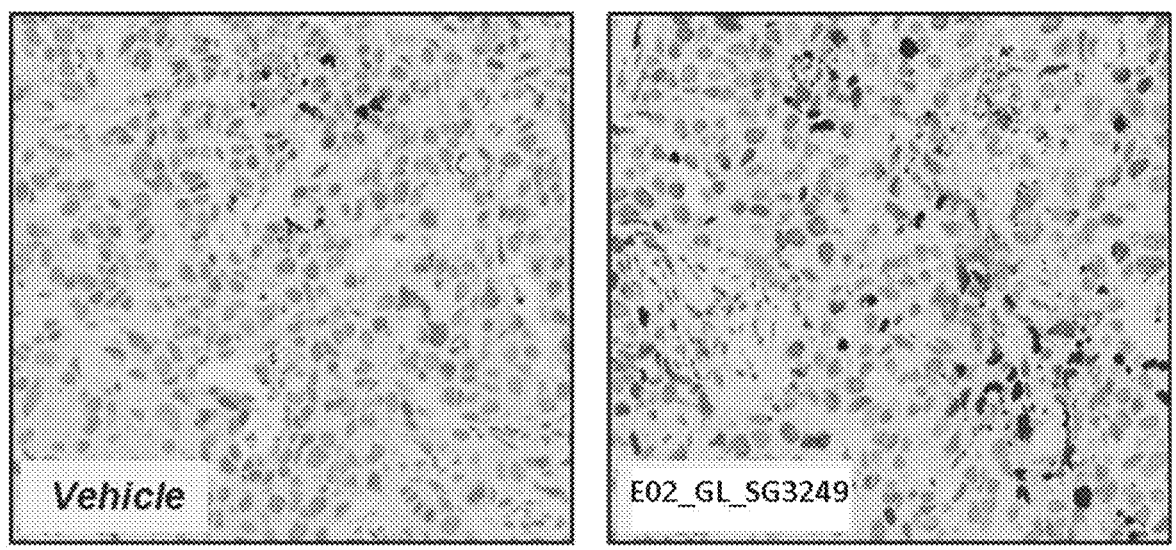
FIG. 25A-25B shows results of (A) gamma-H2AX immunohistochemistry (IHC) in a HCC1954 tumour xenograft (with and without E02-GL-SG3249), quantified in (B) as no. of gamma-H2AX positive cells per mm$^2$ (within a tissue region of interest) (+/−S.E.M.). Image analysis performed using HALO software (with CRO-OracleBio). Increased numbers of gamma-H2AX positive tumour cells were observed up to 10 days following E02-GL-SG3249 treatment.
Figure 25B:
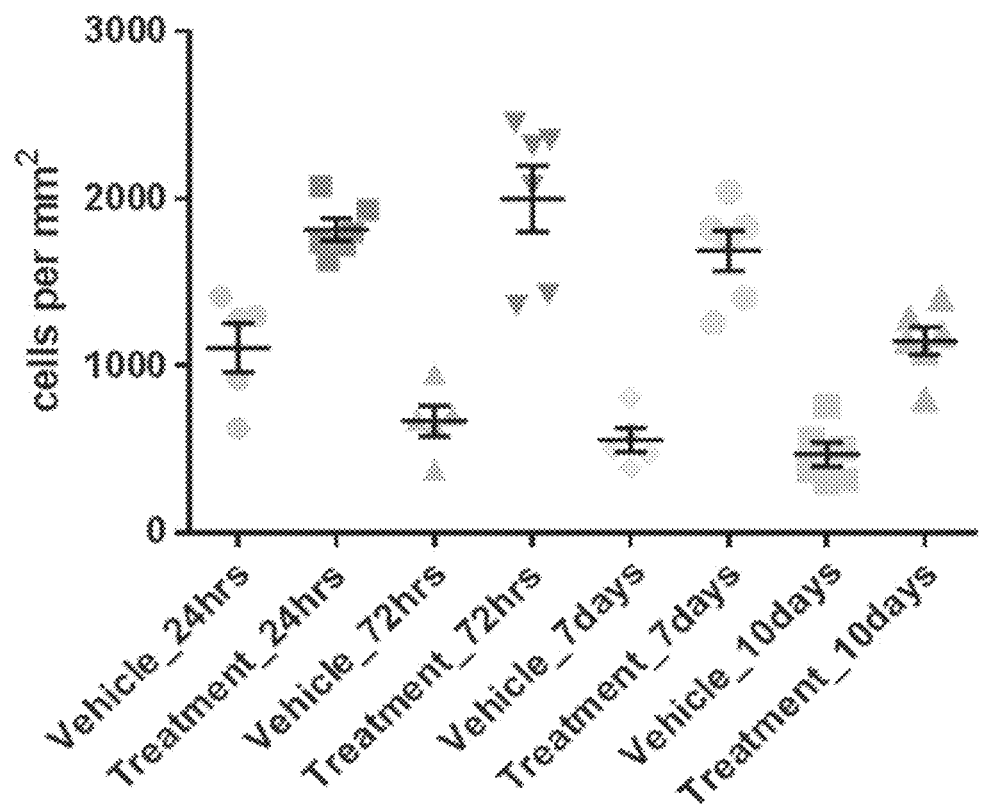

Immunohistochemistry was then performed to determine gamma H2AX (marker of double strand breaks) following treatment. Increased numbers of gamma H2AX positive tumour cells were observed up to 10 days following E02-GL-SG3249 treatment (see FIG. 25).

Example 22

Analysis of the Affinity of E02_GL Using KinExA 3200

Experiments to obtain estimates of affinity (KD) of clone E02_GL anti-B7H4 Fab with human B7H4 was performed using KinExA technology. "E02-GL" antibody has the CDR/VH sequences (e.g. corresponds to) of ZY0EQD-E02 ("GL" means the antibody has been germlined).

A range of human B7H4 concentrations were equilibrated overnight in the presence of 5, 10 or 45 nM fixed concentrations of the Fab at 25° C. These were analysed on the KinExA 3200 and the data sets fitted globally (N-curve analysis). Results are summarised in Table 17.

TABLE 17

| Antibody | B7H4 | Best estimate of $K_D$ | N-curve analysis, comments |
| --- | --- | --- | --- |
| E02_GL | human | 1.2 nM | $K_D$ = 1.21 nM with 95% Confidence Intervals = 0.556-2.22 nM. 62% of h B7H4 epitopically active, 95% Confidence Intervals = 51-77% |

The 62% h B7H4 activity figure matches well with Rmax calculations in accompanying Biacore based affinity assessments of E02_GL.

Example 23

Comparison of E02_GL Binding to B7-H4 with mAb "1D11"

Clone E02_GL was subjected to ELISA analysis for binding to human and mouse B7-H4. Binding was compared directly with the mAb 1D11 (Genentech), and R347 isotype control. "E02-GL" antibody has the CDR/VH sequences (e.g. corresponds to) of ZY0EQD-E02 ("GL" means the antibody has been germlined).

Figure 2A:
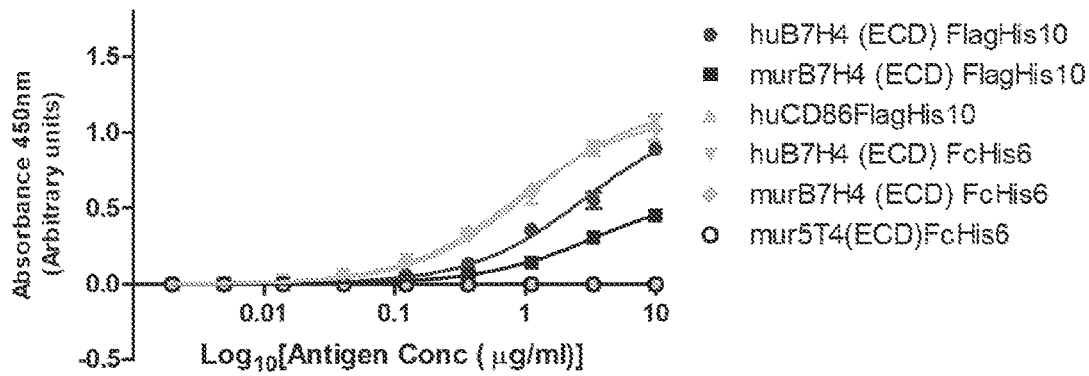
FIG. 2A-2K shows results for species cross-reactivity ELISA analysis.
Figure 2B:
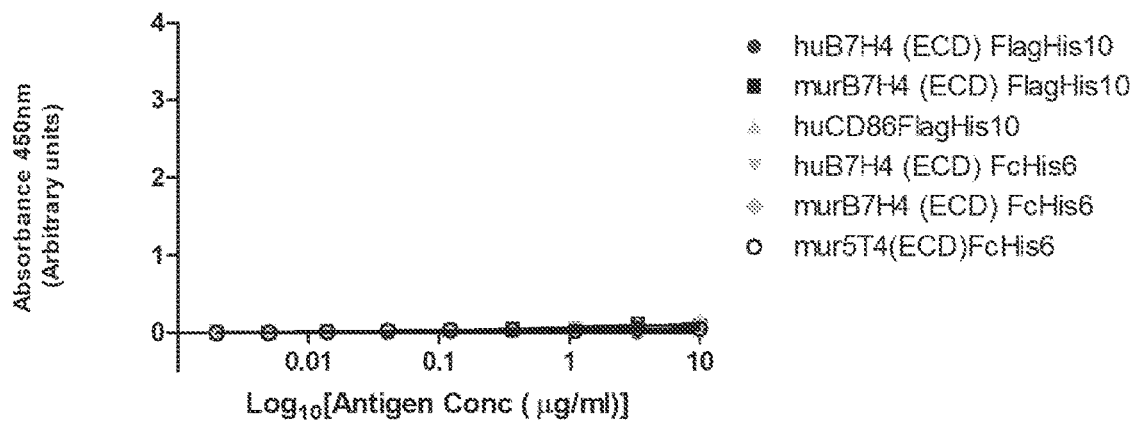
Figure 2C:
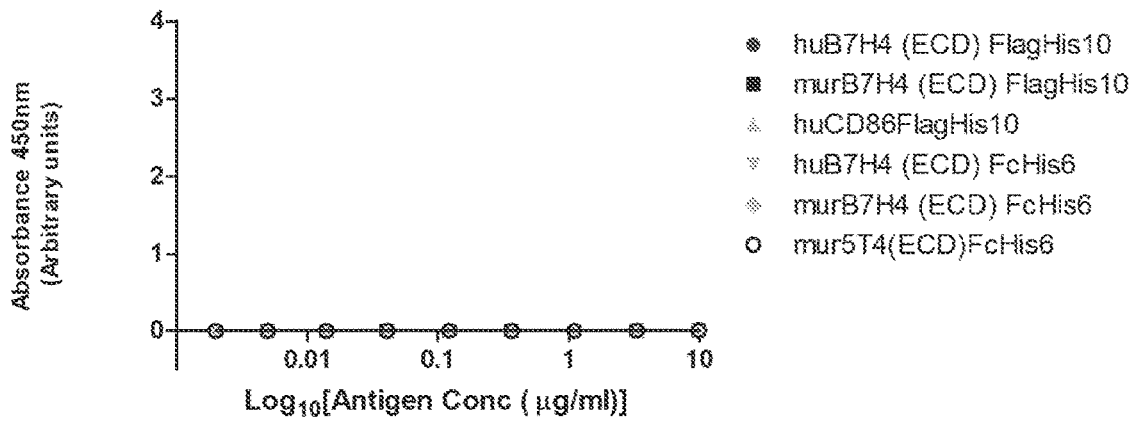
Figure 2D:
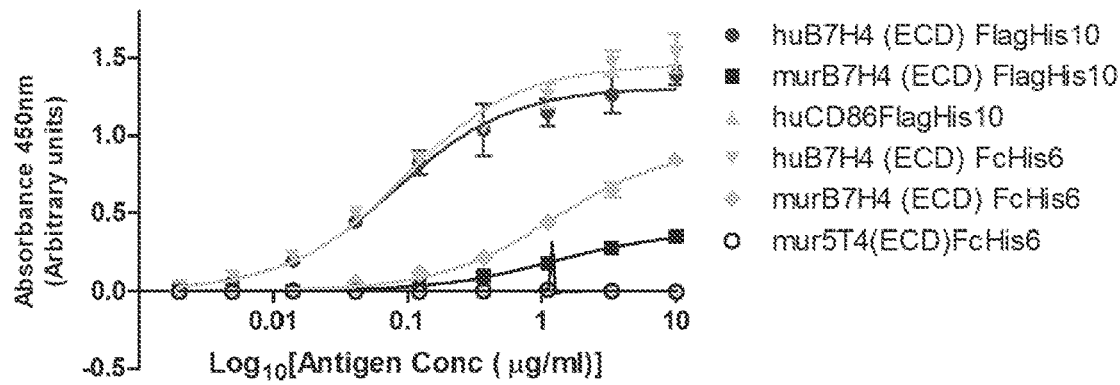
Figure 2E:
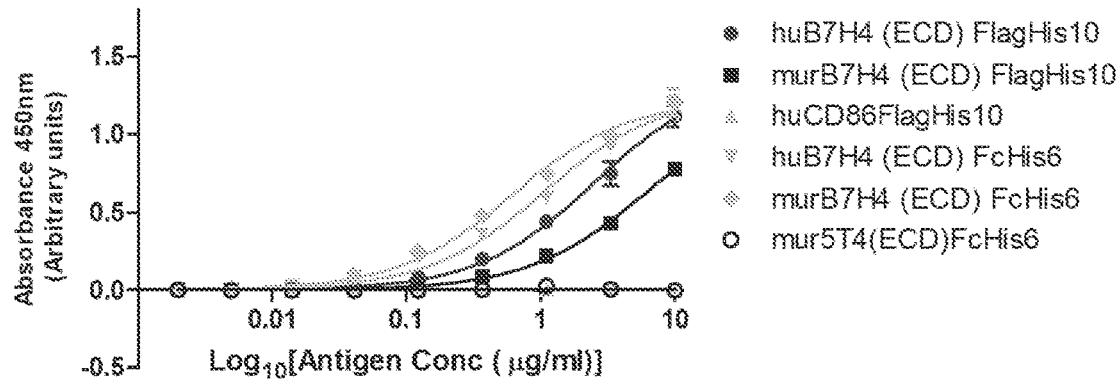
Figure 2F:
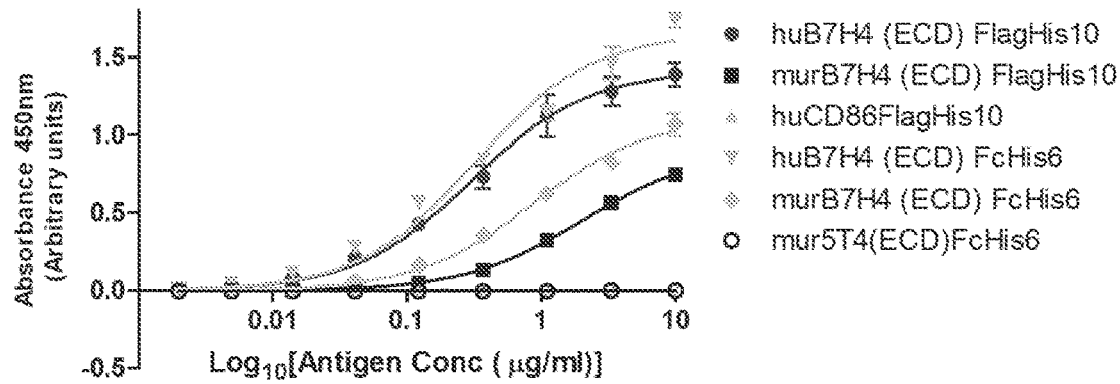
Figure 2G:
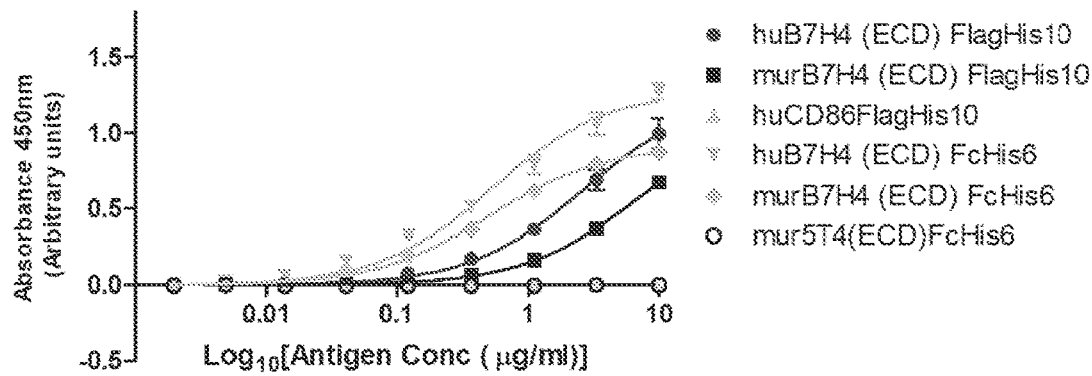
Figure 2H:
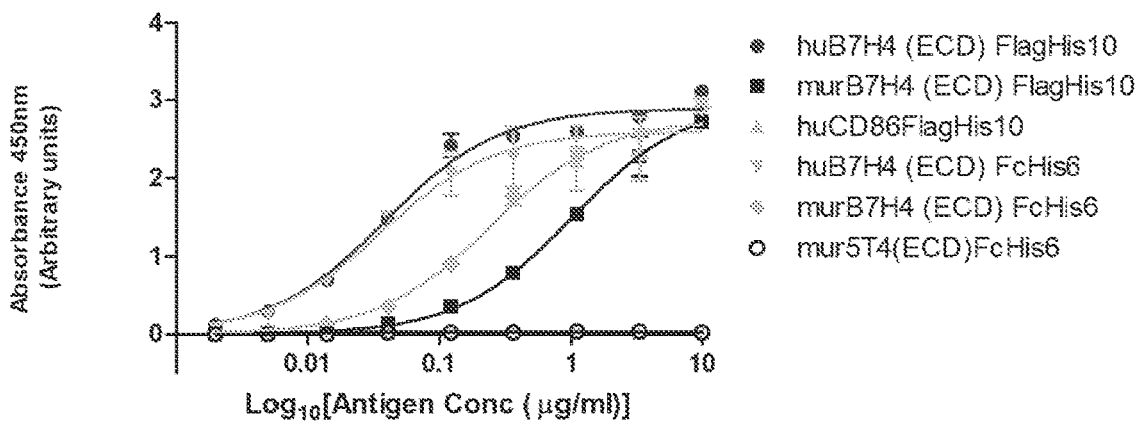
Figure 2I:
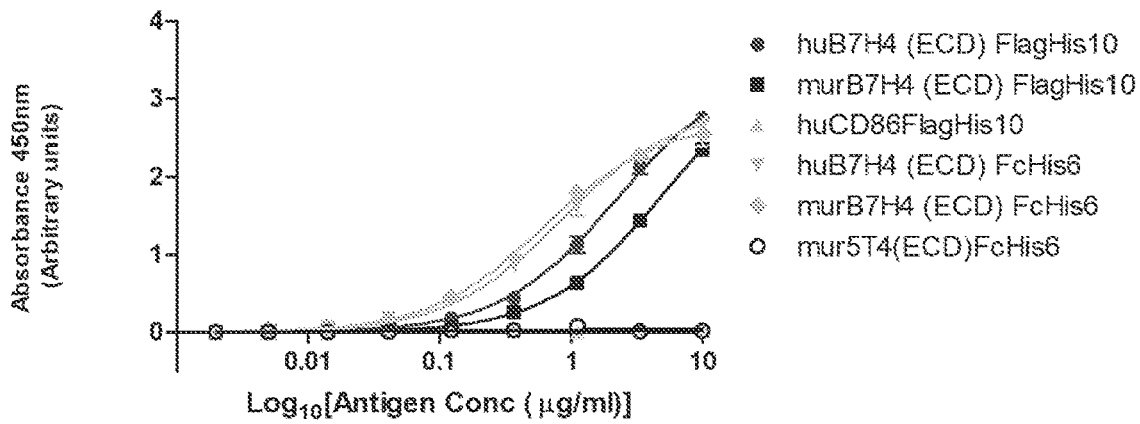
Figure 2J:
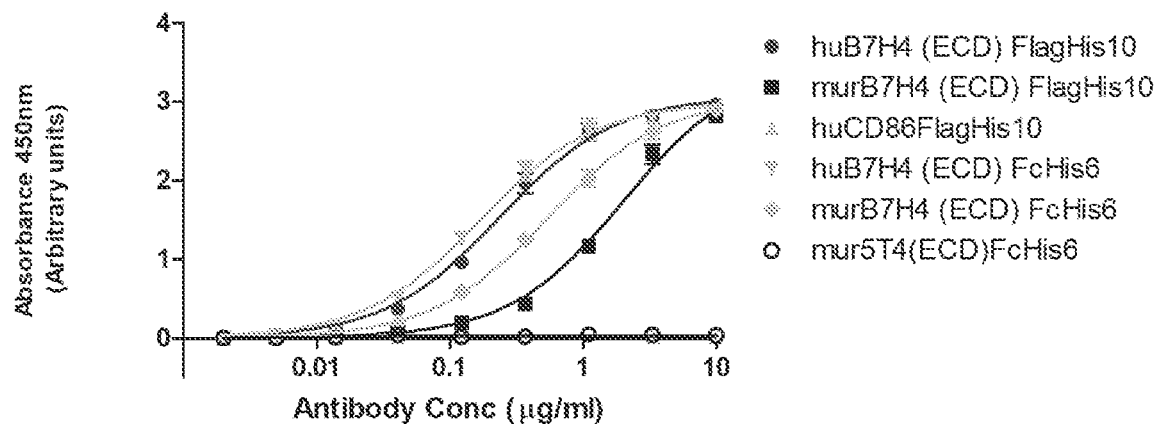
Figure 2K:
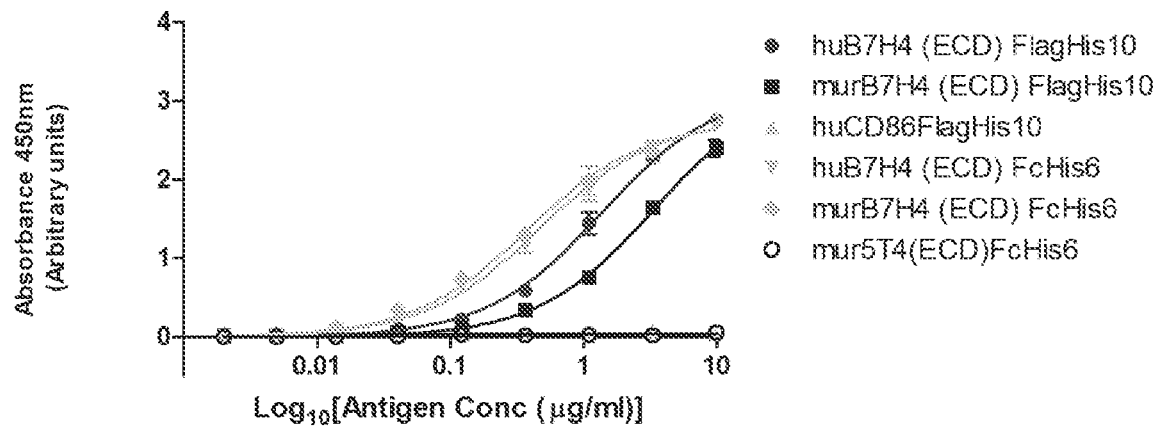
Figure 3A:
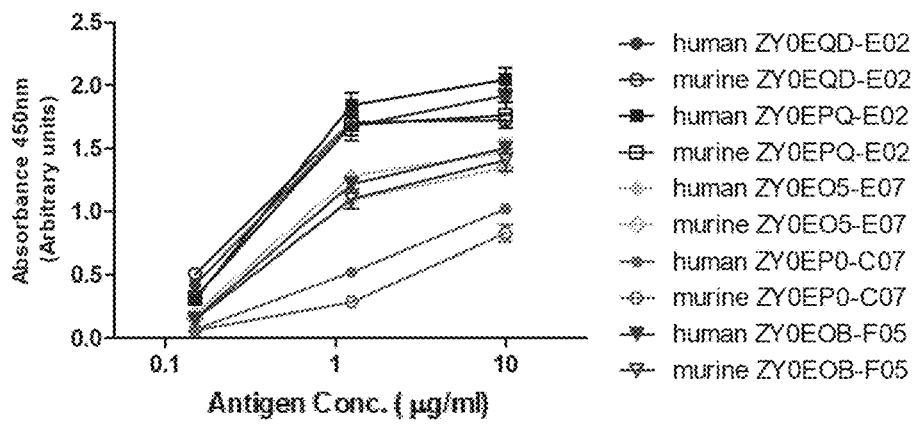
FIG. 3A-3G shows results of ELISA analysis of clone binding to B7-H4 family members and homologues.
Figure 3B:
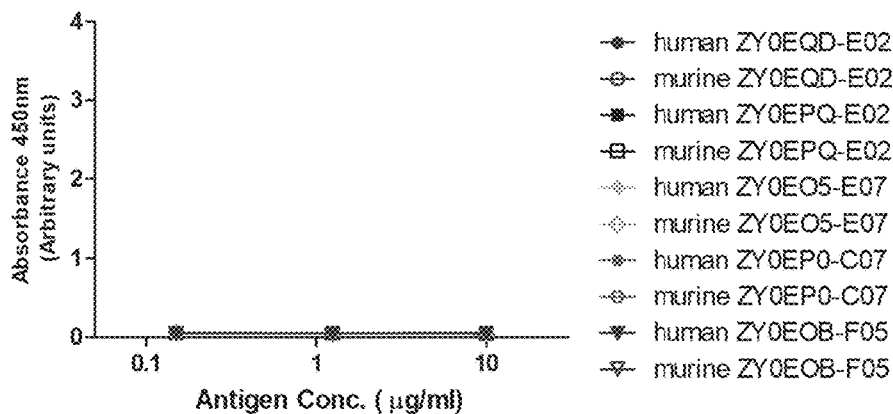
Figure 3C:
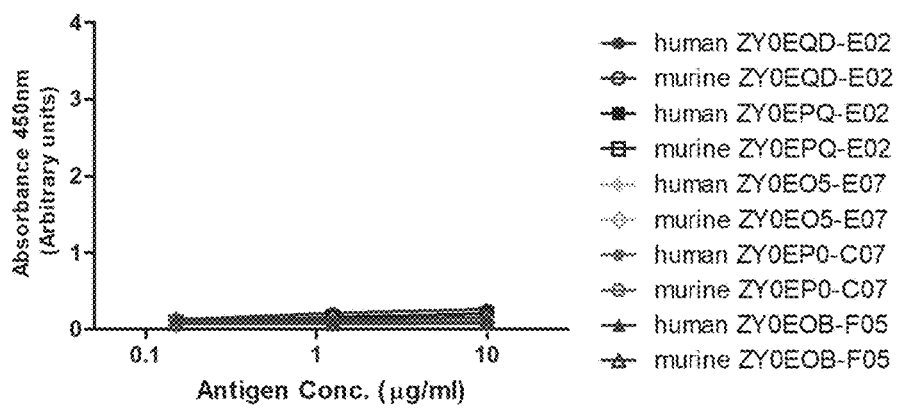
Figure 3D:
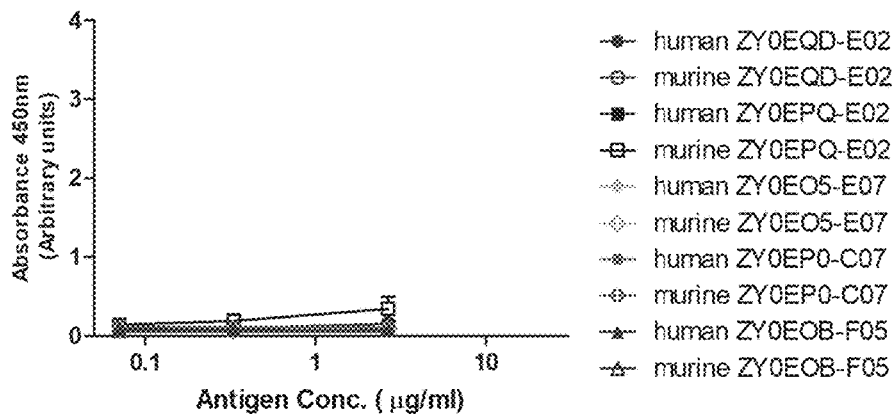
Figure 3E:
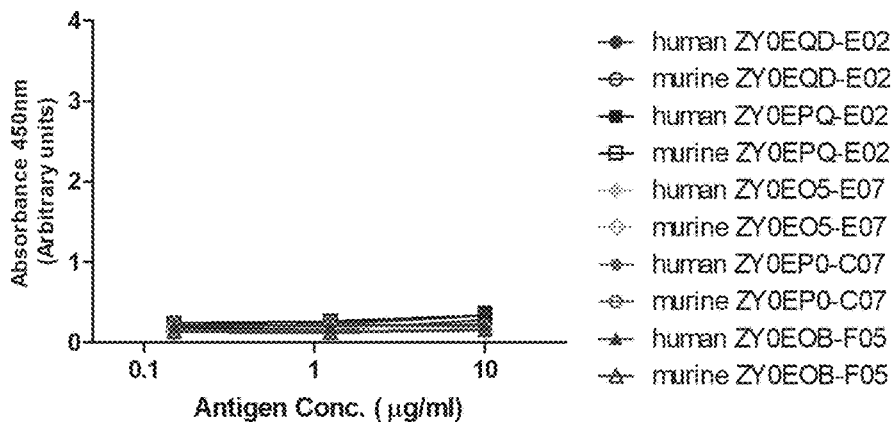
Figure 3F:
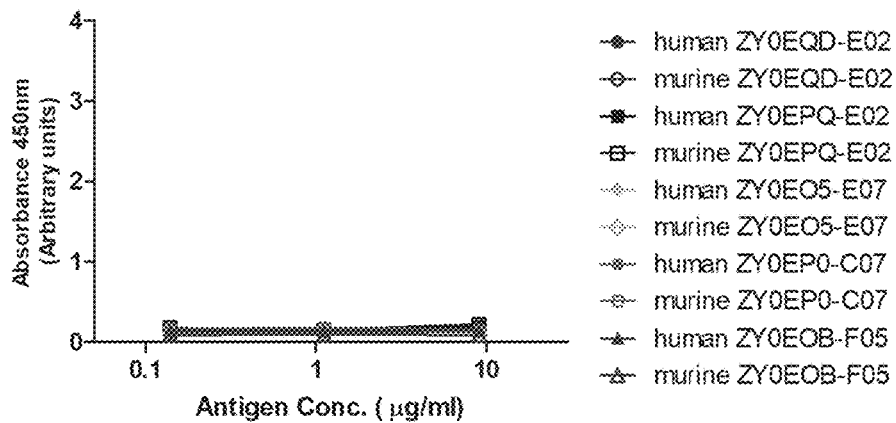
Figure 3G:
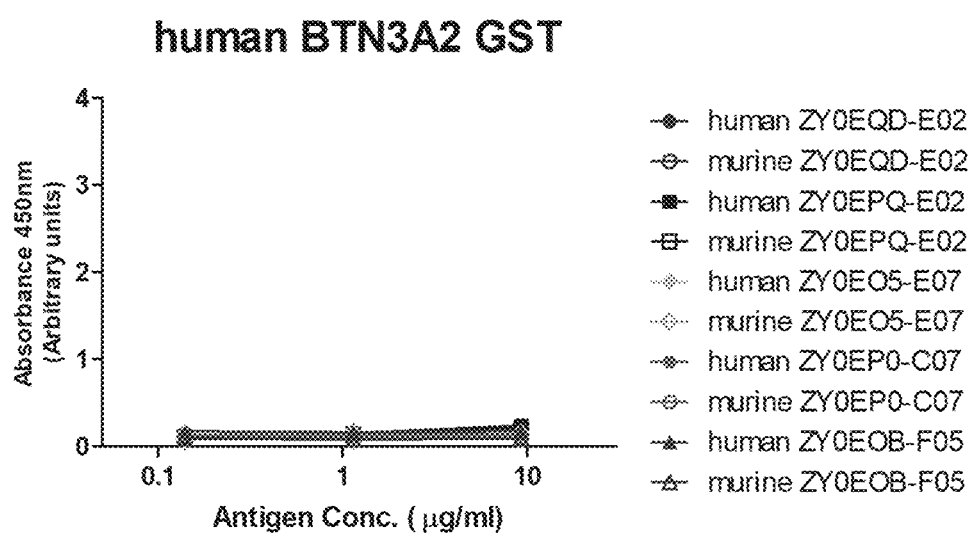

E02_GL shows higher binding affinity for human B7-H4 compared to mouse B7-H4 (see e.g. FIG. 2D). Advantageously, E02-GL shows significantly stronger binding (affinity) to human B7-H4 than the Genentech "1D11" mAb (which shows much weaker binding), as demonstrated by both ELISA and FACs analysis—see FIGS. 7 and 8, respectively. Indeed, Genentech "1D11" mAb binds human B7-H4 at similar levels (low) to mouse B7-H4 (showing that "1D11" has less specificity for the human protein, when compared with E02_GL).

Example 24

Imaging Studies Showing Tumour Localisation of E02_GL

In vivo imaging studies were performed as outlined under Materials and Methods (above), namely with 800 CW labelled antibody (E02_GL). "E02-GL" antibody has the CDR/VH sequences (e.g. corresponds to) of ZY0EQD-E02 ("GL" means the antibody has been germlined).

Preferential localization of B7-H4 Ab (E02_GL) to the B7-H4 expressing tumour compared to the WT tumour was observed for the HT29 on days 3, 7, 14; the CT26 on day 3 and 7, and p=0.06 on day 10; and the 4T1 on day 7—see FIGS. 26 and 27.

Total radiant efficiency produced the clearest results. Similar trends were observed when normalizing to tumour volume.

Example 25

Toxicology Studies with E02-GL-SG3249

E02-GL-SG3249 was administered to male cynomolgus monkeys (N=2/dose level). The "E02-GL" antibody has the CDR/VH sequences (e.g. corresponds to) of ZY0EQD-E02 ("GL" means the antibody has been germlined).

No abnormal toxicities were observed, and toxicities were consistent with other similar PBD-ADCs (by monitoring standard target organs: kidney, bone marrow, skin; no evidence of target-related effects).

Pharmacology Studies

Figure 29A:
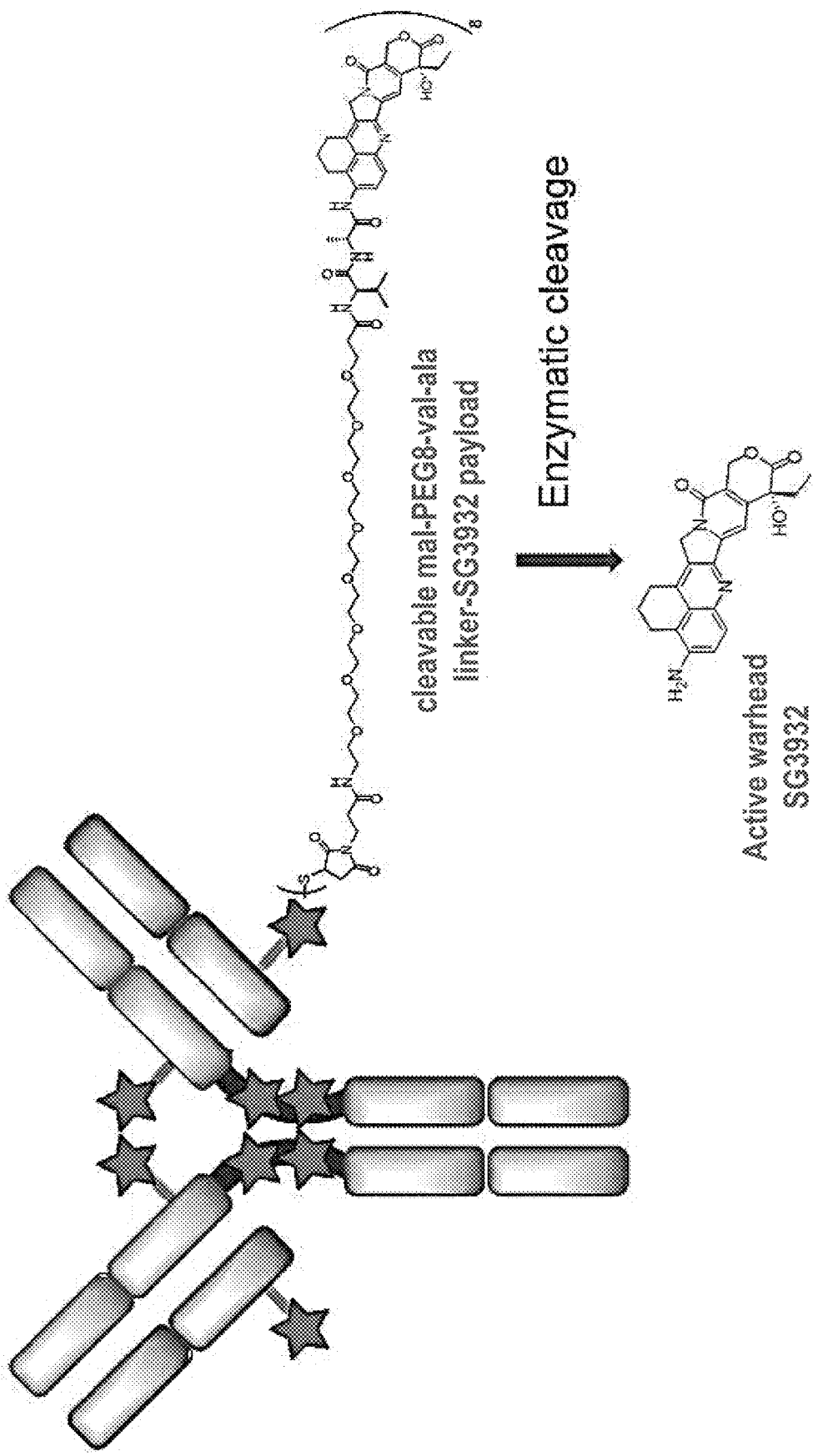
FIG. 29A is a schematic of the B7-H4 targeting TOP1i-ADC.
Figure 29B:
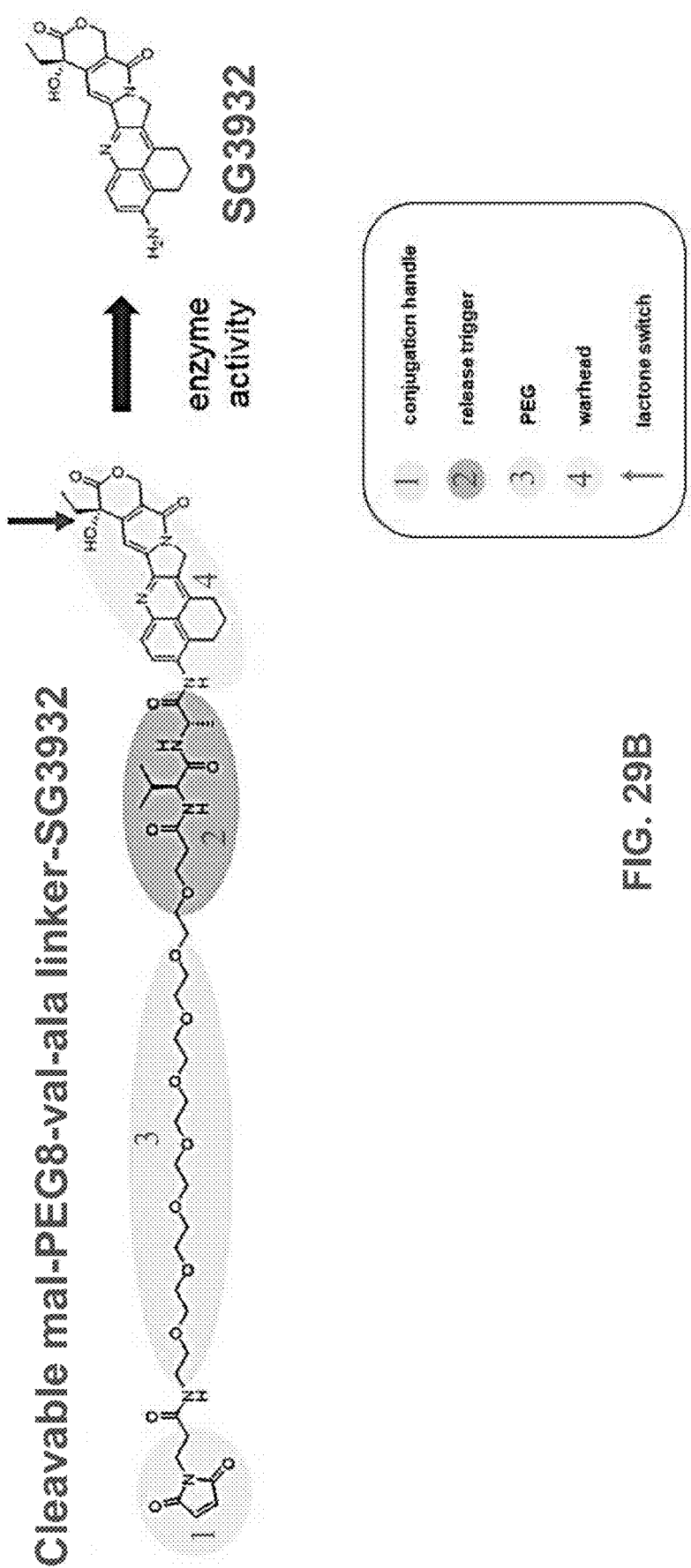
FIG. 29B shows the key features of the B7-H4 targeting TOP1i-ADC E02-GL-SG3249.

In vitro and in vivo pharmacology studies were undertaken to further characterize the effects and mechanism of action of the E02-GL antibody (the E02-GL antibody and antigen-binding Fab intermediate thereof, are referred to herein as "E02-INT"). The E02-GL-SG3932 ADC-GL-SG3932 is an ADC directed against B7-H4 and is comprised of an anti-B7-H4 human IgG1K monoclonal antibody (i.e., E02-GL) conjugated via a cleavable maleimide-PEG8-valine-alanine linker (cleavable mal-PEG8-val-ala linker) to a TOP1i warhead. The TOP1i warhead is referred to herein as SG3924. The TOP1i drug is covalently bound to native cysteines in the antibody through a thiosuccinimide linkage, with approximately 8 drugs bound per antibody (i.e., DAR of 8). A schematic of the E02-GL-SG3932 ADC is shown in FIG. 29A. The key features that differentiate E02-GL-SG3932 ADC from competitor ADCs are shown in FIG. 29B.

The E02-GL-SG3932 characteristics are set forth below and further described elsewhere herein:
mAb E02-INT: Specific binding to human and cynomolgus monkey B7-H4 (3.7 nM, 3.94 nM affinity respectively)
Warhead SG3932
Linker-warhead: cleavable mal-PEG8-val-ala linker-SG3932

In Vitro Studies

Example 26

B7-H4 Expression Profiling by Immunohistochemistry

The expression profile of B7-H4 was assessed using a validated IHC protocol to demonstrate B7-H4 expression in FFPE normal cynomolgus monkey and human tissues and human tumor tissues.

Figure 30:
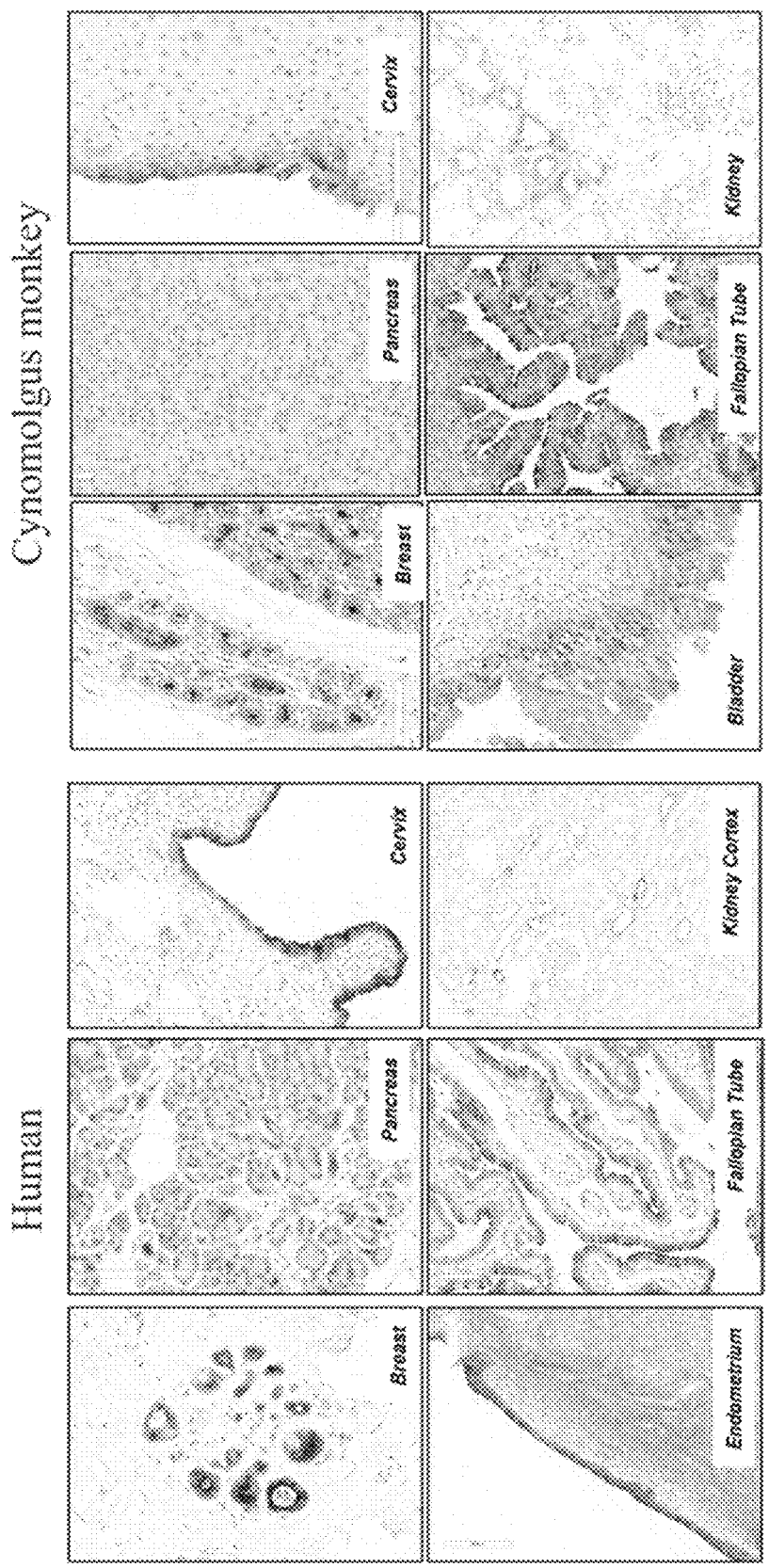
FIG. 30 shows example images of representative immunohistochemical staining of B7-H4 expression in normal human and normal cynomolgus monkey breast, pancreas, cervix, endometrium, fallopian tube/oviduct and kidney tissues.

B7-H4 was shown to be expressed in a limited number of normal human tissues, and when present, was generally expressed in <10% of the total cells in the sample (except for fallopian tube and lung bronchus), restricted towards ductal or tubular epithelium, and primarily located on the apical luminal membrane (Table 18). A similar B7-H4 expression pattern was detected in normal cynomolgus monkey tissues (Tables 2 and 19), where B7-H4 was shown to be expressed in a limited number of tissues, with an expression pattern that is restricted towards ductal or tubular epithelium and primarily located on the apical luminal membrane and within cytoplasm. Representative images of immunohistochemical staining of B7-H4 in selected normal human and cynomolgus monkey tissues are shown in FIG. 30.

TABLE 18

Results of B7-H4 Expression in Human Normal Tissue Using Immunohistochemistry

| Tissue | Donor Number demonstrating B7-H4 IHC Staining | Relative proportion of Tissue demonstrating positive B7-H4 staining | Intensity[a] | Cellular Localisation | Details |
| --- | --- | --- | --- | --- | --- |
| Breast | 6/6 | <10% | +/+++ | Luminal m | Ductal epithelial cells |
| Epididymis | 3/3 | <5% | ++ | Luminal m | Luminal membrane in ducts |
| Fallopian Tube | 3/3 | <30% | ++/+++ | Luminal m | Ductal epithelial staining |
| Kidney | 11/11 | <5% | ++/+++ | Luminal m > c | Luminal membrane and some cytoplasmic staining in occasional tubules |
| Liver | 2/3 | 1% | +/++ | Luminal m | Luminal membrane of occasional small bile ducts |
| Lung - Bronchus | 7/7 | <20% | ++/+++ | Luminal m > c | Basal cells in bronchial epithelium and occasional ductal epithelium from bronchial glands |
| Oesophagus | 1/3 | 1% | + | Luminal m | Basolateral membrane of occasional epithelial cells in sub-mucosal glands |
| Ovary | 3/6 | 1% | +/++ | c > m | Individual mature oocyte showing granulosa cells |
| Pancreas | 8/8 | <5% | +/+++ | Luminal m | Luminal membrane and cytoplasm of centroacinar cells and luminal staining of intercalated ducts |
| Pituitary | 3/3 | <5% | ++/+++ | m > c | Occasional localised cells within Pars Intermedia cells showing staining of colloid in follicles and |

TABLE 18-continued

Results of B7-H4 Expression in Human Normal Tissue Using Immunohistochemistry

| Tissue | Donor Number demonstrating B7-H4 IHC Staining | Relative proportion of Tissue demonstrating positive B7-H4 staining | Intensity[a] | Cellular Localisation | Details |
|---|---|---|---|---|---|
| Prostate | 3/3 | <10% | ++/+++ | m > c | Rathke's Cleft epithelial cells Basal epithelial cells in some ducts |
| Seminal Gland | 3/3 | <10% | ++/+++ | Luminal m | Several ductular epithelial cells |
| Skin | 15/16 | <5% | ++/+++ | Luminal m | Membrane of occasional sweat gland duct epithelium, membrane of hair follicle epithelium |
| Ureter | 3/3 | <5% | +/++ | m > c | Cytoplasmic staining in some basal urothelial cells |
| Urinary Bladder | 8/8 | <10% | ++/+++ | Luminal m > c | Apical aspect of urothelial cells |
| All other tissues demonstrated no positive B7-H4 IHC staining | | | Adrenal, Aorta, Artery, Bone Marrow, Brain, Caecum, Colon, Duodenum, Eye, Heart, Ileum, Jejunum, Lung, Lymph Node, Nerve, Rectum, Salivary Gland, Skeletal muscle, Spinal cord, Spleen, Stomach, Testis, Thymus, Thyroid, Tongue, Vagina | | | c: cytoplasmic; m: membrane.
[a]All stained slides were reviewed and scored by a Pathologist assessing both the proportion of cells expressing B7-H4, the intensity of staining, and cellular localisation of staining. Intensity is reported as weak (+), moderate (++), or strong (+++).

Figure 31:
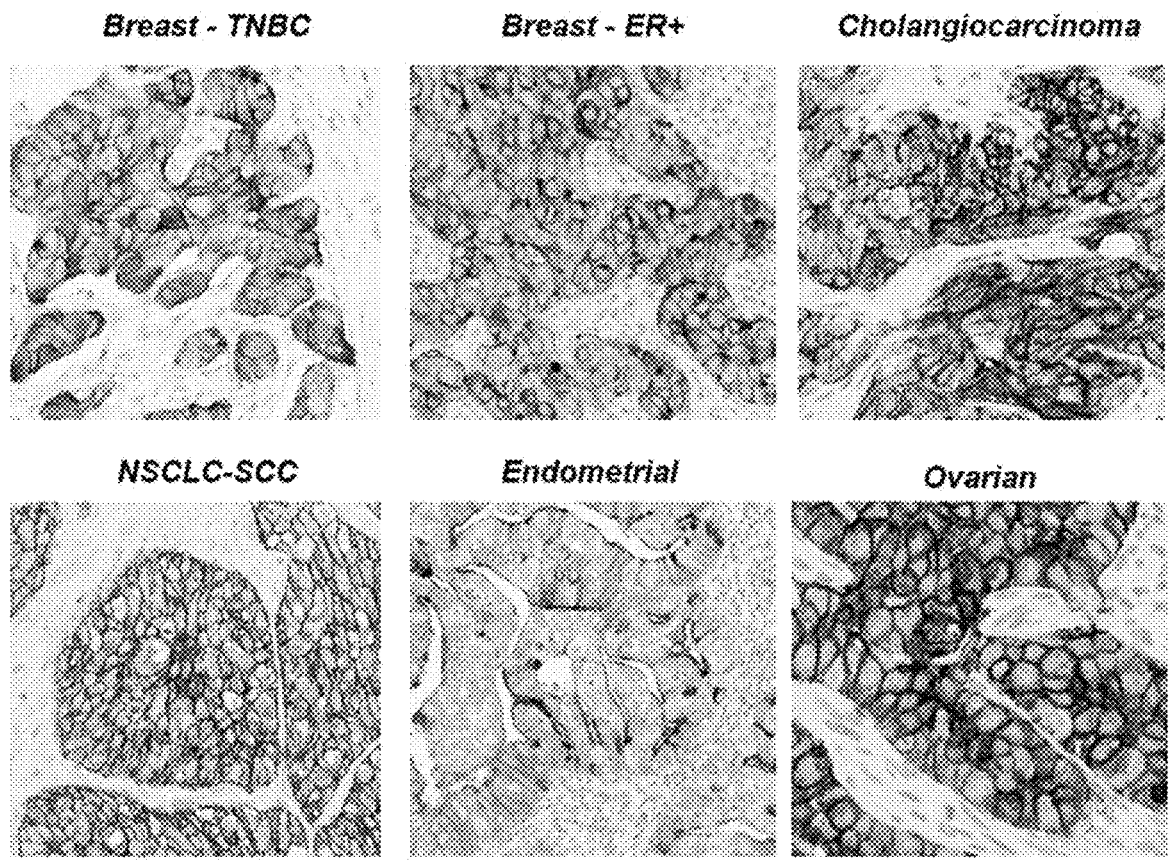
FIG. 31 shows example images of representative immunohistochemical staining of B7-H4 expression in human tumor tissues including breast (TNBC and ER+, see individual FIGS. 1A-1B), cholangiocarcinoma, NSCLC-SCC, endometrial and ovarian tumor.

B7-H4 expression was assessed in a range of human tumor tissues using IHC and scored by a pathologist. A summary of the human tumor tissue expression is detailed in Table 19, with representative images shown in FIG. 31.

TABLE 19

Results of B7-H4 Expression in Human Tumor Tissue Using Immunohistochemistry

| Tumor Indication | Proportion of Donors (%) with HIGH B7-H4+ tumors [a] | Proportion of Donors (%) with LOW B7-H4+ tumors [b] | Proportion of Donors (%) with Positive B7-H4+ tumors [c] | Total Proportion of Donors (%) with B7-H4+ tumors [d] | Total Number of Donors |
|---|---|---|---|---|---|
| Endometrial Adenocarcinoma | 42.4 | 45.5 | 6.1 | 93.9 | 66 |
| Breast (TNBC) | 28.8 | 35.1 | 12.6 | 76.6 | 111 |
| Breast (ER+) | 32.6 | 32.3 | 10.8 | 75.7 | 288 |
| Breast (HER2+) | 46.7 | 23.3 | 13.3 | 83.3 | 30 |
| Ovarian (Serous Papillary) | 49.3 | 28.0 | 6.7 | 84.0 | 75 |
| Cholangiocarcinoma | 33.3 | 30.3 | 21.2 | 84.8 | 66 |
| NSCLC-SCC | 15.0 | 27.5 | 23.5 | 66.0 | 153 |

[a] HIGH B7-H4: human tumor tissue samples containing 50% to 100% of B7-H4 positive cells.
[b] LOW B7-H4: human tumor tissue samples containing 5% to 49% of B7-H4 positive cells.
[c] Positive B7-H4: human tumor tissue samples containing 1% to 4% of B7-H4 positive cells.
[d] Indicates the proportion of human tumor tissue samples containing 1% to 100% of B7-H4 positive cells.

This example demonstrates that B7-H4 was expressed in many types of human cancers, including breast cancer, cholangiocarcinoma, endometrial carcinoma, non-small cell lung cancer squamous cell carcinoma, and ovarian serous carcinoma.

Example 27

Sequence Homology Comparison of Human B7-H4 with Orthologs in Cynomolgus Monkey, Rhesus Monkey, Mouse, and Rat Amino acid sequences for human B7-H4 were identified and aligned to orthologs in cynomolgus monkey, rhesus monkey, mouse and rat. Percentage identity was calculated based on the results of these alignments. B7-H4 is well conserved among non human primates; human B7-H4 (hB7-H4) shares 98% and 99% sequence identity for both full-length and extracellular domain regions, respectively, in both cynomolgus monkey (cyB7 H4) and rhesus monkey (rhB7-H4) (FIG. 32). Rodent species are less conserved; mouse and rat B7-H4 share 87% and 86% sequence identity with hB7-H4 for full length B7-H4, respectively, and 90% and 89% sequence identity in the extracellular domain with hB7-H4, respectively.

This example demonstrates that the high amino acid sequence identity in B7-H4 across human and non-human primates suggests that E02-GL-SG3932 is likely to bind to cynomolgus monkey and rhesus monkey B7-H4. In contrast, the amino acid identity comparison between human, mouse and rat B7-H4 is lower, indicating that binding of E02-GL-SG3932 to murine or rat B7-H4 is less likely.

Example 28

E02-GL-SG3932 Stability after Fifteen Days Incubation in Mouse, Rat, Cynomolgus Monkey, and Human Serum ADCs bearing drug linked to cysteines via a thiosuccinimide are known to exhibit some drug loss in physiological milieu due to the retro-Michael reaction. This process regenerates the cysteine used for conjugation and the maleimide-bearing drug, thus reducing the DAR of the ADC over time. This deconjugation process is a known property of ADCs containing drug linked to antibodies through thiosuccinimides.

The stability of E02-GL-SG3932 in cynomolgus monkey, mouse, and rat serum was evaluated using immunoprecipitation followed by reduced reverse phase mass spectrometry (rLCMS). Measurements indicate that less than 20% drug loss occurs from E02-GL-SG3932 after incubation in mouse, rat and cynomolgus monkey serum, with 84.5%, 83.5% and 82.0% of SG3924 remaining attached to E02-GL-SG3932 at day 15 in mouse, rat, and cynomolgus monkey serum samples, respectively. The stability of E02-GL-SG3932 in human serum was evaluated by immunocapture using human B7-H4 coated resin, followed by rLCMS. Measurements indicate that drug loss after incubation in human serum was modest, with 81% of SG3924 remaining attached to E02-GL-SG3932 at day 15.

This example indicates the mechanism of drug release is deconjugation through the retro-Michael reaction and not linker cleavage, consistent with other ADCs prepared by maleimide conjugation to cysteine amino acids involved with interchain disulfides.

Example 29

Binding Affinity of Antibody Intermediate E02-INT Fab for Recombinant B7-H4 Antigens The binding affinity of anti-B7-H4 antibody E02-INT Fab for recombinant human, cynomolgus monkey, and mouse B7-H4 variants were determined by surface plasmon resonance (SPR). The dissociation constant ($K_D$) values, shown in Table 20, demonstrate that E02-INT Fab binds to immobilized human and cynomolgus B7-H4 with similar affinities. In contrast, the affinity of E02-INT Fab for mouse B7-H4 antigen is approximately 100-fold lower than for human B7-H4 antigen.

TABLE 20

Binding Affinity of Anti-B7-H4 Antibody Intermediate E02-INT Fab to Human, Cynomolgus Monkey and Mouse B7-H4 Determined by SPR

| Species | $K_D$ |
|---|---|
| Human | 3.70 nM |
| Cynomolgus Monkey | 3.94 nM |
| Mouse | 405 (±15) nM |

Fab: antigen binding fragment

Example 30

Binding Affinity of E02-GL-SG3932 for Human FcRn and Fcγ Receptors

The binding affinity of E02-GL-SG3932 to human FcRn and Fcγ receptors was assessed by SPR. The steady state binding affinity ($K_D$) of human FcRn to E02-GL-SG3932 is 4360 nM. The equilibrium KD of E02-GL-SG3932 to huFcγ RI was 4.35 nM. The equilibrium $K_D$ of E02-GL-SG3932 to huFcγ RIIa, huFcγ RIIb, huFcγ RIIIA-158V, and huFcγ RIIIA-158F ranged from 3307 to 21640 nM.

Example 31

Figure 33:
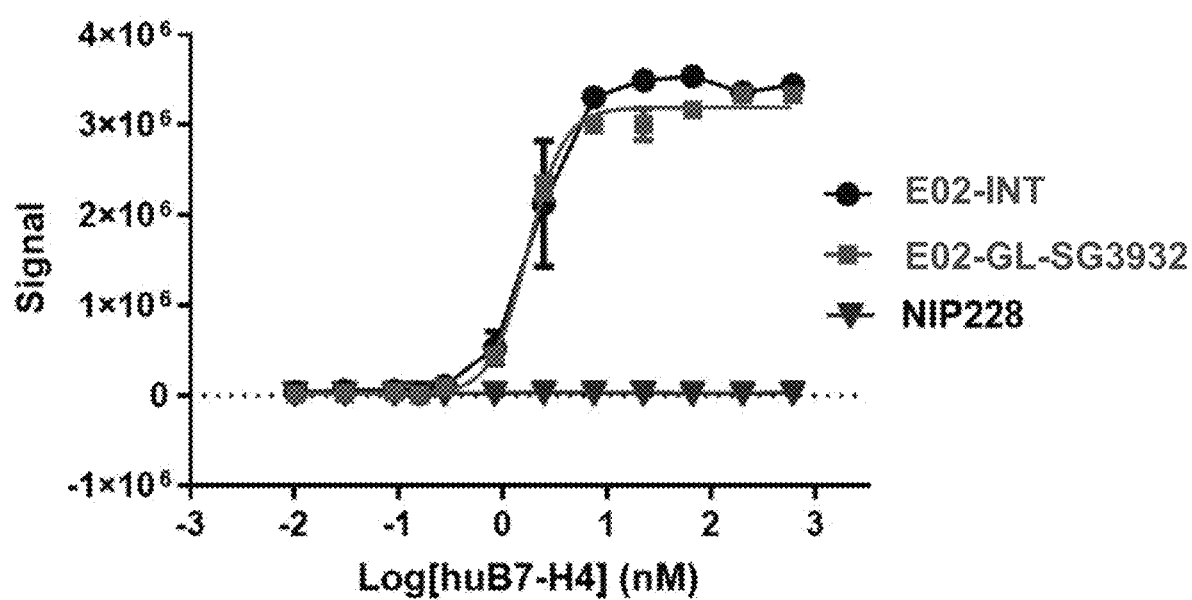
FIG. 33 shows binding of antibody intermediate E02-INT and E02-GL-SG3932 to human B7 H4 by DELFIA-ELISA method and anti-human IgG (H+L). E02-INT: antibody intermediate of E02-GL-SG3932; NIP228: isotype-matched control; huB7-H4: recombinant human B7-H4.

Comparative Binding Affinity of Antibody Intermediate E02-INT and E02-GL-SG3932 for Recombinant Human B7-H4 Antigen To assess whether conjugation of the topoisomerase 1 linker-warhead affected binding properties of the E02-INT antibody, the binding affinity of E02-INT and E02-GL-SG3932 were measured using a DELFIA-ELISA method and an SPR method. As shown in FIG. 33, results from the DELFIA-ELISA assay indicate that E02-INT and E02-GL-SG3932 bind similarly to immobilized recombinant human B7-H4, with EC50 values of 1.98 nM and 1.71 nM, respectively. The kinetic rate constants ($k_{on}$ and $k_{off}$) and equilibrium dissociation constants ($K_D$) of E02-INT and E02-GL-SG3932 for human B7-H4 antigen was also determined by SPR, using an antibody capture method. As shown in Table 21, E02-INT and E02-GL-SG3932 bind similarly to human B7-H4 with KD values of 31.1 nM and 29.3 nM, respectively.

TABLE 21

Binding Affinity of Antibody Intermediate E02-INT
and E02-GL-SG3932 to Human B7-H4 Determined by SPR

| Species | $K_a$ (M$^{-1}$s$^{-1}$) | $K_d$ (s$^{-1}$) | $K_D$ (nM) | $R_{max}$ (RU) |
|---|---|---|---|---|
| E02-INT | 9.38 × 10$^4$ | 2.92 × 10$^{-3}$ | 31.1 | 56.8 |
| E02-GL-SG3932 | 9.55 × 10$^4$ | 2.80 × 10$^{-3}$ | 29.3 | 49.7 |

RU: resonance unit

The results for Examples 30 and 31 show that binding properties of the E02-INT antibody are maintained after conjugation to the topoisomerase 1 linker-warhead.

Example 32

Cellular Binding of Antibody Intermediate E02-INT to Engineered HEK 293 Cells Expressing Human, Cynomolgus Monkey, or Mouse B7-H4

Figure 34:
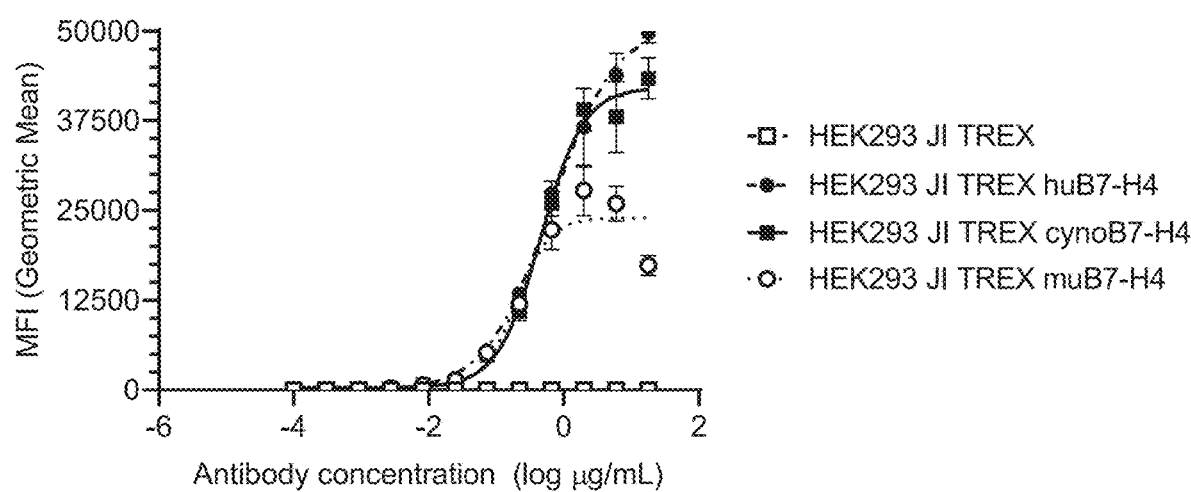
FIG. 34 shows binding of antibody intermediate E02-INT to HEK 293 cells stably expressing human, murine, or cynomolgus monkey B7-H4. E02-INT: antibody intermediate of E02-GL-SG3932; HEK293 JI TREX: non-transduced HEK293 JI TREX cells; HEK293 JI TREX cynoB7-H4: HEK 293 cells stably expressing cynomolgus monkey B7-H4; HEK293 JI TREX huB7-H4: HEK 293 cells stably expressing human B7-H4; HEK293 JI TREX muB7-H4: HEK 293 cells stably expressing murine B7-H4; MFI: mean fluorescence intensity. The y-axis is the mean fluorescence intensity geometric mean. Data are presented as the average of triplicate determinations±SD.

Flow cytometry was used to measure binding of antibody E02-INT to non-transduced HEK 293 Jump In TREX cells and to HEK 293 Jump In TREX cells stably expressing human, murine, or cynomolgus monkey B7-H4. Antibody E02-INT bound to HEK 293 Jump In TREX cells stably expressing human, murine and cynomolgus monkey B7-H4 but did not bind to the B7-H4-negative non-transduced HEK 293 Jump In TREX cells (FIG. 34). Binding to HEK 293 Jump In TREX cells expressing murine B7-H4 was reduced compared to cells expressing human or cynomolgus monkey B7-H4.

Example 33

Cellular Binding of Antibody Intermediate E02-INT and E02-GL-SG3932 to Human Breast Cancer Cell Lines and to HT29 Cells Stably Expressing Human B7-H4

Figure 35:
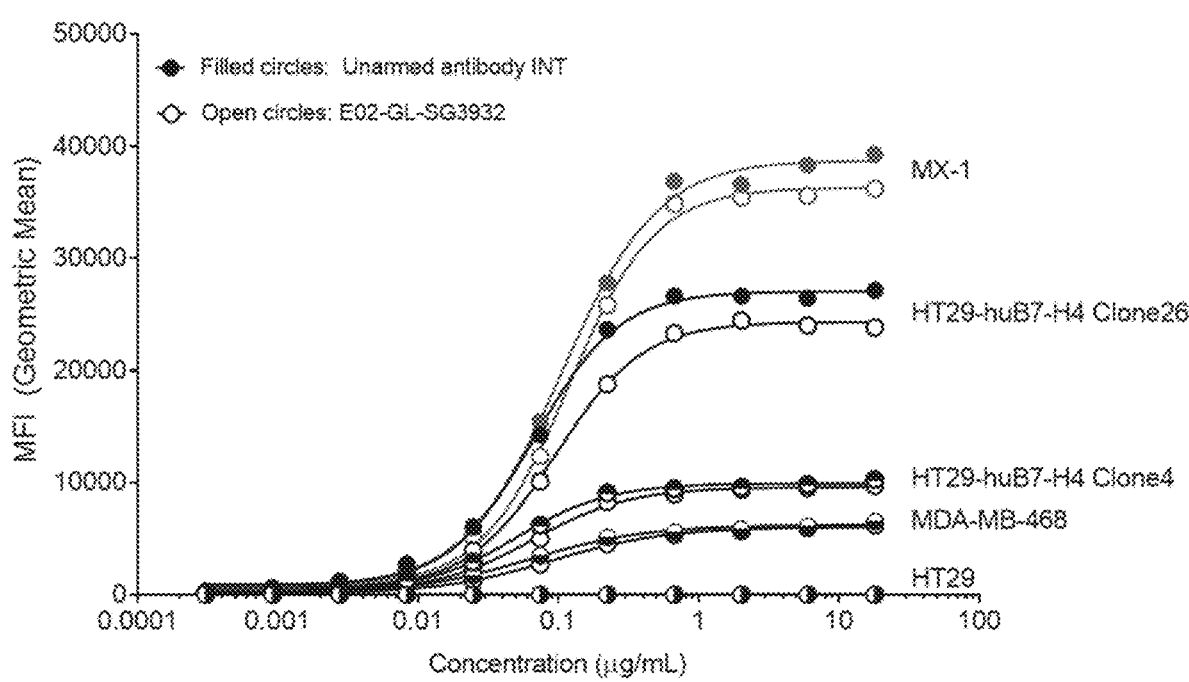
FIG. 35 shows binding of antibody intermediate E02-INT and E02-GL-SG3932 to human breast cancer cell lines and to HT29 cells stably expressing human B7-H4. E02-INT: antibody intermediate of E02-GL-SG3932; HT29-huB7-H4 Clone 4 and HT29-huB7-H4 Clone 26: HT29 cells stably expressing human B7-H4; MFI: mean fluorescence intensity. The y-axis is the mean fluorescence intensity geometric mean.

Flow cytometry was used to measure binding of antibody E02-INT and E02-GL-SG3932 to the human breast cancer cell lines MX-1 and MDA-MB-468, and to engineered HT29 colon cancer cells stably expressing human B7-H4. As shown in FIG. 35, E02-INT and E02-GL-SG3932 bound similarly to HT29 cells stably expressing human B7-H4 (HT29-huB7-H4 Clone 4 and HT29-huB7-H4 Clone 26) but did not bind to the B7-H4-negative non-transduced HT29. E02-INT and E02-GL-SG3932 also bound to MX-1 and MDA-MB-468 cells, demonstrating that the antibody intermediate and ADC can recognize endogenously-expressed B7-H4 in human cancer cell lines. The binding of E02-INT and E02-GL-SG3932 was comparable, Examples 32 and 33 demonstrate that the cellular binding properties of the parental antibody are maintained after conjugation to the topoisomerase 1 linker-warhead.

Example 34

In-Vitro Cytotoxicity of E02-GL-SG3932

The effect of E02-GL-SG3932 treatment on cell viability was determined using a target-negative human colon cancer cell line HT29, the engineered human colon cancer cell line HT29-huB7-H4 Clone 26, and a human breast cancer cell line, MX-1, using a CellTiter-Glo assay. As shown in FIG. 36, E02-GL-SG3932 was cytotoxic to the B7-H4 expressing HT29-huB7-H4 Clone 26 and MX-1 cells, with an IC50 value of 0.036 µg/mL and 0.029 µg/mL, respectively. In contrast, no difference in activity was observed between E02-GL-SG3932 and the isotype-matched control ADC (NIP228-SG3932) in the B7-H4 negative HT29 cell line, suggesting that E02-GL-SG3932 can specifically kill cancer cells expressing human B7-H4.

Example 35

In-Vitro Cytotoxicity of E02-GL-SG3932

Figures 36A, 36B, 36C:
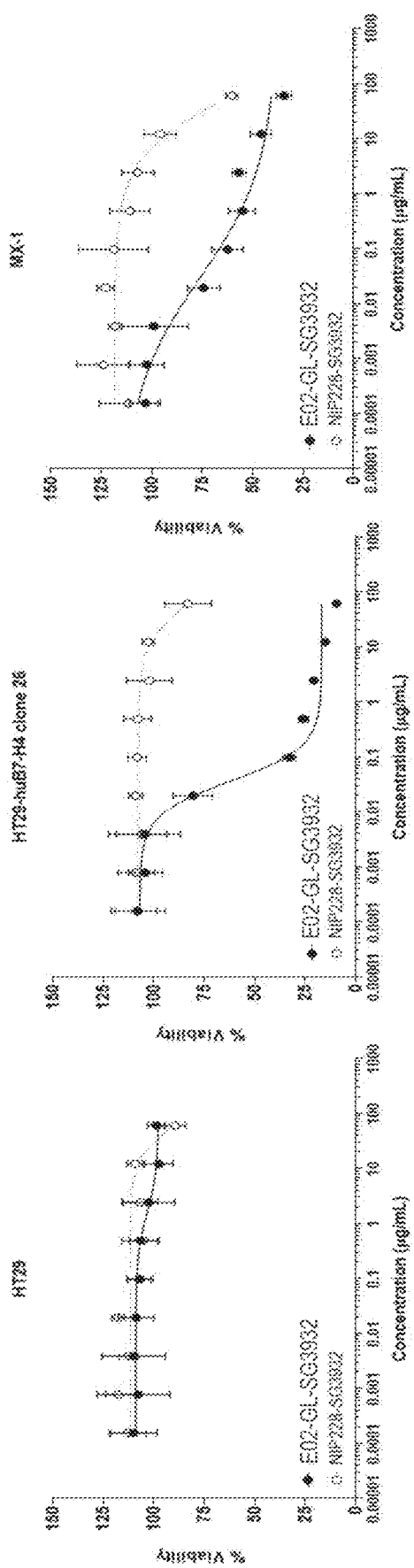
FIGS. 36A-36C show the in vitro cytotoxic activity of E02-GL-SG3932 in cell lines HT29, HT29-huB7-H4 Clone 26, and MX-1. Data are presented as the average of triplicate determinations±SD.

When IgG antibodies bind cell surface antigens via their Fab domains, the Fc portion of the antibodies can engage with FcγRIIIa on natural killer cells. The interaction of the Fc domain with FcγRIIIa induces cross-linking of the FcγRs, which triggers the release of cytotoxic granules containing perforin and granzymes, leading to the death of the target cell, a process called antibody-dependent cellular cytotoxicity (ADCC). The potential of antibody E02-INT and E02-GL-SG3932 to initiate ADCC activity was evaluated utilizing isolated primary human NK cells and the human breast cancer SKBR3 cell line as the target cell. In this assay, both E02-INT and E02-GL-SG3932 yielded a significant increase in ADCC activity beyond untreated co-cultured cells (FIGS. 36A-36C). E02-GL-SG3932 activity is slightly reduced when compared to E02-INT, however this difference is not statistically significant, suggesting that E02-INT and E02-GL-SG3932 can elicit ADCC activity in vitro.

Figure 37:
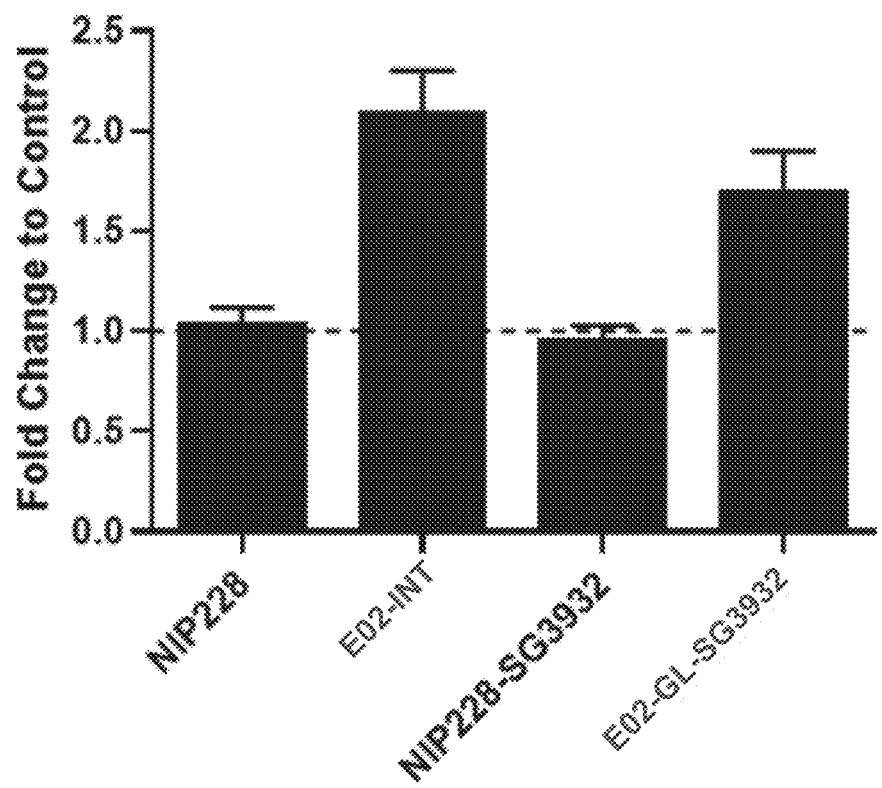
FIG. 37 shows in vitro antibody-dependent cell-mediated cytotoxicity activity of E02-GL-SG3932. The graph displays mean fold change±SEM of six experiments.

Next, human breast cancer SK-BR-3 cells were co-cultured with NK cells isolated from six healthy donors in the presence of 1 µg/mL E02-GL-SG3932, antibody intermediate E02-INT, isotype-matched control antibody NIP228, and the isotype-matched control ADC NIP228-SG3932 (FIG. 37). ADCC activity was evaluated by Incycte® Annexin V Dye binding of extracellular surface exposure of phosphatidyl serine on apoptotic cells, yielding a bright and stable red fluorescent signal. The fold-change was based on maximum cell death of non-drug treated NK/SK-BR-3 co-cultured cells. Maximum cell death was calculated by dividing the average red objects in experimental wells by the average maximum cell death in Staurosporine treated SK-BR-3 cells.

Example 36

Internalization and Lysosomal Trafficking of Antibody E02-INT

Figure 38:
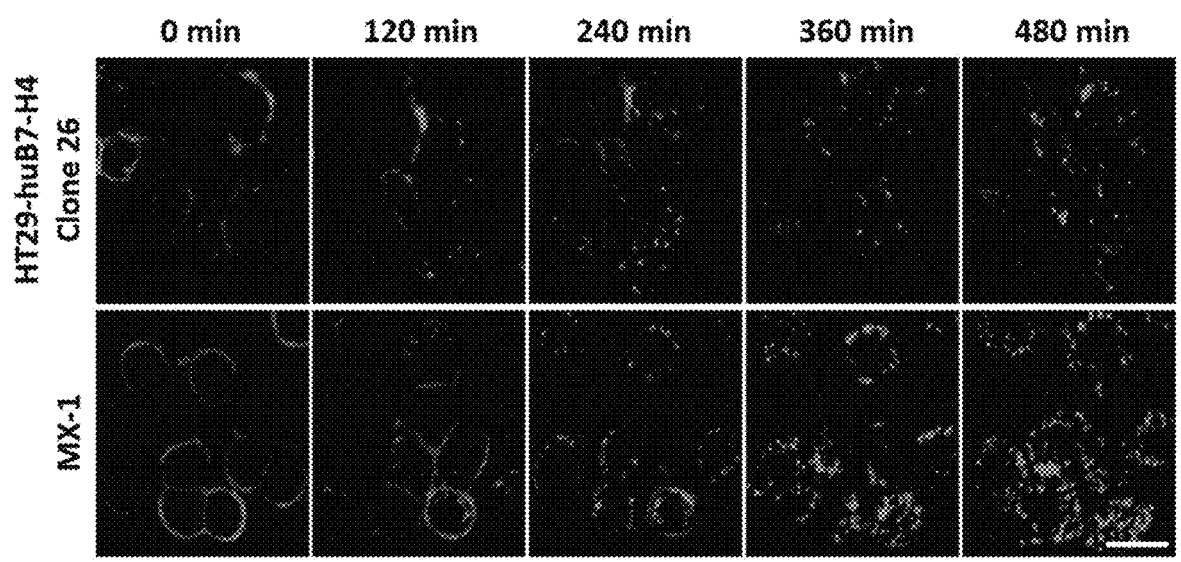
FIG. 38 shows the time course of E02-INT internalization presented as an image sequence. Human colon cancer cells HT29-huB7-H4 Clone 26 (1st row) and human breast cancer cells MX-1 (2nd row) are labelled with 5 μg/mL E02-INT conjugated with Alexa Fluor™ 568 (red). The scale bar is 20 μm.
Figure 39A:
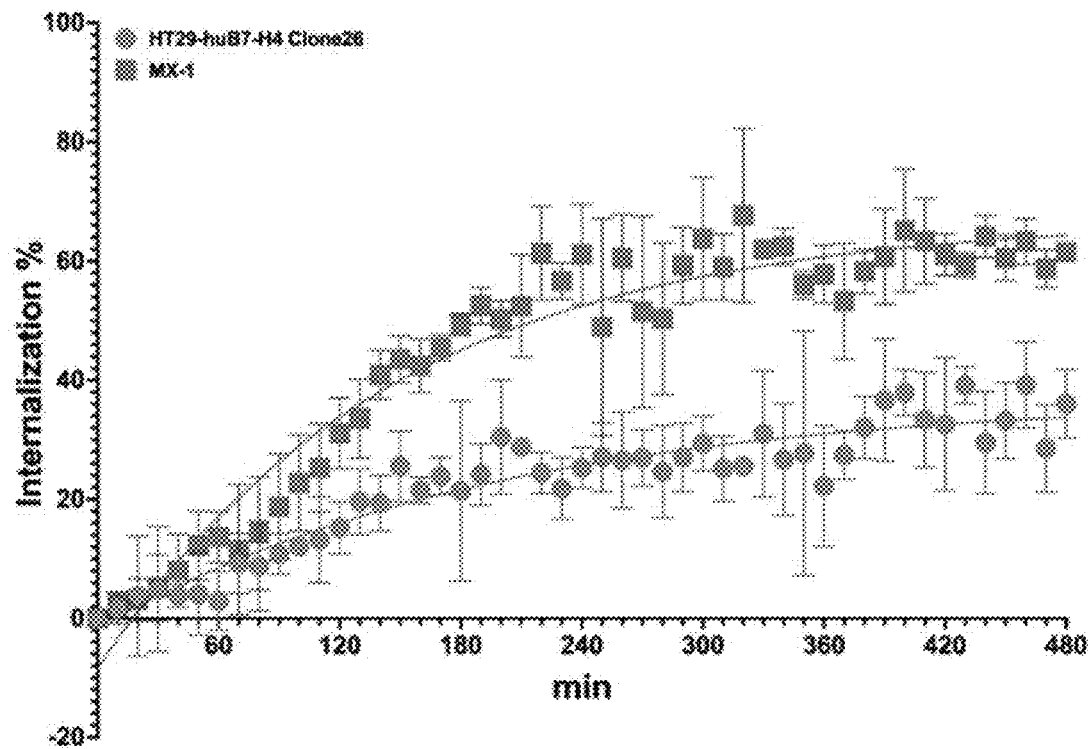
FIGS. 39A-39C show live cell imaging of E02-INT internalization in the human cancer cell lines HT29-huB7-H4 clone 26 and MX-1. (A) Each point represents mean internalization percentage±standard deviation of 3 independent wells at 10 minute intervals for 480 minutes. (B) Internalization percentage after 8 hours and (C) The predicted half-life from 3 independent wells is shown. These values were derived using the Dissociation—One phase exponential decay equation. Horizontal bars indicate intragroup arithmetic mean; Statistic significance was evaluated by one-way ANOVA, Tukeys multiple comparison test. ns: not significant, p>0.05; ** p<0.05.
Figure 39B:
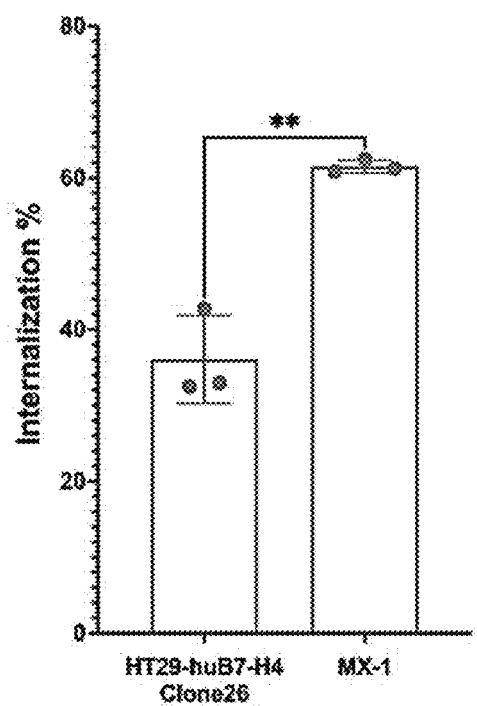
Figure 39C:
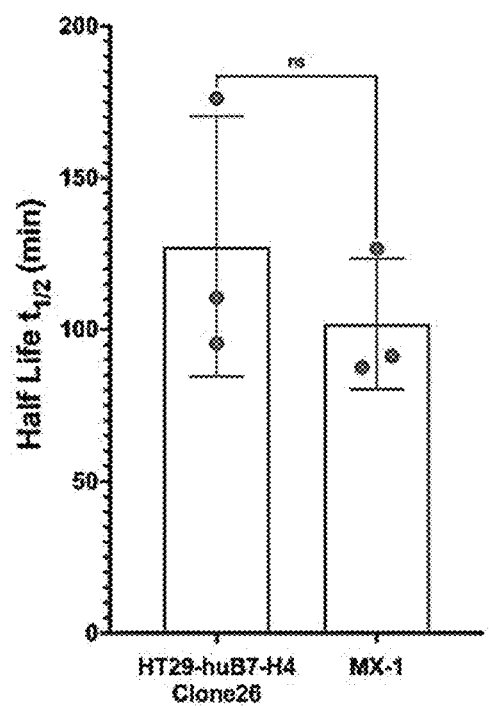

The internalization and intracellular trafficking properties of antibody E02-INT was evaluated using a quantitative live cell imaging assay in MX-1 human breast cancer cells and HT29 huB7-H4 Clone 26 human colon cancer cells overexpressing B7-H4. Time-lapse sequence images showed that in both human breast cancer (MX-1) and colon cancer (HT29-huB7-H4 Clone 26) cell lines, intense E02-INT membrane signal persists from 0 minutes to 120 minutes, with increased internalization of E02-INT by 240 minutes (FIG. 38, FIG. 39A and FIG. 39B). Measurement of internalization kinetics across two cell lines showed internalization half-life of 127 (±35 SD) minutes and 102 (±18 SD) minutes for the HT29-huB7-H4 Clone 26 and MX-1 cells, respectively (FIG. 39C).

Figures 40A, 40B:
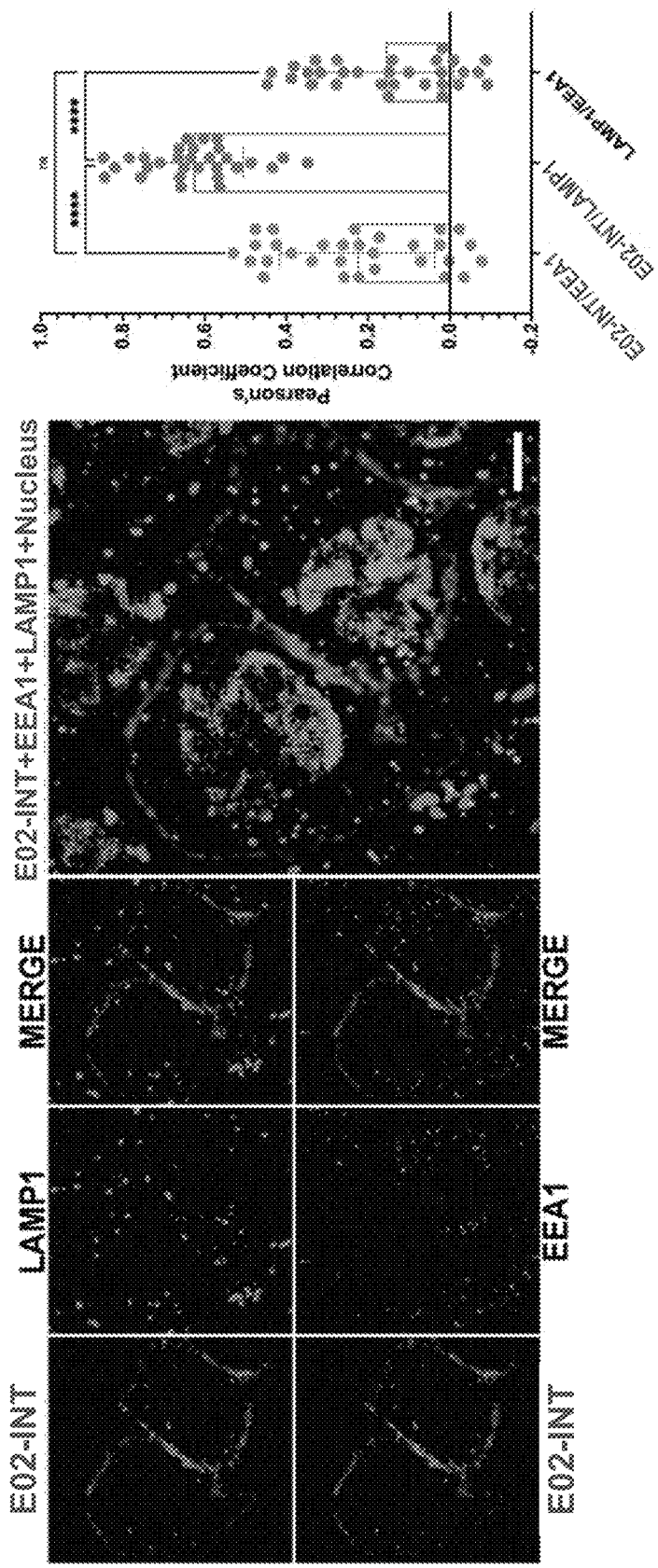
FIGS. 40A-40B show that antibody E02-INT colocalizes with lysosomes in HT29-huB7-H4 Clone 26 Cells. (A) HT29-huB7-H4 Clone 26 cells were incubated for 24 hours with 5 μg/mL E02-INT conjugated with Alexa Fluor™ 568 antibody [(A) red—top and bottom left]. Lysosomes were stained with mouse anti-human LAMP1-Alexa Fluor™ 488 antibodies [(A) green—top middle]. Endosomes were stained with rabbit anti-human EEA1 antibodies and detected with goat anti-rabbit IgG1-DyLight™ 650 [(A) green—bottom middle]. Colocalization of E02-INT with LAMP1 or EEA1 is shown in merged images. (B) Colocalization of E02-INT with EEA1 and LAMP1 analysed by Pearson's correlation coefficient using Zeiss Zen software. Each spot represents single cell measurement. Statistical significance was evaluated by one-way ANOVA, Tukeys multiple comparison test. ns: not significant, p>0.05; **** p<0.0001.

Confocal microscopy was used to determine intracellular trafficking of E02-INT by measuring co-localization with the early endosomal marker, Early Endosome Antigen 1 (EEA1) and the lysosomal marker, lysosomal-associated membrane protein 1 (LAMP1). As shown in FIG. 40, E02-INT was enriched in the LAMP1 decorated subcellular compartment with limited colocalization with EEA1, indicating that after internalization, E02-INT is trafficked to the lysosomal compartment of cells.

Example 37

In Vitro Activation of DNA Damage Response Signaling by E02-GL-SG3932 and SG3924

Figure 41:
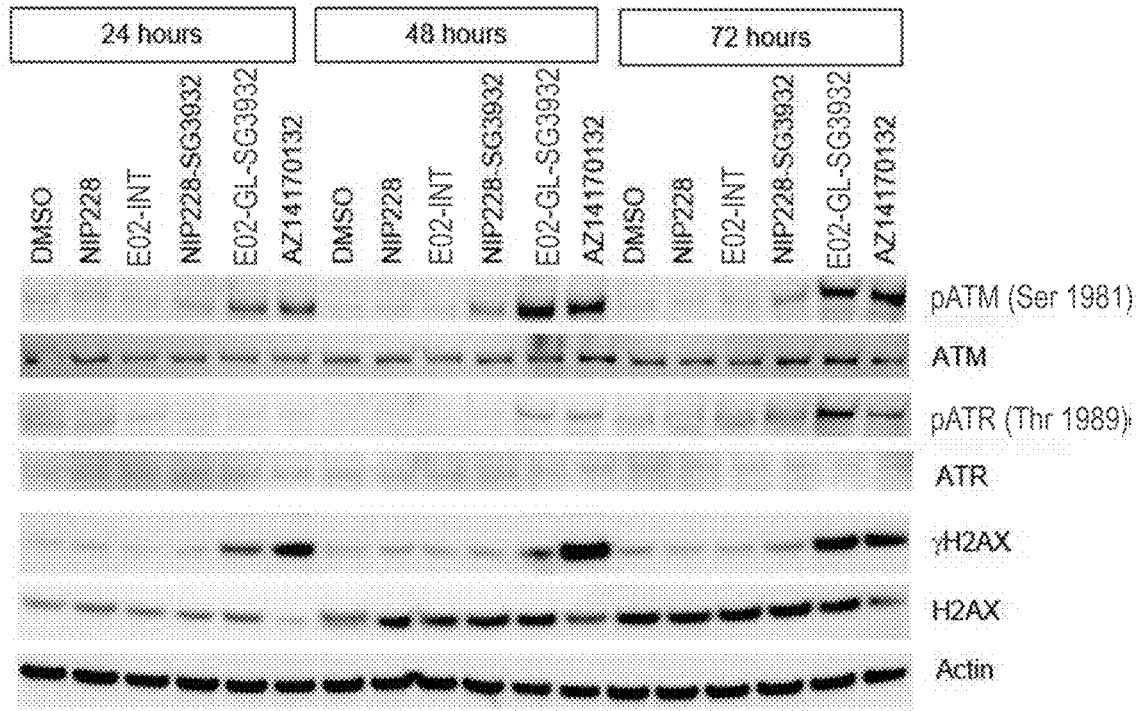
FIG. 41 is a picture of a gel showing DNA damage response signaling in MX-1 Cells treated with E02-GL-SG3932 or the TOP1i warhead SG3924. Data presented is a representative of n: 2 experiments.

Western blotting was used to evaluate DDR pathway activation in the MX-1 human breast cancer cell line and the engineered colon cancer cell line HT29-huB7-H4 Clone 26 following treatment with either E02-GL-SG3932 or its TOP1i warhead, SG3924. As shown in FIG. 41, treatment of MX-1 cells with either 10 µg/mL E02-GL-SG3932 or 10 nM SG3924 resulted in activation of the ATM signalling pathway, evident by an increase in phosphorylation of ATM (Ser 1981) as early as 24-hours and persisting over the 72-hour treatment period. Similarly, E02-GL-SG3932 and SG3924 induced activation of ATR (Thr 1989 phosphorylation), observed at the 48-hour and 72-hour timepoint. An increase in γH2AX was observed following treatment after 24 hours and persisting through the 72-hour treatment period, indicating DNA damage.

Figure 42:
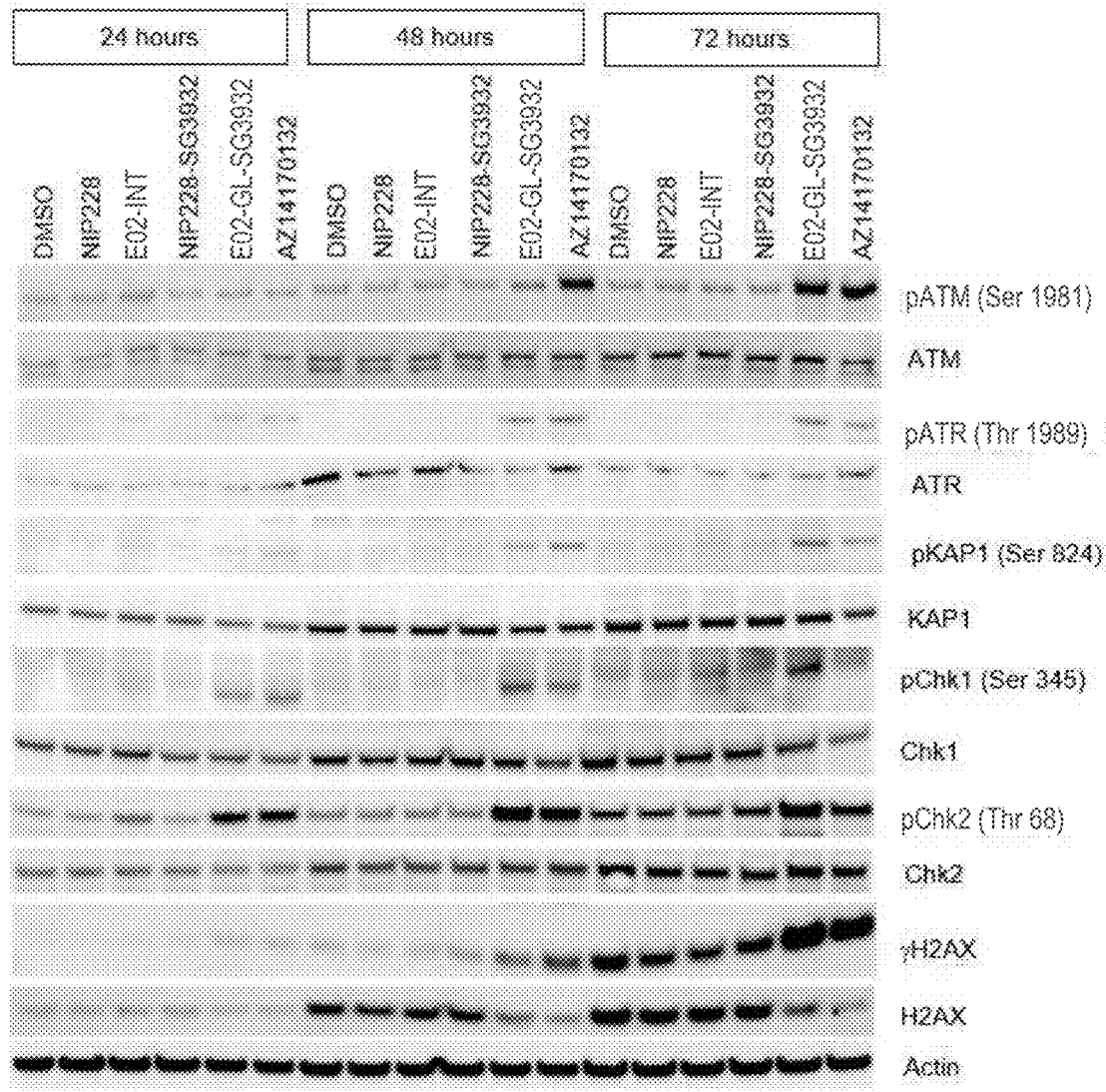
FIG. 42 is a picture of a gel showing DNA damage response signaling in HT29-huB7-H4 cells treated with E02-GL-SG3932 or the TOP1i Warhead SG3924. Data presented is a representative of n: 2 experiments.
Figure 44A:
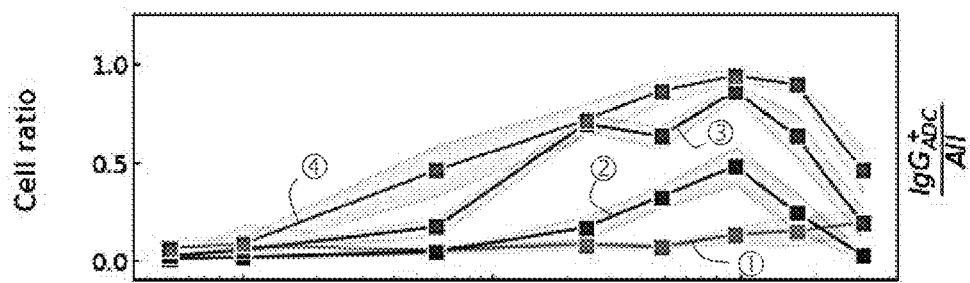
FIGS. 44A-44D show image analysis data of human IgG, γH2AX and cleaved Caspase-3 IHC staining across all timepoints and treatments in the HT29 huB7 H4 clone 26 xenograft study. Top panel (44A): Epithelial cell analysis, showing the change in the fraction of human IgG-positive epithelial cells from all epithelial cells over time. Second panel (44B): γH2AX analysis, showing the fraction of epithelial cells found positive for foci in the γH2AX assay. Third panel (44C): Cleaved caspase 3 (CC-3), showing the percent of cleaved caspase-3-positive tumor cells in the samples over time. Bottom panel (44D): Cell density of all epithelial cells in the sample over time, indicating cell death resulting from E02-GL-SG3932 treatment compared to the isotype-matched control ADC NIP228-SG3932.
Figure 44B:
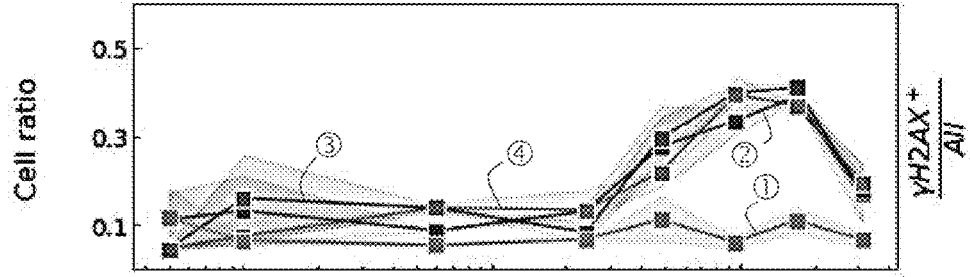
Figure 44C:
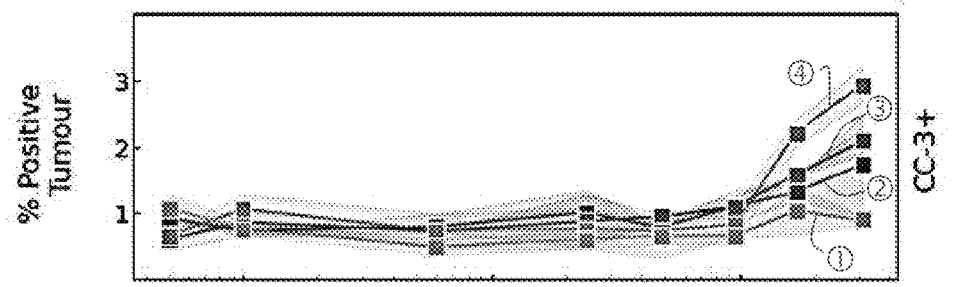
Figure 44D:
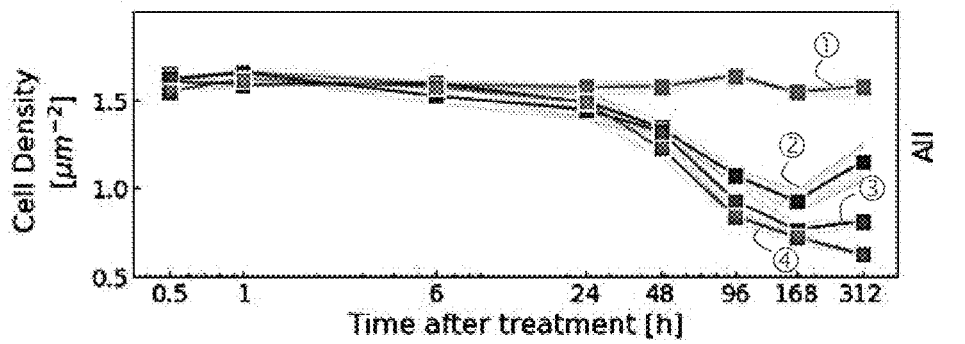

The effect of E02-GL-SG3932 or its TOP1i warhead on DDR signalling was also examined in the colorectal cancer cell line HT29-huB7-H4 Clone 26, engineered to express B7-H4. As shown in FIG. 42, treatment with either 10 µg/mL E02-GL-SG3932 or 10 nM SG3924 resulted in an activation of the DDR signalling pathway, evidenced by an increase in phosphorylation of ATR (Thr 1989), its downstream target Chk1 (Ser 345) and Chk2 (Thr 68). This increase in phosphorylation persisted over the 72-hour treatment period. Similarly, activation of ATM (Ser 1981) and its downstream target KAP1 (Ser 824), was observed after treatment with E02-GL-SG3932 and TOP1i warhead at the 48-hour and 72-hour timepoint. An increase in γH2AX was observed following treatment after 48 hours and persisting through the 72-hour treatment period, indicating DNA damage.

Taken together, these results confirmed, in two different cell lines, that E02-GL-SG3932 activates a DDR pathway consistent with the mechanism of action of its TOP1i warhead.

In Vivo Studies

The in vitro studies demonstrated the ability of E02-GL-SG3932 to bind to human and cynomolgus monkey B7-H4 with similar affinity, that E02-GL-SG3932 specifically binds, and is cytotoxic to, B7-H4 expressing tumor cells and could elicit modest ADCC activity in an isolated primary NK cell co-culture assay, that the antibody intermediate of E02-GL-SG3932 (E02-INT) is internalized into tumor cells, and is trafficked to the lysosomal compartment, and that treatment with E02-GL-SG3932 or its TOP1i warhead activates the DDR signaling pathway in B7-H4 expressing cell lines. To further elucidate the mechanism of action of E02-GL-SG3932 and determine if these in vitro findings translate into antitumor activity, in vivo mouse models were employed.

Example 38

Pharmacodynamic Study of E02-GL-SG3932 in the HT29-huB7-H4 Clone 26 Xenograft Model Pharmacodynamic effects following E02-GL-SG3932 treatment were evaluated in a human tumor xenograft mouse model using immunodeficient CB-17 SCID mice. Animals were inoculated subcutaneously (SC) with the human colon cancer cell line HT29-huB7-H4 Clone 26, engineered to express human B7-H4 and after tumors grew in volume to approximately 250 to 300 mm3, animals were randomized and each mouse received an IV injection of either E02-GL-SG3932 or control articles. Tumors were collected at designated timepoints, fixed in 10% neutral buffered formalin and subsequently processed and embedded into paraffin blocks. IHC and image analysis techniques were used to examine human IgG, γH2AX foci, cleaved caspase-3, and epithelial cell density in tumor samples over time. Representative IHC images of human IgG, γH2AX, and cleaved caspase-3 in tumors collected 168 hours after a single IV administration of 7 mg/kg E02-GL-SG3932 or isotype-matched control ADC NIP228 SG3932 are shown in FIGS. 43A-43F.

As shown in FIGS. 44A-44D, dose-dependent accumulation of E02-GL-SG3932 was observed in tumor cells over time, as visualized by a human IgG IHC assay. Accumulation of E02-GL-SG3932 correlated with increased positive staining for γH2AX foci, signifying induction of DNA damage. Elevated cleaved caspase-3 and an overall decrease in epithelial cell density were observed over time in E02-GL-SG3932-treated tumors compared to the control.

Taken together, these data suggest that E02-GL-SG3932 binds to B7-H4 on tumor cells, causing DNA damage and apoptotic cell death.

Example 39

Antitumor Efficacy of E02-GL-SG3932 in Subcutaneous Human Breast and Colon Cancer Xenograft Models In Vivo Efficacy, PDX The antitumor activity of antibody intermediate E02-INT and E02-GL-SG3932 was investigated in human tumor xenograft mouse models using immunodeficient CB-17 SCID mice.

HT29 or HT29-huB7-H4 Clone 26 Xenograft Models

Figure 45A:
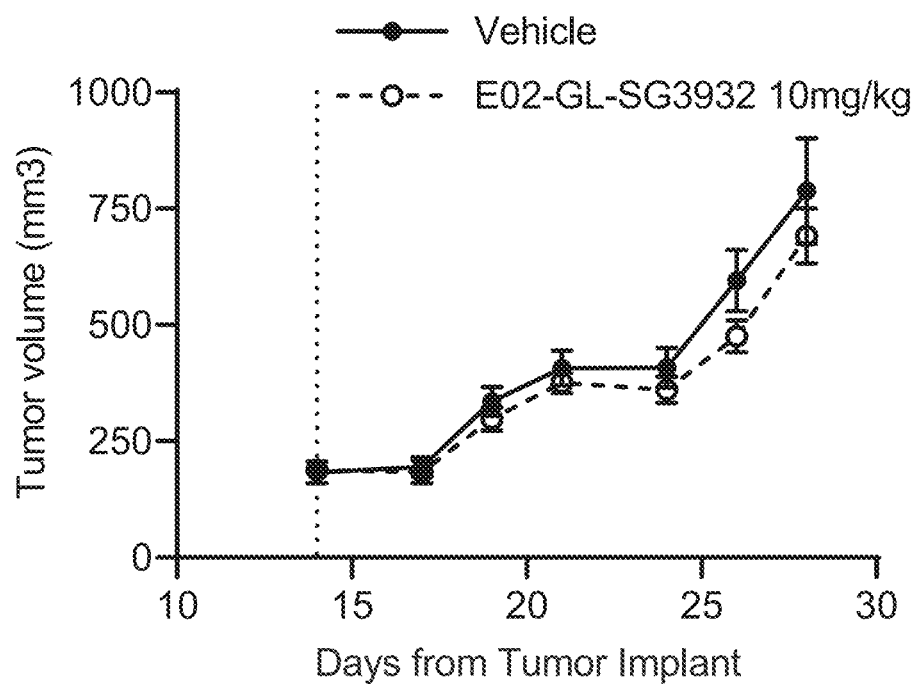
FIGS. 45A-45B show E02-GL-SG3932 efficacy in the B7-H4 negative HT29 xenograft model (See also FIG. 11). Values are mean±SEM tumor volumes for n: 8 animals per group. Dotted line denotes the day of dosing.
Figure 45B:
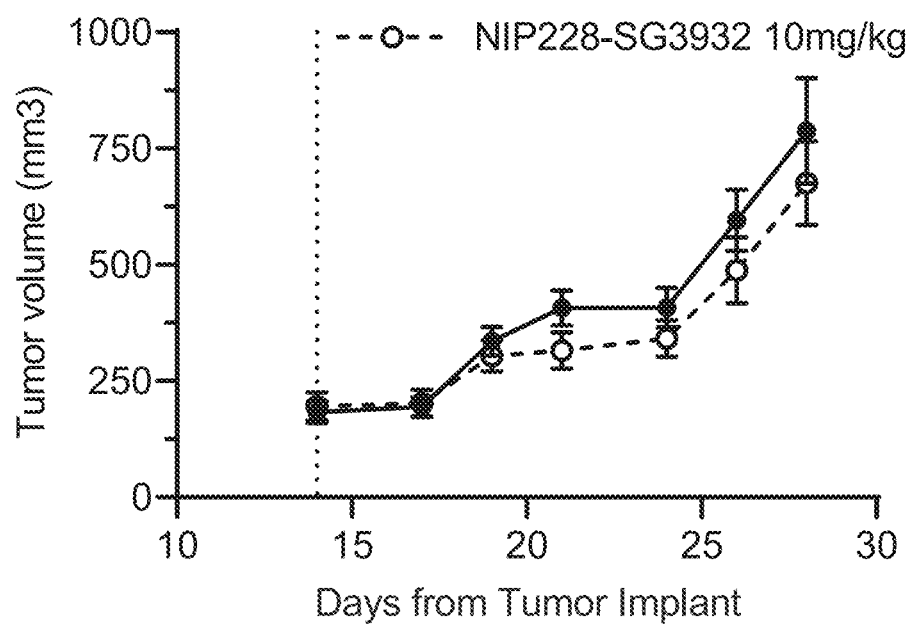
Figure 46A:
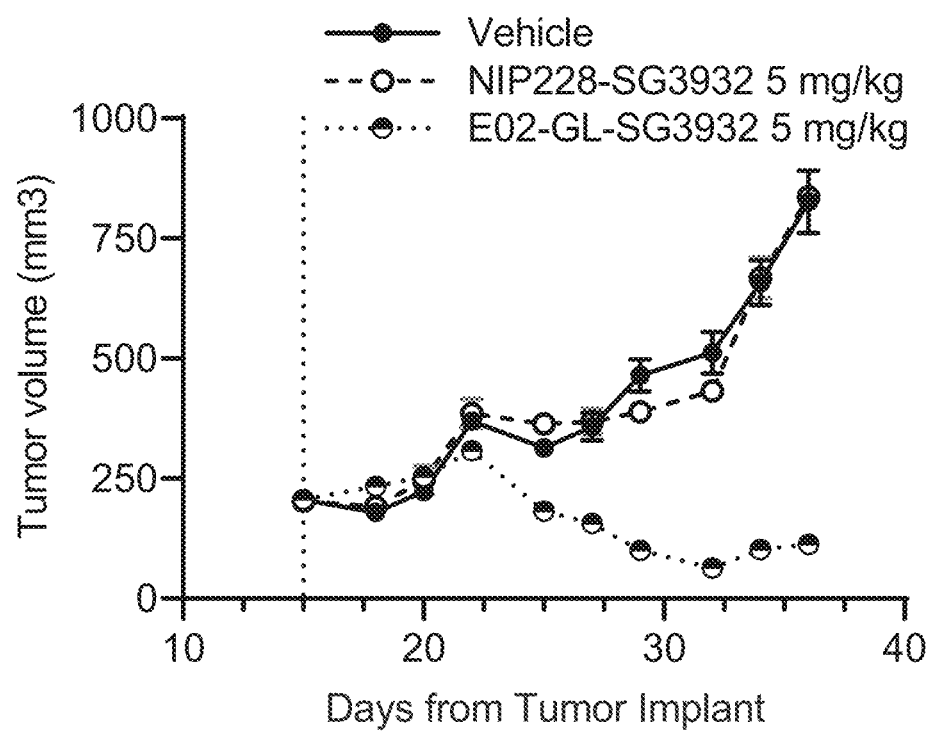
FIGS. 46A-46C show E02-GL-SG3932 efficacy in the HT29-huB7-H4 clone 26 xenograft model. Values are mean±SEM tumor volumes for n: 10 or 8 animals per group. Dotted line denotes the day of dosing.
Figure 46B:
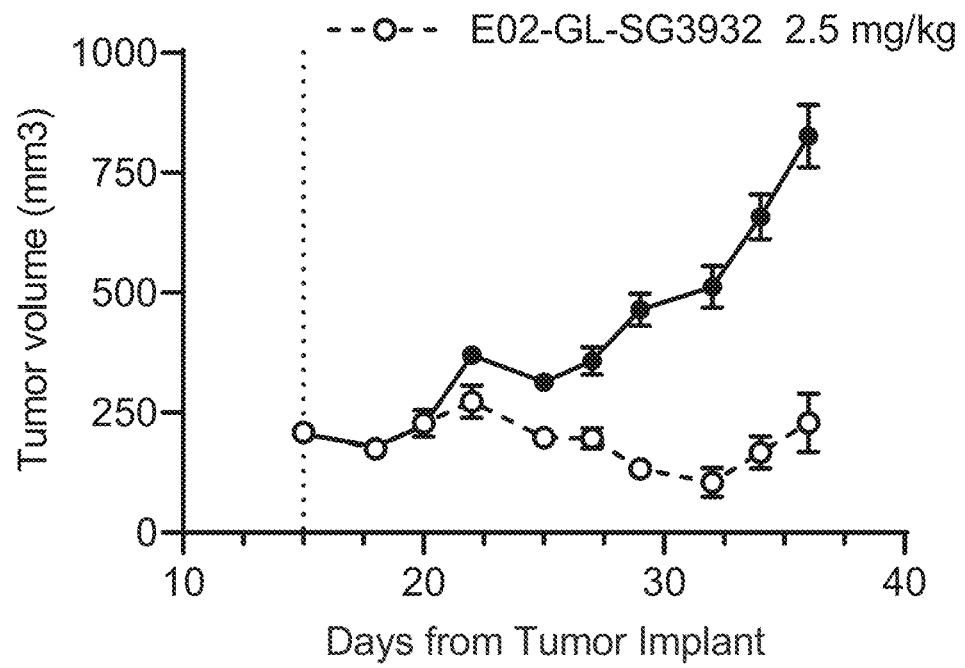
Figure 46C:
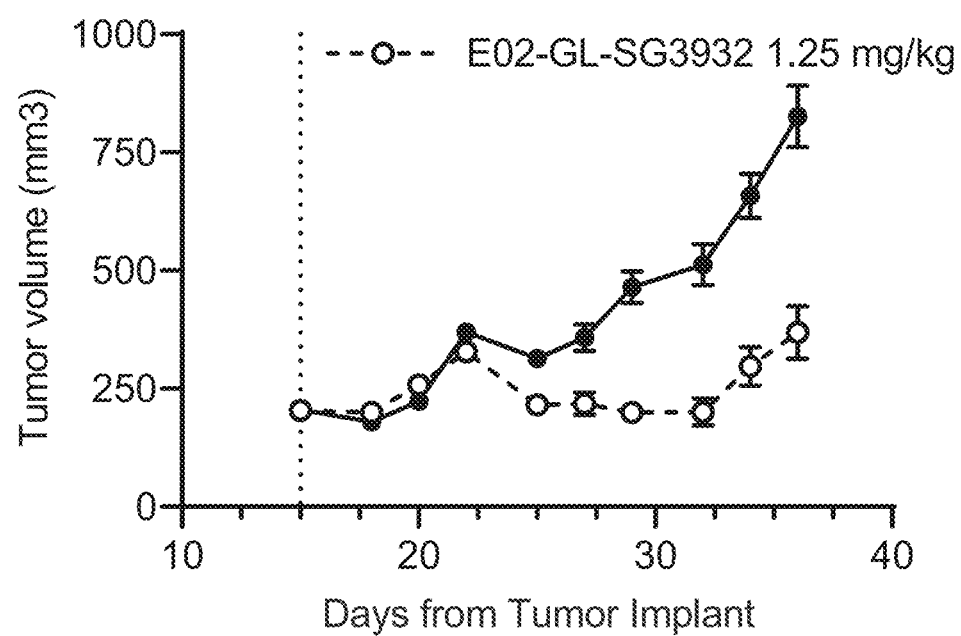

E02-GL-SG3932 was first evaluated in a pair of colon cancer cell line xenograft models in two separate studies; HT29, which is B7-H4 negative, and HT29-huB7-H4 Clone 26, which is derived from the HT29 cell line and engineered to express human B7-H4. In both studies, animals were injected SC with either the HT29 or HT29-huB7-H4 Clone 26 cells and after tumors grew in volume to a mean of 178 mm3 (HT29) or 194 mm3 (HT29-huB7-H4 Clone 26), animals were randomized and each mouse received an IV injection of either E02-GL-SG3932 or control articles. As shown in FIGS. 45A and 45B, compared to the vehicle treated control group, neither E02-GL-SG3932 nor the isotype-matched control ADC NIP228-SG3932 significantly inhibited the growth of HT29 xenograft tumors when administered as a single IV dose at 10 mg/kg, demonstrating 12% (p=0.7006) and 14% (p=0.6593) TGI, respectively. In contrast, compared to the vehicle treated control group or the isotype-matched control ADC NIP228-SG3932, E02-GL-SG3932 significantly inhibited the growth of HT29-huB7-H4 Clone 26 xenograft tumors when dosed as a single IV dose at 5 mg/kg, 2.5 mg/kg and 1.25 mg/kg (FIGS. 46A-46C), with TGI relative to vehicle of 42% (p<0.001), 37% (p=0.0005), and 31% (p=0.0039), respectively.

MX-1 Breast Cancer Xenograft Model

Figure 47A:
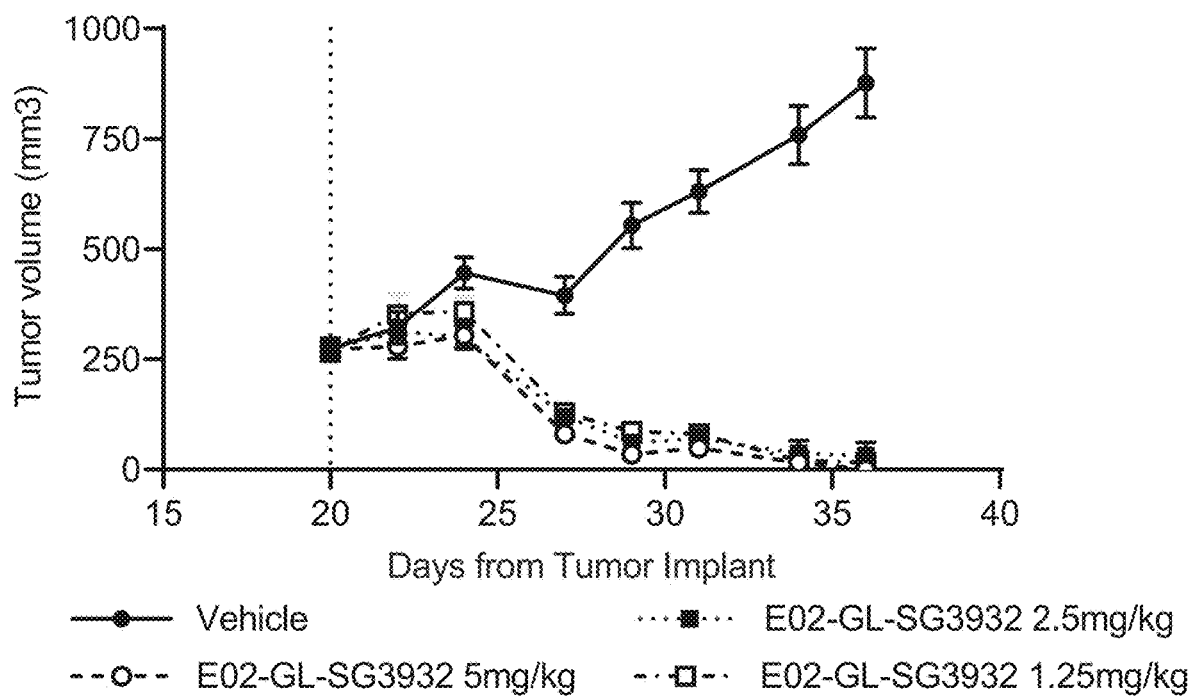
FIGS. 47A and 47B show efficacy of E02-GL-SG3932, NIP228-SG3932, and E02-INT in the MX-1 xenograft model. Values are mean±SEM tumor volumes for n: 8 animals per group. Dotted line denotes the day of dosing.
Figure 47B:
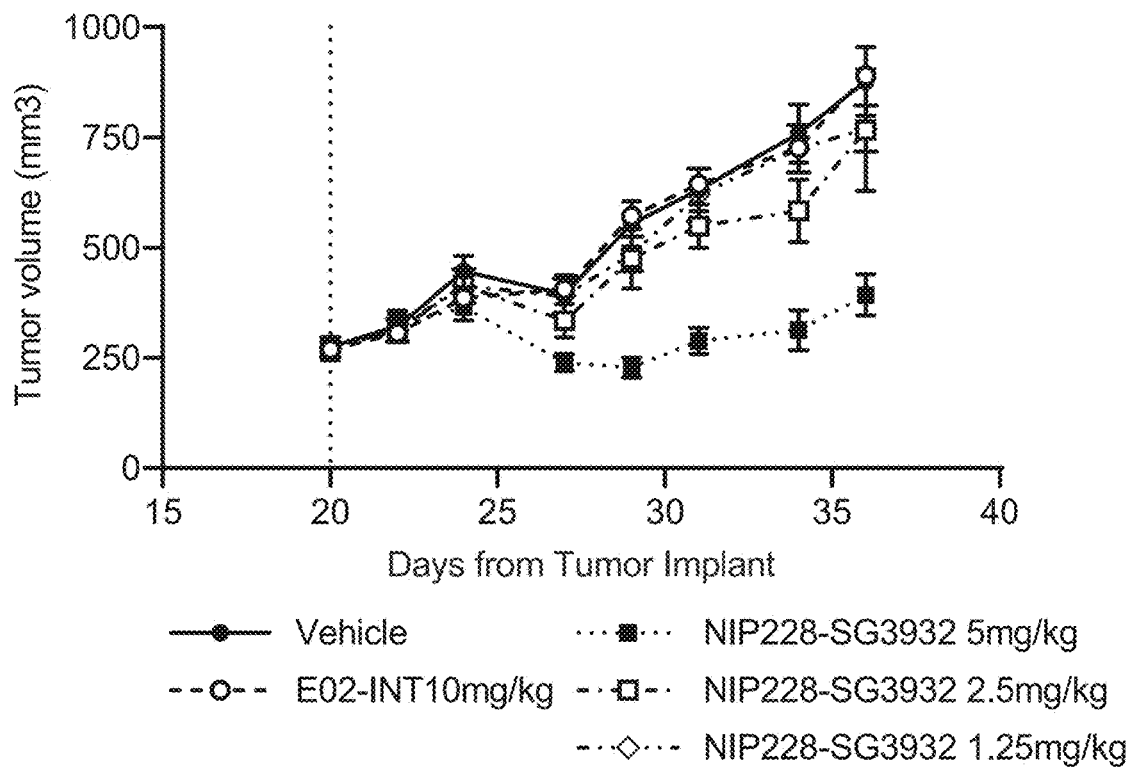

The effect of E02-GL-SG3932, the isotype-matched control ADC NIP228-SG3932, and E02-INT, the antibody intermediate of E02-GL-SG3932 was evaluated in the MX-1 breast cancer xenograft model. Animals were injected SC with MX-1 cells and after tumors grew in volume to a mean of 270 mm3, animals were randomized and each mouse received an IV injection of test or control articles. Compared to the vehicle treated control group, E02-GL-SG3932 significantly inhibited the growth of MX-1 xenograft tumors when dosed as a single IV dose at 5 mg/kg, 2.5 mg/kg and 1.25 mg/kg (FIGS. 47A and 47B), resulting in TGI of 100% (p<0.001), 96% (p<0.001) and 98% (p<0.001), respectively.

The antibody intermediate, E02-INT, dosed at 10 mg/kg, did not significantly inhibit tumor growth (TGI=–1%, p>0.9999). The lack of activity of E02-INT at this high dose level in SCID mice suggests that ADCC may not be a significant contributor to the activity of E02-GL-SG3932 in vivo and that the antitumor effects of E02-GL-SG3932 are driven through its TOP1i warhead.

MX-1 and MDA-MB-468 Breast Cancer Xenograft Models

Figure 48:
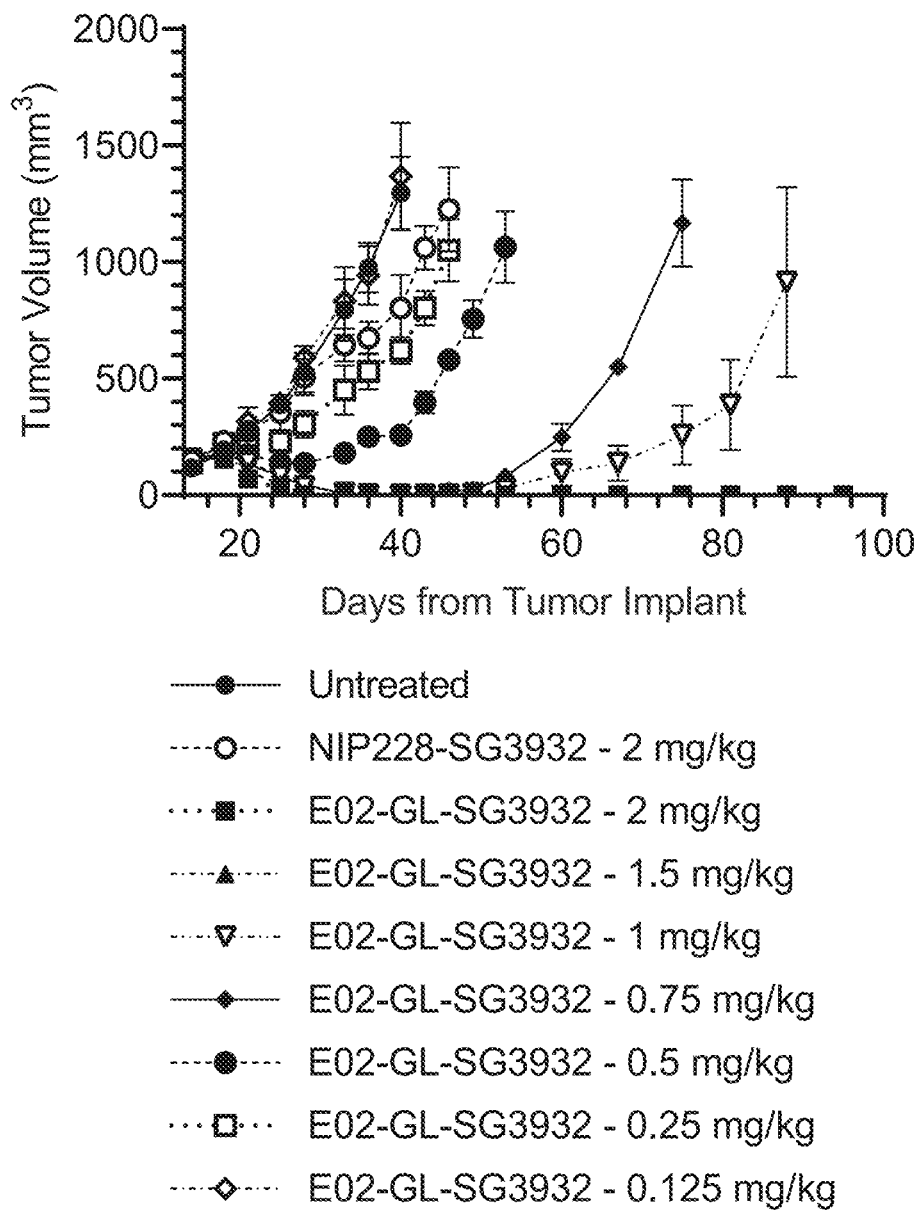
FIG. 48 shows efficacy of E02-GL-SG3932 and NIP228-SG3932 in the MX-1 xenograft model. Values are mean±SEM tumor volumes for n: 3 or 6 animals per group.
Figure 49:
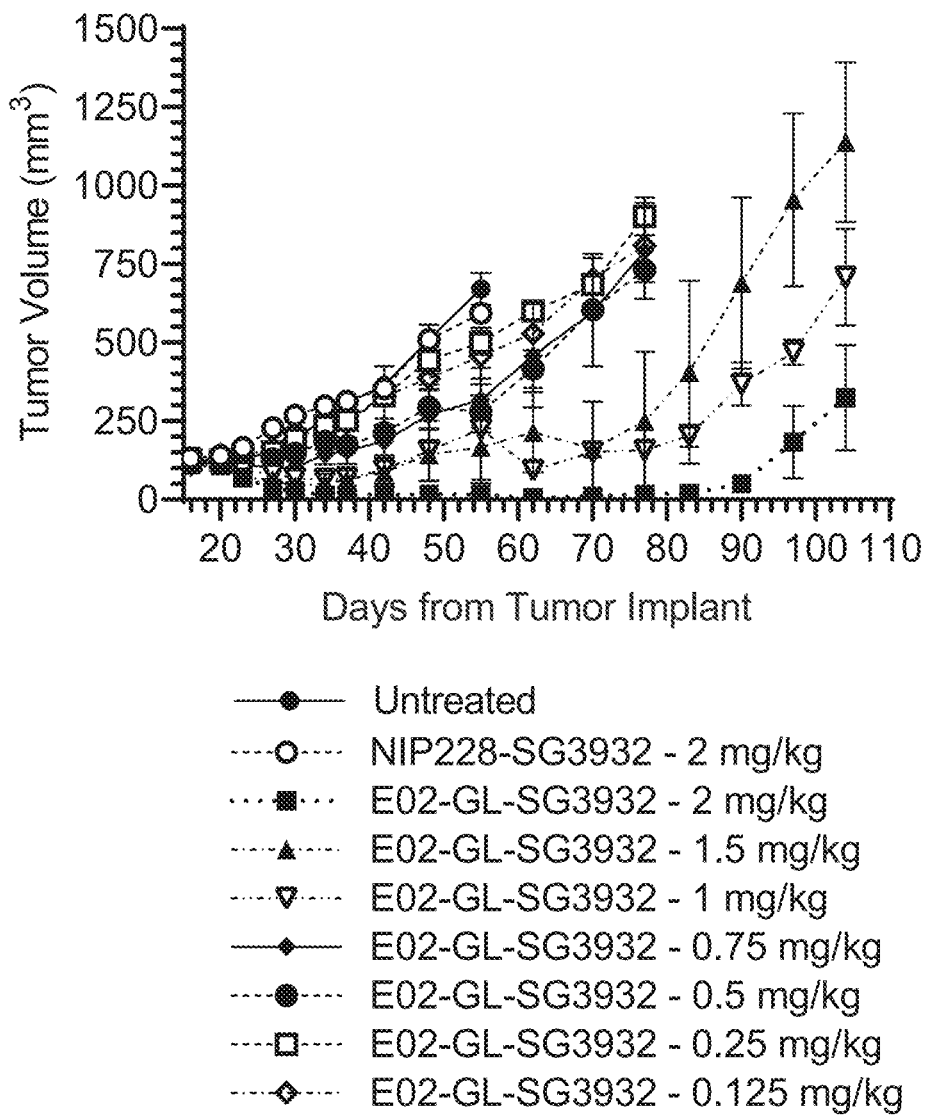
FIG. 49 shows efficacy of E02-GL-SG3932 and NIP228-SG3932 in the MDA-MB-468 xenograft model. Values are mean±SEM tumor volumes for n: 3 or 6 animals per group.

To further elucidate the dose-dependent effect of E02-GL-SG3932 treatment in vivo, dose levels ranging from 0.125 mg/kg to 2 mg/kg were evaluated in MX-1 and MDA-MB-468 breast cancer xenograft models. In both studies, animals were injected SC with either the MX-1 or MDA-MB-468 cells and after tumors grew in volume to a mean of approximately 138 mm3 (MX-1) or 120 mm3 (MDA-MB-468), animals were randomized and each mouse received an IV injection of either E02-GL-SG3932 or control articles. As shown in FIG. 48, a single intravenous dose of E02-GL-SG3932 resulted in dose-dependent inhibition of MX-1 xenografts. When compared to the untreated group at day 40, E02-GL-SG3932 treatment resulted in 100% TGI at the 2 mg/kg, 1.5 mg/kg and 1 mg/kg dose levels. E02-GL-SG3932 doses of 0.75 mg/kg, 0.5 mg/kg, 0.25 mg/kg and 0.125 mg/kg resulted in dose-dependent % TGI of 99.7%, 80.1%, 52.1% and –5.5%, respectively. Similarly, a single intravenous dose of E02-GL-SG3932 resulted in dose-dependent inhibition of MDA-MB-468 xenografts (FIG. 49). When compared to the untreated group at day 55, E02-GL-SG3932 treatment resulted in 97.7%, 75.2% and 66.6% TGI at the 2 mg/kg, 1.5 mg/kg and 1 mg/kg dose levels, respectively. E02-GL-SG3932 doses of 0.75 mg/kg, 0.5 mg/kg, 0.25 mg/kg and 0.125 mg/kg resulted in dose-dependent % TGI of 52.8%, 58.4%, 25.5% and 31.8%, respectively.

Example 40

Antitumor Efficacy of E02-GL-SG3932 in Patient-Derived Xenograft Models of Triple-Negative Breast Cancer The antitumor activity of E02-GL-SG3932 was investigated in a panel of 26 human TNBC PDX models using immunocompromised athymic nude mice. These PDX models have been established from human tumor samples without prior in vitro culture and have been studied for histology, cytogenetics, genetic and other biological markers, and for their response to standard-of-care therapies. Tumor fragments were subcutaneously transplanted into mice, and once tumors grew in volume to approximately 94 to 189 mm3, animals were randomized and each mouse received a single IV injection of either E02-GL-SG3932 or control articles, at a dose of 1.25 mg/kg or 3.5 mg/kg. To assess the relationship between B7-H4 expression and efficacy, fresh untreated tumors with a volume of around 500 to 1183 mm3 from 3 additional mice from each model were collected, fixed in 10% neutral buffered formalin and subsequently processed and embedded into paraffin blocks. IHC and image analysis techniques were then used to characterize the expression of B7-H4 on tumor cell membranes in each model.

Figure 50:
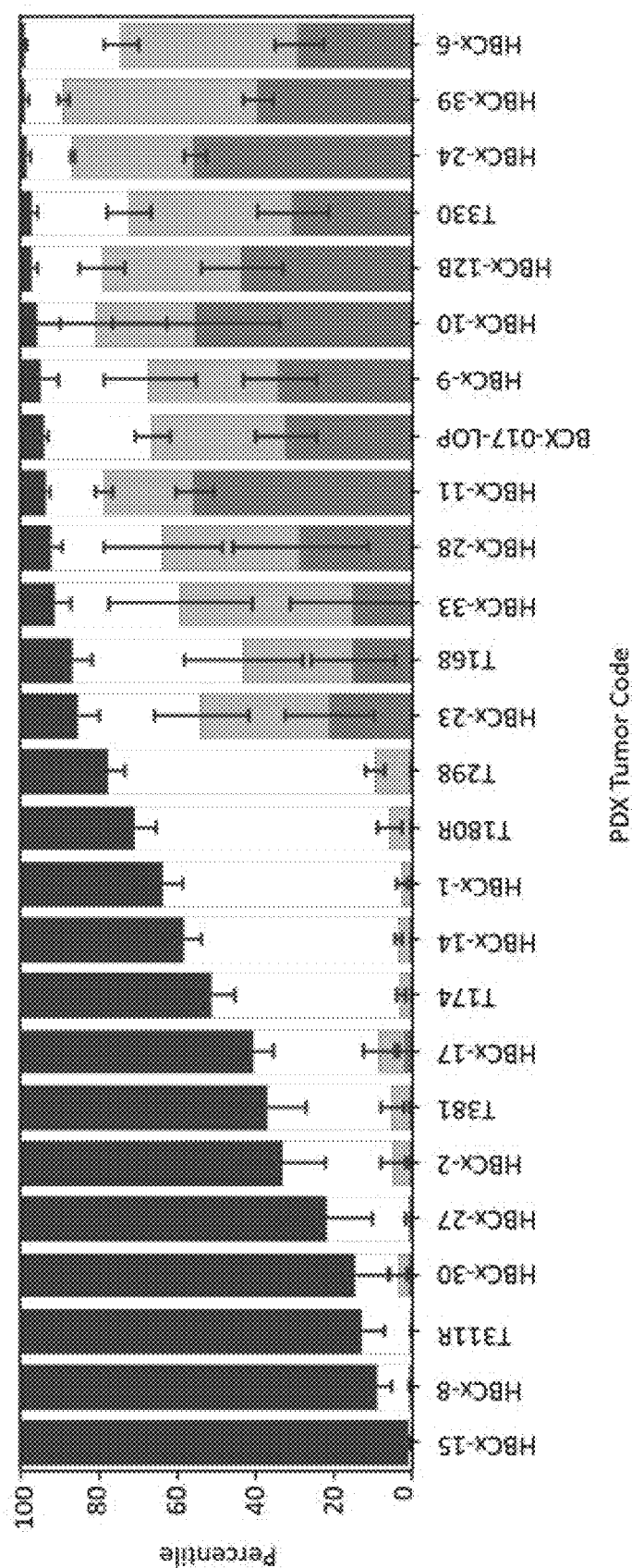
FIG. 50 shows quantitative image analysis B7-H4 expression data in patient derived xenograft (PDX) models, sorted by case average of mean of cell membrane OD mean value. Expression is color encoded by IHC cell intensity class (negative: black, 1+: white, 2+: light gray, 3+: dark gray.

IHC analysis demonstrated that these PDX models represented heterogenous tumor expression of B7-H4, with different levels of IHC staining intensity and proportion of tumor staining, including one model with nearly undetectable levels of B7-H4 (HBCx-15) (FIG. 50).

Figure 51:
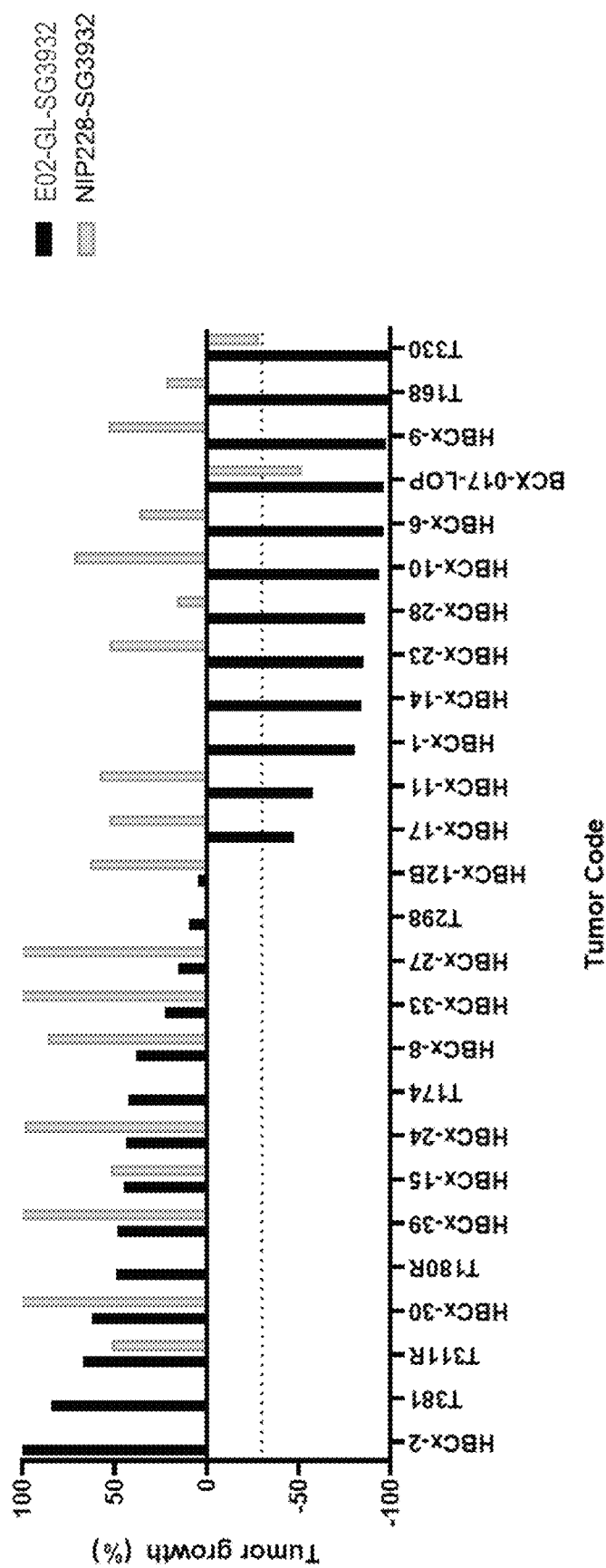
FIG. 51 shows antitumor activity resulting from a single administration of 1.25 mg/kg E02-GL-SG3932 or NIP228-SG3932 in patient derived xenograft models.
Figure 52A:
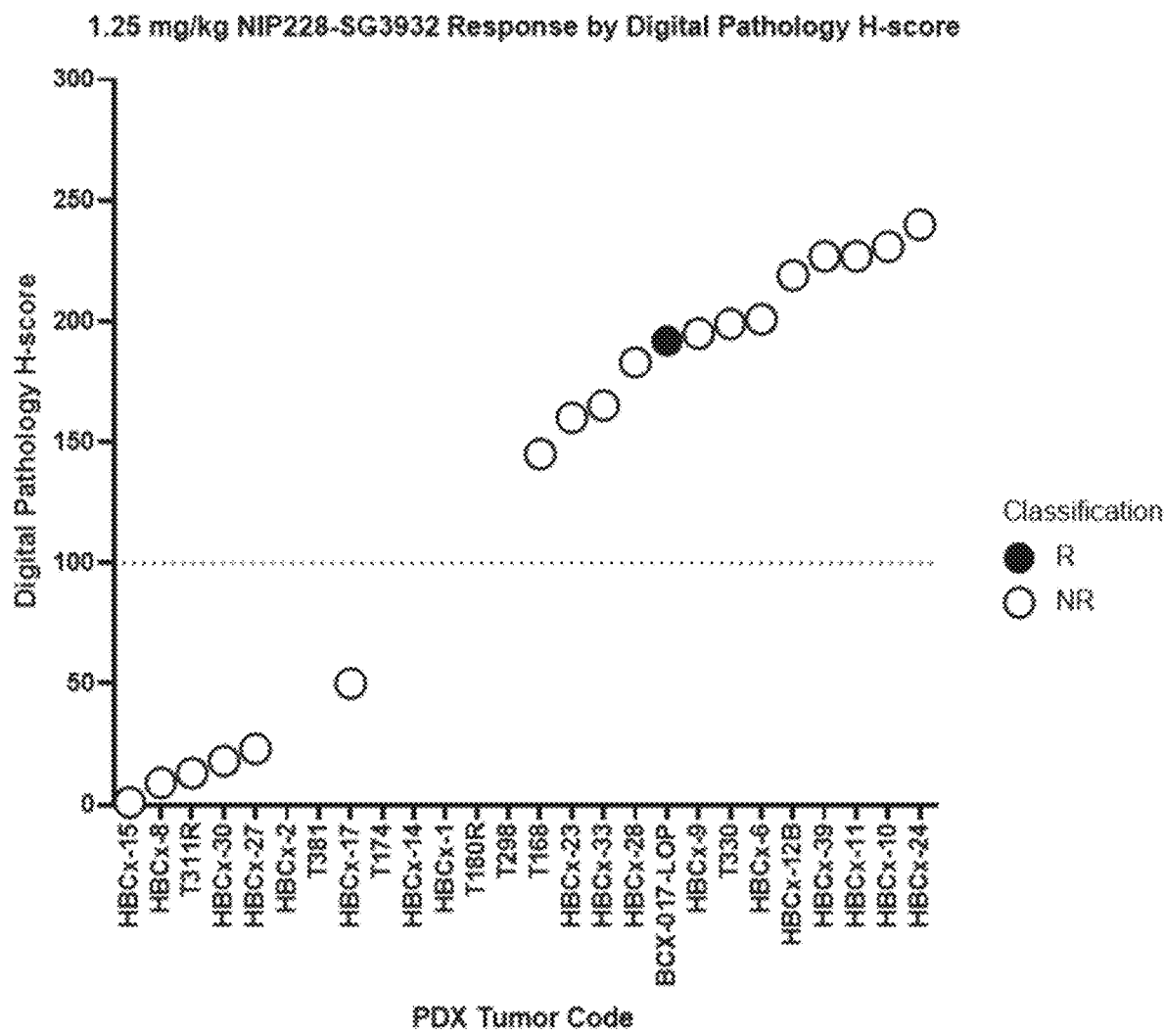
FIGS. 52A and 52B show B7-H4 expression in PDX models grouped according to tumor response to E02-GL-SG3932 or NIP228-SG3932 at the 1.25 mg/kg dose level. Models were considered to be responsive (R) to test agents if the percent change in tumor volume from baseline was −30% to −100%, inclusive. Models were considered to be non-responders (NR) if the percent change in tumor volume from baseline was greater than −30%. The y-axis indicates the level of B7-H4 in each model, as determined by H-score.
Figure 52B:
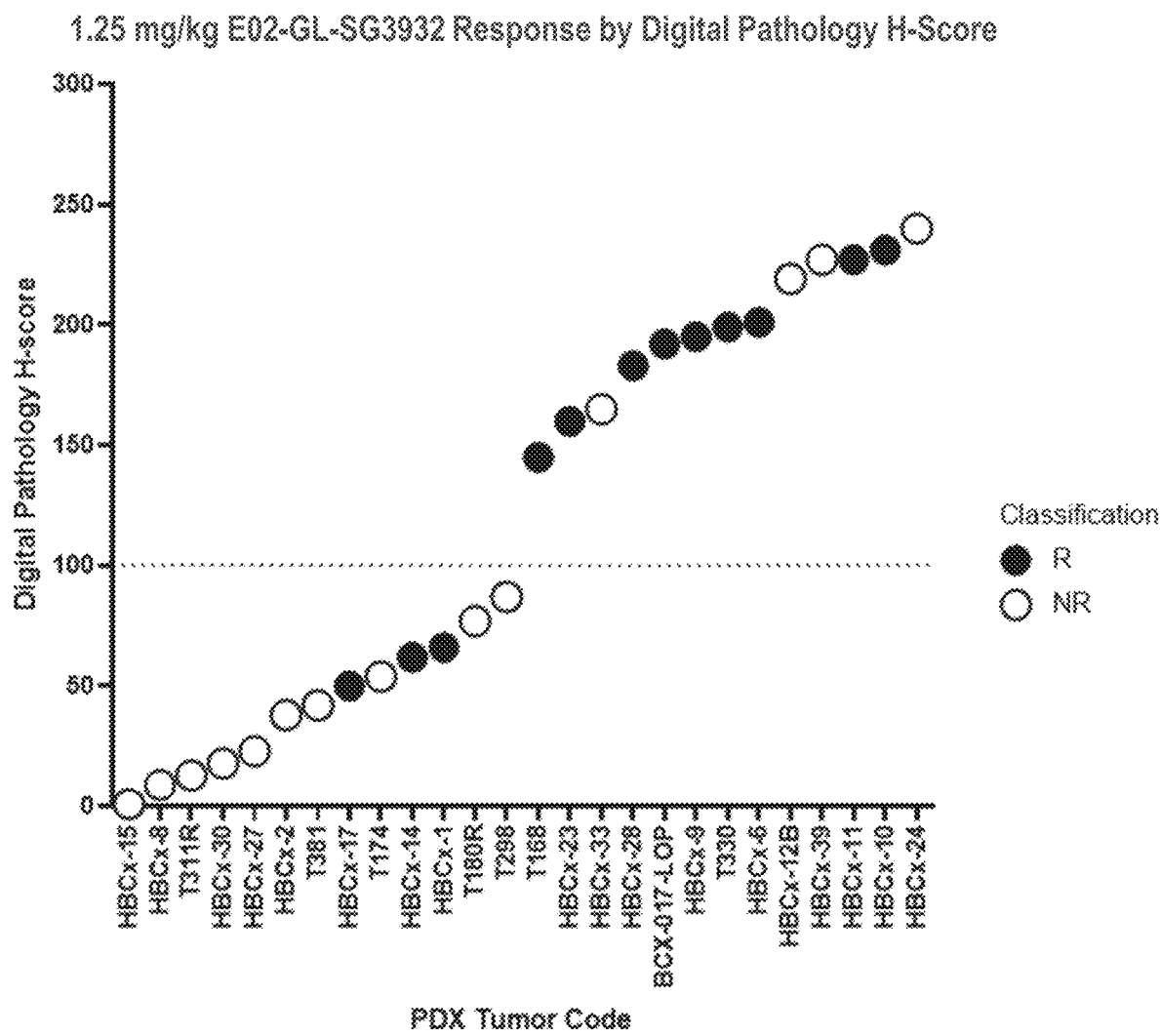
Figure 53A:
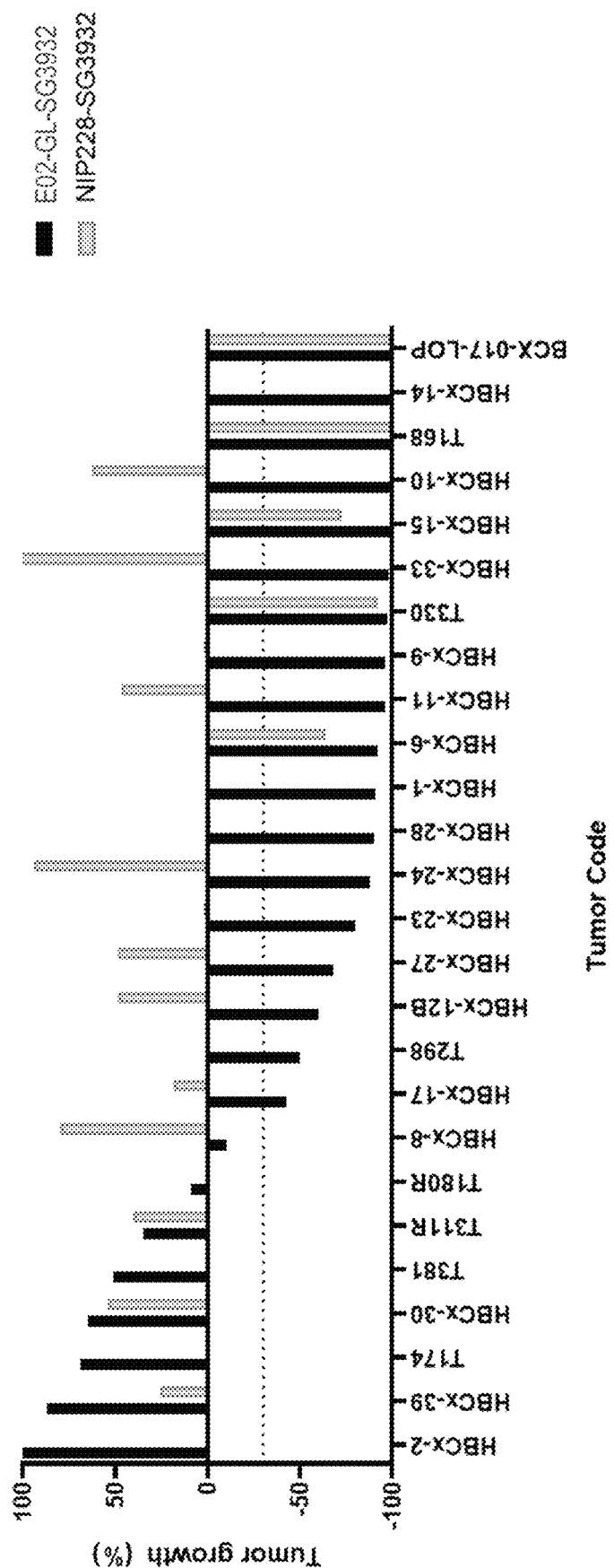
FIG. 53A shows antitumor activity resulting from a single administration of 3.5 mg/kg E02-GL-SG3932 or NIP228-SG3932 in patient derived xenograft models.
Figure 53B:
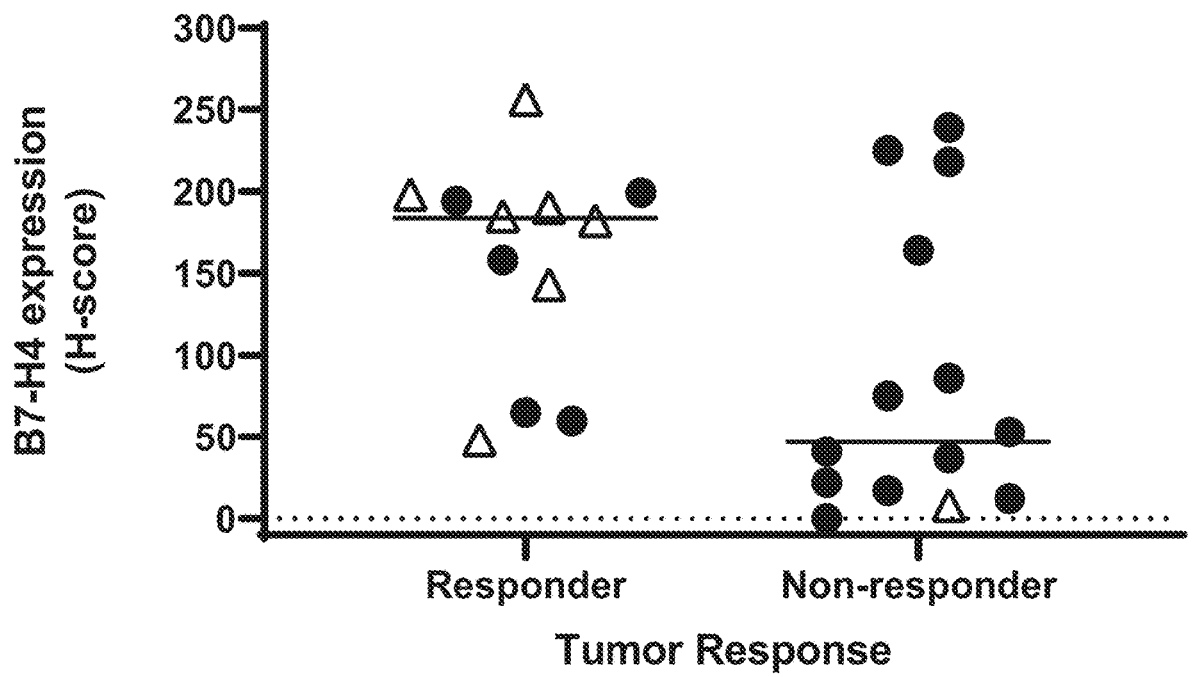
FIGS. 53B-53E show results of the study protocol to determine correlation of E02-GL-SG3932 administration, B7-H4 expression level and HR-deficiency at (A) 1.25 mg/kg E02-GL-SG3932, (B) 3.5 mg/kg E02-GL-SG3932, (C) 1.25 mg/kg isotype control ADC, and (D) 3.5 mg/kg isotype control ADC.
Figure 53C:
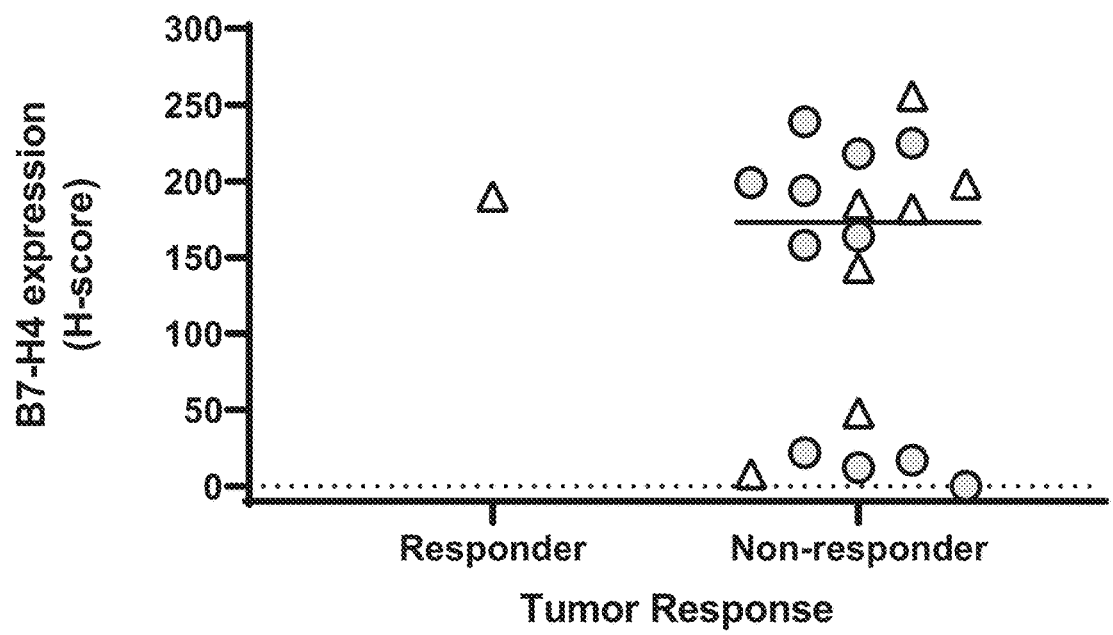
Figure 53D:
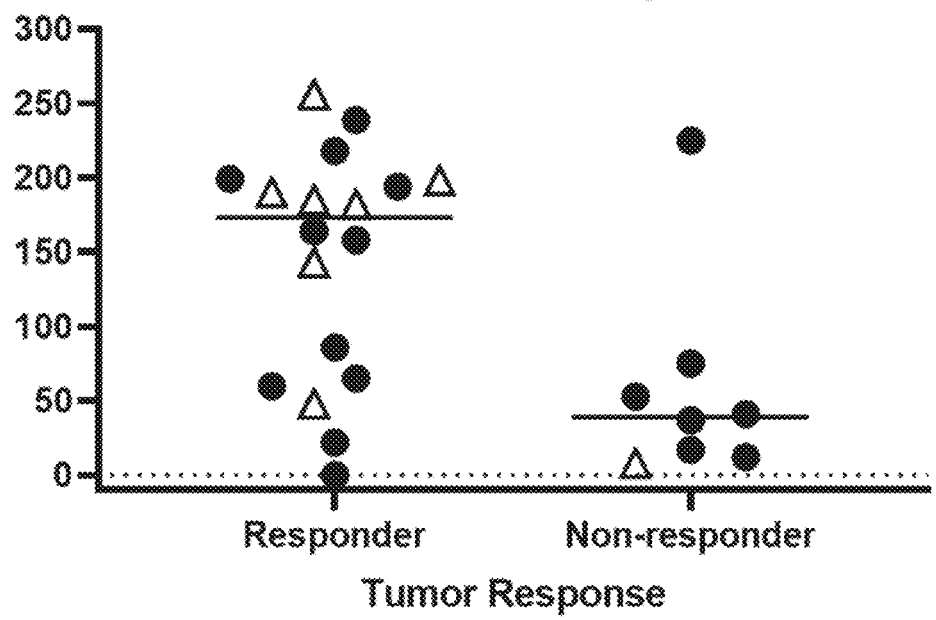
Figure 53E:
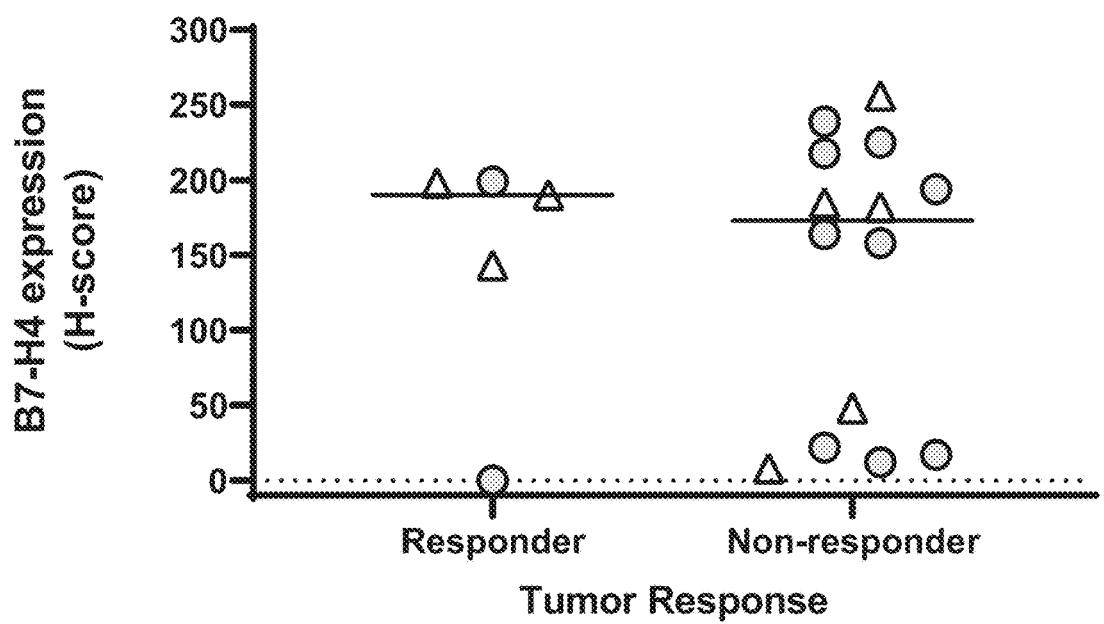

Tumor growth inhibition was observed after a single dose of 1.25 mg/kg E02-GL-SG3932, with 46.2% of models (12 of 26) exhibiting a reduction in tumor volume from baseline of 30% or greater (FIG. 51). Of these, 75% (9 of 12) expressed elevated levels of B7-H4, with an H-score of 100 or greater (FIGS. 52A and 52B). A significant association between H-score classification and responder status was identified for E02-GL-SG3932 at the 1.25 mg/kg dose level (Fisher's exact tests, p=0.047), suggesting that elevated levels of B7-H4 are associated with response to treatment with 1.25 mg/kg E02-GL-SG3932.

Figure 54A:
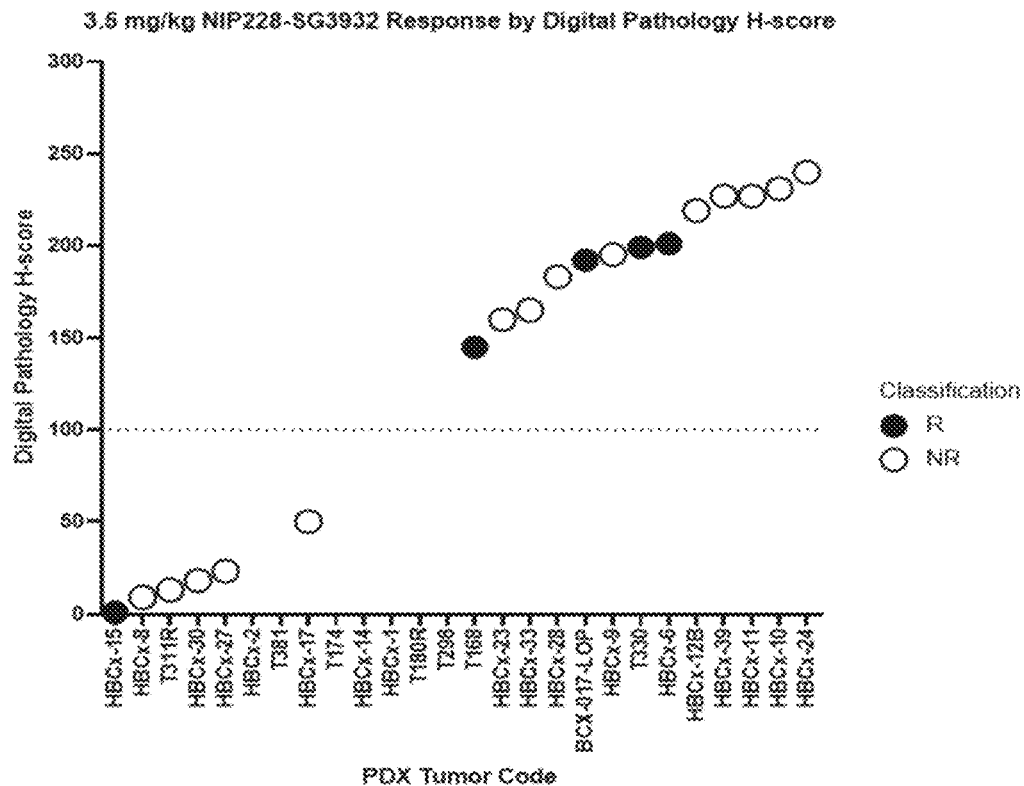
FIGS. 54A and 54B show B7-H4 expression in PDX models grouped according to tumor response to E02-GL-SG3932 or NIP228-SG3932 at the 3.5 mg/kg dose level. Models were considered to be responsive (R) to test agents if the percent change in tumor volume from baseline was −30% to −100%, inclusive. Models were considered to be NR if the percent change in tumor volume from baseline was greater than −30%. The y-axis indicates the level of B7 H4 in each model, as determined by H-score.
Figure 54B:
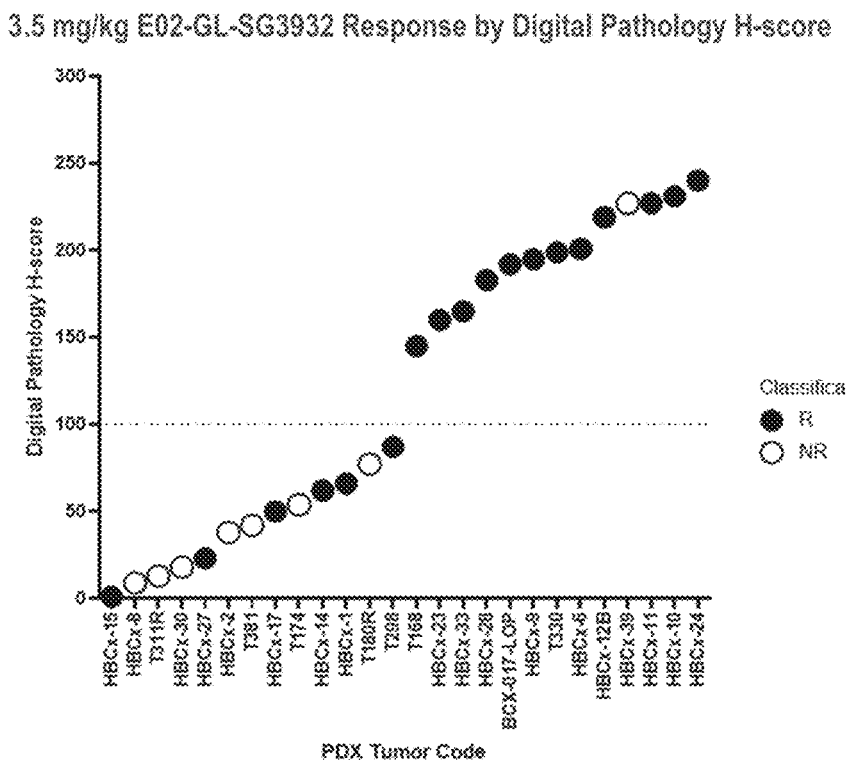
Figure 55A:
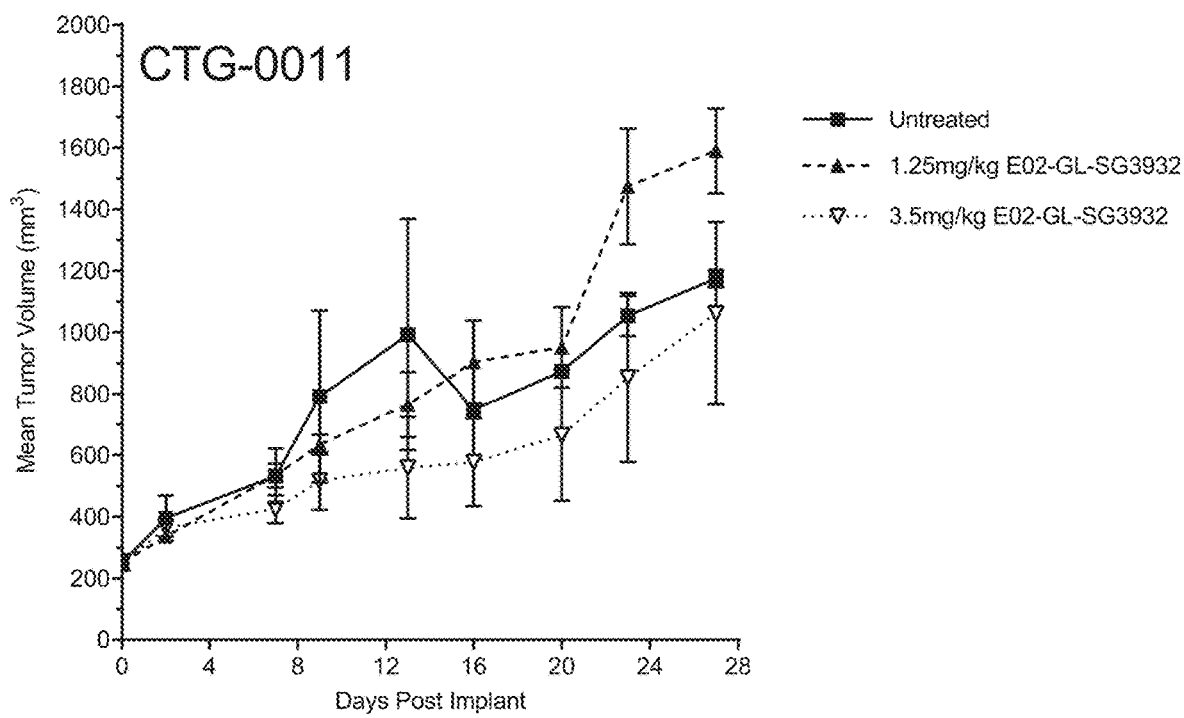
FIGS. 55A-55G show the mean tumor volume over time for a first panel of cholangiocarcinoma PDX mouse models treated with a single dose of 1.25 mg/kg or 3.5 mg/kg E02-GL-SG3932, as compared to untreated mice.
Figure 55B:
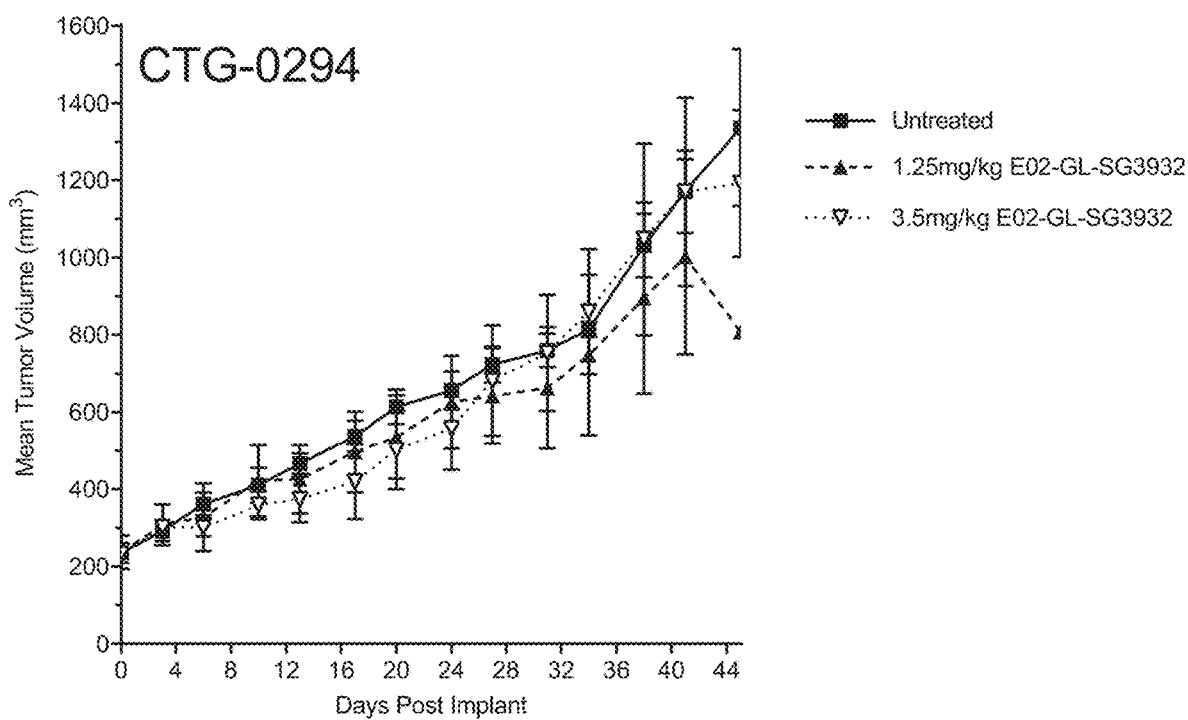
Figure 55C:
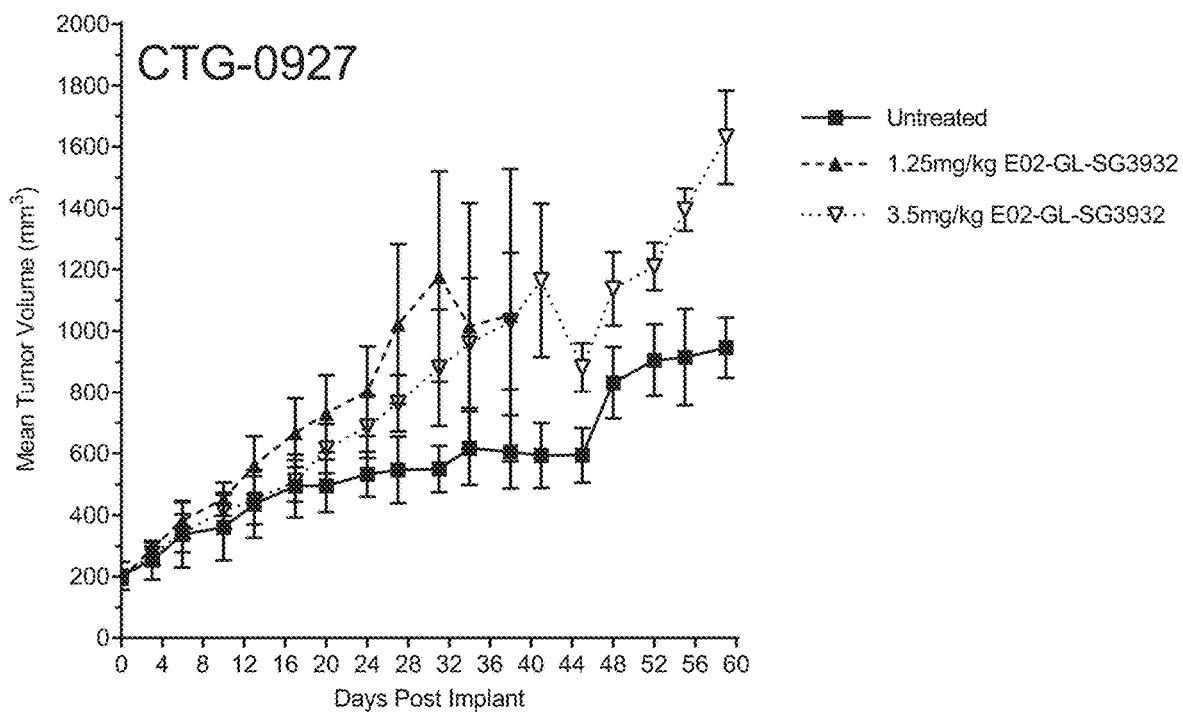
Figure 55D:
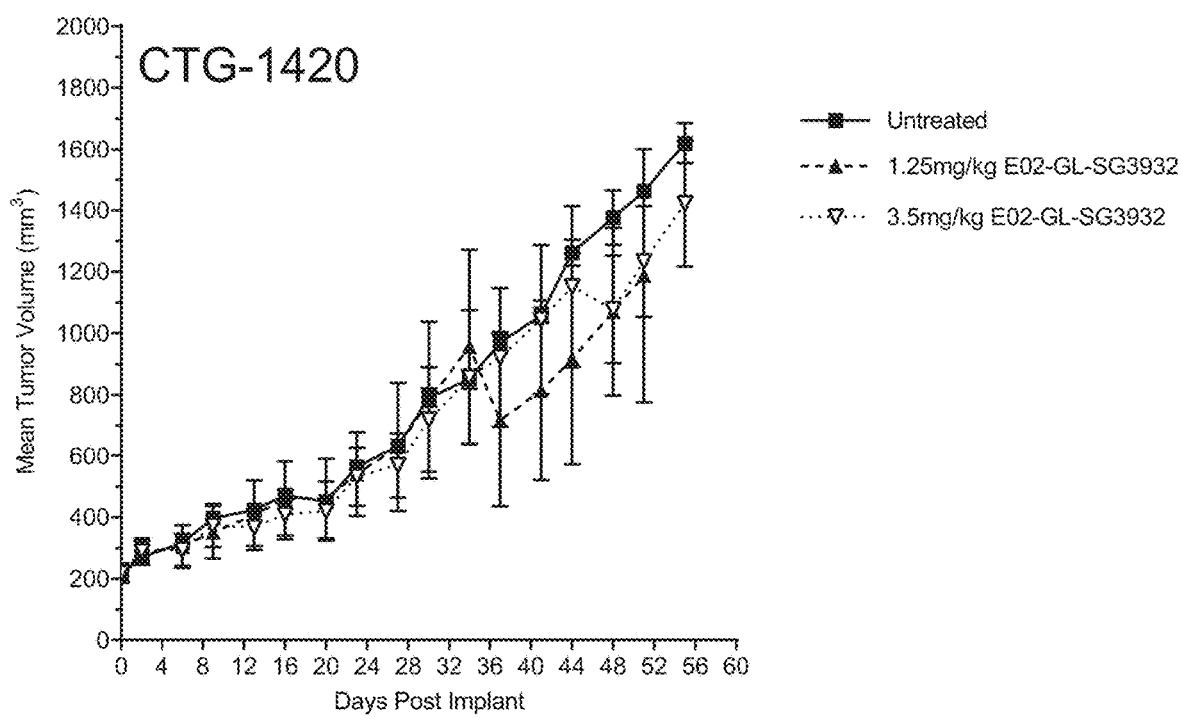
Figure 55E:
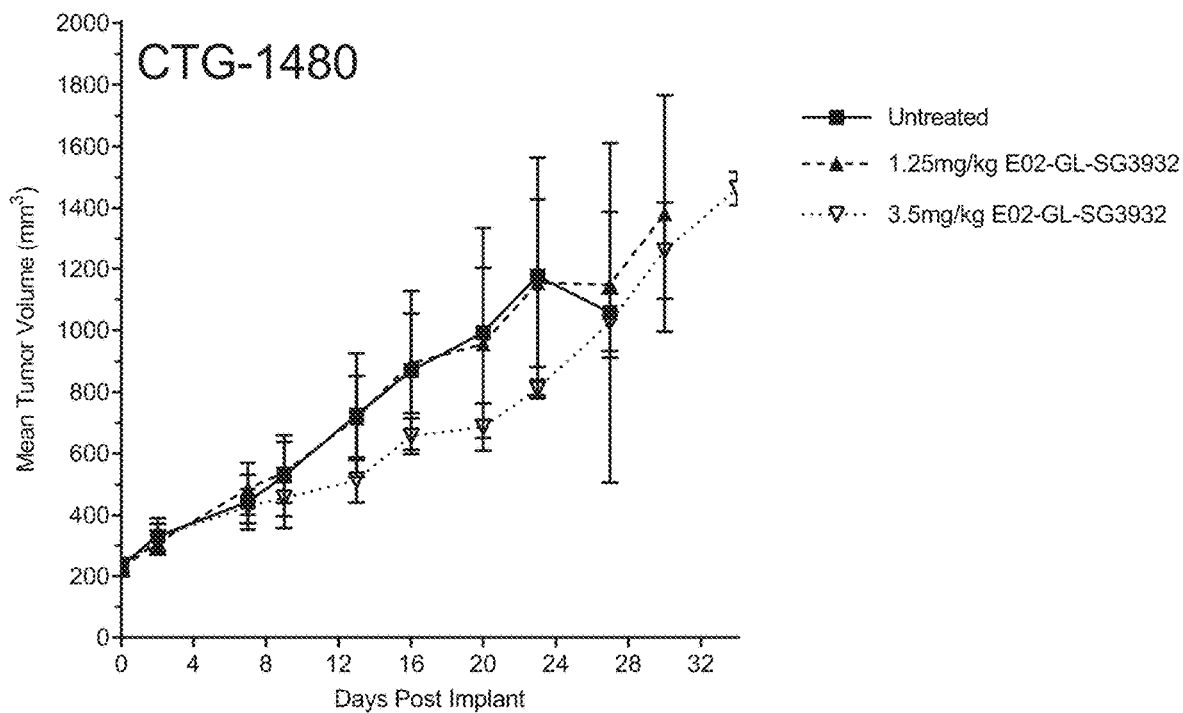
Figure 55F:
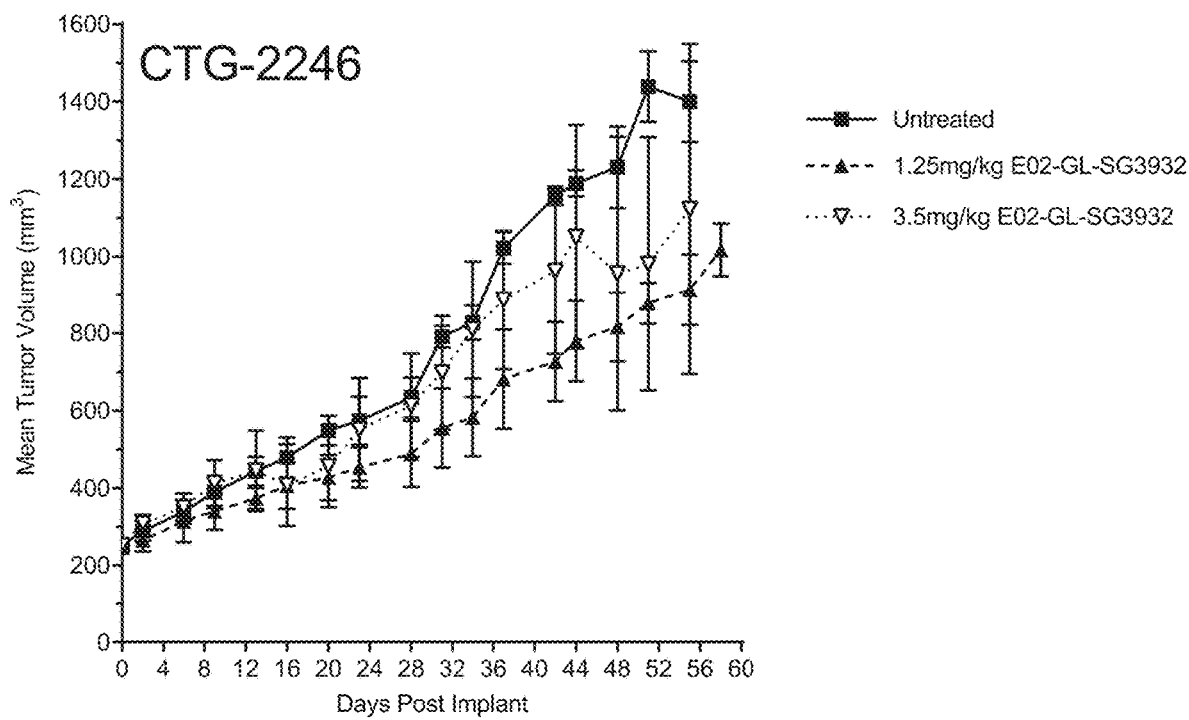
Figure 55G:
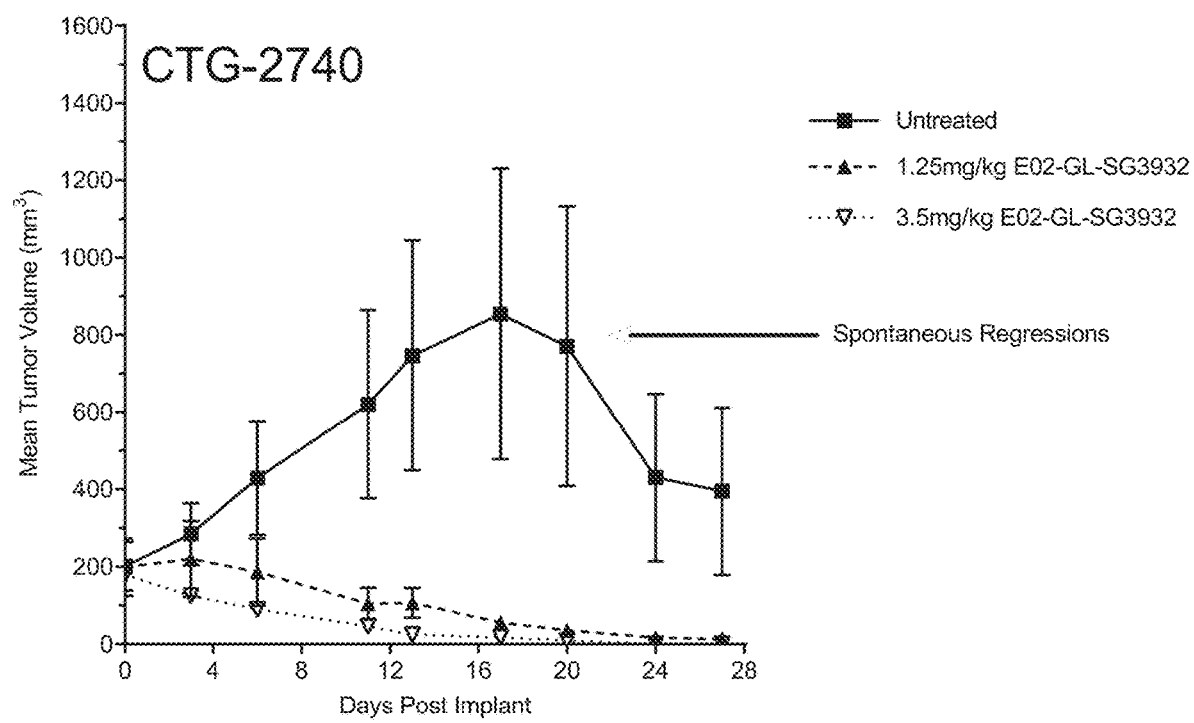
Figure 56A:
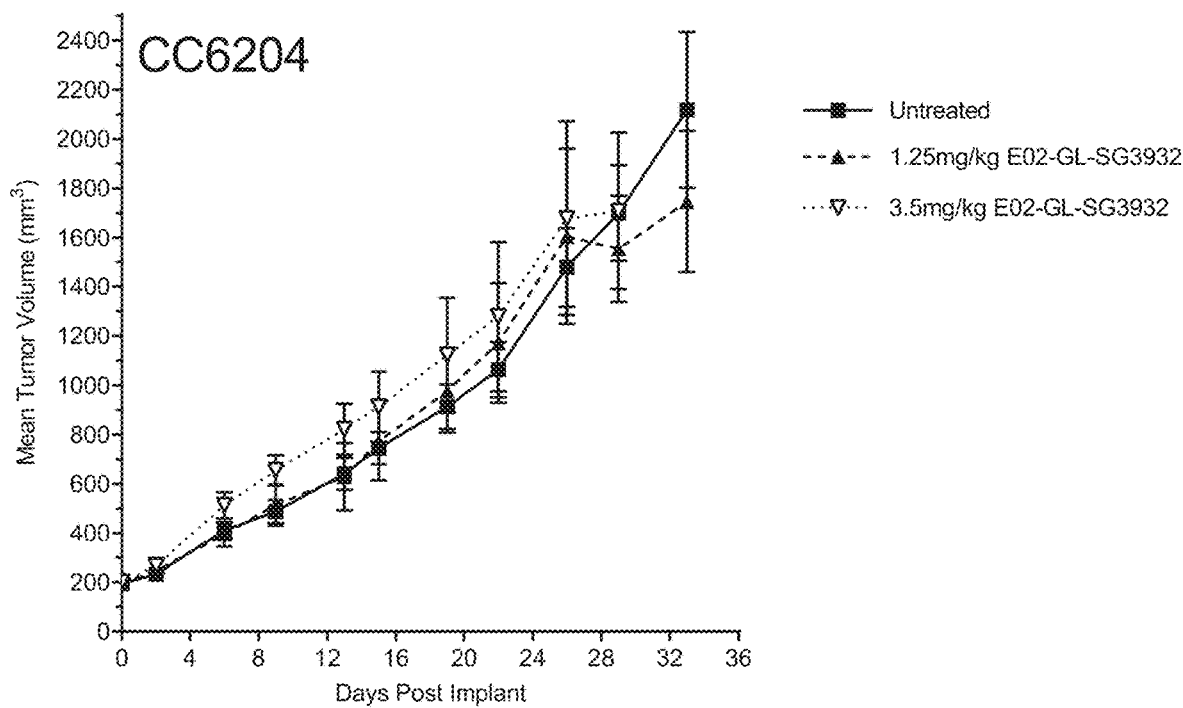
FIGS. 56A-56K show the mean tumor volume over time for a second panel of cholangiocarcinoma PDX mouse models treated with a single dose of 1.25 mg/kg or 3.5 mg/kg E02-GL-SG3932, as compared to untreated mice.
Figure 56B:
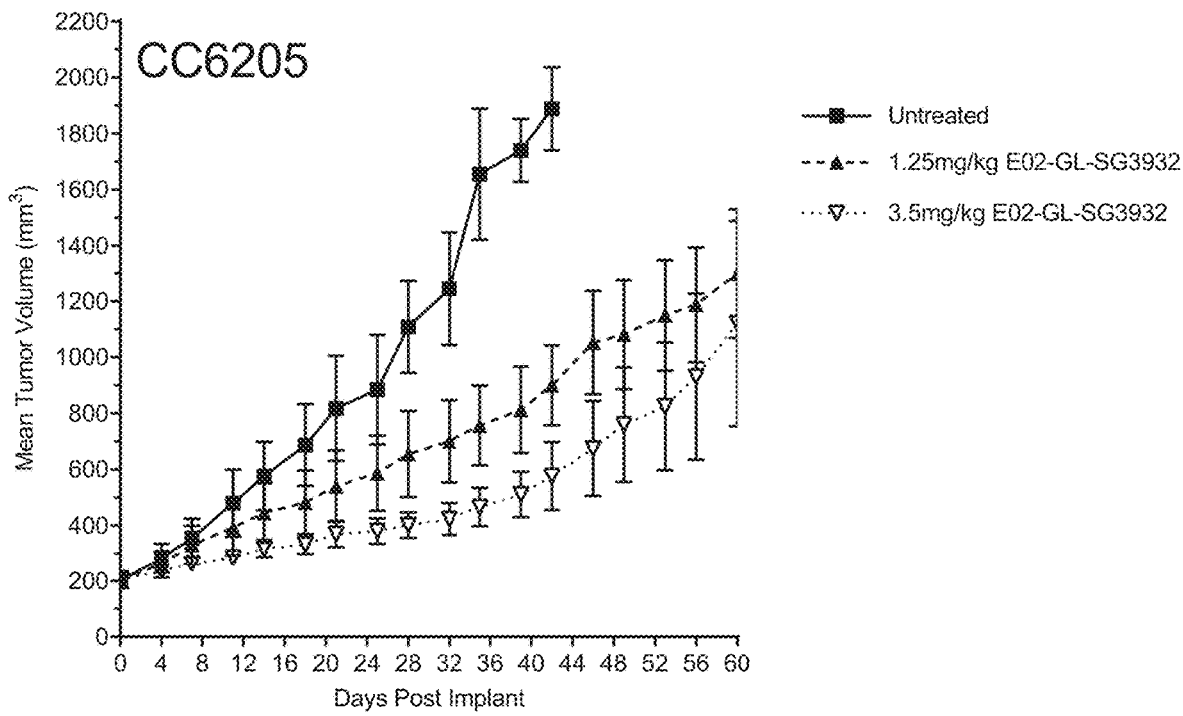
Figure 56C:
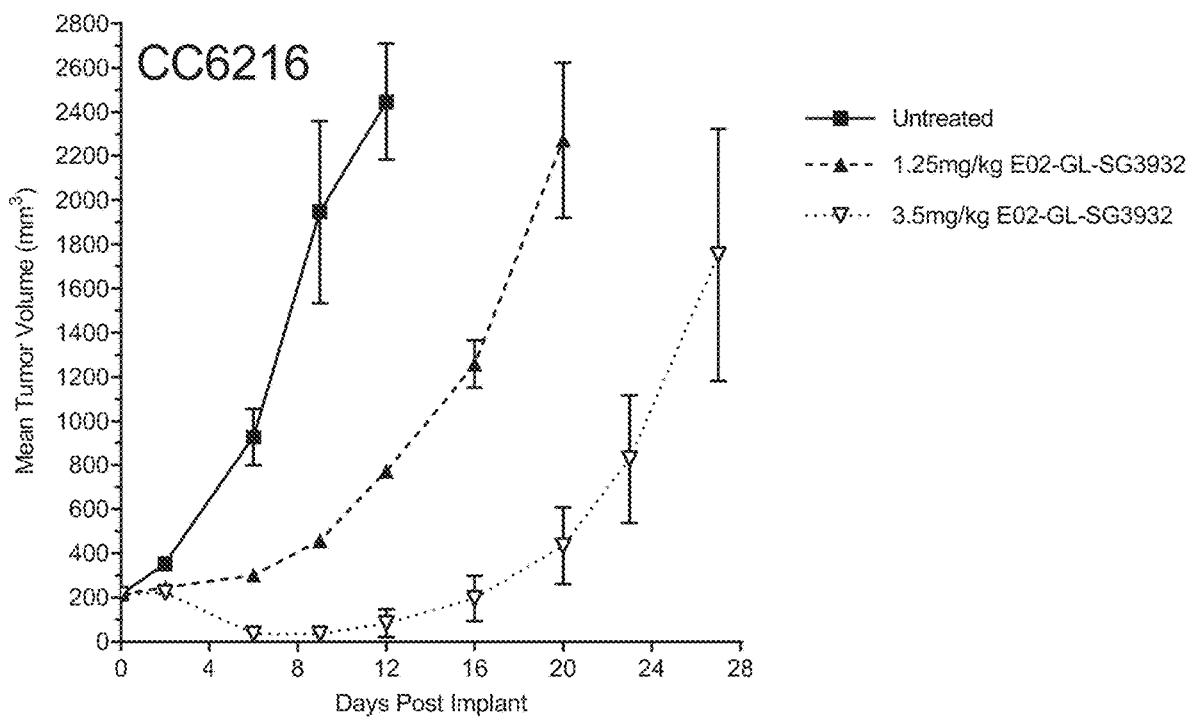
Figure 56D:
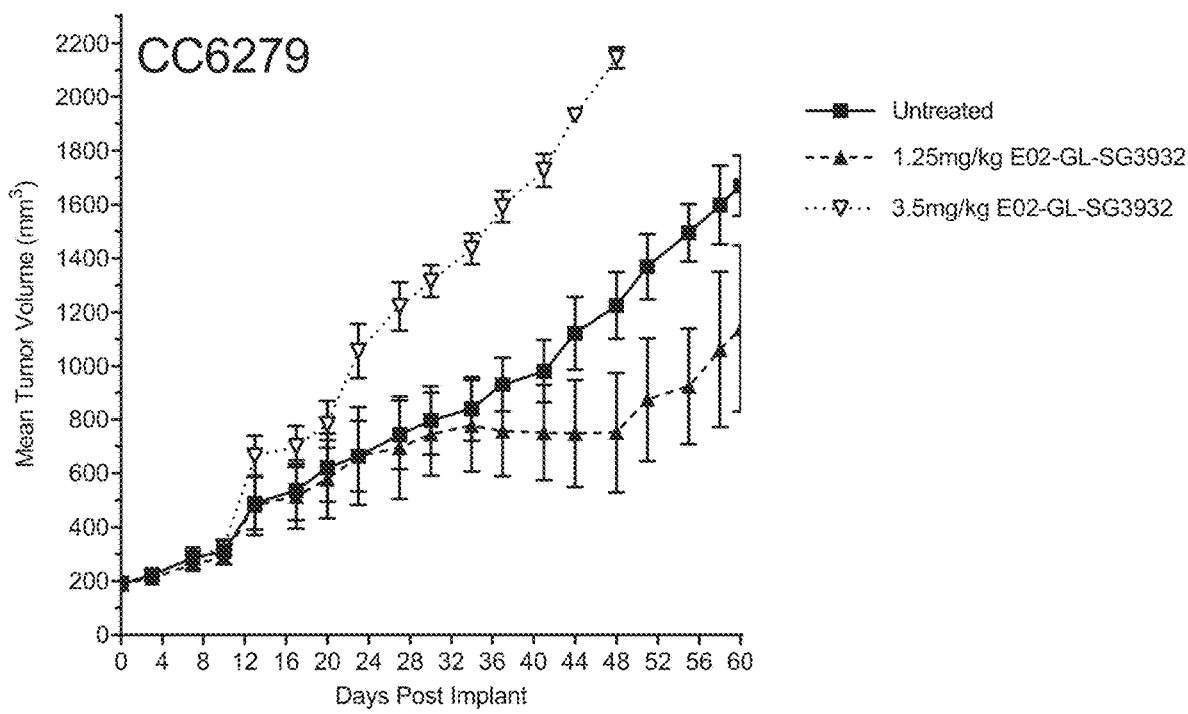
Figure 56E:
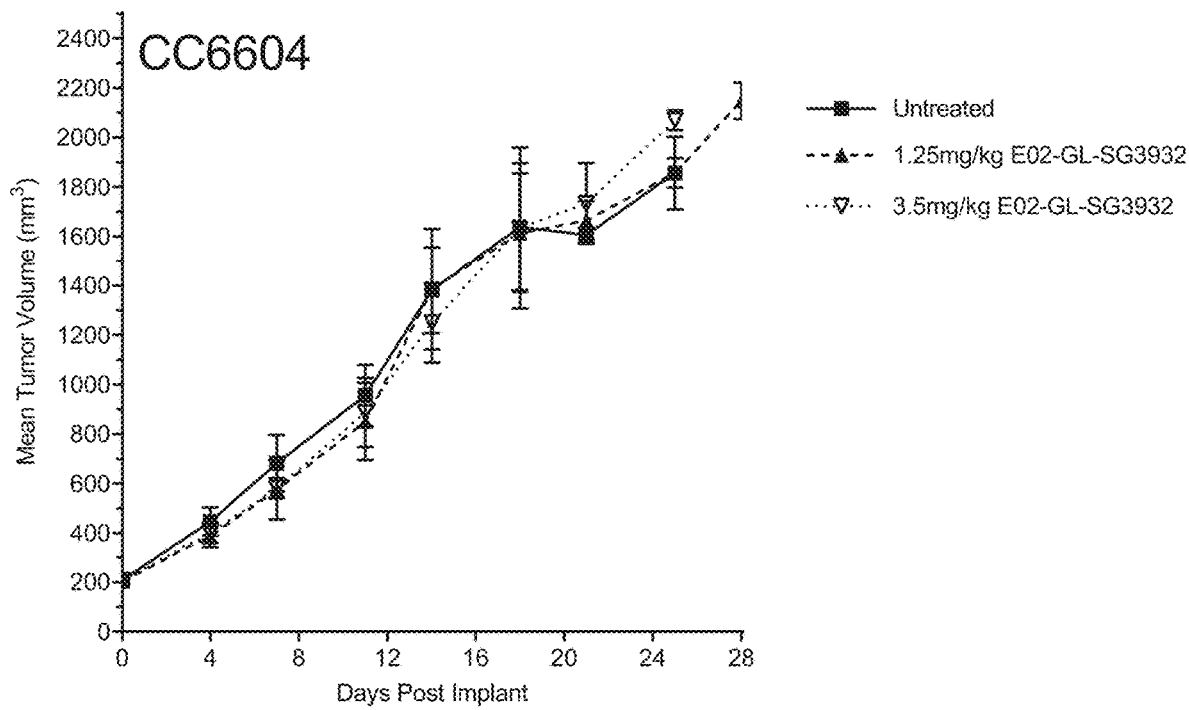
Figure 56F:
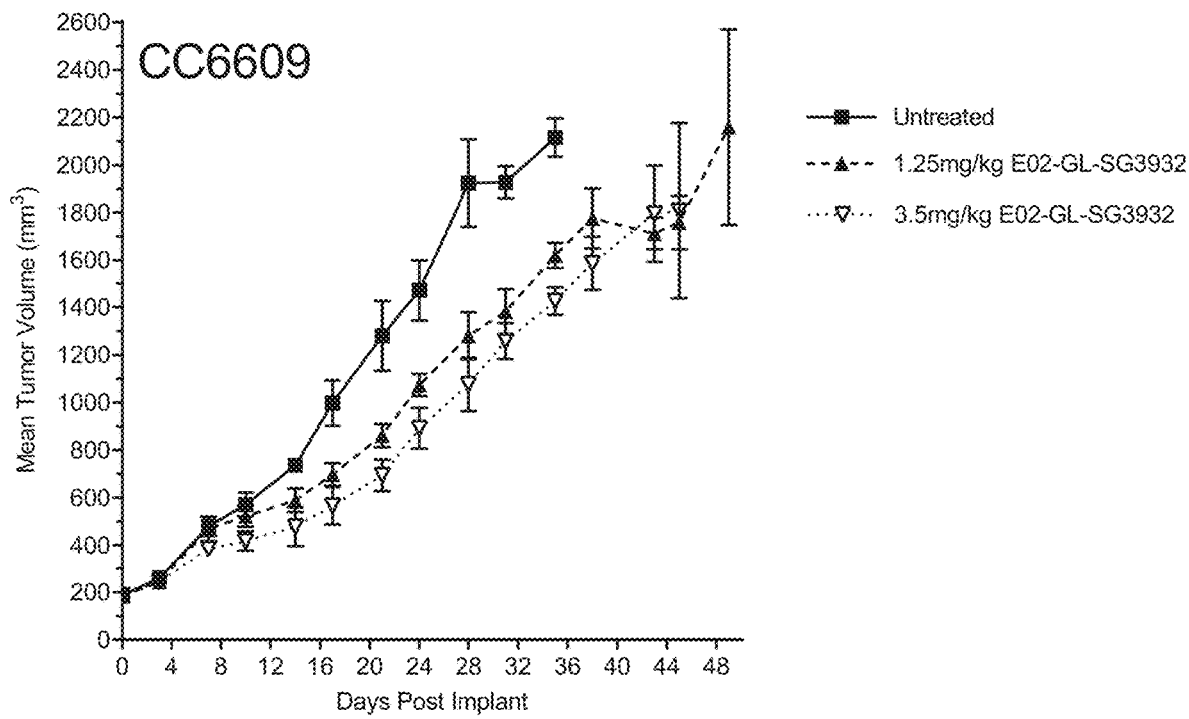
Figure 56G:
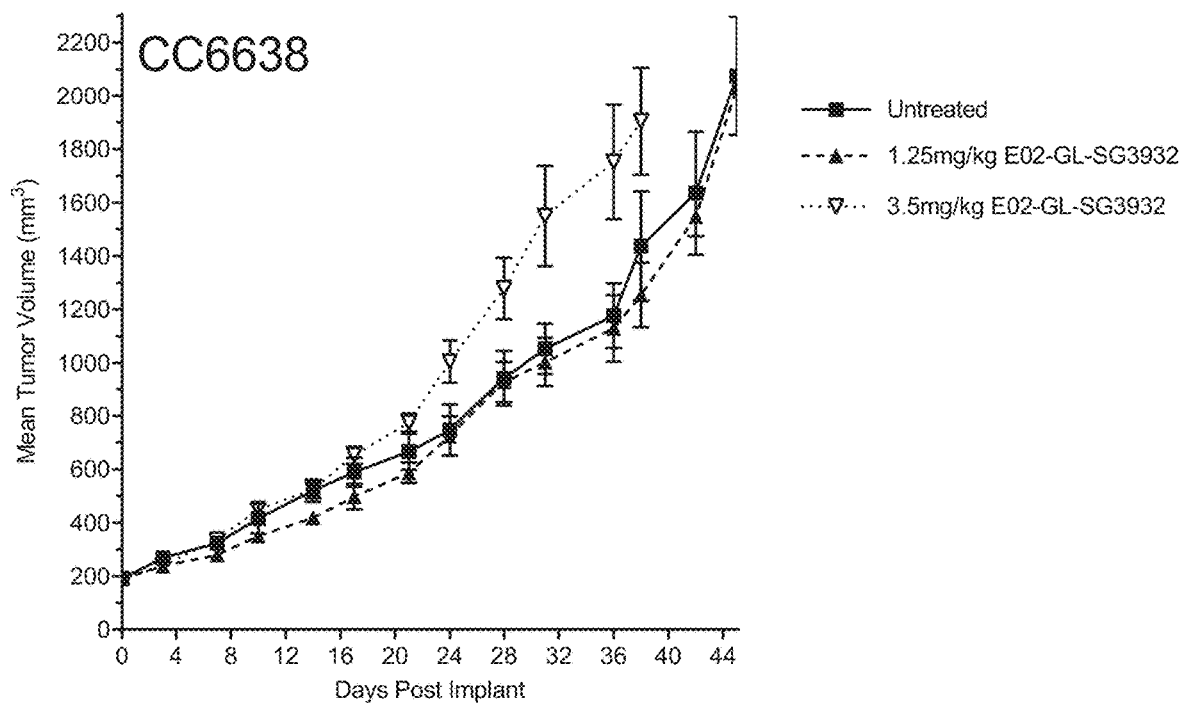
Figure 56H:
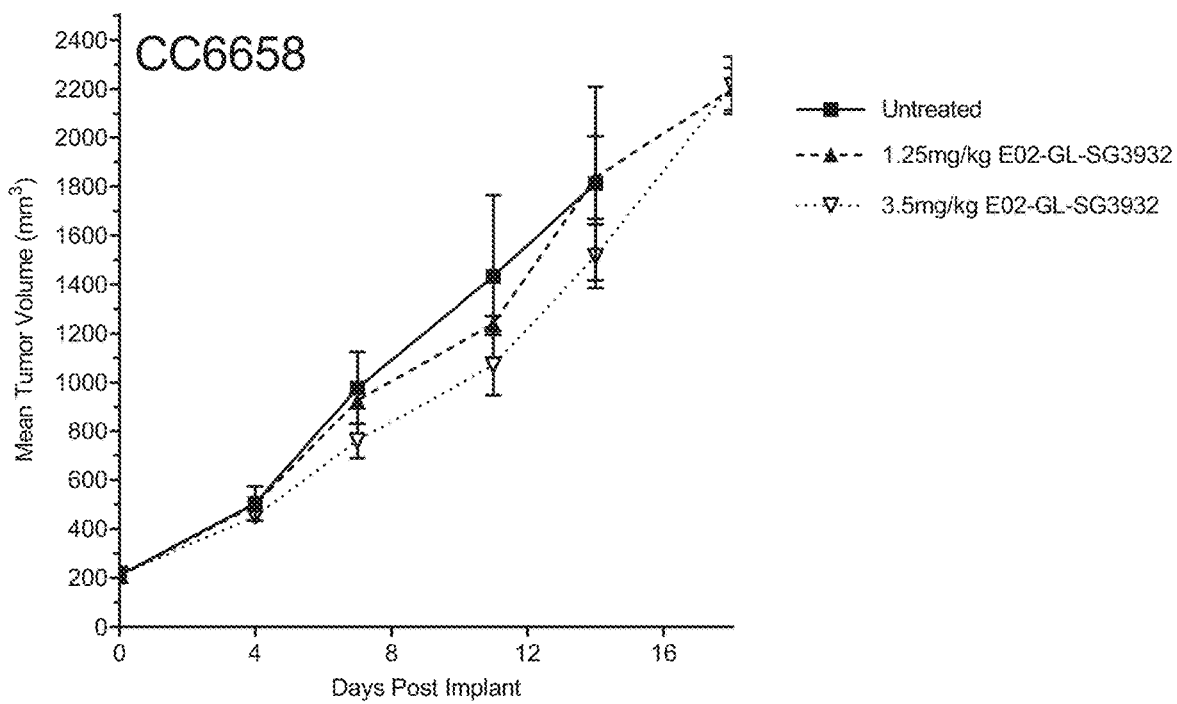
Figure 56I:
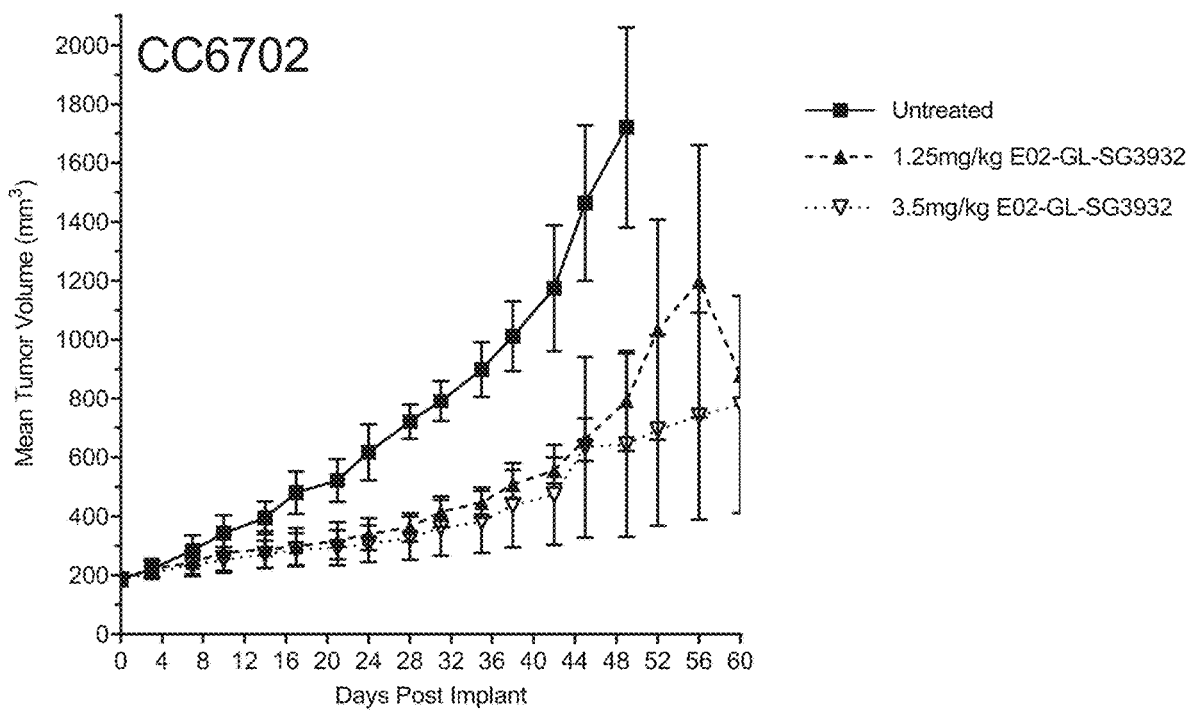
Figure 56J:
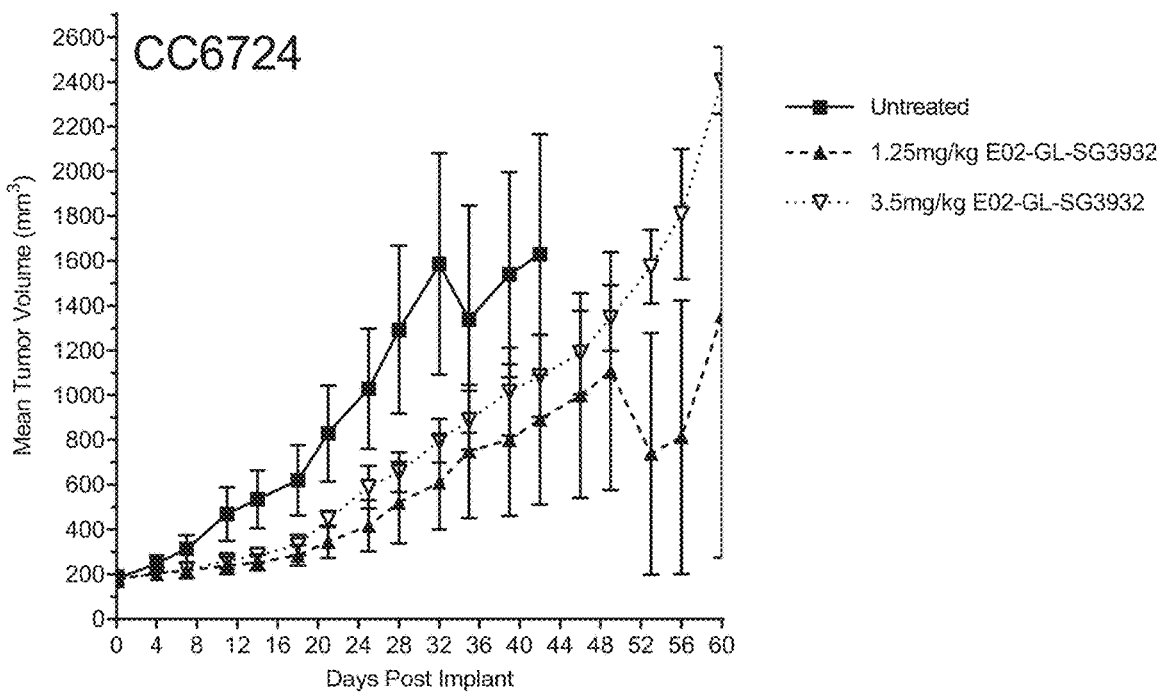
Figure 56K:
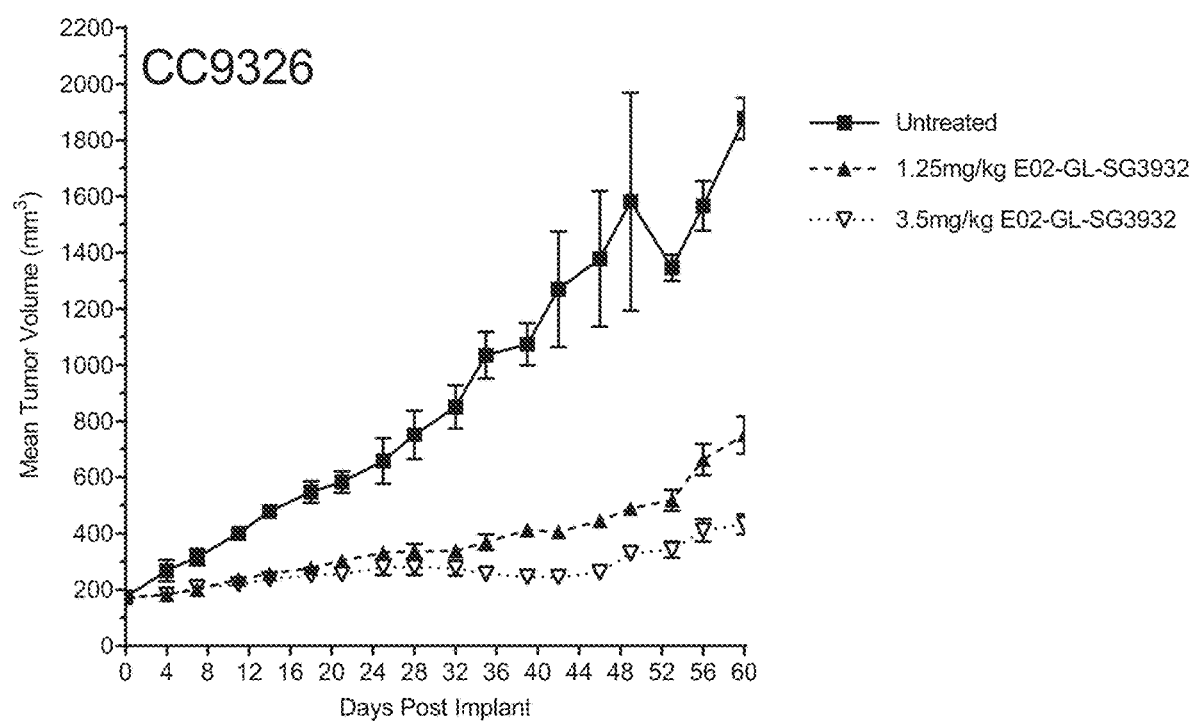

Compared with the 1.25 mg/kg dose level, greater antitumor activity was observed after a single dose of 3.5 mg/kg E02-GL-SG3932, with 69.2% (18 of 26) of the models tested exhibiting a reduction in tumor growth from baseline of 30% or greater (FIG. 53). Of these, 66.7% (12 of 18) expressed elevated levels of B7-H4, with an H-score of 100 or greater (FIGS. 54A and 54B). At this dose level, the association between H-score classification and responder status was not statistically significant (Fisher's exact tests, p=0.073).

Increased activity was also observed for the NIP228-SG3932 isotype ADC at this dose level, with 5 models (T330, BCX-017-LOP, T168, HBCx-15, and HBCx-6) exhibiting a reduction in tumor growth from baseline of 30% or greater (FIG. 53). These 5 models have a shared characteristic; defective homologous DNA repair, defined by the presence of either a BRCA1 mutation or a negative score in a RAD51 foci formation assay, proposed as a functional measure of homologous DNA repair capacity.

Figure 60A:
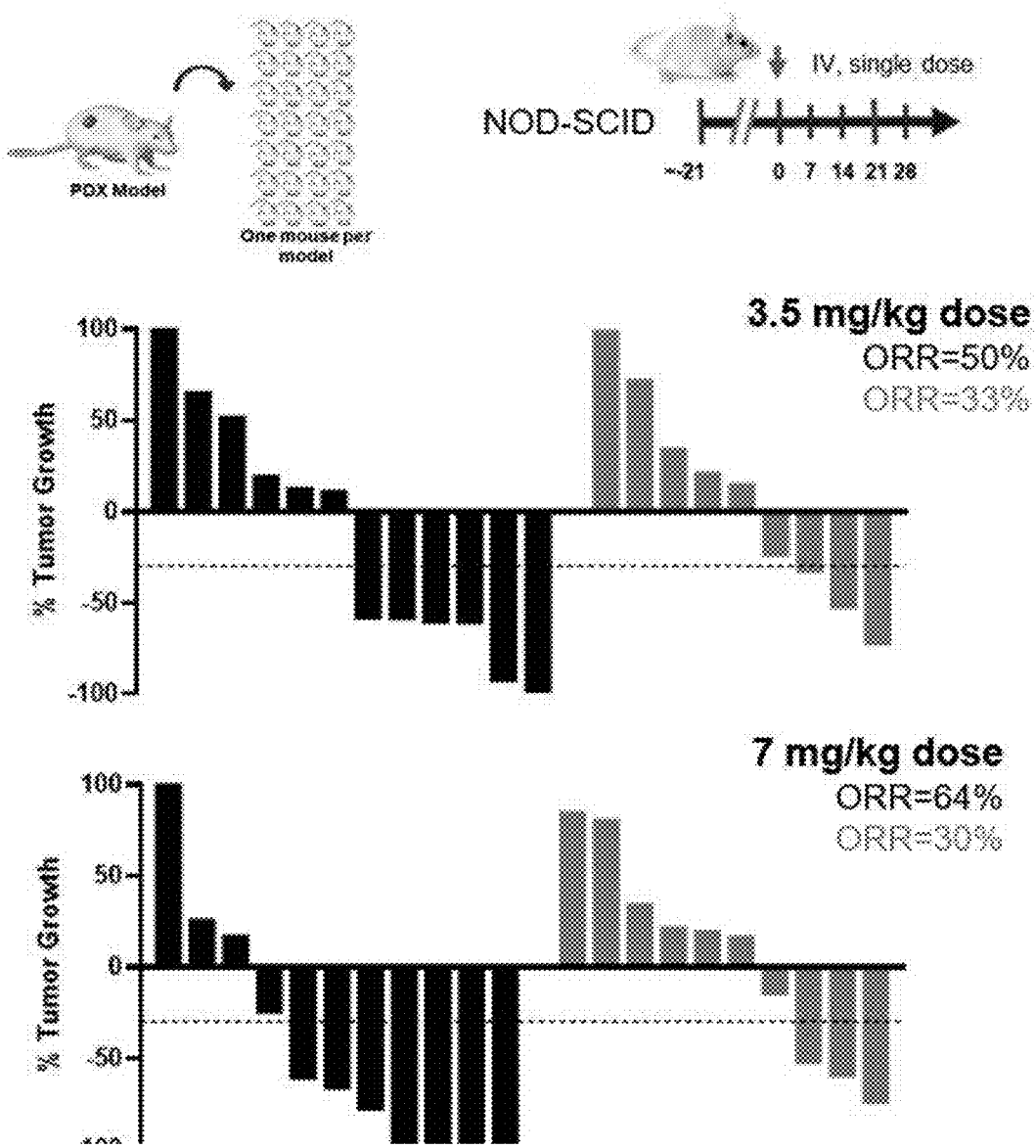
FIGS. 60A-60B show that E02-GL-SG3932 has robust activity in breast and ovarian PDX mouse models.
Figure 60B:
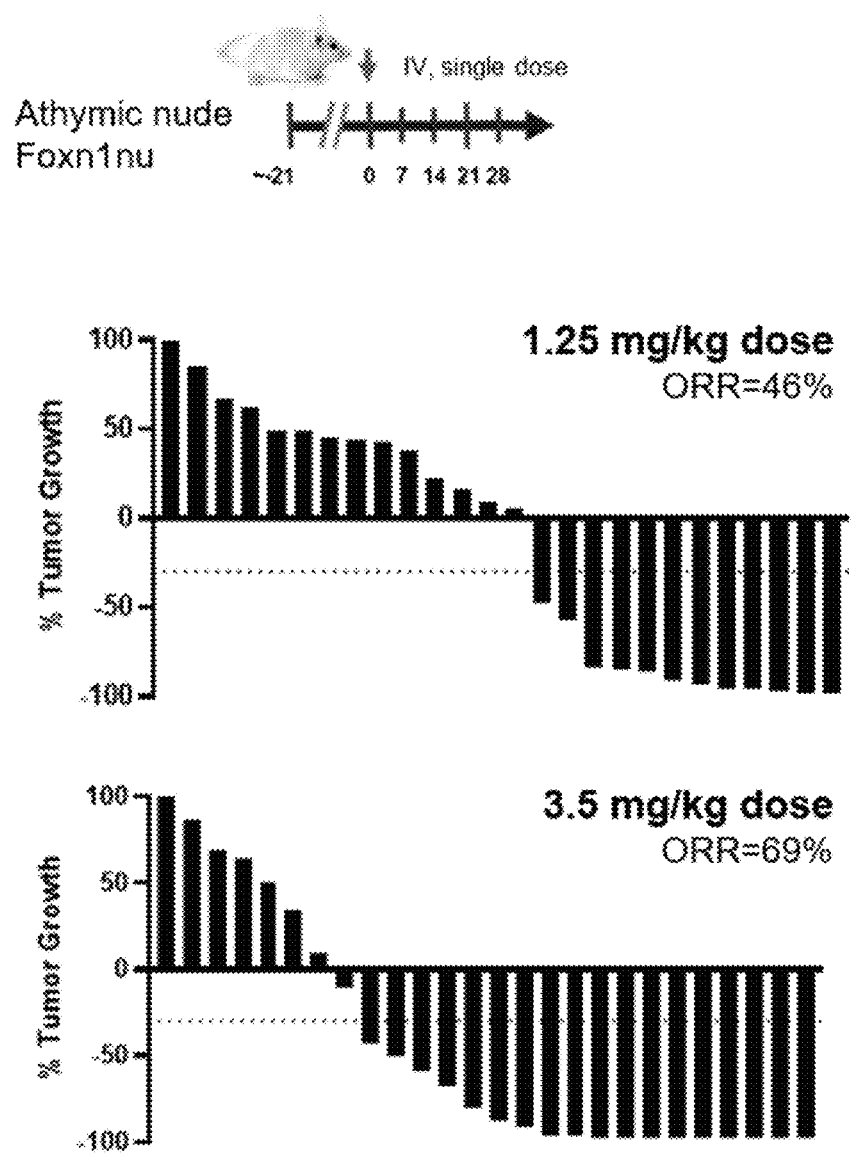
Figure 61:
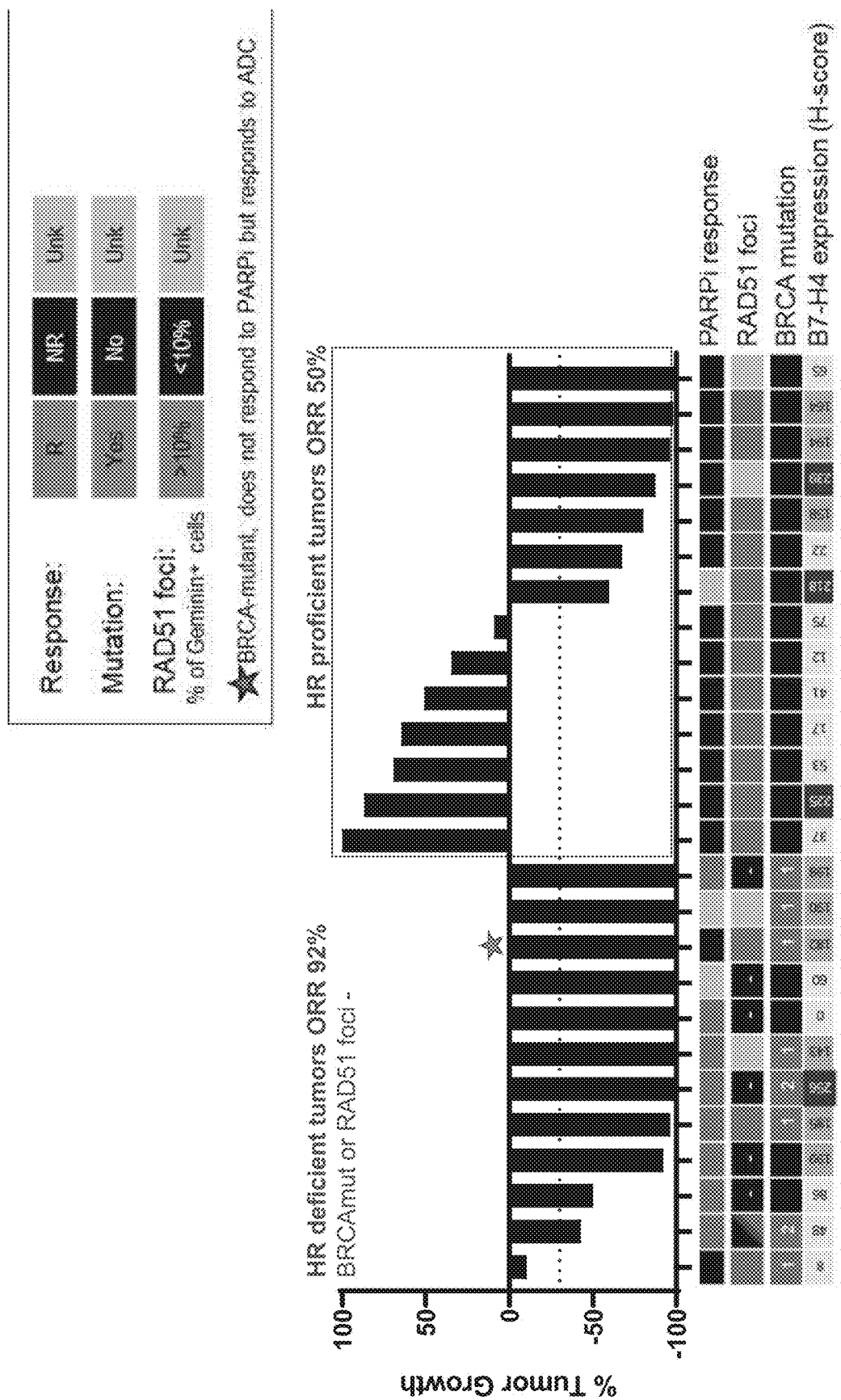
FIG. 61 shows that E02-GL-SG3932 has robust activity in HR-deficient tumors and in HR-proficient tumors with elevated B7-H4.
Figure 62A:
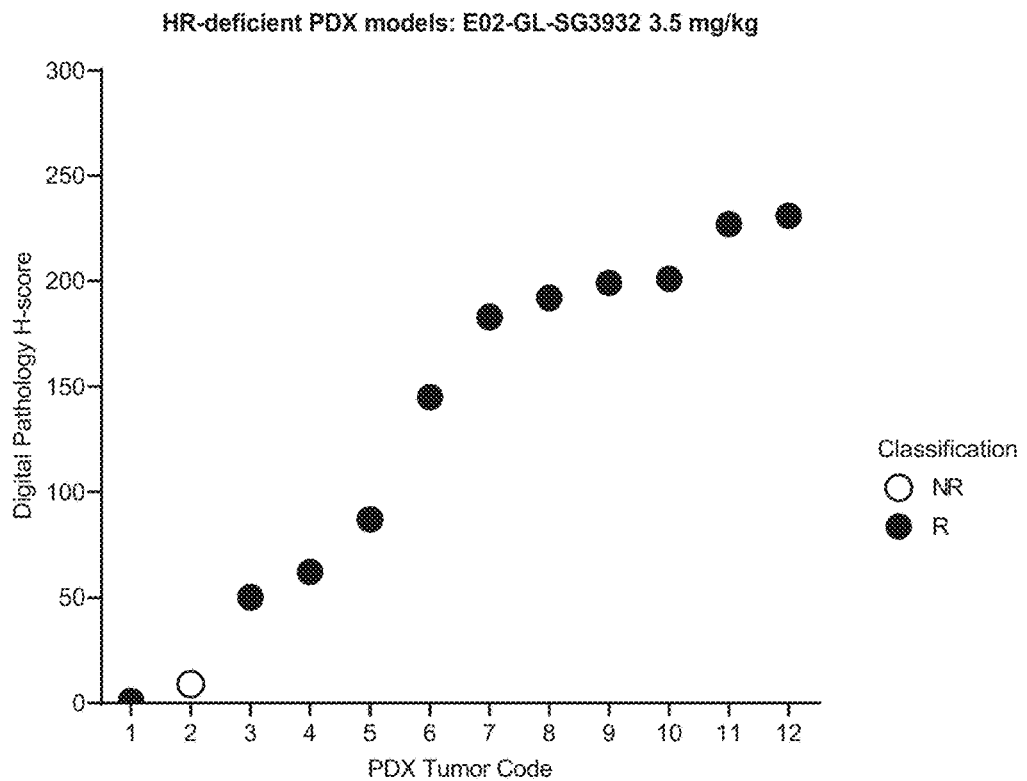
FIGS. 62A-62B show the tumor response in HR-deficient (A) and HR-proficient (B) PDX models grouped according to tumor response to E02-GL-SG3932 at the 3.5 mg/kg dose level. (R) indicates that models were considered to be responsive to test agents. (NR) indicates that models were considered to be non-responders. The y-axis indicates the level of B7-H4 in each model, as determined by H-score.
Figure 62B:
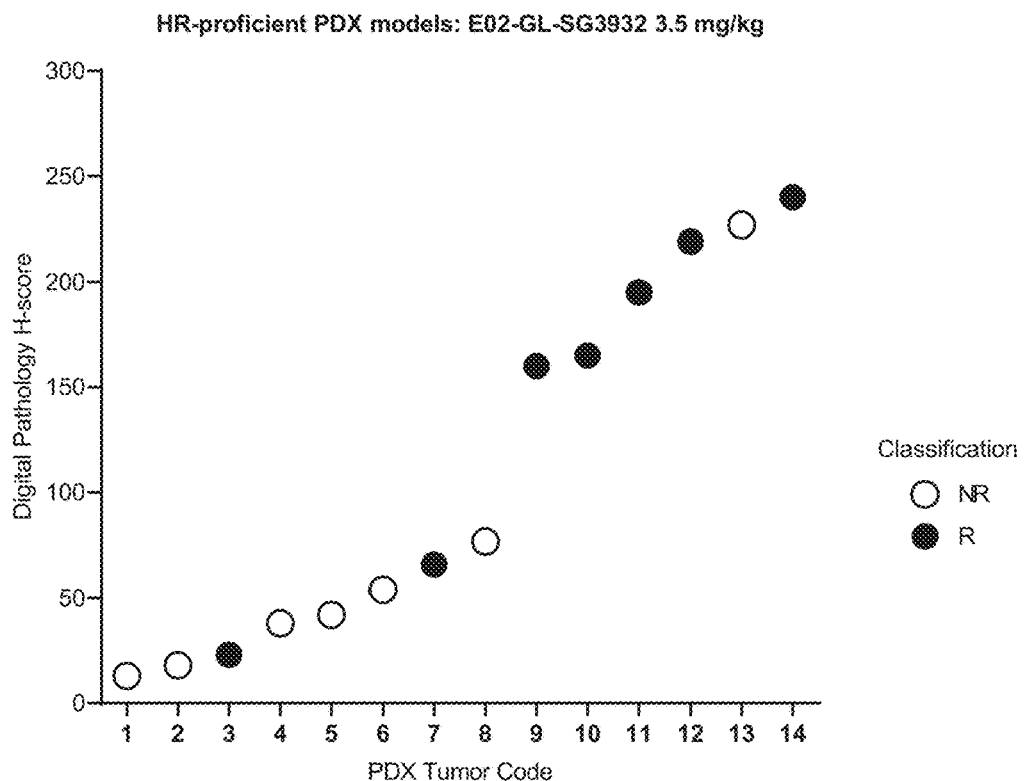
Figure 62C:
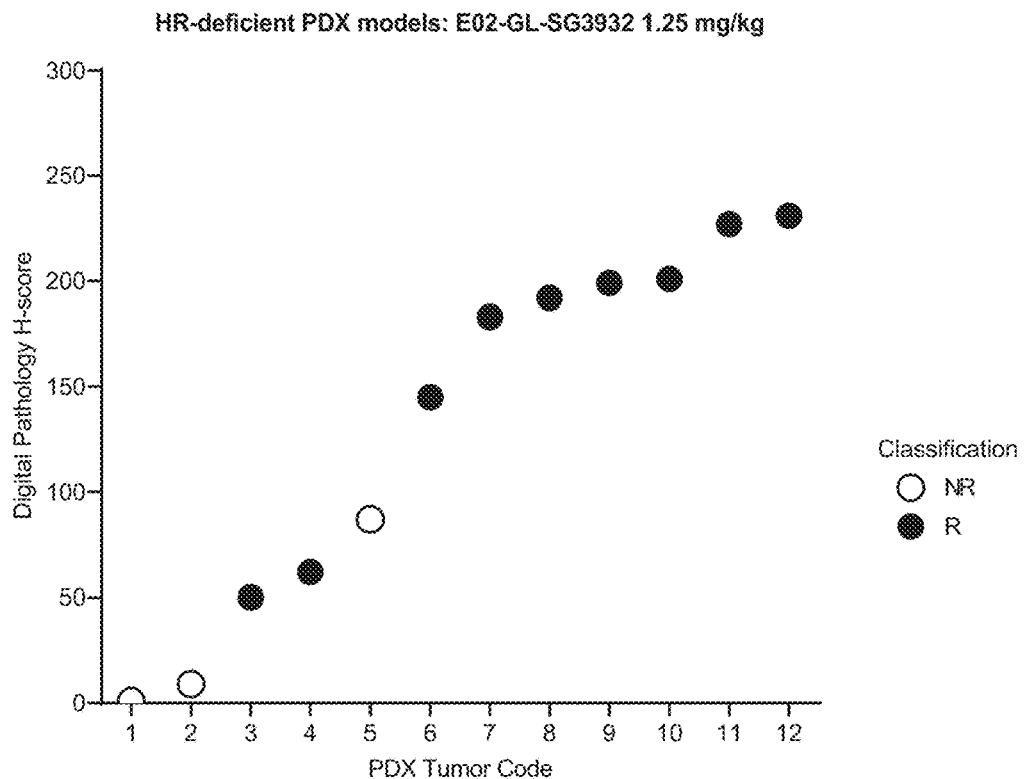
FIGS. 62C-62D show the tumor response in HR-deficient (A) and HR-proficient (B) PDX models grouped according to tumor response to E02-GL-SG3932 at the 1.25 mg/kg dose level. (R) indicates that models were considered to be responsive to test agents. (NR) indicates that models were considered to be non-responders. The y-axis indicates the level of B7-H4 in each model, as determined by H-score.
Figure 62D:
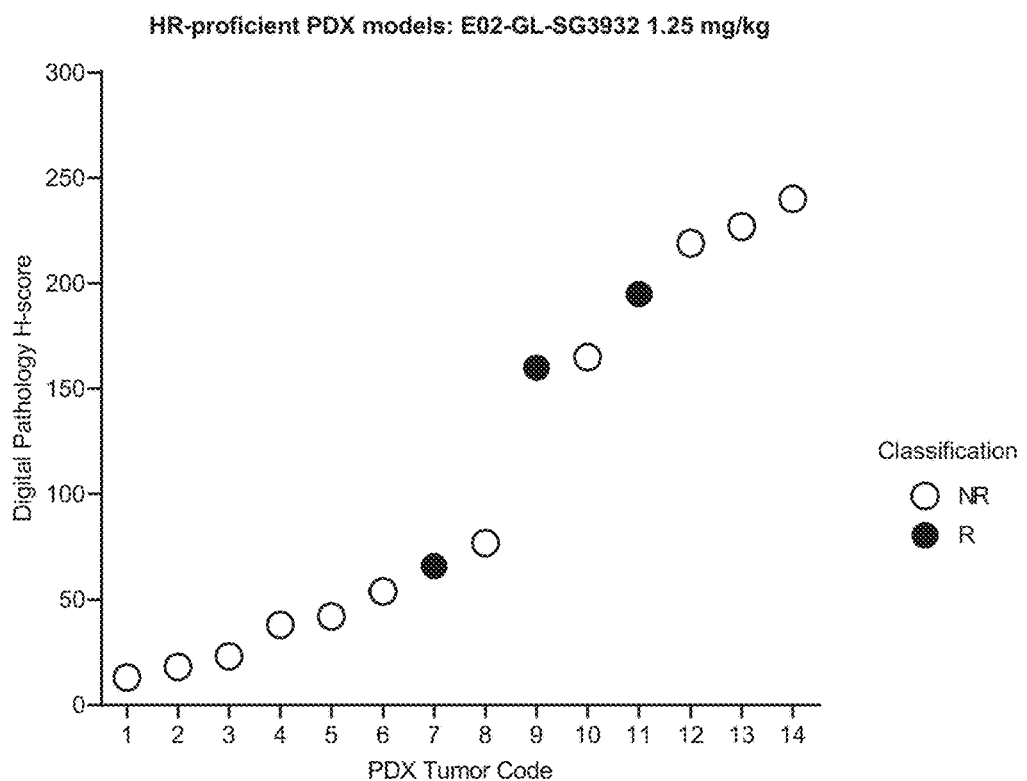

This example demonstrates that administration of E02-GL-SG3932 in tumors that have elevated levels of B7-H4 expression and are defective in homologous DNA repair, defined by (1) the presence of a BRCA1 mutation, (2) a negative score in a RAD51 foci formation assay, can reduce tumor volume. FIGS. 53B-53E show that at low doses, E02-GL-SG3932 response correlates with B7-H4 expression level and HR-deficiency. In a separate study, PDX models treated at 7 mg/kg showed a high level of isotype-control ADC activity (FIGS. 60A-60B and FIG. 61).

This example also demonstrates that E02-GL-SG3932 shows robust activity in HR-deficient tumors and in HR-proficient tumors with elevated B7-H4, and that HR-deficient tumors are more sensitive to damage by TOP1i and will have a lower B7-H4 expression threshold for activity.

Example 41

Antitumor Efficacy of E02-GL-SG3932 in Patient-Derived Xenograft Models of Cholangiocarcinoma The antitumor activity of E02-GL-SG3932 was investigated in a panel of 37 human cholangiocarcinoma PDX models. In the pre-study phase, female mice of various backgrounds (athymic nude mice, Balb/c Nude or NOD/SCID) were implanted with human cholangiocarcinoma PDX fragments and allowed to grow to approximately 1000-1500 mm3 in size. These tumors were then harvested and reimplanted into study mice. When tumors reached an average tumor volume of 150-300 $mm^3$, animals were then matched by tumor volume into treatment or control groups and dosing initiated on Day 0. Each mouse received a single IV injection of E02-GL-SG3932 or a control (untreated), at a dose of 1.25 mg/kg or 3.5 mg/kg. FIGS. 55A-55G provide results for a first investigated panel. The results shown in FIGS. 56A-56K provide results for a second investigated panel.

Example 42

E02-GL-SG3932 TOP1i Linker-Warhead is Related to Wider Therapeutic Index (TI)

Head to head comparative studies of the AZ'0133 linker-warhead selected for E02-GL-SG3932 were conducted to determine efficacy, pharmacokinetics, and toxicity of the SG3932 warhead with four alternative linkers. The cleavable mal-PEG8-val-ala linker-SG3932 linker-warhead ADC offers the widest relative TI and compares favorably to benchmark. The four comparative linker-warheads are provided below. Data collected from the comparative studies is provided set forth in Table 22.

Comparative Linker-Warheads

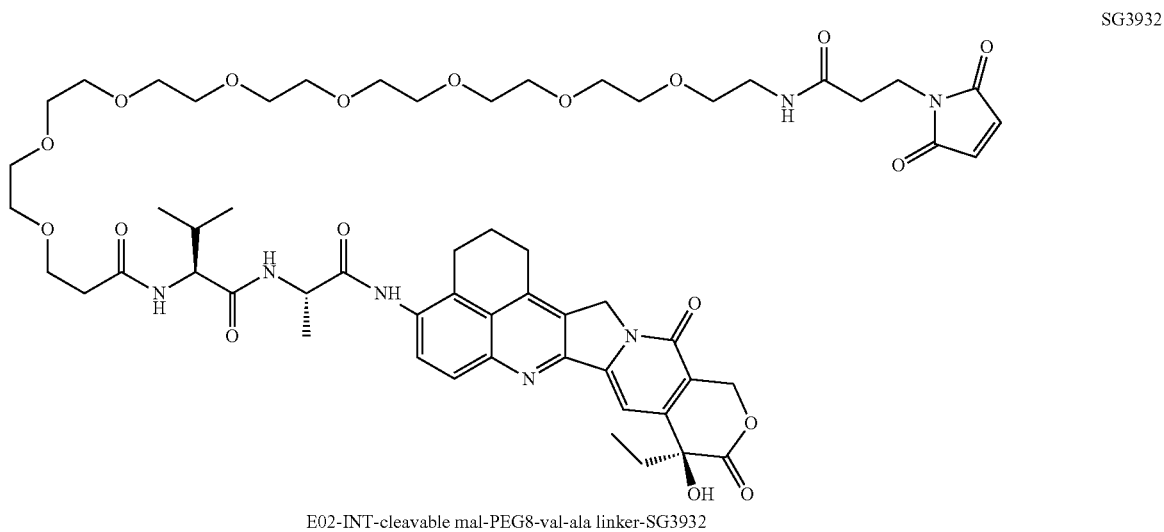

E02-INT-cleavable mal-PEG8-val-ala linker-SG3932

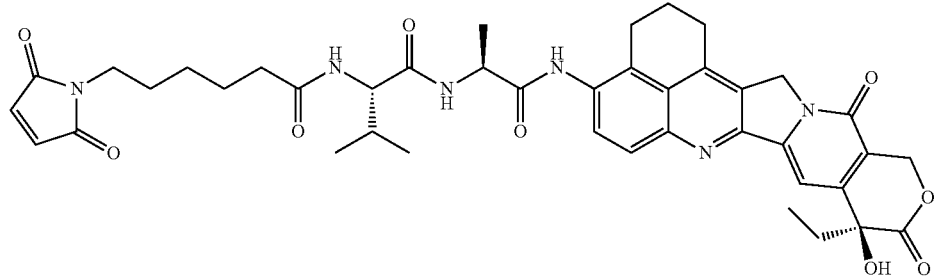

E02-INT-SG4010

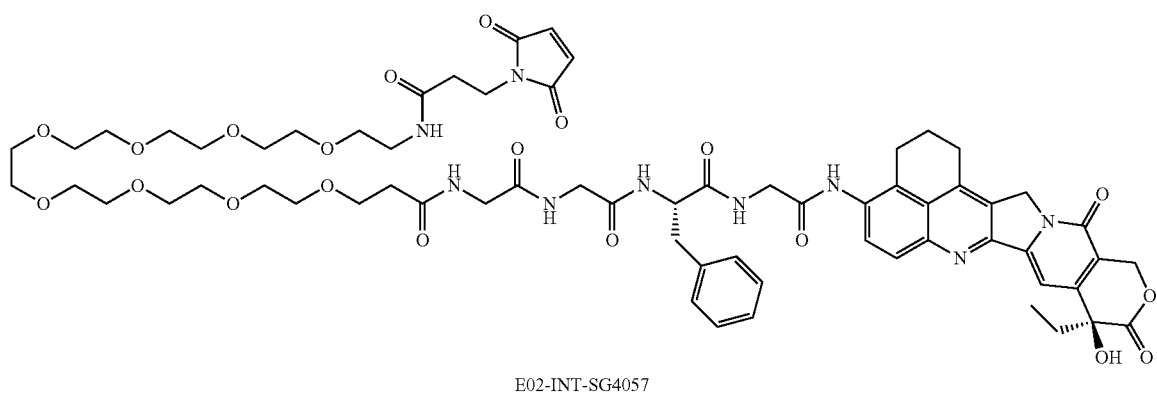

E02-INT-SG4057

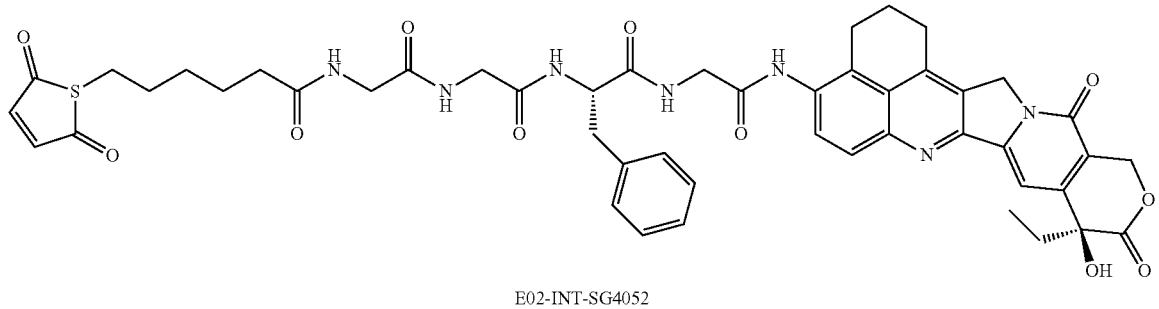

SG4052

E02-INT-SG4052

TABLE 22

Head-to-head comparative studies of efficacy, PK and toxicity of the E02-INT antibody with four alternative linkers

| | E02-INT-SG3932 | E02-INT-SG4010 | E02-INT-SG4057 | E02-INT-SG4052 |
|---|---|---|---|---|
| | | Linker + Warhead | | |
| | mp-PEG8-Val-Ala-SG3932 | mc-Val-Ala-SG3932 | mp-PEG8-GGFG-SG3932 | mc-GGFG-SG3932 |
| Hydrophobicity (HIC), Retention time (min) | 3.41 | 3.37 | 3.76 | 3.53 |
| In vitro serum stability (avg % deconjug. at day 15 vs 0) | 24 | 68.4 | 28.4 | 69 |
| In vitro cytotoxicity IC50 MX1/HT29 clone 26 (ng/mL) | 8.81/53.3 | 5.54/40.6 | 14.4/44.0 | 6.21/67.6 |
| In vivo efficacy-MX-1, dose for tumor stasis/30% regression (mg/kg) | 0.57/1.27 | 0.83/1.18 | 0.92/1.02 | 1.02/1.85 |
| In vivo efficacy-MDA-MB-468, dose for tumor stasis/30% regression (mg/kg) | 0.89/1.35 | 0.71/1.47 | 1.12/1.85 | 1.16/1.98 |
| SCID mouse PK - CL (ml/day/kg) @ 1.25 mg/kg | 11.3 | 20.4 | 14.6 | 19.0 |
| Rat PK - CL (ml/day/kg) @ 60 mg/kg (HNSTD) | 7.57 | 13.3 | 10.3 | 24.3 |
| Rat toxicology study (# of findings with severity over background/control after 20 or 60 mg/kg dose) | 1/7 | 3/7 | 3/7 | 4/7 |
| Relative TI for tumor stasis in MX-1 | 152 | 101 | 82 | 44 |
| Relative TI for 30% tumor regression at day 7 in MX-1 | 68 | 71 | 45 | 39 |

Figures 57A, 57B:
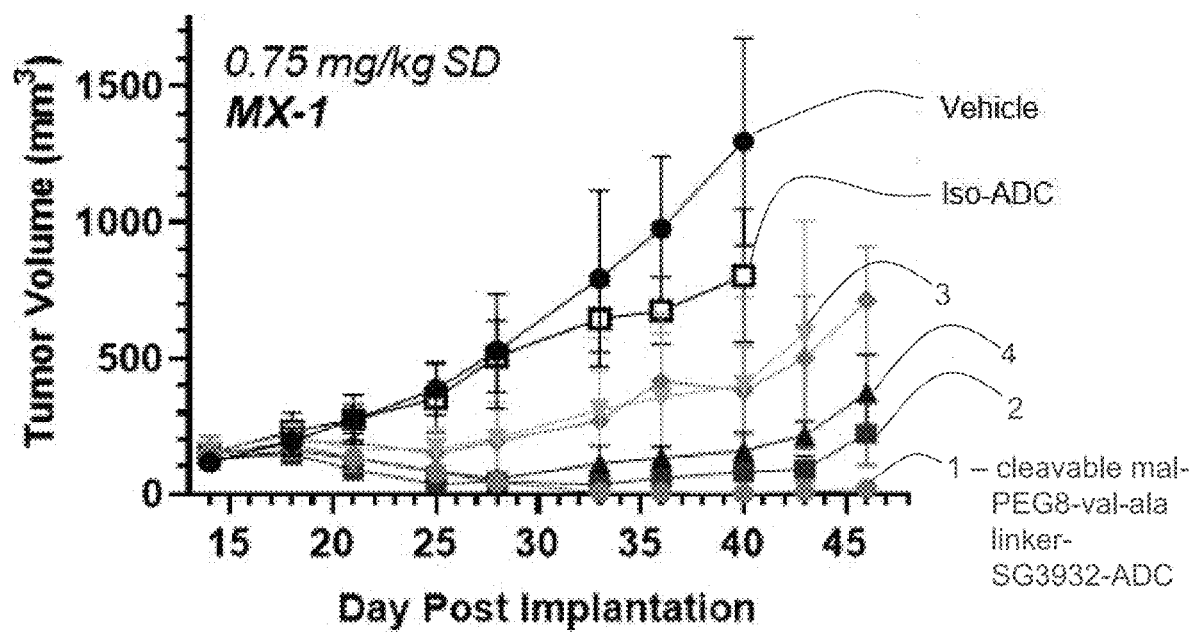
FIG. 57A-57B show that the ADC prepared with the cleavable mal-PEG8-val-ala linker-warhead is the most active in vivo, as compared to ADCs 2-4.
Figure 58:
FIG. 58 shows that the cleavable mal-PEG8-val-ala linker-warhead ADC exhibits the cleanest safety profile in a rat toxicity study, as compared to ADCs 2-4.
Figures 59A, 59B:
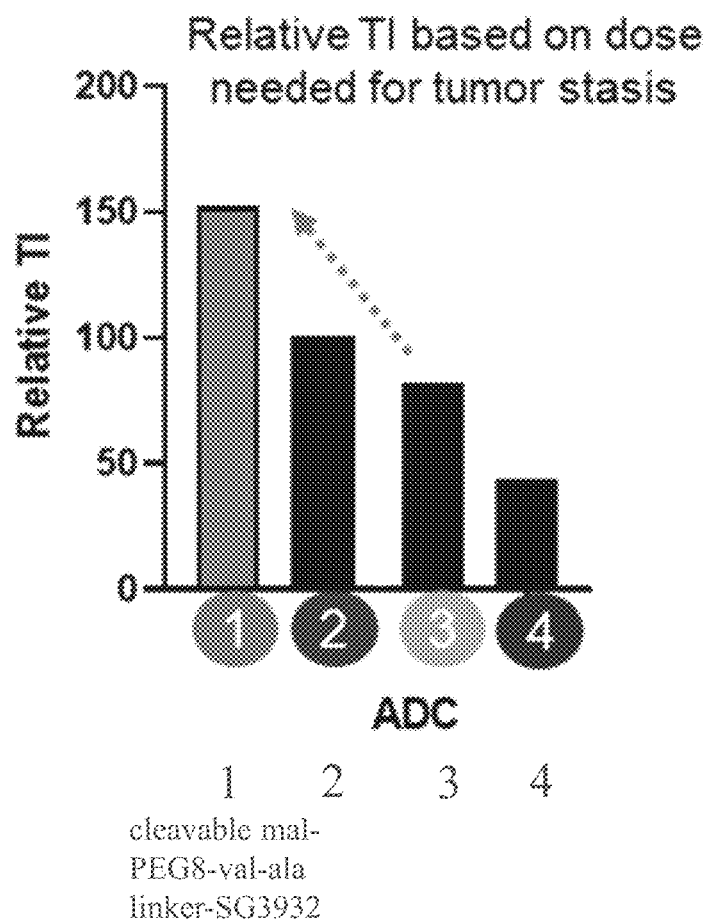
FIG. 59A-59B show that the cleavable mal-PEG8-val-ala linker-warhead ADC has good PK properties and widest relative TI, as compared to ADCs 2-4. Relative TI=exposure ratio of AUC at the highest dose tested in rat (NOAEL not HNSTD) to the AUC that provides tumor stasis (MX-1 model).

The mp-PEG8-Val-Ala-SG3932 linker-warhead for E02-GL-SG3932 performed better than each comparator. The ADC prepared with the cleavable mal-PEG8-val-ala linker-SG3932 linker-warhead is the most active in vivo, when conjugated to the E02-INT antibody (FIGS. 57A and 57B). The cleavable mal-PEG8-val-ala linker-SG3932 linker-warhead ADC exhibits the cleanest safety profile in rat toxicity study, as shown in FIG. 58. The cleavable mal-PEG8-val-ala linker-SG3932 linker-warhead ADC has good PK properties and widest relative TI, as shown in FIG. 59. Relative TI=exposure ratio of AUC at the highest dose tested in rat (NOAEL not HNSTD) to the AUC that provides tumor stasis (MX-1 model).

As shown in FIG. 29B, the cleavable mal-PEG8-val-ala linker-SG3932 linker-warhead can be differentiated from competitor TOP1i conjugated ADC and contains key features thought to contribute to TI and provide advantages. In particular, the mp-PEG in the cleavable mal-PEG8-val-ala linker-SG3932 stabilizes the conjugate and contributes to ADC stability, and the lactone switch in cleavable mal-PEG8-val-ala linker-SG3932 can open while attached to the ADC, which increases warhead potency following internalization by receptor-mediated endocytosis (RME). (FIG. 29B)

FIGS. 60A-60B show that E02-GL-SG3932 has robust activity in Breast and Ovarian PDX. Panel A: The antitumor activity of E02-GL-SG3932 was investigated in a panel of breast and ovarian PDX models. Each mouse (N=1 per group) received a single IV injection of E02-GL-SG3932 or a control (untreated), at a dose of 7 mg/kg or 3.5 mg/kg. FIG. 60B shows antitumor activity in a panel of TNBC PDX models. Each mouse received a single IV injection of E02-GL-SG3932 or a vehicle control at a dose of 3.5 mg/kg or 1.25 mg/kg.

E02-GL-SG3932 also shows robust activity in HR-deficient tumors and in HR-proficient tumors with elevated B7-H4 (FIGS. 61 and 62A-D).

Figure 63:
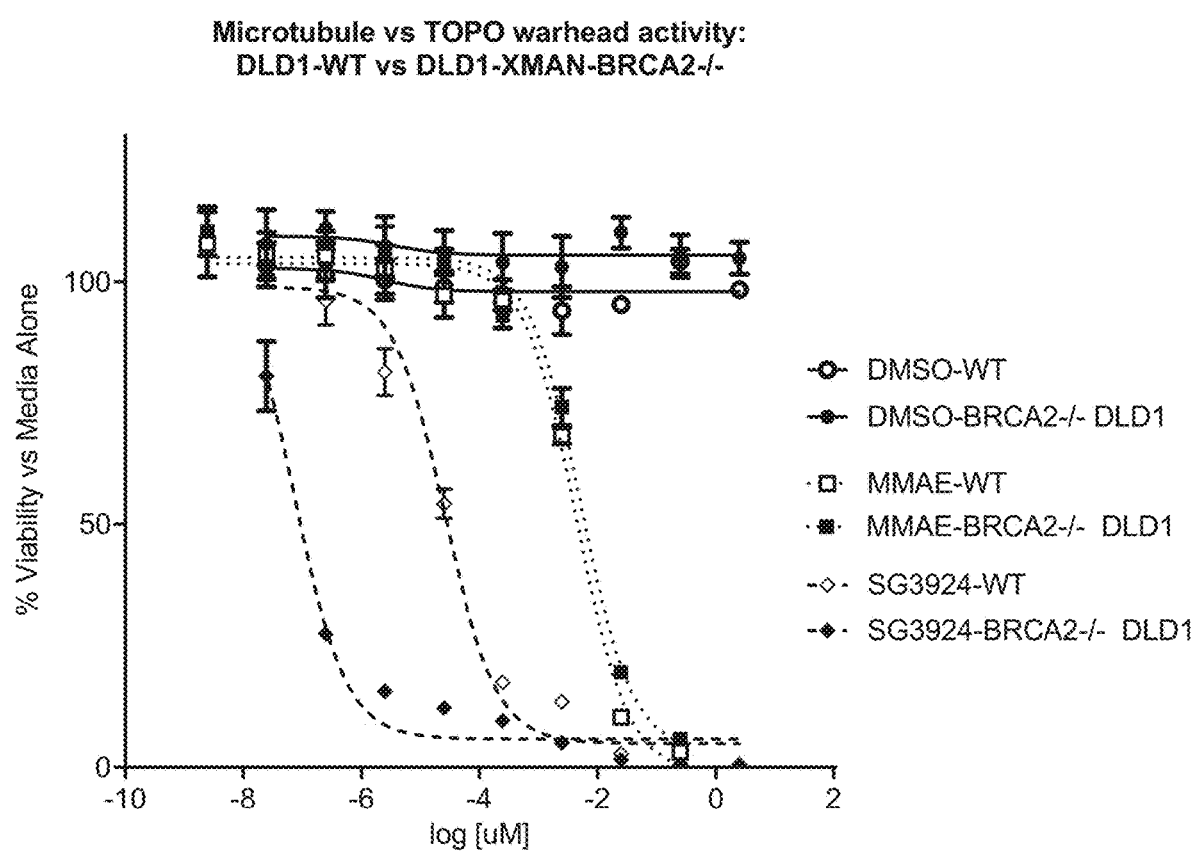
FIG. 63 shows the results of 6-day cytotoxicity assays of different warheads in DLD1 wt or BRCA2−/− cells. MMAE=negative control, microtubule-inhibitor warhead.

Additionally, HR-deficiency increases sensitivity to the SG3932 warhead. As shown in FIG. 63, a shift in potency with the SG3932 warhead as compared to Dimethylsulfoxide (DMSO) treatment and a negative control microtubule-inhibitor warhead (MMAE). As shown in FIG. 63, cell viability was over 100% when wild-type and BRCA2−/− cells were treated with DMSO. Cell viability was reduced in both wild-type and BRCA2−/− cells when treated with the MMAE warhead. A large decrease in viability was seen when wild-type cells were treated with the SG3932 warhead as compared to the MMAE warhead. However, the largest decrease in viability (~349 fold shift in potency) was seen when BRCA2−/− cells were treated with the SG3932 warhead. This demonstrates that HR-deficiency increases sensitivity to the SG3932 warhead.

Synthesis of Topoisomerase I Inhibitors
General Information

Flash chromatography was performed using a Biotage® Isolera™ and fractions checked for purity using thin-layer chromatography (TLC). TLC was performed using Merck Kieselgel 60 F254 silica gel, with fluorescent indicator on aluminium plates. Visualisation of TLC was achieved with UV light.

Extraction and chromatography solvents were bought and used without further purification from VWR U.K.

All fine chemicals were purchased from Sigma-Aldrich unless otherwise stated. Pegylated reagents were obtained from Quanta biodesign US via Stratech UK.

LC/MS Conditions

Method A

Positive mode electrospray mass spectrometry was performed using a Waters Aquity H-class SQD2. Mobile phases used were solvent A (water with 0.1% formic acid) and solvent B (acetonitrile with 0.1% formic acid). Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Detection was at 254 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm.

Method B

The HPLC (Waters Alliance 2695) was run using a mobile phase of water (A) (formic acid 0.1%) and acetonitrile (B) (formic acid 0.1%). Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Wavelength detection range: 190 to 800 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm.

Method C

The HPLC (Waters Alliance 2695) was run using a mobile phase of water (A) (formic acid 0.1%) and acetonitrile (B) (formic acid 0.1%).

Initial composition 5% B held over 1 min, then increase from 5% B to 100% B over a 9 min period. The composition was held for 2 min at 100% B, then returned to 5% B in 0.10 minutes and hold there for 3 min. Total gradient run time equals 15 min. Flow rate 0.6 mL/min. Wavelength detection range: 190 to 800 nm. Oven temperature: 50° C. Column: ACE Excel 2 C18-AR, 2μ, 3.0×100 mm.

HPLC Conditions

Reverse-phase ultra-fast high-performance liquid chromatography (UFLC) was carried out on a Shimadzu Prominence™ machine using a Phenomenex™ Gemini NX 5μ C18 column (at 50° C.) dimensions: 150×21.2 mm. Eluents used were solvent A (H₂O with 0.1% formic acid) and solvent B (CH₃CN with 0.1% formic acid). All UFLC experiments were performed with gradient conditions: Initial composition 13% B increased to 30% B over a 3 minutes period, then increased to 45% B over 8 minutes and again to 100% over 6 minutes before returning to 13% over 2 min and hold for 1 min. The total duration of the gradient run was 20.0 minutes. Flow rate was 20.0 mL/minute and detection was at 254 and 223 nm.

NMR Method

Proton NMR chemical shift values were measured on the delta scale at 400 MHz using a Bruker AV400. The following abbreviations have been used: s, singlet; d, doublet; t, triplet; q, quartet; quin, quintet; m, multiplet; br, broad. Coupling constants are reported in Hz.

Synthesis of Key Intermediates

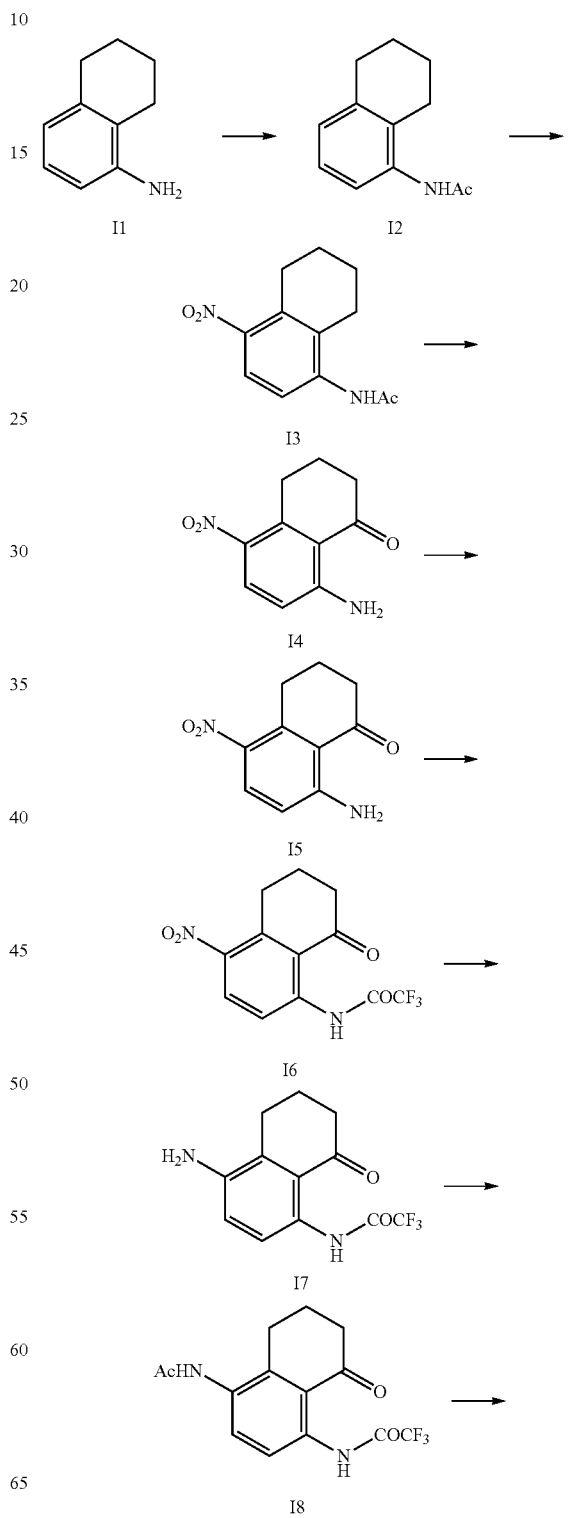

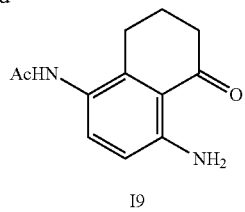

I9 a) N-(5,6,7,8-tetrahydronaphthalen-1-yl)acetamide (I2)

5,6,7,8-tetrahydronaphthalen-1-amine I1 (8.54 g, 58.0 mmol) was dissolved in dichloromethane (80 mL). Triethylamine (18 mL, 129 mmol) was added and the mixture cooled to 0° C. Dropwise, acetic anhydride (11.5 mL, 122 mmol) was added, upon completion of the addition, the reaction mixture was warmed to rt and stirred for 45 min, whereupon LCMS indicated the reaction was complete. The mixture was diluted with $CH_2Cl_2$, washed with $H_2O$, sat. $NaHCO_3$, 10% citric acid, the organic phase dried over $MgSO_4$ and concentrated in vacuo. The off-white solid was triturated with 1:3 $Et_2O$/isohexane to afford 12 (10.8 g, 57.1 mmol, 98% Yield) as a white solid which was used without further purification. LC/MS (method A): retention time 1.44 mins (ES+) m/z 190 [M+H]$^+$ b) N-(4-nitro-5,6,7,8-tetrahydronaphthalen-1-yl)acetamide (I3)

N-(5,6,7,8-tetrahydronaphthalen-1-yl)acetamide I2 (1.00 g, 5.2840 mmol) was added portion-wise to sulfuric acid (15 mL, 281 mmol) at −5° C. Sodium nitrate (450 mg, 5.2945 mmol) was added portion-wise to the reaction mixture and stirred for 30 min at −5° C. whereupon LCMS indicated no further reaction progress. The reaction mixture was poured onto ice with external cooling, the aqueous mixture extracted with $CH_2Cl_2$, the organic phase dried over $MgSO_4$ and purified by Isolera (10-80% EtOAc in isohexane) to afford a mixture of N-(4-nitro-5,6,7,8-tetrahydronaphthalen-1-yl)acetamide I3 and N-(2-nitro-5,6,7,8-tetrahydronaphthalen-1-yl)acetamide (956 mg, 4.0811 mmol, 77% Yield) as a white/yellow solid. LC/MS (method A): retention time 1.53 mins (ES+) m/z 235 [M+H]$^+$.

c) N-(4-nitro-8-oxo-5,6,7,8-tetrahydronaphthalen-1-yl)acetamide (I4)

N-(4-nitro-5,6,7,8-tetrahydronaphthalen-1-yl)acetamide I3 (1.01 g, 4.31 mmol) was dissolved in acetone (30 mL). Magnesium sulfate in water (3.9 mL, 5.9 mmol, 1.5 mol/L) was added and the mixture was cooled to 0° C. Potassium permanganate (2.07 g, 13.0 mmol) was added portionwise to the reaction mixture and the mixture warmed to rt and stirred for 50 min, whereupon TLC indicated the reaction was complete. The reaction mixture was filtered through Celite, the solids washed with $CHCl_3$ and the resulting organic mixture washed with $H_2O$, brine, dried over $MgSO_4$ and purified by isolera (20-50% EtOAc in isohexane) to afford a mixture of N-(4-nitro-8-oxo-5,6,7,8-tetrahydronaphthalen-1-yl)acetamide I4 and N-(2-nitro-8-oxo-5,6,7,8-tetrahydronaphthalen-1-yl)acetamide (709 mg, 2.86 mmol, 66%) as a white/yellow solid. LC/MS (method A): retention time 1.44 mins (ES+) m/z 190 [M+M]$^+$ d) 8-amino-5-nitro-3,4-dihydronaphthalen-1(2H)-one (I5)

A mixture of N-(4-nitro-8-oxo-5,6,7,8-tetrahydronaphthalen-1-yl)acetamide I4 and N-(2-nitro-8-oxo-5,6,7,8-tetrahydronaphthalen-1-yl)acetamide (709 mg, 2.8561 mmol) and 6N hydrochloric acid (7 mL) were stirred at 80° C. for 2.5 h, whereupon LCMS indicated the reaction was complete. The reaction mixture was cooled in an ice bath and 6N NaOH solution was added until the pH was basic. The aqueous mixture was extracted with $CH_2Cl_2$, the organic phase dried over $MgSO_4$ and concentrated in vacuo. Isolera (0-50% EtOAc in isohexane) afforded 8-amino-5-nitro-3,4-dihydronaphthalen-1(2H)-one I5 (320 mg, 1.552 mmol, 54% Yield) as a yellow/orange solid. LC/MS (method A): retention time 1.54 mins (ES+) m/z 207 [M+M]$^+$ e) 2,2,2-trifluoro-N-(4-nitro-8-oxo-5,6,7,8-tetrahydronaphthalen-1-yl)acetamide (I6)

8-amino-5-nitro-3,4-dihydronaphthalen-1(2H)-one I5 (430 mg, 2.0854 mmol) was dissolved in dichloromethane (20 mL). Pyridine (340 μL, 4.20 mmol) was added and the mixture cooled to 0° C. Trifluoroacetic anhydride (590 μL, 4.197 mmol) was added and stirred for 30 min, whereupon LCMS indicated the reaction was complete. The mixture was diluted with $CH_2Cl_2$, washed with $H_2O$, the organic phase dried over $MgSO_4$ and concentrated in vacuo to afford 2,2,2-trifluoro-N-(4-nitro-8-oxo-5,6,7,8-tetrahydronaphthalen-1-yl)acetamide I6 (630 mg, 2.0846 mmol, >99% Yield) as a yellow solid, which was used without further purification. LC/MS (method A): retention time 1.86 min (ES+) m/z 301X [M−H]$^-$ f) N-(4-amino-8-oxo-5,6,7,8-tetrahydronaphthalen-1-yl)-2,2,2-trifluoroacetamide (I7)

Zinc (2.73 g, 41.7 mmol) was suspended in methanol (80 mL), formic acid (4 mL) and water (4 mL) and the mixture cooled to 0° C. 2,2,2-trifluoro-N-(4-nitro-8-oxo-5,6,7,8-tetrahydronaphthalen-1-yl)acetamide I6 (568 mg, 2.0865 mmol) was added portion-wise and the mixture stirred at 0° C. for 30 min, whereupon LCMS indicated the reaction was complete. The reaction mixture was filtered, the filtrate diluted with EtOAc and washed with sat $NaHCO_3$. The organic phase was dried over $MgSO_4$ and concentrated in vacuo to afford N-(4-amino-8-oxo-5,6,7,8-tetrahydronaphthalen-1-yl)-2,2,2-trifluoroacetamide I7 (568 mg, 2.0865 mmol, >99% Yield) as a yellow solid, which was used without further purification. LC/MS (method A): retention time 1.65 min (ES+) m/z 273 [M+H]$^+$ g) N-(4-acetamido-8-oxo-5,6,7,8-tetrahydronaphthalen-1-yl)-2,2,2-trifluoroacetamide (I8)

N-(8-amino-4-oxo-tetralin-5-yl)-2,2,2-trifluoro-acetamide I7 (568 mg, 2.0865 mmol) was dissolved in dichloromethane (20 mL). Triethylamine (580 μL, 4.16 mmol) then acetyl chloride (297 μL, 4.173 mmol) were added and the mixture stirred for 30 min, whereupon LCMS indicated the reaction was complete. The reaction mixture was diluted with $CH_2Cl_2$, washed with $H_2O$, the organic phase dried over $MgSO_4$ and concentrated in vacuo to afford N-(8-acetamido-4-oxo-tetralin-5-yl)-2,2,2-trifluoro-acetamide I8 (655 mg, 2.084 mmol, >99% yield) as a yellow solid, which was used without further purification. LC/MS (method A): retention time 1.55 min (ES+) m/z 315 [M+H]+ h) N-(4-amino-5-oxo-5,6,7,8-tetrahydronaphthalen-1-yl)acetamide (I9)

N-(8-acetamido-4-oxo-tetralin-5-yl)-2,2,2-trifluoro-acetamide I8 (2.77 g, 8.81 mmol) was dissolved in methanol (240 mL) and water (17 mL). Potassium carbonate (4.88 g, 35.3 mmol) was added and the mixture stirred for 1.5 h at 50° C., whereupon LCMS indicated the reaction was complete. The reaction mixture was cooled, concentrated in vacuo, dissolved in 10% MeOH in $CH_2Cl_2$ and washed with $H_2O$. The organic phase was dried over $MgSO_4$ and purified by isolera chromatography (2-15% MeOH in $CH_2Cl_2$) to afford N-(8-amino-1-oxo-tetralin-5-yl)acetamide I9 (1.20 g, 5.50 mmol, 62.3% Yield) as a yellow solid. LC/MS (method A): retention time 0.98 min (ES+) m/z 219 [M+H]+ i) (S)—N-(9-ethyl-9-hydroxy-10,13-dioxo-2,3,9,10,13,15-hexahydro-1H,12H-benzo[de]pyrano[3',4':6,7]indolizino[1,2-b]quinolin-4-yl)acetamide (I10)

N-(8-amino-1-oxo-tetralin-5-yl)acetamide I9 (641 mg, 2.94 mmol, 1.0 eq.), (S)-4-ethyl-4-hydroxy-7,8-dihydro-1H-pyrano[3,4-f]indolizine-3,6,10(4H)-trione A3 (840 mg, 3.19 mmol, 1.1 eq.) and PPTS (740 mg, 2.95 mmol, 1.0 eq.) were dissolved in toluene (60 mL) and stirred at reflux for 3 h, whereupon LCMS indicated I9 had been consumed. The reaction mixture was cooled and concentrated in vacuo. The resulting solids were triturated with acetonitrile, then acetone to afford I10 as a brown solid with minor TsOH contamination (1.26 g, 96%). LC/MS (method A): retention time 1.32 mins (ES+) m/z 447 [M+M]+ j) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11)

(S)—N-(9-ethyl-9-hydroxy-10,13-dioxo-2,3,9,10,13,15-hexahydro-1H,12H-benzo[de]pyrano[3',4':6,7]indolizino[1,2-b]quinolin-4-yl)acetamide (I10) (1.26 g, 2.83 mmol, 1.0 eq.) was dissolved in hydrochloric acid (6 mol/L) in $H_2O$ (12 mL) and the mixture stirred for 5 h at 80° C., whereupon LCMS indicated I10 had been consumed. The reaction mixture was diluted with $H_2O$ and concentrated in vacuo to afford (S)-4-amino-9-ethyl-9-hydroxy-1,2,3,9,12,15-hexahydro-10H,13H-benzo[de]pyrano[3',4':6,7]indolizino[1,2-b]quinoline-10,13-dione I11 (1.51 g, 2.85 mmol, 90 mass %, 101% Yield) as a red crystalline solid. LC/MS (method A): retention time 1.36 mins (ES+) m/z 405 [M+H]+.

Alternate Synthesis of I11

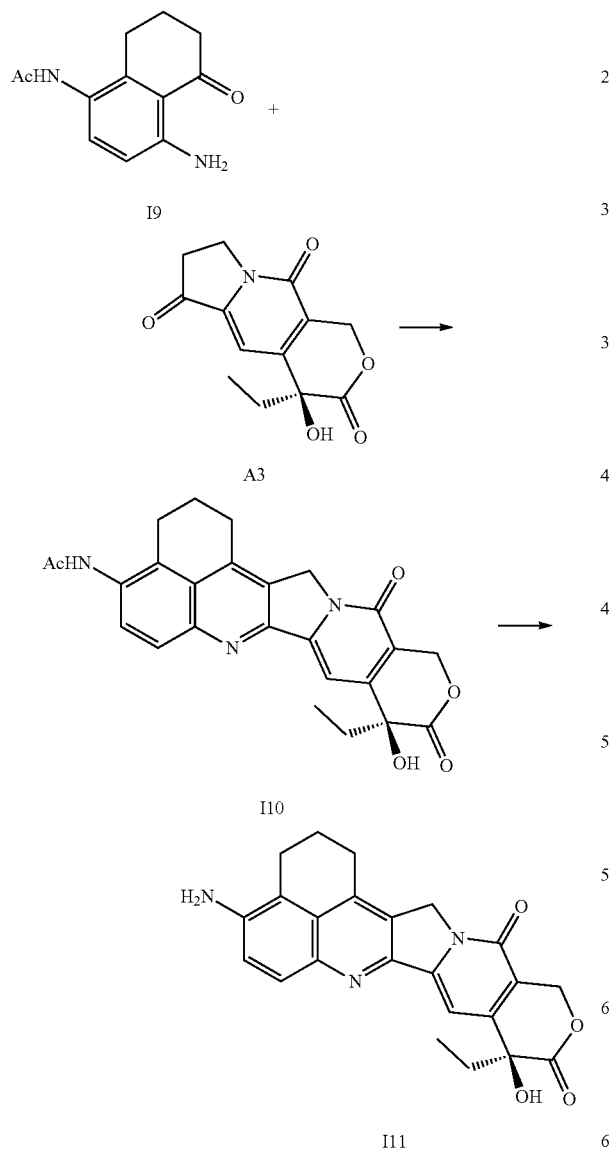

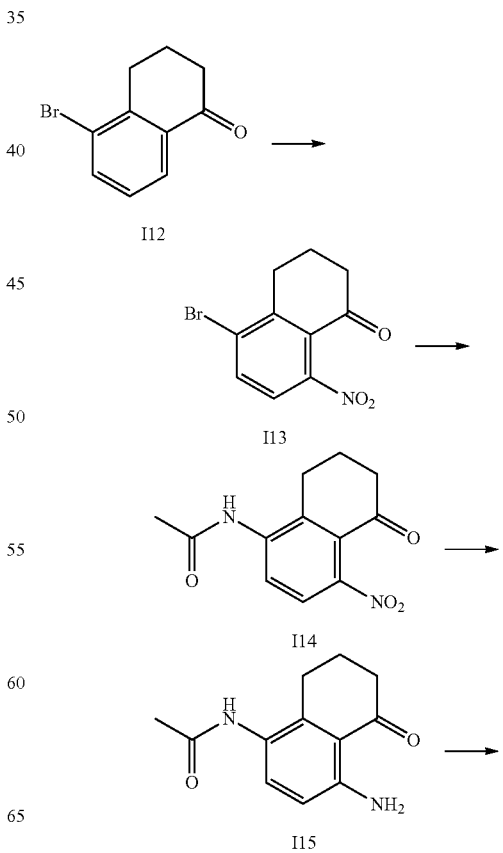

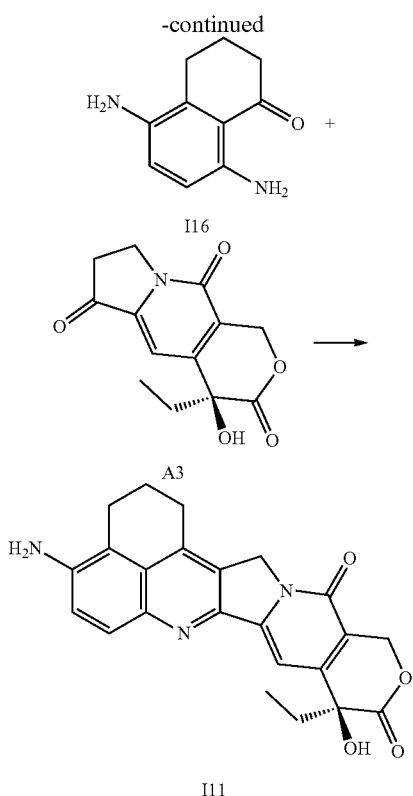

IPC, Purity and Assay Method for this Synthesis

| Instrument | Thermo U-3000 |
| --- | --- |
| Column | ACE Excel 3 C18- PFP (3.0 mm × 150 mm) |
| Oven | 40° C. |
| Mobile phase | A: 10 mM Ammomium Formate in water pH = 3.5 |
| | B: CAN |

| Gradient program | Time (min) | A % | B % |
| --- | --- | --- | --- |
| | 0.0 | 90 | 10 |
| | 20.0 | 10 | 90 |
| | 23.0 | 10 | 90 |
| | 24.0 | 90 | 10 |
| | 30.0 | 90 | 10 |
| | Re-equilibration time: 6 min | | |

| Flow rate | 1.0 ml/min |
| --- | --- |
| Detector | UV 220 nm |
| Diluent | CAN | a) 5-bromo-8-nitro-tetralin-1-one (I13)

A solution of potassium nitrate (1.15 eq., 13.83 g) dissolved in sulphuric acid (Conc., 5.0 rel. vol., 160 mL), was added (addition time 4-12 h, maintaining the temperature below 10° C.) to a solution of 5-bromotetralin-1-one (I12) (1.0 equiv., 26.77 g) in sulfuric acid (Conc., 5.0 rel. vol., 160 mL) under nitrogen. When the reaction was complete the reaction mixture was transferred to flask containing water (36 rel. vol., 1.15 L) adjusting the transfer rate to keep the temperature below 10° C. The resulting solid was filtered, washed with water (4.0 rel. vol., 128 mL) three times and then dried at ~40° C. for 24 h. The dry cake was dissolved in a mixture of acetone (2.5 rel. vol., 80 mL) and water (0.38 rel. vol., 12.2 mL) heated to ~75° C. and then cooled to ~20° C. The resulting solid was removed by filtration. The solvent was swapped to ethanol by distillation and the solution volume reduced to a 2.0 rel. vol. (64 mL). The solution was cooled to ~25° C. and the resulting solid collected by filtration. The solid was washed with ethanol (1.0 Rel. Vol., 32 mL) then dried under vacuum at 40° C. to give 5-bromo-8-nitro-tetralin-1-one I13 (15.36 g, 40%) as a brown solid; RT 14.0 min Method 1 IPC, Purity and Assay Method for bromo-8-nitro-tetralin-1-one.

| Instrument | Thermo U-3000 |
| --- | --- |
| Column | ACE Excel 3 C18-PFP (3.0 mm × 150 mm) |
| Oven | 40° C. |
| Mobile phase | A: 10 mM Ammomium Formate in water pH = 3.5 |
| | B: CAN |

| Gradient program | Time (min) | A % | B % |
| --- | --- | --- | --- |
| | 0.0 | 90 | 10 |
| | 20.0 | 10 | 90 |
| | 23.0 | 10 | 90 |
| | 24.0 | 90 | 10 |
| | 30.0 | 90 | 10 |
| | Re-equilibration time: 6 min | | |

| Flow rate | 1.0 ml/min |
| --- | --- |
| Detector | UV 220 nm |
| Diluent | CAN | b) N-(8-nitro-1-oxo-tetralin-5-yl)acetamide (I14)

A solution of bromo-8-nitro-tetralin-1-one (I13)(1.0 eq., 18.0 g, 90.6% ww), acetamide (1.2 eq., 4.72 g), tris(dibenzylideneacetone)dipalladium(0) (0.01 eq., 0.61 g) and potassium phosphate (1.4 eq., 19.8 g) in dioxane (15 rel. vol., 270 mL) under nitrogen was heated to ~70° C. When the reaction was complete the solution was cooled to ~20° C. and diluted with dioxane (5 rel. vol., 90.0 mL) and filtered. The solvent was swapped to ethanol and the volume reduced to a total reaction volume of 3 rel. vol. (54.0 mL). the solution was cooled to ~20° C. and the resulting solid collected by filtration and washed with MTBE (methyl tert-butyl ether) (1.0 rel. vol., 18.0 mL). The solid was dried under vacuum at 40° C. to give N-(8-nitro-1-oxo-tetralin-5-yl)acetamide I14 (10.0 g, 60.6%) as a dark yellow solid; RT 8.86 min.

c) N-(8-amino-1-oxo-tetralin-5-yl)acetamide (I15)

Palladium hydroxide on carbon (20% w/w, 0.15 eq., 5.25 g) was added to a solution of N-(8-nitro-1-oxo-tetralin-5-yl)acetamide (I14)(1.0 eq., 32.6 g) in methanol (40 rel. vol., 1250 mL). The reaction mixture was placed under a hydrogen atmosphere at ~40 psi, at ~40° C. for 8 h. The hydrogen was removed and replaced with nitrogen and the catalyst was removed by filtration over cellulose, washing the cellulose with methanol (4.0 rel. vol., 130 mL). The solution volume was reduced to 4.0 rel. vol. by distillation and then diluted with MTBE (4 rel. vol, 130 mL). The resulting solid was collect by filtration, washed with MTBE (2 rel. vol., 65 mL) and dried under vacuum at 40° C. to give N-(8-amino-1-oxo-tetralin-5-yl)acetamide I15 (21.1 g, 77.8%) as a grey green solid; RT 5.44 min.

d) 5,8-diaminotetralin-1-one (I16)

A solution of N-(8-amino-1-oxo-tetralin-5-yl)acetamide (I15)(1.0 eq., 10.0 g) in hydrochloric acid (5 M, 6.0 rel. vol., 60 mL), was held at ~90° C. for 3 h. The temperature was reduced to 25° C. and sodium hydroxide (2 M, 4.0 rel. vol., 40 mL) was added until pH 10.0 was achieved, maintaining the temperature 25° C. The resulting solid was collected by filtration and washed with water (2.0 rel. vol., 20 mL). The wet cake was dissolved in tetrahydrofuran (60 rel. vol., 600 mL) and filtered. The solution was concentrated to 5.0 rel. vol. and heptane (20 rel. vol., 200 mL) added. The solution was concentrated to 10.0 rel. vol. and further heptane (20 rel. vol., 200 mL) added, and then the volume reduced to 10.0 rel. vol. again. The resulting solid was collected by filtration and washed with heptane (5.0 rel. vol., 50 mL). The solid was dried under vacuum at 40° C. for 17 h to give 5,8-diaminotetralin-1-one (I16)(6.90 g, 82.7%) as a yellow solid; 1H NMR (400 MHz DMSO-d6) δ ppm 1.82 (m, 2H), 2.38 (t, J=2.0 Hz, 2H), 2.47 (t, J=2.0 Hz, 2H), 6.34 (d, J=2.0 Hz, 1H), 6.68 (d, J=2.0 Hz, 1H); RT 3.90 e) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11)

A solution of 5,8-diaminotetralin-1-one (I16)(1.0 eq., 5.0 g), (4S)-4-ethyl-4-hydroxy-7,8-dihydro-1H-pyrano[3,4-f]indolizine-3,6,10-trione (A3)(1.06 eq., 7.9 g), and pyridinium para-toluenesulfonate (1.0 eq., 7.2 g) in toluene (50.0 rel. vol., 250 mL) was held at 120° C. for 15 h. The volume of the solution was reduced to 2.0 rel. vol. and then diluted with acetonitrile (20 rel. vol., 100 mL) and water (20 rel. vol., 100 mL). The resulting slurry was filtered and the solid washed with aqueous acetonitrile (1:1, 20 rel. vol., 100 mL). The solid was slurried with aqueous methanol (water:MeOH 3:1, 40 rel. vol., 200 mL), filtered and washed with aqueous methanol (1:1, 20 rel. vol., 100 mL). The solid was slurried with water (60 rel. vol., 300 mL) at 50° C., filtered and washed with water (10 rel. vol., 50 mL). The solid was slurried with aqueous acetonitrile (water: acetonitrile, 1:3, 40 rel. vol., 200 mL) at 30° C., filtered and washed with aqueous acetonitrile (water: acetonitrile, 1:3, 5 rel. vol., 50 mL) and then dried under vacuum at 40° C. to give (S)-4-amino-9-ethyl-9-hydroxy-1,2,3,9,12,15-hexahydro-10H, 13H-benzo[de]pyrano[3',4':6,7]indolizino[1,2-b]quinoline-10,13-dione (I11) as white solid (5.0 g, 43.7%); RT 5.13.

Synthesis of I18

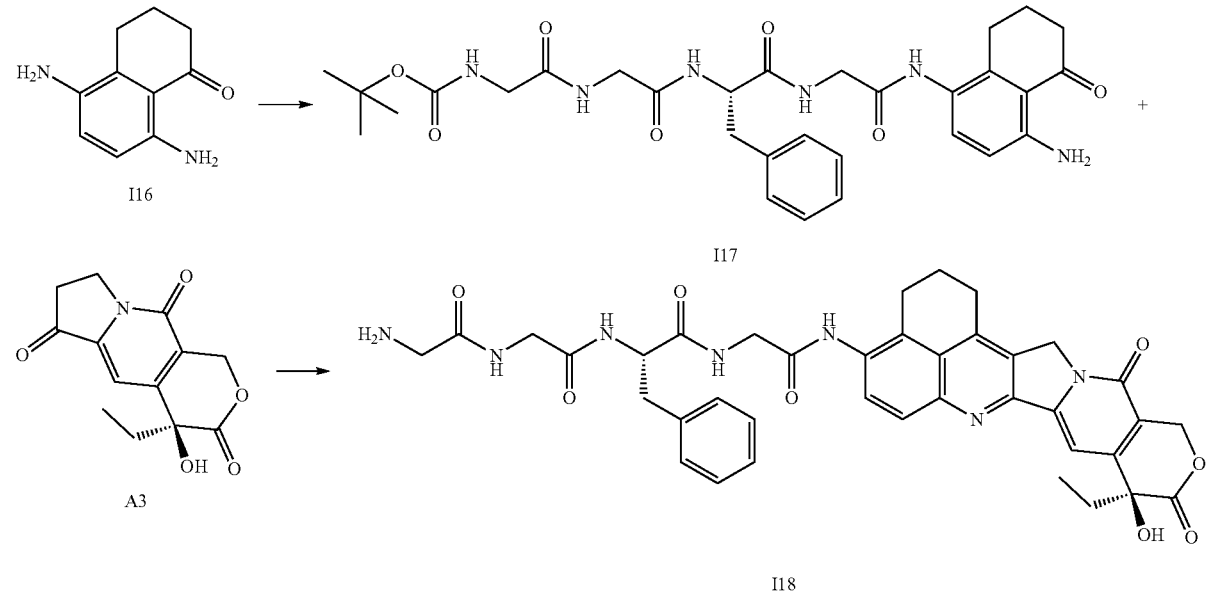

a) tert-butyl (S)-(2-((2-((1-((2-((4-amino-5-oxo-5,6,7,8-tetrahydronaphthalen-1-yl)amino)-2-oxoethyl)amino)-1-oxo-3-phenylpropan-2-yl)amino)-2-oxoethyl)amino)-2-oxoethyl)carbamate (I17)

Boc-GGFG-OH (227 mg, 0.52 mmol) and EEDQ (157 mg, 0.634 mmol) were solubilised in CH$_2$Cl$_2$ (25 mL) and the mixture stirred for 15 min, until the peptide has gone into solution. Compound 116 (100 mg, 0.56747 mmol) was subsequently added and the mixture left to stir until complete. After 1 h, the reaction looked 90% complete by LVMC. The mixture has gone thicker as the product is crashing out. The mixture was left for another hour before vaccing down to dryness. The crude was taken up in Et$_2$O (50 mL). The solid was filtered and subsequently taken up in CH$_2$Cl$_2$ (50 mL) to purify further. The solid was filtered and dried to give product 117 (273 mg, 0.459 mmol, 80.9% Yield) as a grey solid. Analytical data: LCMS 3 min: ES$^+$=1.46 min, m/z 595.7 [M+H]$^+$.

b) (S)-2-(2-(2-aminoacetamido)acetamido)-N-(2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)-3-phenylpropanamide (I18)

Aniline I17 (450 mg, 1.045 mMol), lactone A5 (280 mg, 1.064 mMol) and pyridinium p-toluenesulfonate (273 mg, 1.086 mMol) were solubilised in toluene (20 mL) and the mixture was heated to 150° C. (high reflux). MeOH (4 mL) was added to help solubilise the mixture. After 7 h the crude reaction was vacced down to dryness. The crude product was purified by silica gel chromatography (CHCl$_3$/MeOH, 100% to 65:35) to give product I18 (259 mg, 0.359 mMol, 78.1 yield). Analytical data: LCMS 3 min: ES$^+$=1.17 min, m/z 722.8 [M+H]$^+$.

Alternative Synthesis of 116

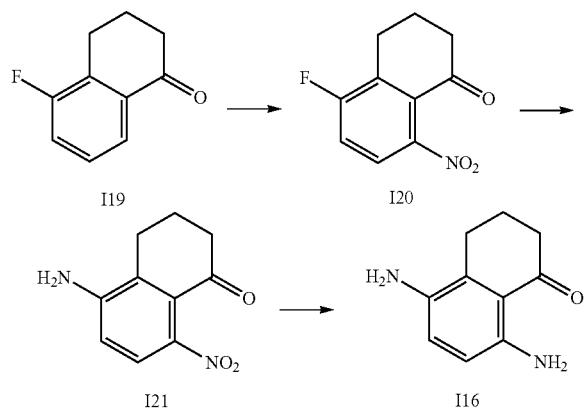

a) 5-Fluoro-8-nitro-tetralin-1-one (I20)

5-fluorotetralin-1-one I19 (4.7 g, 29 mmol) was solubilised in ½ the amount of sulfuric acid (120 mL) in a 3 neck round bottom flask. The mixture was stirred until all the solid has dissolved and then cooled to 0-5° C. In a dropping funnel, dissolve potassium nitrate (3 g, 29.6730 mmol) into the remaining half of sulfuric acid (120 mL) at 0-5° C. Slowly add to the SM mixture making sure to maintain the solution cool (45 min). Stir at 0-5° C. until complete. The reaction mixture was subsequently quenched with water (250 mL) and left to stir at 0-5° C. The solid was filtered and washed with water (50 mL). The solid was dried in a vacuum oven for 2 h at 50° C. The crude solid was slurried in $Et_2O$ overnight before being cooled to 0° C. and filtered. The wet cake was washed with more cold $Et_2O$ (50 mL) and left to dry in a vacuum oven at 50° C. to give pure product I20 (5.5 g, 26 mmol, 92% yield) as a light pink fine powder. LCMS (Method B): $ES^+$=1.55 min, m/z 210.1 $[M+H]^+$.

b) 5-Amino-8-nitro-tetralin-1-one (I21)

Compound I20 (2.7 g, 13 mmol) was solubilised in $CH_3CN$ (2.5 mL) and $NH_4OH$ (21 mass %) in $H_2O$ (8 mL, 40 mmol) was added to a sealed pressure resistant tube and heated to 185° C. Once complete, the mixture was transferred to a round bottom flask and vacced down. The crude was purified by silica gel column chromatography ($CHCl_3$/MeOH; 100 to 99:1) to give pure product I21 (1.1 g, 5.3 mmol, 41% yield) as a black solid. LCMS (Method B): $ES^+$=1.34 min, m/z 207.1 $[M+H]^+$.

c) 5,8-diaminotetralin-1-one (I16)

Compound 121 (1.35 g, 6.55 mmol) was dissolved in a mixture of methanol (20 mL), $H_2O$ (1 mL) and formic acid (1 mL) at 0° C. Zinc (8.5 g, 130 mmol) was slowly added, making sure to keep the temperature below 40° C. A little more formic acid/$H_2O$ (0.5 mL) was added to push the reaction to completion. The reaction mixture was filtered, and the filtrate diluted with EtOAc and $CH_2Cl_2$ before being vacced down. The crude was dry loading onto silica gel column chromatography ($CHCl_3$/EtOAc; 100 to 7:3 then $CHCl_3$/MeOH; 99:1 to 98:2) to give pure product 116 (1.015 g, 5.760 mmol, 88.0% Yield). LCMS (Method B): $ES^+$=0.2 min, m/z not observed.

Synthesis Example 1 (e.g. Synthesis of SG3932)

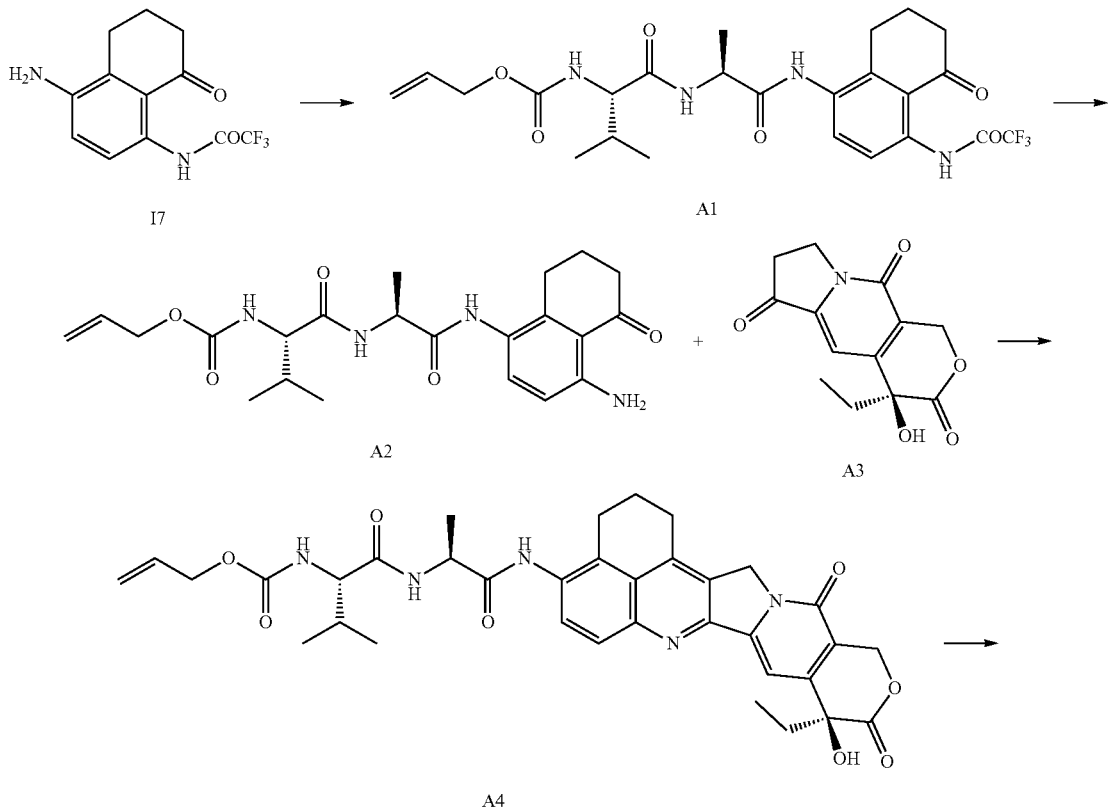

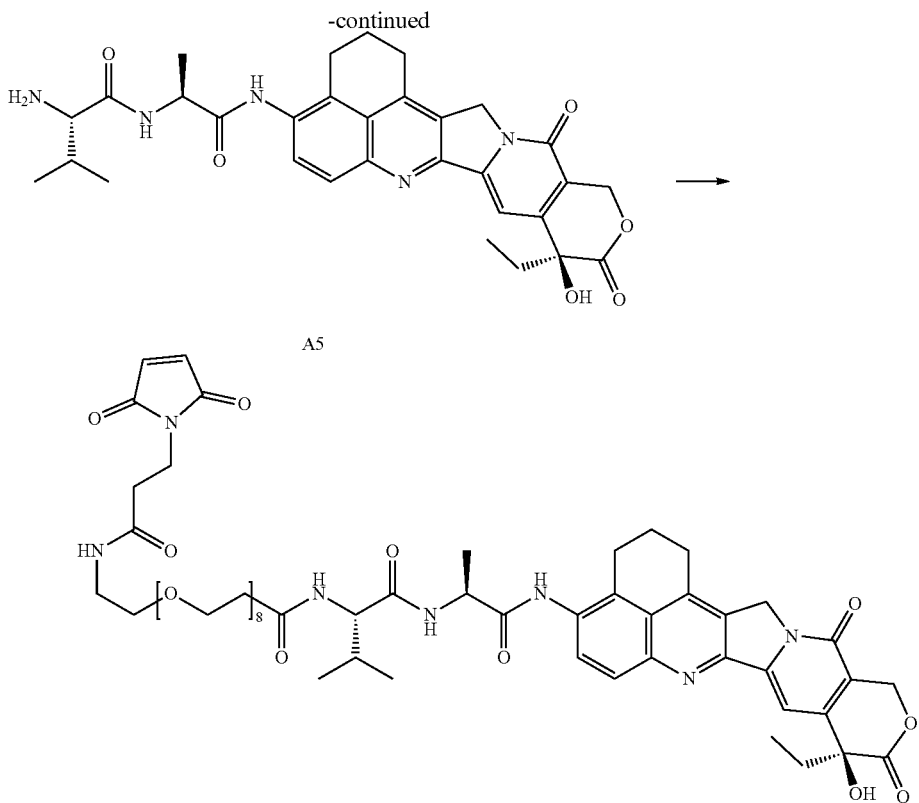

A5 a) Allyl ((S)-3-methyl-1-oxo-1-(((S)-1-oxo-1-((5-oxo-4-(2,2,2-trifluoroacetamido)-5,6,7,8-tetrahydronaphthalen-1-yl)amino)propan-2-yl)amino)butan-2-yl)carbamate (A1)

DCC (6.54 g, 31.7 mMol) and HOPO (3.36 g, 30.2 mMol) were added to a solution of alloc-Val-Ala-OH (9.09 g, 31.7 mmol) and 17 (7.85 g, 28.8 mMol) in CH$_2$Cl$_2$ (300 mL) at 25° C. The resulting mixture was left to stir overnight. The white solid that formed during the reaction was filtered out and washed with cold CH$_2$Cl$_2$. The filtrate was washed with water (150 mL) and brine (150 mL). The organic layer was dried over MgSO$_4$, filtered and evaporated. The crude product was purified by silica gel chromatography (Hex/EtOAc, 60:40). Product A1 isolated was contaminated with co-eluting DCU (21.1 g, 140% yield). LC/MS (Method B): ES$^+$=1.81 min, m/z 527.6 [M+H]$^+$.

b) Allyl ((S)-1-(((S)-1-((4-amino-5-oxo-5,6,7,8-tetrahydronaphthalen-1-yl)amino)-1-oxopropan-2-yl)amino)-3-methyl-1-oxobutan-2-yl)carbamate (A2)

Protected aniline A1 (18 g, 34.19 mMol) was solubilised in a mixture of MeOH and H$_2$O 10:1 (165 mL) and K$_2$CO$_3$ was added (10 g, 72.36 mMol). The mixture was stirred at 50° C. until complete. The mixture was vacced down to almost dryness and the residue was taken up with CH$_2$Cl$_2$ and washed with H$_2$O and brine, before being dried over MgSO$_4$, filtered and evaporated. The crude product was purified by silica gel chromatography (CHCl$_3$/MeOH, 100% to 7:3). The isolated product A2 was contaminated with a co-eluting impurity (10.71 g, 73% yield). LC/MS (Method B): ES+=1.46 min, m/z 431.7 [M+H]$^+$.

c) Allyl ((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methylbutan-2-yl)carbamate (A4)

Aniline A2 (450 mg, 1.045 mMol), lactone A3 (280 mg, 1.064 mMol) and pyridinium p-toluenesulfonate (273 mg, 1.086 mMol) were solubilised in toluene (20 mL) and the mixture was heated to 130° C. (high reflux). Every now and then a few drops of MeOH is added to help solubilise the mixture. After 7 h the crude reaction was vacced down to dryness. The crude product was purified by silica gel chromatography (CHCl$_3$/MeOH, 100% to 95:5) to give product A4 (360 mg, 52.3% yield). LC/MS (Method B): ES$^+$=1.51 min, m/z 658.8 [M+H]$^+$.

d) Allyl (S)-2-amino-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (A5)

Excess piperidine was added (642 µL) to a solution of A4 (543 mg, 0.82 mMol) and PdP(Ph$_3$)$_4$ (89 mg, 0.08 mMol) in CH$_2$Cl$_2$ (15 mL). The mixture was allowed to stir at room temperature for 20 min, at which point the reaction had gone to completion (as monitored by LC/MS). The reaction mixture was diluted with CH$_2$Cl$_2$ (25 mL) and the organic phase was washed with H$_2$O (25 mL) and brine (25 mL). The organic phase was dried over MgSO$_4$, filtered and excess solvent removed by rotary evaporation under reduced pressure to afford crude product A5 which was used as such in the next step. LC/MS (Method B): ES$^+$=1.15 min, m/z 574.6 [M+H]$^+$.

e) 1-(3-(2,5-dioxo-2,5-dihydro-1H-pyrrol-1-yl)pro-panamido)-N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-3,6,9,12,15,18,21,24-octaoxaheptacosan-27-amide (1)

Pyridine (83 μL, 1.03 mMol) and Mal-dPEG$_8$-OTFP (767 mg, 1.03 mMol) were added to a solution of crude A5 (assumed 1.03 mMol) in dry CH$_2$Cl$_2$ (50 mL) under an argon atmosphere. The reaction was stirred overnight and as the reaction was not complete 0.5 eq. of Mal-dPEG$_8$-OTFP was added to try to push the reaction. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by reverse phase HPLC (gradient of H$_2$O/CH$_3$CN+0.05% FA) and freezedried to give 1 (1.189 g, 31% yield over 2 steps). LC/MS (Method B): ES$^+$=1.43 min, m/z 1149.3 [M+H]$^+$.
LC/MS (Method C): ES$^+$=5.37 min, m/z 1149.4 [M+H]$^+$.

Synthesis Example 2 (e.g. Synthesis of SG4010)

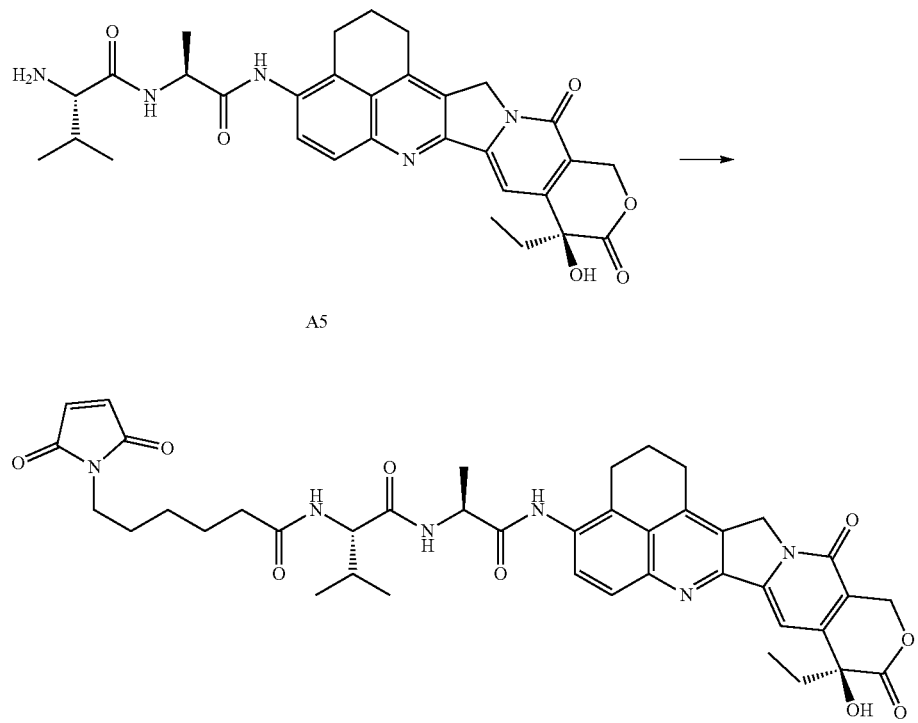

6-(2,5-dioxo-2,5-dihydro-1H-pyrrol-1-yl)-N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)hexanamide (2)

Mal-caproic acid (56 mg, 0.26 mMol) and EDCI·HCl (51 mg, 0.26 mMol) were added to a solution of crude A5 (assumed 0.26 mMol) in dry CH$_2$Cl$_2$ (20 mL) under an argon atmosphere. The reaction was stirred overnight and as the reaction was incomplete, another 0.5 eq of Mal-caproic acid and EDCI·HCl were added. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by silica gel column chromatography (CHCl$_3$/MeOH 95:5) to give 2 (31.6 mg, 20% yield over 2 steps). LC/MS (Method B): ES$^+$=1.56 min, m/z 767.8 [M+H]$^+$. LC/MS (Method C) 15 min: ES$^+$=6.05 min, m/z 767.8 [M+H]$^+$.

Synthesis Example 3

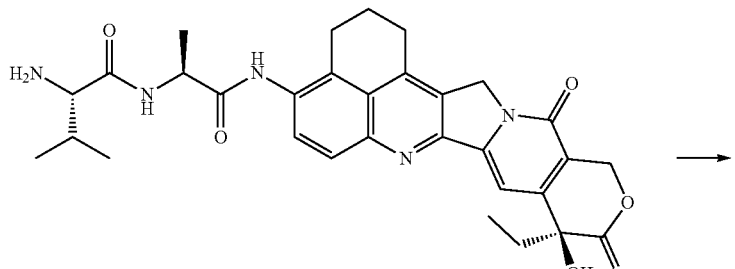

A5

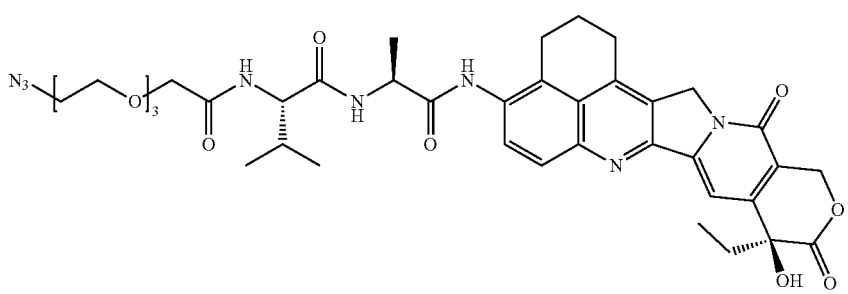

3

(S)-2-(2-(2-(2-(2-azidoethoxy)ethoxy)ethoxy)acetamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (3)

Azido-dPEG$_3$-acid (77.5 mg, 0.31 mMol) and EDCI·HCl (60 mg, 0.31 mMol) were added to a solution of crude A5 (assumed 0.31 mMol) in dry CH$_2$Cl$_2$ (20 mL) under an argon atmosphere. The reaction was stirred overnight and as the reaction was incomplete, another 0.5 eq. of azido-dPEG$_3$-OH and EDCI·HCl were added. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by preparative HPLC and the fractions were freezedried to give pure 3 (92.2 mg, 24.7% yield over 2 steps). LC/MS (Method B): ES'=1.69 min, m/z 789.9 [M+H]$^+$. LC/MS (Method C): ES'=6.68 min, m/z 790.0 [M+H]$^+$.

Synthesis Example 4

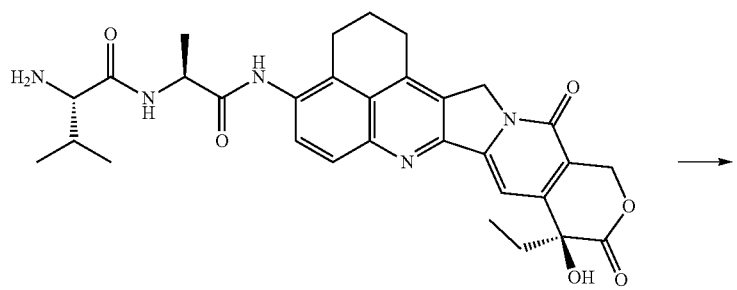

A5

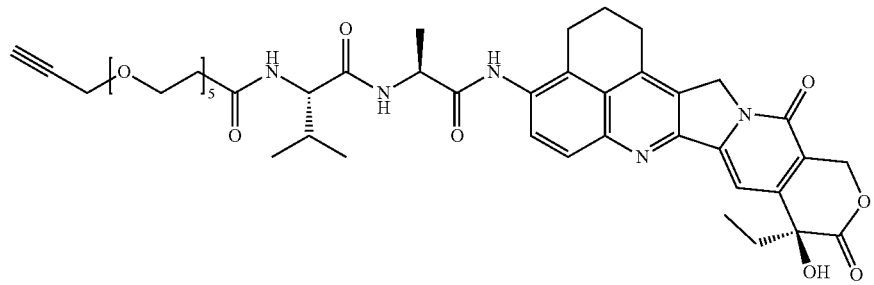

4

N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-4,7,10,13,16-pentaoxanonadec-18-ynamide (4)

Propargyl-dPEG$_5$-acid (56 mg, 0.19 mMol) and EDCI·HCl (37 mg, 0.19 mMol) were added to a solution of crude A5 (assumed 0.19 mMol) in dry CH$_2$Cl$_2$ (10 mL) under an argon atmosphere. The reaction was stirred overnight and as the reaction was incomplete, another 0.5 eq. of Propargyl-dPEG$_5$-OH and EDCI·HCl were added. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by preparative HPLC and the fractions were freezedried to give pure 4 (22 mg, 16.7% yield over 2 steps). LC/MS (Method B): ES$^+$=1.54 min, m/z 860.9 [M+H]$^+$. LCMS (Method C): ES$^+$=5.57 min, m/z 860.9 [M+H]$^+$.

Synthesis Example 5

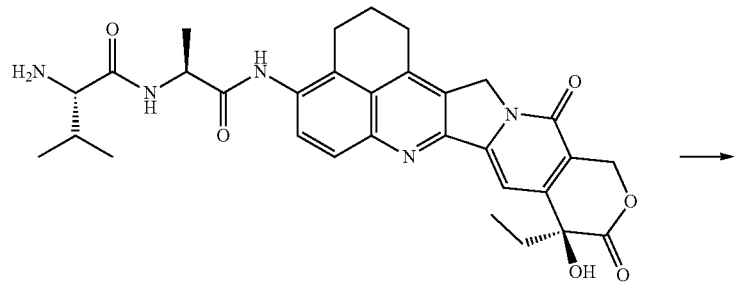

A5

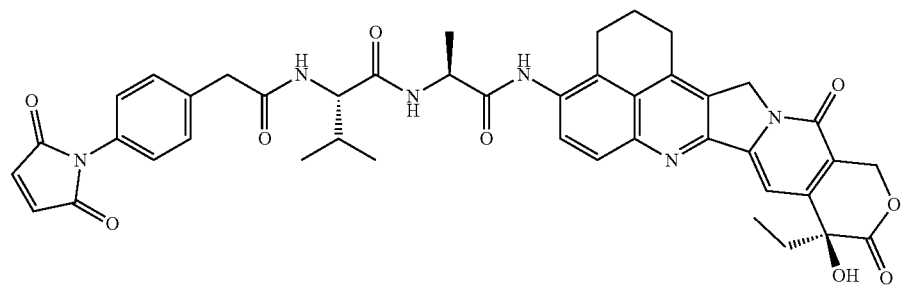

5

(S)-2-(2-(4-(2,5-dioxo-2,5-dihydro-1H-pyrrol-1-yl)phenyl)acetamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (5)

PM-acetic-OSu (64 mg, 0.19 mMol) was added to a solution of crude A5 (assumed 0.19 mMol) in dry CH$_2$Cl$_2$ (10 mL) under an argon atmosphere. The reaction was not proceeding so DIPEA (51 μL, 0.28 mMol) was added. The reaction was stirred until complete. The mixture was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by preparative HPLC and the fractions were freezedried to give pure 5 (2.5 mg, 1.6% yield over 2 steps). LC/MS (Method B): ES$^+$=1.54 min, m/z 787.7 [M+H]$^+$. LC/MS (Method C): ES$^+$=5.61 min, m/z 787.8 [M+H]$^+$.

Synthesis Example 6

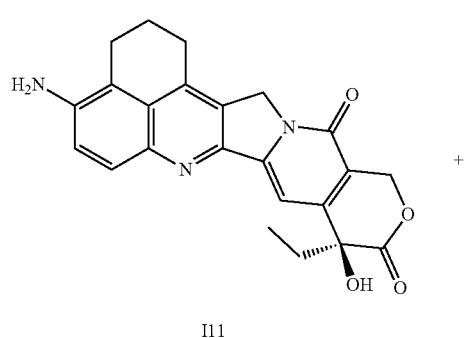

I11

+

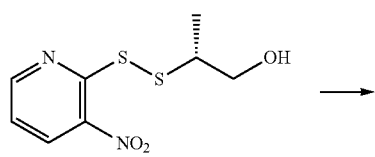

A6

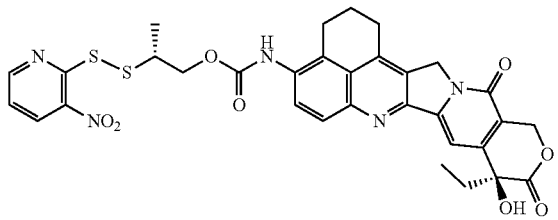

6

(R)-2-((3-nitropyridin-2-yl)disulfanyl)propyl ((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)carbamate (6)

(i) (2R)-2-[(3-nitro-2-pyridyl)disulfanyl]propan-1-ol A6 (25 mg, 0.1015 mmol, 1.0 eq.) was dissolved in dichloromethane (1 mL). Pyridine (8.5 μL, 0.11 mmol, 1.0 eq.), then triphosgene (11 mg, 0.0370685 mmol, 0.33 eq.) were added and the mixture stirred under Ar for 45 min, whereupon LCMS (Et$_2$NH quench) indicated the formation of the corresponding carbamate.

(ii) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11) (43 mg, 0.09026 mmol, 1.0 eq.) was dissolved in dichloromethane (2 mL), N,N-diisopropylethylamine (42 μL, 0.241 mmol, 2.7 eq.) and pyridine (25 μL, 0.309 mmol, 3.4 eq.). The reaction mixture from step (i) was added and the mixture stirred for 30 min, whereupon LCMS indicated the reaction was complete. The reaction mixture was concentrated in vacuo and purified by isolera chromatography (0-4% MeOH in CH$_2$Cl$_2$) to afford 6 (22 mg, 0.03256 mmol, 36% Yield, QC=96.8%) as a yellow solid. LC/MS (Method B): RT=1.86 min, 676.6 [M+H]$^+$.

Synthesis Example 7 (e.g. Synthesis of SG4052)

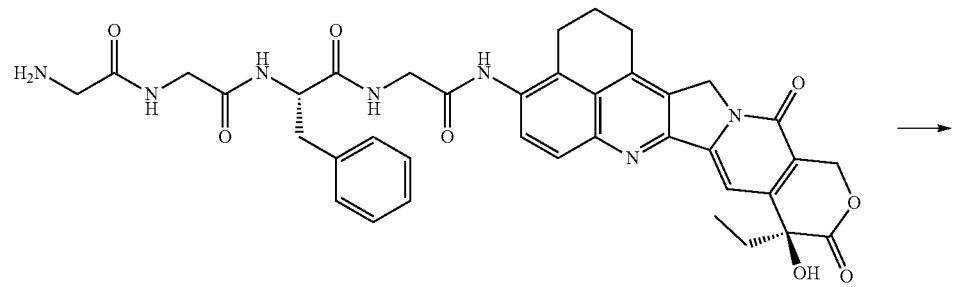

I18

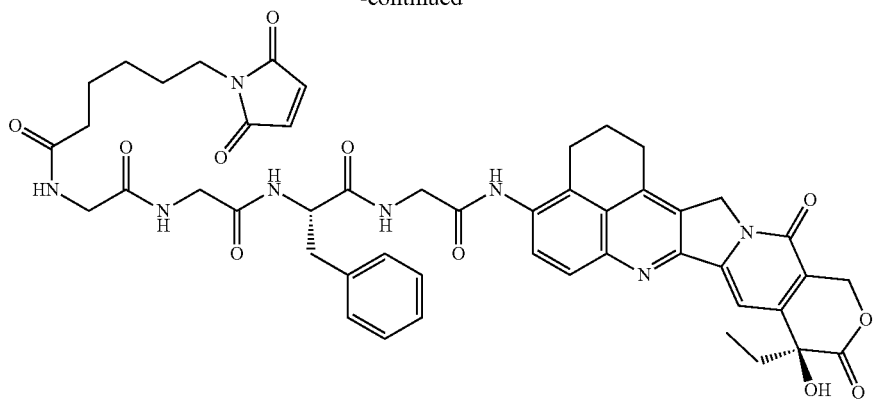

7

6-(2,5-dioxo-2,5-dihydro-1H-pyrrol-1-yl)-N-(2-((2-(((S)-1-((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)amino)-1-oxo-3-phenylpropan-2-yl)amino)-2-oxoethyl)amino)-2-oxoethyl)hexanamide (7)

Compound I18 (259 mg, 0.3588 mmol) was solubilised in CH$_2$Cl$_2$ (25 mL). The starting material was not soluble at all so DMA (1 mL) was added. As no improvement was observed, DIPEA (68 μL, 0.390 mmol) was added and all the solid went in solution. Maleimide caproic acid (69 mg, 0.358 mmol) was added and the mixture left to stir at r.t. overnight and which point LCMS analysis revealed the reaction to be complete. The reaction mixture was quenched with MeOH (2 mL) and vacced down to dryness. The crude product was purified by preparative HPLC and subsequently freezedried to give compound 7 as an ochre solid (38.2 mg, 11% yield). Analytical data: LCMS 3 min: ES+=1.47 min, m/z 916.2 [M+H]$^+$. LCMS 15 min: ES$^+$=5.46 min, m/z 916.1 [M+H]$^+$.

Synthesis Example 8 (e.g. Synthesis of SG4057)

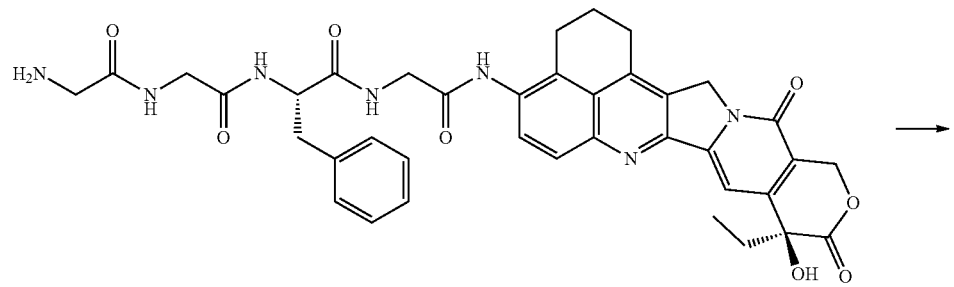

I18

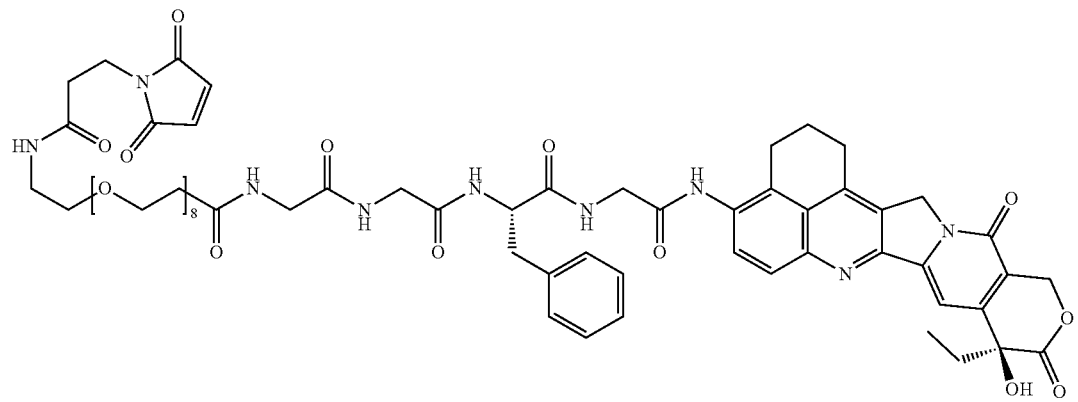

8

1-(3-(2,5-dioxo-2,5-dihydro-1H-pyrrol-1-yl)propanamido)-N-(2-((2-(((S)-1-((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)amino)-1-oxo-3-phenylpropan-2-yl)amino)-2-oxoethyl)amino)-2-oxoethyl)-3,6,9,12,15,18,21,24-octaoxaheptacosan-27-amide (8)

Compound I18 (70 mg, 0.096 mmol) was solubilised in CH₂Cl₂ (5 mL). The starting material was not soluble at all so DMA (0.5 mL) was added. As no improvement was observed, DIPEA (19 µL, 0.106 mmol) was added and all the solid went in solution. Mal-dPEG$_{8-0}$H (63 mg, 0.106 mmol) and EDCI·HCl (19 mg, 0.099 mMol) were added and the mixture left to stir at r.t. overnight and which point LCMS analysis revealed the reaction to be complete. The reaction mixture was quenched with MeOH (2 mL) and vacced down to dryness. The crude product was purified by preparative HPLC and subsequently freezedried to give 8 as an ochre solid (30 mg, 24% yield). LCMS 3 min: ES⁺=1.44 min, m/z 1297.6 [M+H]⁺.

Synthesis Example 9—Alternative Synthesis of 1
(e.g. Alternative Synthesis of SG3932)

[[(2S)-2-[3-[2-[2-[2-[2-[2-[2-[2-[2-[3-(2,5-dioxopyrrol-1-yl)propanoylamino]ethoxy]ethoxy]ethoxy]ethoxy]ethoxy]ethoxy]ethoxy]propano yl amino]-3-methylbutanoyl]amino]propanoic acid (664 mg, 0.871 mmol, 1.1 eq.) in N,N-dimethylacetamide (l0 mL) were added, followed by EDCI·HCl (226 mg, 1.18 mmol, 1.5 eq.) and the mixture stirred for 2 h, whereupon LCMS indicated good conversion, but that the reaction had stalled. The reaction mixture was warmed to 30° C. and stirred for 30 min, LCMS indicated no change so CH₂Cl₂ was removed in vacuo and Et₂O added to the resulting DMA solution. The precipitated oil was collected, Et₂O removed in vacuo and the precipitation process repeated. The combined precipitates were purified by HPLC (10-60% B in A over 13 min) to afford 1 (200 mg, 0.174 mmol, 98% purity, 22% Yield) as a yellow residue after freeze-drying. LC/MS (method A): retention time 1.44 mins (ES+) m/z 1149 [M+H]⁺ ¹H NMR (600 MHz, Chloroform-d) δ 8.81 (s, 1H), 7.83 (s, 2H), 7.48 (s, 1H), 7.18 (dd, J=18.7, 7.5 Hz, 2H), 6.69 (s, 2H), 6.43 (s, 1H), 5.68 (d, J=16.1 Hz, 1H), 5.27 (d, J=16.1 Hz, 1H), 5.03 (d, J=18.4 Hz, 1H), 4.90 (d, J=18.4 Hz, 1H), 4.75 (p, J=7.2 Hz, 1H), 4.32 (dd, J=7.4, 5.8 Hz, 1H), 4.05 (s, 1H), 3.83 (t, J=7.2 Hz, 3H), 3.78-3.68 (m, 3H), 3.68-3.57 (m, 31H), 3.53

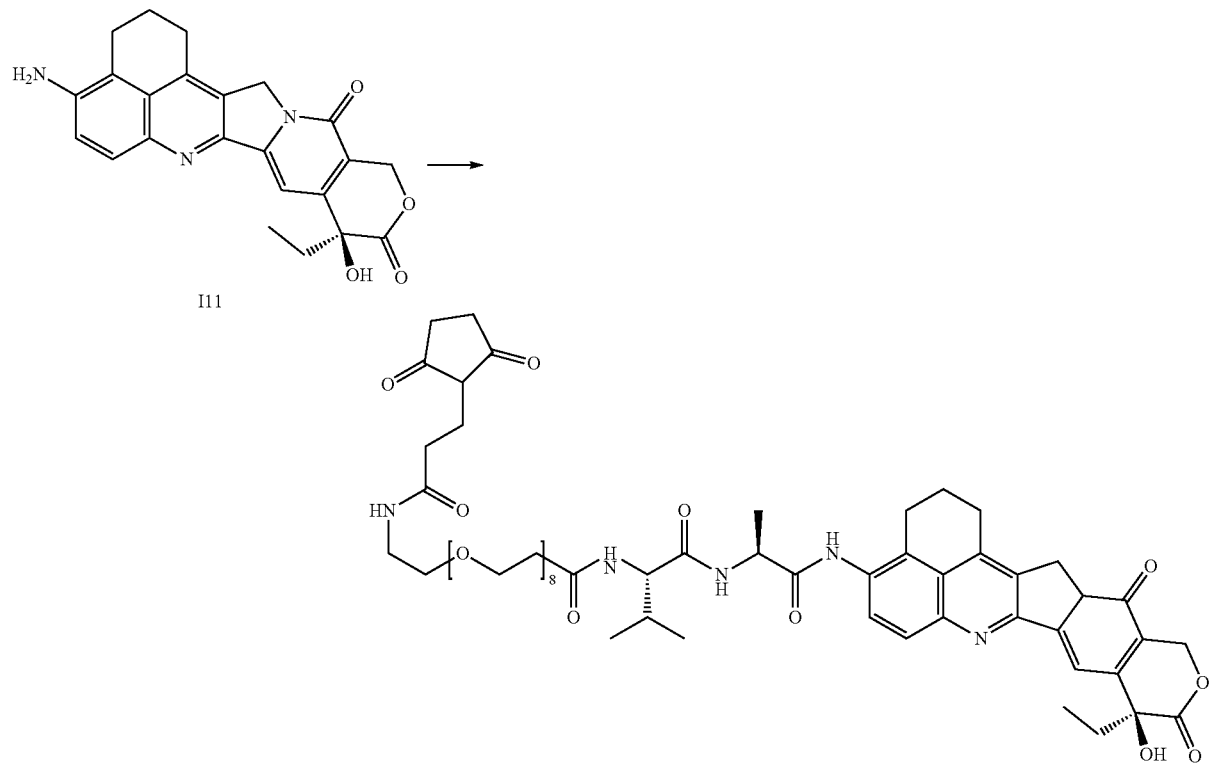

(S)-4-amino-9-ethyl-9-hydroxy-1,2,3,9,12,15-hexahydro-10H,13H-benzo[de]pyrano[3',4':6,7]indolizino[1,2-b]quinoline-10,13-dione I11 (371 mg, 0.779 mmol, 1.0 eq.) was dissolved in dichloromethane (30 mL). N,N-diisopropylethylamine (69 µL, 0.396 mmol, 0.51 eq.), and (2S)-2-

(t, J=5.1 Hz, 3H), 3.40 (q, J=5.3 Hz, 2H), 3.06-2.91 (m, 3H), 2.84 (dt, J=16.3, 6.2 Hz, 1H), 2.63 (ddd, J=14.8, 8.5, 4.2 Hz, 1H), 2.57-2.44 (m, 4H), 2.30 (dq, J=13.4, 6.7 Hz, 1H), 2.10 (p, J=6.4 Hz, 3H), 1.91 (ddt, J=16.8, 14.3, 7.2 Hz, 3H), 1.54 (d, J=7.1 Hz, 3H), 1.02 (dd, J=15.5, 6.9 Hz, 10H).

Synthesis Example 10—Alternate Synthesis of A2

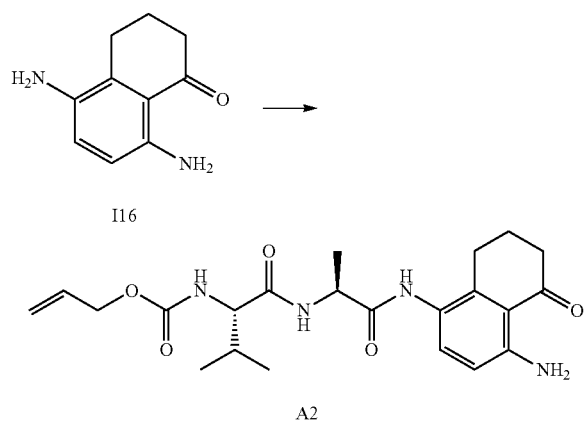

Allyl ((S)-1-(((S)-1-((4-amino-5-oxo-5,6,7,8-tetra-hydronaphthalen-1-yl)amino)-1-oxopropan-2-yl)amino)-3-methyl-1-oxobutan-2-yl)carbamate (A2)

EDCI·HCl (7.71 g, 31.2 mMol) was added to a solution of alloc-Val-Ala-OH (8.49 g, 31.2 mmol) in $CH_2Cl_2$ (200 mL) and stirred for 15 min or until solubilised. 116 (5 g, 28.3 mMol) was subsequently added and the resulting mixture was left to stir until the reaction was completed. The volatiles were removed under reduced pressure. The crude product was taken up in $Et_2O$ (50 mL) and the mixture sonicated for 3 min. The solid was filtrated and taken up again in $CH_2Cl_2$ (50 mL), sonicated for 3 min and filtered again to give pure product A2 as a grey solid (12.21 g, 79% yield). LC/MS (Method B): ES+=1.47 min, m/z 431.5 $[M+H]^+$.

Synthesis Example 11

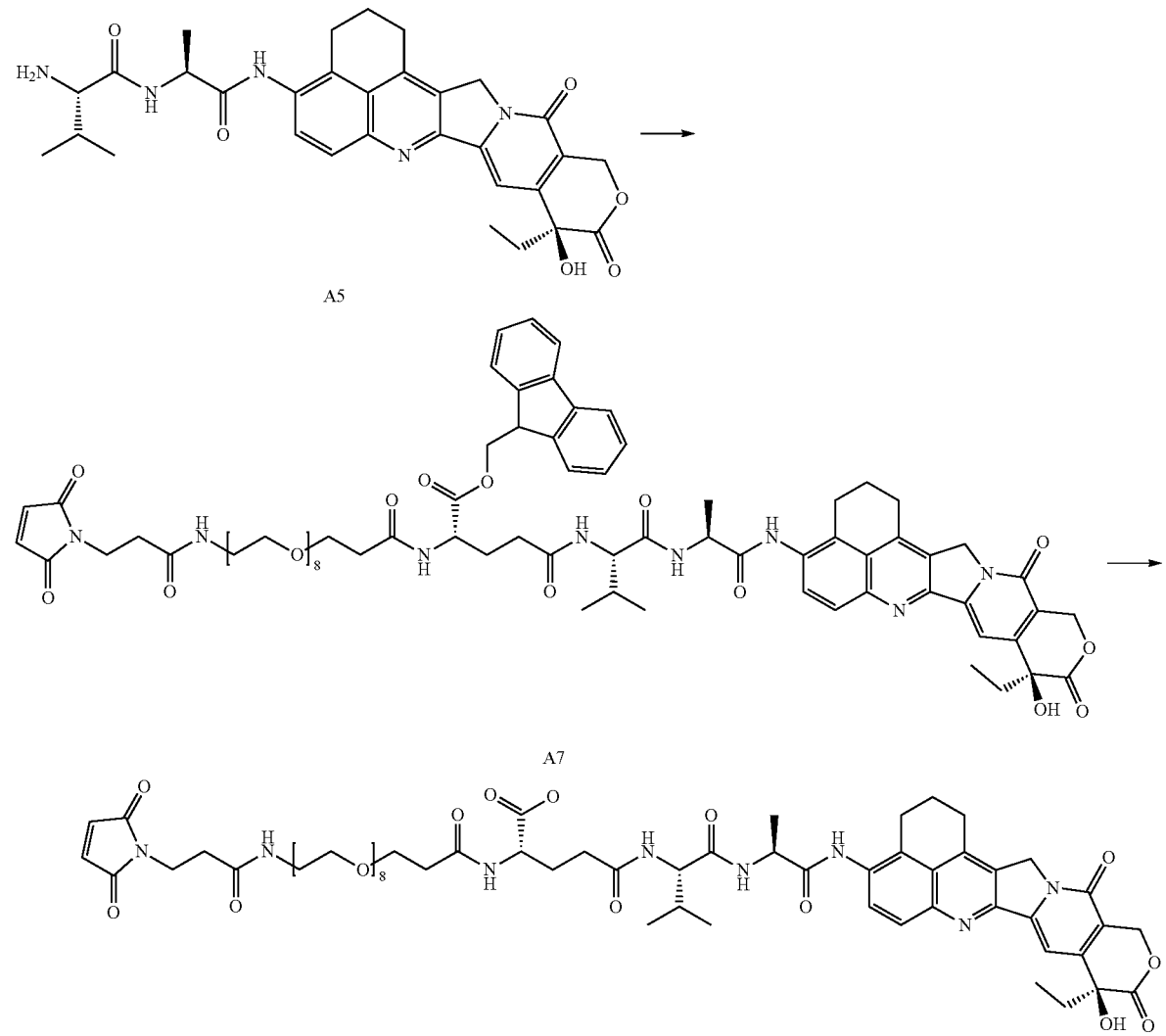

a) (9H-fluoren-9-yl)methyl N2-(1-(2,5-dioxo-2,5-dihydro-1H-pyrrol-1-yl)-3-oxo-7,10,13,16,19,22,25,28-octaoxa-4-azahentriacontan-31-oyl)-N5-((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-L-glutaminate (A7)

EDCI·HCl (0.10 mmol, 1.2 eq) was added to a solution of A5 (0.087 mmol, 1.0 eq) and Mal-PEG8-Glu-OH (0.10 mmol, 1.2 eq) in DCM (5 mL) and the resulting mixture stirred at room temperature overnight. The reaction mixture was evaporated to dryness and purified by column (8-12% MeOH/DCM) to leave the product as a white solid. Yield=80 mg (63%). LC/MS (Method B) rt 1.66 min m/z (1456.2) M+H.

b) N2-(1-(2,5-dioxo-2,5-dihydro-1H-pyrrol-1-yl)-3-oxo-7,10,13,16,19,22,25,28-octaoxa-4-azahentriacontan-31-oyl)-N5-((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-L-glutamine (9)

1-Methylpyrrolidine (200 µL) was added to a solution of A7 (0.06 mmol) in DMF (0.8 mL) and stirred at room temperature for 10 mins. The solvent was removed under vacuum and the residue purified by prep HPLC (30% MeCN/water+0.05% formic acid over 8.5 mins). Fractions containing product were freeze dried to give the product as an off-white solid. Yield=23 mg (30%). LC/MS (Method B) rt 1.43 min m/z (1278.4) M+H.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

| SEQUENCES | | |
|---|---|---|
| Identifier | Sequence | |
| ZY0EPQ-E02; CHDR1 | SEQ ID NO: 1: | GYYWN |
| ZY0EPQ-E02; CHDR2 | SEQ ID NO: 2: | EINHSGSTNYNPSLKS |
| ZY0EPQ-E02; CHDR3 | SEQ ID NO: 3: | NLYNWNLDS |
| ZY0EPQ-E02; CLDR1 | SEQ ID NO: 4: | RASQGIRNDLG |
| ZY0EPQ-E02; CLDR2 | SEQ ID NO: 5: | VASSLQS |
| ZY0EPQ-E02; CLDR3 | SEQ ID NO: 6: | LQHNSYPRT |
| ZY0EQD-E02; CHDR1 | SEQ ID NO: 7: | GYYWN |
| ZY0EQD-E02; CHDR2 | SEQ ID NO: 8: | EINHSGSTSYNPSLKS |
| ZY0EQD-E02; CHDR3 | SEQ ID NO: 9: | VLYNWNVDS |
| ZY0EQD-E02; CLDR1 | SEQ ID NO: 10: | RASQDIRNDVG |
| ZY0EQD-E02; CLDR2 | SEQ ID NO: 11: | AASRLQS |
| ZY0EQD-E02; CLDR3 | SEQ ID NO: 12: | LQHNSYPRT |
| ZY0EOB-F05; CHDR1 | SEQ ID NO: 13: | SGGYYWS |
| ZY0EOB-F05; CHDR2 | SEQ ID NO: 14: | NIYYSGSTYYNPSLKS |
| ZY0EOB-F05; CHDR3 | SEQ ID NO: 15: | EKALATVTPSGYENYYTVDV |
| ZY0EOB-F05; CLDR1 | SEQ ID NO: 16: | WASQGISSYLA |
| ZY0EOB-F05; CLDR2 | SEQ ID NO: 17: | AASTLQS |
| ZY0EOB-F05; CLDR3 | SEQ ID NO: 18: | QHLNSYPLT |
| ZY0EO5-E07; CHDR1 | SEQ ID NO: 19: | SGGYYWS |
| ZY0EO5-E07; CHDR2 | SEQ ID NO: 20: | NIYYSGSTYYNPSLKS |
| ZY0EO5-E07; CHDR3 | SEQ ID NO: 21: | EKALASVIPSGYENYYVVDV |
| ZY0EO5-E07; CLDR1 | SEQ ID NO: 22: | WASQGIAGYLA |

| SEQUENCES | | |
|---|---|---|
| ZY0E05-E07; CLDR2 | SEQ ID NO: 23: | AASTLQS |
| ZY0E05-E07; CLDR3 | SEQ ID NO: 24: | QHLNSYPLT |
| ZY0EP0-C07; CHDR1 | SEQ ID NO: 25: | DYYMS |
| ZY0EP0-C07; CHDR2 | SEQ ID NO: 26: | YISSSGSTIYYTDSVKG |
| ZY0EP0-C07; CHDR3 | SEQ ID NO: 27: | DGVGFDY |
| ZY0EP0-C07; CLDR1 | SEQ ID NO: 28: | RASQSVSSSYLA |
| ZY0EP0-C07; CLDR2 | SEQ ID NO: 29: | AASSRAT |
| ZY0EP0-C07; CLDR3 | SEQ ID NO: 30: | QQYGSSPLYT |

SEQ ID NO: 31 (ZY0EPQ-E02, variable heavy chain)
QVQLQQWGAGLLKPSETLSLTCAVYGGSFSGYYWNWIRQPPGKGLEWIGEINHSGST
NYNPSLKSRVTILVDTSKNQFSLKLSSVTAADTAVYYCARNLYNWNLDSWGQGTLVTV
SS SEQ ID NO: 32 (ZY0EPQ-E02, variable light chain)
DIQMTQSPSSLSASVGDRVTITCRASQGIRNDLGWYQQKPGRAPKRLIYVASSLQSGV
PSRFSGSGSGTEFTLTISSLQPEDFATYYCLQHNSYPRTFGQGTKVEIK SEQ ID NO: 33 (ZY0EQD-E02, variable heavy chain, e.g.
pre-germlining)
QVQLQQWGAGLLKPSETLSLTCAVYGGSFSGYYWNWIRQPPGKGLEWIGEINHSGST
SYNPSLKSRVTISVDTSKNQFSLKLSSVTAADTAVYYCARVLYNWNVDSWGQGTLVTV
SS SEQ ID NO: 34 (ZY0EQD-E02, variable light chain)
DIQMTQSPSSLSASVGDRVTITCRASQDIRNDVGWYQQKPGKAPKRLIYAASRLQSGV
PSRFSGSGSGTEFTLTISSLQPEDFATYYCLQHNSYPRTFGQGTKVEIK SEQ ID NO: 35 (ZY0EOB-F05, variable heavy chain)
QVQLQESGPGLVKPSQTLSLTCTVSDGSISSGGYYWSWIRQHPGKGLEWIGNIYYSG
STYYNPSLKSRVTISVDTSKNQFSLKLNSVTAADTAVYYCATEKALATVTPSGYENYYT
VDVWGQGTTVTVSS SEQ ID NO: 36 (ZY0EOB-F05, variable light chain)
DIQLTQSPSFLSASVGDRVTITCWASQGISSYLAWYQQKPGKAPKLLIYAASTLQSGVP
SRFSGSGSGTEFTLTISSLQPEDFATYYCQHLNSYPLTFGGGTKVEIK SEQ ID NO: 37 (ZY0E05-E07, variable heavy chain)
QVQLQESGPGLVKPSQTLSLTCTVSGGSISSGGYYWSWIRQHPGKGLEWIGNIYYSG
STYYNPSLKSRVTISVDTSKNQFSLKLSSVTAADTAVYYCAREKALASVIPSGYENYYV
VDVWGQGTTVTVSS SEQ ID NO: 38 (ZY0E05-E07, variable light chain)
DIQLTQSPSFLSASVGGRVTITCWASQGIAGYLAWYQQKPGKAPKLLIYAASTLQSGVP
SRFSGSGSGTEFTLTISSLQPEDFATYYCQHLNSYPLTFGGGTKVEIK SEQ ID NO: 39: (ZY0EP0-C07, variable heavy chain)
QVQLVESGGVLVKPGGSLRLSCAASGFTLSDYYMSWIRQAPGMGLEWVSYISSSGST
IYYTDSVKGRFTISRDSAKNSLYLQMNSLRAEDTAVYYCARDGVGFDYWGQGTLVTVS
S SEQ ID NO: 40 (ZY0EP0-C07, variable light chain)
EIVLTQSPGTLSLFPGERATLSCRASQSVSSSYLAWYQQKPGQSPRLLIYAASSRATGI
PDRFSGSGSGTDFTLTISRLEPEDFAVYYCQQYGSSPLYTFGQGTKLEIK SEQ ID NO: 41 (Maia heavy chain constant region, cysteine
insertion underlined):
ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPE
LLGGPS<u>C</u>VFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK SEQ ID NO: 42 (light chain constant region)
RTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC -continued

SEQUENCES

SEQ ID NO: 43 (ZY0EQD-E02, variable heavy chain, e.g.
pre-germlining, e.g. variant of SEQ ID NO: 33/SEQ ID NO: 45)
QVQLQQWGAGLLKPSETLSLTCTVYGGSFSGYYWNWIRQPPGRGLEWIGEINHSGST
SYNPSLKSRITISIDTSKNQFSLKLSSVTAADTAVYYCARVLYNWNVDSWGQGTLVTVS
S SEQ ID NO: 44 (ZY0EQD-E02, light chain):
DIQMTQSPSSLSASVGDRVTITCRASQDIRNDVGWYQQKPGKAPKRLIYAASRLQSGV
PSRFSGSGSGTEFTLTISSLQPEDFATYYCLQHNSYPRTFGQGTKVEIKRTVAAPSVFI
FPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC SEQ ID NO: 45 (EQD-E02_GL, variable heavy chain,
GL = germlined)
QVQLQQWGAGLLKPSETLSLACTVYGGSFSGYYWNWIRQPPGKGLEWIGEINHSGST
SYNPSLKSRVTISVDTSKNQFSLKLSSVTAADTAVYYCARVLYNWNVDSWGQGTLVTV
SS SEQ ID NO: 46 (EQD-E02-GLY, variable heavy chain,
GLY = germlined with a Y substitution)
QVQLQQWGAGLLKPSETLSLACTVYGGSFSGYYWNWIRQPPGKGLEWIGEIYHSGST
SYNPSLKSRVTISVDTSKNQFSLKLSSVTAADTAVYYCARVLYNWNVDSWGQGTLVTV
SS SEQ ID NO: 47 (EQD-E02-GLQ, variable heavy chain,
GLQ = germlined with a Q substitution)
QVQLQQWGAGLLKPSETLSLACTVYGGSFSGYYWNWIRQPPGKGLEWIGEIQHSGST
SYNPSLKSRVTISVDTSKNQFSLKLSSVTAADTAVYYCARVLYNWNVDSWGQGTLVTV
SS SEQ ID NO: 48 (E02-GL-Maia-heavy chain, cysteine insertion
underlined)
QVQLQQWGAGLLKPSETLSLACTVYGGSFSGYYWNWIRQPPGKGLEWIGEINHSGST
SYNPSLKSRVTISVDTSKNQFSLKLSSVTAADTAVYYCARVLYNWNVDSWGQGTLVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPA
PELLGGPSCVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 49 (E02-GLY-Maia-heavy chain, GLY = germlined
with a Y substitution)
QVQLQQWGAGLLKPSETLSLACTVYGGSFSGYYWNWIRQPPGKGLEWIGEIYHSGST
SYNPSLKSRVTISVDTSKNQFSLKLSSVTAADTAVYYCARVLYNWNVDSWGQGTLVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPA
PELLGGPSCVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 50 (E02-GLQ-Maia-heavy chain, GLQ = germlined
with a Q substitution)
QVQLQQWGAGLLKPSETLSLACTVYGGSFSGYYWNWIRQPPGKGLEWIGEIQHSGST
SYNPSLKSRVTISVDTSKNQFSLKLSSVTAADTAVYYCARVLYNWNVDSWGQGTLVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPA
PELLGGPSCVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 51 (E02-GL-WT-heavy chain)
QVQLQQWGAGLLKPSETLSLACTVYGGSFSGYYWNWIRQPPGKGLEWIGEINHSGST
SYNPSLKSRVTISVDTSKNQFSLKLSSVTAADTAVYYCARVLYNWNVDSWGQGTLVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO: 52 (heavy chain constant region)
ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPE

SEQUENCES

LLGGPSCVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK

SEQ ID NO: 53 (Human B7H4 nucleic acid
sequence, including 5' and 3' UTR)
GCCACCatggcttccctggggcagatcctcttctggagcataattagcatcatcattat
tctggctggagcaattgcactcatcattggctttggtatttcagggagacactccatca
cagtcactactgtcgcctcagctgggaacattggggaggatggaatcctgagctgcact
tttgaacctgacatcaaactttctgatatcgtgatacaatggctgaaggaaggtgtttt
aggcttggtccatgagttcaaagaaggcaaagatgagctgtcggagcaggatgaaatgt
tcagaggccggacagcagtgtttgctgatcaagtgatagttggcaatgcctctttgcgg
ctgaaaaacgtgcaactcacagatgctggcacctacaaatgttatatcatcacttctaa
aggcaaggggaatgctaaccttgagtataaaactggagccttcagcatgccggaagtga
atgtggactataatgccagctcagagaccttgcggtgtgaggctccccgatggttcccc
cagcccacagtggtctgggcatcccaagttgaccagggagccaacttctcggaagtctc
caataccagctttgagctgaactctgagaatgtgaccatgaaggttgtgtctgtgctct
acaatgttacgatcaacaacacatactcctgtatgattgaaaatgacattgccaaagca
acaggggatatcaaagtgacagaatcggagatcaaaaggcggagtcacctacagctgct
aaactcaaaggcttctctgtgtgtctcttctttctttgccatcagctgggcacttctgc
ctctcagcccttacctgatgctaaaaTAATAA SEQ ID NO: 54 (Human B7H4 nucleic acid
sequence, coding sequence)
atggcttccctggggcagatcctcttctggagcataattagcatcatcattattctggc
tggagcaattgcactcatcattggctttggtatttcagggagacactccatcacagtca
ctactgtcgcctcagctgggaacattggggaggatggaatcctgagctgcactttttgaa
cctgacatcaaactttctgatatcgtgatacaatggctgaaggaaggtgttttaggctt
ggtccatgagttcaaagaaggcaaagatgagctgtcggagcaggatgaaatgttcagag
gccggacagcagtgtttgctgatcaagtgatagttggcaatgcctctttgcggctgaaa
aacgtgcaactcacagatgctggcacctacaaatgttatatcatcacttctaaaggcaa
ggggaatgctaaccttgagtataaaactggagccttcagcatgccggaagtgatgtgg
actataatgccagctcagagaccttgcggtgtgaggctccccgatggttcccccagccc
acagtggtctgggcatcccaagttgaccagggagccaacttctcggaagtctccaatac
cagctttgagctgaactctgagaatgtgaccatgaaggttgtgtctgtgctctacaatg
ttacgatcaacaacacatactcctgtatgattgaaaatgacattgccaaagcaacaggg
gatatcaaagtgacagaatcggagatcaaaaggcggagtcacctacagctgctaaactc
aaaggcttctctgtgtgtctcttctttctttgccatcagctgggcacttctgcctctca
gcccttacctgatgctaaaa SEQ ID NO: 55 (Human B7H4 polypeptide
sequence; UniProt Accession No.: Q7Z7D3)
MASLGQILFWSIISIIILAGAIALIIGFGISGRHSITVTTVASAGNIGEDGILSCTFE
PDIKLSDIVIQWLKEGVLGLVHEFKEGKDELSEQDEMFRGRTAVFADQVIVGNASLRLK
NVQLTDAGTYKCYIITSKGKGNANLEYKTGAFSMPEVNVDYNASSETLRCEAPRWFPQP
TVVWASQVDQGANFSEVSNTSFELNSENVTMKVVSVLYNVTINNTYSCMIENDIAKATG
DIKVTESEIKRRSHLQLLNSKASLCVSSFFAISWALLPLSPYLMLK

Embodiments

E1. An antibody or antigen binding fragment thereof which binds to B7-H4, comprising:
  i. a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof;
  ii. a HCDR1, a HCDR2, a HCDR3, a LCDR1, a LCDR2, and a LCDR3 comprising the amino acid sequence of SEQ ID NO: 1, SEQ ID NO: 2, SEQ ID NO: 3, SEQ ID NO: 4, SEQ ID NO: 5, and SEQ ID NO: 6, respectively, or a functional variant thereof;
  iii. a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively, or a functional variant thereof;
  iv. a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively, or a functional variant thereof; or
  v. a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively, or a functional variant thereof.

E2. The antibody or antigen binding fragment thereof according to E1, wherein the antibody or antigen binding fragment thereof comprises:
  i. a variable heavy (VH) chain and a variable light (VL) chain comprising the amino acid sequence of SEQ ID NO: 45 and SEQ ID NO: 34, respectively, or a functional variant thereof;
  ii. a variable heavy (VH) chain and a variable light (VL) chain comprising the amino acid sequence of SEQ ID NO: 33 and SEQ ID NO: 34, respectively, or a functional variant thereof;

iii. a variable heavy (VH) chain and a variable light (VL) chain comprising the amino acid sequence of SEQ ID NO: 43 and SEQ ID NO: 34, respectively, or a functional variant thereof;

iv. a variable heavy (VH) chain and a variable light (VL) chain comprising the amino acid sequence of SEQ ID NO: 46 and SEQ ID NO: 34, respectively, or a functional variant thereof;

v. a variable heavy (VH) chain and a variable light (VL) chain comprising the amino acid sequence of SEQ ID NO: 47 and SEQ ID NO: 34, respectively, or a functional variant thereof;

vi. a VH chain and a VL chain comprising the amino acid sequence of SEQ ID NO: 31, and SEQ ID NO: 32, respectively, or a functional variant thereof;

vii. a VH chain and a VL chain comprising the amino acid sequence of SEQ ID NO: 35 and SEQ ID NO: 36, respectively, or a functional variant thereof;

viii. a VH chain and a VL chain comprising the amino acid sequence of SEQ ID NO: 37 and SEQ ID NO: 38, respectively, or a functional variant thereof; or ix. a VH chain and a VL chain comprising the amino acid sequence of SEQ ID NO: 39 and SEQ ID NO: 40, respectively, or a functional variant thereof.

E3. The antibody or antigen binding fragment thereof according to E1 or E2, wherein the antibody or antigen binding fragment thereof comprises:
  i. a HCDR1, a HCDR2, a HCDR3, a LCDR1, a LCDR2, and a LCDR3 comprising the amino acid sequence of SEQ ID NO: 7, SEQ ID NO: 8, SEQ ID NO: 9, SEQ ID NO: 10, SEQ ID NO: 11, and SEQ ID NO: 12, respectively, or a functional variant thereof.

E4. The antibody or antigen binding fragment thereof according to E1-E3, wherein the antibody or antigen binding fragment thereof comprises:
  i. a VH chain and a VL chain comprising the amino acid sequence of SEQ ID NO: 45 and SEQ ID NO: 34, respectively, or a functional variant thereof.

E5. The antibody or antigen binding fragment thereof according E1-E4, wherein the antibody or antigen binding fragment thereof binds an OVCAR4 cell line.

E6. The antibody or antigen binding fragment thereof according to E1-E5, wherein the antibody or antigen binding fragment thereof comprises a heavy chain constant region comprising the amino acid sequence of SEQ ID NO: 41.

E7. The antibody or antigen binding fragment thereof according to E1-E5, wherein the antibody or antigen binding fragment thereof comprises a heavy chain constant region comprising the amino acid sequence of SEQ ID NO: 52.

E8. The antibody or antigen binding fragment thereof according to E1-E7, wherein the antibody or antigen binding fragment thereof comprises a light constant region comprising the amino acid sequence of SEQ ID NO: 42.

E9. The antibody or antigen binding fragment thereof according to any one of E1-E5, wherein the antibody or antigen binding fragment thereof comprises a heavy chain comprising the amino acid sequence of SEQ ID NO: 51; and a light chain comprising the amino acid sequence of SEQ ID NO: 44.

E10. The antibody or antigen binding fragment thereof according to any one of E1-E5, wherein the antibody or antigen binding fragment thereof comprises a heavy chain comprising the amino acid sequence of SEQ ID NO: 48; and a light chain comprising the amino acid sequence of SEQ ID NO: 44.

E11. The antibody or antigen binding fragment thereof according to any one of E1-E10, wherein the antibody or antigen binding fragment thereof is conjugated to a heterologous agent.

E12. The antibody or antigen binding fragment thereof according to any one of E1-E11, wherein the antibody or antigen binding fragment thereof is conjugated to one or more heterologous agent selected from the group consisting of a topoisomerase I inhibitor, a tubulysin derivative, a pyrrolobenzodiazepine, an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, or a combination thereof.

E13. The antibody or antigen binding fragment thereof according to any one of E1-E12, wherein the antibody or antigen binding fragment thereof is conjugated to one or more heterologous agent selected from a topoisomerase I inhibitor, tubulysin derivative, a pyrrolobenzodiazepine, or a combination thereof.

E14. The antibody or antigen binding fragment thereof according to any one of E1-E13, wherein the antibody or antigen binding fragment thereof is conjugated to a heterologous agent selected from the group consisting of tubulysin AZ1508, pyrrolobenzodiazepine SG3315, pyrrolobenzodiazepine SG3249, or a combination thereof.

E15. The antibody or antigen binding fragment thereof according to any one of E1-E14, wherein the antibody or antigen binding fragment thereof is conjugated to a pyrrolobenzodiazepine SG3249 cytotoxin: (SG3249).

E16. The antibody or antigen binding fragment thereof according to any one E1-E14, wherein the antibody or antigen binding fragment thereof is conjugated to: (SG3932); (SG4010); (SG4057); and/or (SG4052).

E17. The antibody or antigen binding fragment thereof according to any one of E1-E14, or E16, wherein the antibody or antigen binding fragment thereof is conjugated to: (SG3932).

E18. The antibody or antigen binding fragment thereof according to any one of E1-E17, wherein said antibody or antigen binding fragment thereof is a monoclonal antibody.

E19. The antibody or antigen binding fragment thereof according to any one of E1-E18, wherein said antibody or antigen binding fragment thereof is a humanised monoclonal antibody.

E20. A pharmaceutical composition comprising an antibody or antigen binding fragment thereof according to any one of E1-E19.

E21. A polynucleotide encoding the antibody or antigen binding fragment thereof according to any one of E1-E19.

E22. A host cell comprising the polynucleotide of E21.

E23. A method for producing an antibody or antigen binding fragment thereof that binds to B7-H4, comprising expressing a polynucleotide according to E22 in a host cell.

E24. An antibody or antigen binding fragment thereof obtainable by the method of E23.

E25. A method of treating a cancer comprising a cancer cell which expresses B7-H4, the method comprising administering to a subject the antibody or antigen binding fragment of any one of E1-E19 or E24, the pharmaceutical composition of E20, or a combination thereof.

E26. An antibody or antigen binding fragment thereof according to any one of E1-E19 or 24, or the pharmaceutical composition of E20, for use in treating a cancer, wherein said cancer comprises a cancer cell which expresses B7-H4.

E27. The method according to E25, or antibody or antigen binding fragment thereof or pharmaceutical composition for use according to E26, where said cancer is selected from breast cancer, ovarian cancer, endometrial cancer, cholangiocarcinoma, NSCLC (squamous and/or adenocarcinoma), pancreatic cancer, and gastric cancer.

E28. The method, or antibody or antigen binding fragment thereof or pharmaceutical composition for use according to any one of E25-E27, wherein said cancer is selected from breast cancer, ovarian cancer, endometrial cancer, and cholangiocarcinoma.

E29. The method, or antibody or antigen binding fragment thereof or pharmaceutical composition for use according to any one of E25-E28, wherein said cancer is a breast cancer selected from hormone receptor-positive (HR+) breast cancer, human epidermal growth factor receptor 2 positive (HER2+) breast cancer, and triple negative breast cancer (TNBC).

E30. A method for detecting the presence or absence of a B7-H4 polypeptide in a sample, comprising:
  i. contacting a sample with an antibody or antigen binding fragment thereof according to any one of E1-E19 or E24, or a pharmaceutical composition according to E20, to provide an antibody-antigen complex;
  ii. detecting the presence or absence of said antibody-antigen complex;
  iii. wherein the presence of the antibody-antigen complex confirms the presence of a B7-H4 polypeptide;
  iv. wherein the absence of the antibody-antigen complex confirms the absence of B7-H4 polypeptide.

E31. The method according to E30, wherein the presence of said antibody-antigen complex is indicative of the presence of a cancer cell, and wherein the absence of said antibody-antigen complex is indicative of the absence of a cancer cell.

E32. The method according to E30 or E31, wherein the sample is an isolated sample obtainable from a subject.

E33. The method according to any one of E30-E32, wherein the B7-H4 polypeptide is an integral component of a cancer cell.

E34. An antibody-drug conjugate (ADC) comprising:
  (i) antibody or antigen binding fragment thereof which binds to human B7-H4 comprising: a HCDR1 comprising the amino acid sequence of SEQ ID NO: 7; a HCDR2 comprising the amino acid sequence of SEQ ID NO: 8; a HCDR3 comprising the amino acid sequence of SEQ ID NO: 9; and a LCDR1 comprising the amino acid sequence of SEQ ID NO: 10; a LCDR2 comprising the amino acid sequence of SEQ ID NO: 11; and a LCDR3 comprising the amino acid sequence of SEQ ID NO: 12;
  (ii) a linker; and
  (iii) a cytotoxic agent wherein the cytotoxic agent is SG3932, wherein the ADC has a drug to antibody ratio (DAR) of 8.

E35. The ADC of E34, wherein the antibody or antigen binding fragment thereof comprises a variable heavy (VH) chain comprising the amino acid sequence of SEQ ID NO: 45 and a variable light (VL) chain comprising the amino acid sequence of SEQ ID NO: 34.

E36. The ADC of E34 or E35 comprising a heavy chain (HC) comprising the amino acid sequence of SEQ ID NO: 51, and light chain (LC) comprising the amino acid sequence of SEQ ID NO: 44.

E37. A pharmaceutical composition comprising the ADC of any one of E34-E36.

E38. A method of treating a cancer comprising a cancer cell which expresses B7-H4, the method comprising administering to a subject the ADC of any one of E34-E36, or the pharmaceutical composition of E37, or a combination thereof.

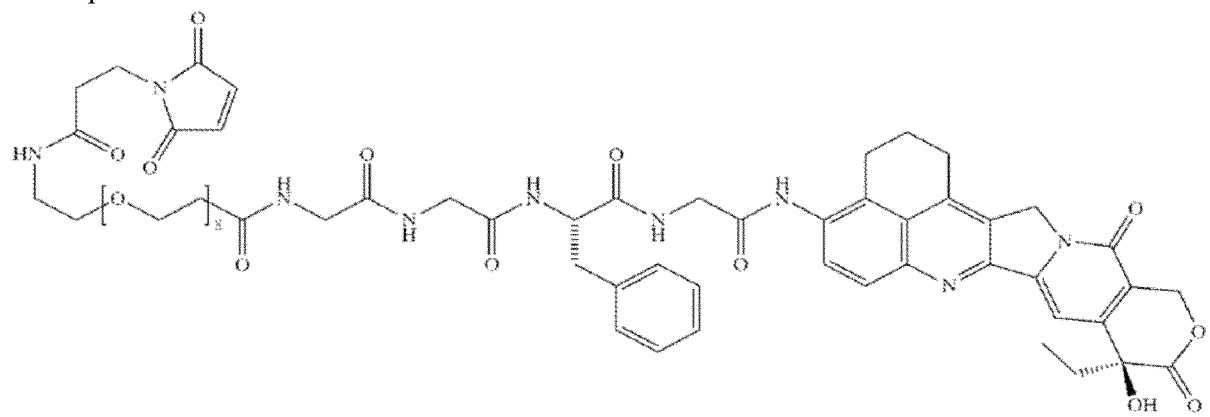

The invention claimed is:

1. An antibody or antigen binding fragment thereof which binds to B7-H4, comprising:
   i) a heavy chain CDR1 (HCDR1), a heavy chain CDR2 (HCDR2), a heavy chain CDR3 (HCDR3), a light chain CDR1 (LCDR1), a light chain CDR2 (LCDR2), and a light chain CDR3 (LCDR3) comprising the amino acid sequence of SEQ ID NO: 7, SEQ ID NO: 8, SEQ ID NO: 9, SEQ ID NO: 10, SEQ ID NO: 11, and SEQ ID NO: 12, respectively;
   ii) a HCDR1, a HCDR2, a HCDR3, a LCDR1, a LCDR2, and a LCDR3 comprising the amino acid sequence of SEQ ID NO: 1, SEQ ID NO: 2, SEQ ID NO: 3, SEQ ID NO: 4, SEQ ID NO: 5, and SEQ ID NO: 6, respectively;
   iii) a HCDR1, a HCDR2, a HCDR3, a LCDR1, a LCDR2, and a LCDR3 comprising the amino acid sequence of SEQ ID NO: 13, SEQ ID NO: 14, SEQ ID NO: 15, SEQ ID NO: 16, SEQ ID NO: 17, and SEQ ID NO: 18, respectively;
   iv) a HCDR1, a HCDR2, a HCDR3, a LCDR1, a LCDR2, and a LCDR3 comprising the amino acid sequence of SEQ ID NO: 19, SEQ ID NO: 20, SEQ ID NO: 21, SEQ ID NO: 22, SEQ ID NO: 23, and SEQ ID NO: 24, respectively; or
   v) a HCDR1, a HCDR2, a HCDR3, a LCDR1, a LCDR2, and a LCDR3 comprising the amino acid sequence of SEQ ID NO: 25, SEQ ID NO: 26, SEQ ID NO: 27, SEQ ID NO: 28, SEQ ID NO: 29, and SEQ ID NO: 30, respectively.

2. The antibody or antigen binding fragment thereof according to claim 1, wherein the antibody or antigen binding fragment thereof comprises:
   i) a variable heavy (VH) chain and a variable light (VL) chain comprising the amino acid sequence of SEQ ID NO: 45 and SEQ ID NO: 34, respectively;
   ii) a variable heavy (VH) chain and a variable light (VL) chain comprising the amino acid sequence of SEQ ID NO: 33 and SEQ ID NO: 34, respectively;
   iii) a variable heavy (VH) chain and a variable light (VL) chain comprising the amino acid sequence of SEQ ID NO: 43 and SEQ ID NO: 34, respectively;
   iv) a variable heavy (VH) chain and a variable light (VL) chain comprising the amino acid sequence of SEQ ID NO: 46 and SEQ ID NO: 34, respectively;
   v) a variable heavy (VH) chain and a variable light (VL) chain comprising the amino acid sequence of SEQ ID NO: 47 and SEQ ID NO: 34, respectively;
   vi) a VH chain and a VL chain comprising the amino acid sequence of SEQ ID NO: 31, and SEQ ID NO: 32, respectively;
   vii) a VH chain and a VL chain comprising the amino acid sequence of SEQ ID NO: 35 and SEQ ID NO: 36, respectively;
   viii) a VH chain and a VL chain comprising the amino acid sequence of SEQ ID NO: 37 and SEQ ID NO: 38, respectively; or
   ix) a VH chain and a VL chain comprising the amino acid sequence of SEQ ID NO: 39 and SEQ ID NO: 40, respectively.

3. The antibody or antigen binding fragment thereof according to claim 2, wherein the antibody or antigen binding fragment thereof comprises a heavy chain comprising the amino acid sequence of SEQ ID NO: 51; and a light chain comprising the amino acid sequence of SEQ ID NO: 44.

4. The antibody or antigen binding fragment thereof according to claim 2, wherein the antibody or antigen binding fragment thereof comprises a heavy chain comprising the amino acid sequence of SEQ ID NO: 48; and a light chain comprising the amino acid sequence of SEQ ID NO: 44.

5. The antibody or antigen binding fragment thereof according to claim 1, wherein the antibody or antigen binding fragment thereof is conjugated to a heterologous agent.

6. The antibody or antigen binding fragment thereof according to claim 5, wherein the heterologous agent is selected from the group consisting of a topoisomerase I inhibitor, a tubulysin derivative, a pyrrolobenzodiazepine, an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, or a combination thereof.

7. The antibody or antigen binding fragment thereof according to claim 5, wherein the heterologous agent is selected from a topoisomerase I inhibitor, a tubulysin derivative, a pyrrolobenzodiazepine, or a combination thereof.

8. The antibody or antigen binding fragment thereof according to claim 5, wherein the antibody or antigen binding fragment thereof is conjugated to a heterologous agent selected from the group consisting of tubulysin AZ1508, pyrrolobenzodiazepine SG3315, pyrrolobenzodiazepine SG3249, or a combination thereof.

9. The antibody or antigen binding fragment thereof according to claim 5, wherein the antibody or antigen binding fragment thereof is conjugated to a pyrrolobenzodiazepine SG3249 cytotoxin and linker comprising SG3249:

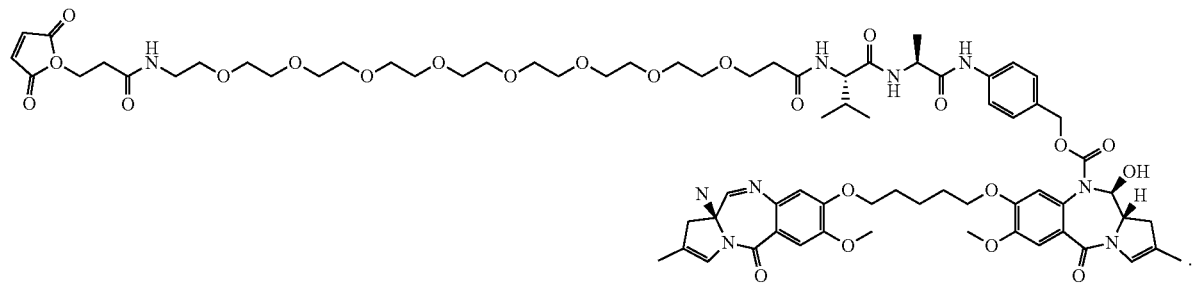
(SG3249)
10. The antibody or antigen binding fragment thereof according to claim 5, wherein the antibody or antigen binding fragment thereof is conjugated to:
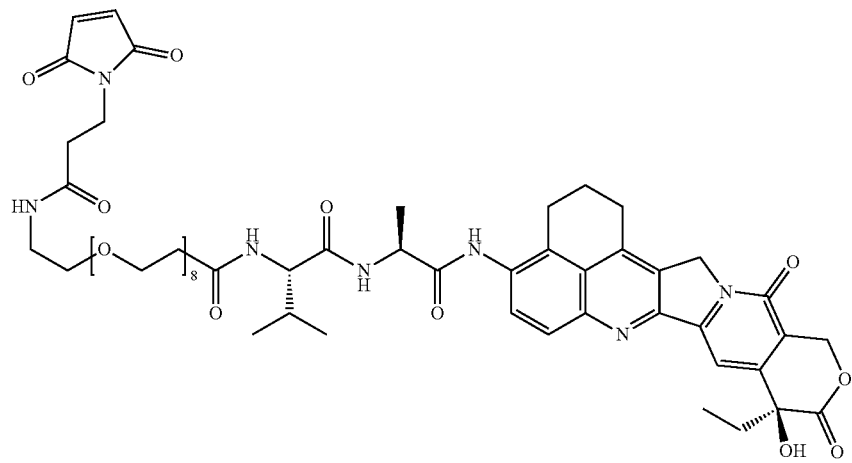
(SG3932)
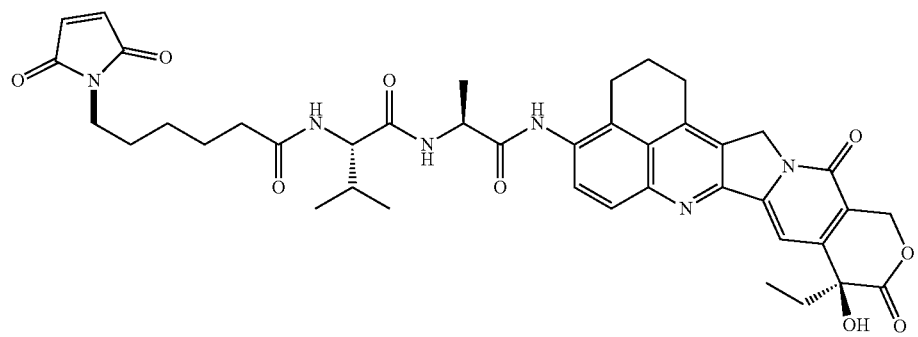
(SG4010)
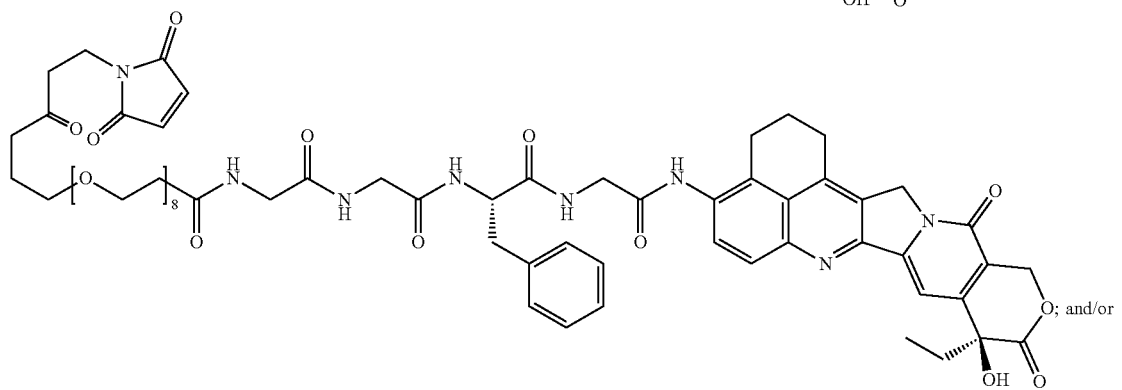
(SG4057)
; and/or -continued (SG4052)

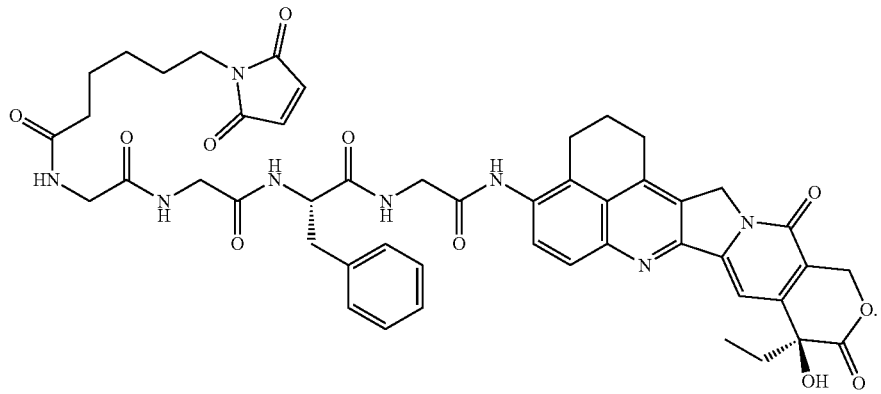

11. The antibody or antigen binding fragment thereof according to claim 10, wherein the antibody or antigen binding fragment thereof is conjugated to:

(SG3932)

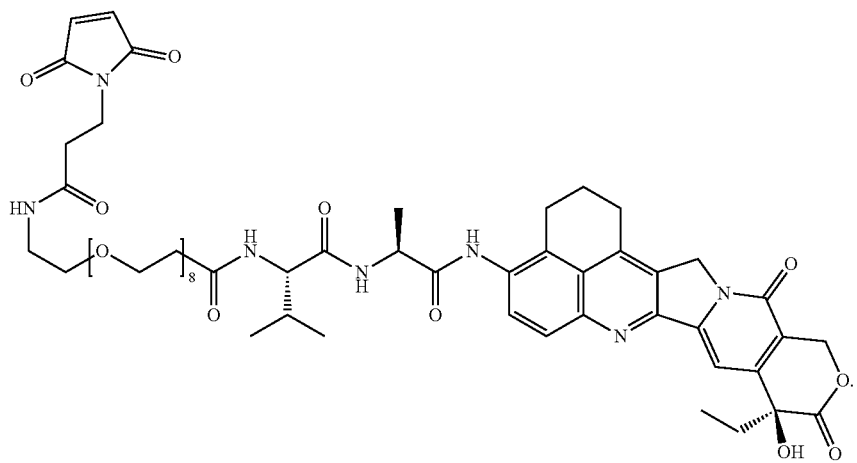

12. A polynucleotide encoding the antibody or antigen binding fragment thereof according to claim 1.

13. A method for producing an antibody or antigen binding fragment thereof that binds to B7-H4, comprising expressing a polynucleotide according to claim 12 in a host cell.

14. A method of treating a cancer comprising a cancer cell which expresses B7-H4, the method comprising administering to a subject having the cancer cell the antibody or antigen binding fragment of claim 11.

15. The method according to claim 14, wherein said cancer is selected from breast cancer, ovarian cancer, endometrial cancer, cholangiocarcinoma, NSCLC (squamous and/or adenocarcinoma), pancreatic cancer, and gastric cancer.

16. A method for detecting the presence or absence of a B7-H4 polypeptide in a sample, comprising:
  i. contacting a sample with an antibody or antigen binding fragment thereof according to claim 1, to provide an antibody-antigen complex;
  ii. detecting the presence or absence of said antibody-antigen complex;
  iii. wherein the presence of the antibody-antigen complex confirms the presence of a B7-H4 polypeptide;
  iv. wherein the absence of the antibody-antigen complex confirms the absence of B7-H4 polypeptide.

17. An antibody-drug conjugate (ADC) comprising:
  (i) antibody or antigen binding fragment thereof which binds to a B7-H4 polypeptide comprising: a HCDR1 comprising the amino acid sequence of SEQ ID NO: 7; a HCDR2 comprising the amino acid sequence of SEQ ID NO: 8; a HCDR3 comprising the amino acid sequence of SEQ ID NO: 9; and a LCDR1 comprising the amino acid sequence of SEQ ID NO: 10; a LCDR2 comprising the amino acid sequence of SEQ ID NO: 11; and a LCDR3 comprising the amino acid sequence of SEQ ID NO: 12;
  (ii) a cleavable mp-PEG8-val-ala linker; and
  (iii) a cytotoxic agent wherein the cleavable mp-PEG8-val-ala linker and the cytotoxic agent are SG3932, and wherein the ADC has a drug to antibody ratio (DAR) of about 8.

18. The ADC of claim 17, wherein the antibody or antigen binding fragment thereof comprises a variable heavy (VH) chain comprising the amino acid sequence of SEQ ID NO: 45 and a variable light (VL) chain comprising the amino acid sequence of SEQ ID NO: 34.

19. The ADC of claim 18 comprising a heavy chain (HC) comprising the amino acid sequence of SEQ ID NO: 51, and a light chain (LC) comprising the amino acid sequence of SEQ ID NO: 44.

20. A method for reducing the volume of a tumor which expresses B7-H4, the method comprising administering to a subject the antibody or antigen binding fragment of claim 11.

21. A pharmaceutical composition comprising the antibody or antigen binding fragment thereof of claim 1.

22. A pharmaceutical composition comprising the ADC of claim 19.

23. A polynucleotide encoding an antibody or antigen binding fragment thereof which binds to a B7-H4 polypeptide comprising: a HCDR1 comprising the amino acid sequence of SEQ ID NO: 7; a HCDR2 comprising the amino acid sequence of SEQ ID NO: 8; a HCDR3 comprising the amino acid sequence of SEQ ID NO: 9; and a LCDR1 comprising the amino acid sequence of SEQ ID NO: 10; a LCDR2 comprising the amino acid sequence of SEQ ID NO: 11; and a LCDR3 comprising the amino acid sequence of SEQ ID NO: 12.

24. The polynucleotide of claim 23, wherein the antibody or antigen binding fragment thereof comprises a variable heavy (VH) chain comprising the amino acid sequence of SEQ ID NO: 45 and a variable light (VL) chain comprising the amino acid sequence of SEQ ID NO: 34.

25. The polynucleotide of claim 24, wherein the antibody or antigen binding fragment thereof comprises a heavy chain (HC) comprising the amino acid sequence of SEQ ID NO: 51, and a light chain (LC) comprising the amino acid sequence of SEQ ID NO: 44.

26. A host cell comprising the polynucleotide of claim 23.

27. A host cell comprising the polynucleotide of claim 24.

28. A method for producing an antibody or antigen binding fragment thereof that binds to B7-H4, comprising expressing a polynucleotide according to claim 24 in a host cell.

29. A method for producing an antibody or antigen binding fragment thereof that binds to B7-H4, comprising expressing a polynucleotide according to claim 25 in a host cell.

30. A method of treating a cancer comprising administering to a subject the ADC of claim 17.

31. A method of treating a cancer comprising administering to a subject the ADC of claim 18.

32. A method of treating a cancer comprising administering to a subject the ADC of claim 19.

33. The method of claim 30, wherein the cancer has a homologous recombination DNA repair defect.

34. The method of claim 33, wherein the homologous recombination DNA repair defect is defined by the presence of a BRCA1 mutation.

35. The method of claim 33, wherein the homologous recombination DNA repair defect is defined by a negative score in a RAD51 foci formation assay.

36. The method of claim 32, wherein the cancer has a homologous recombination DNA repair defect.

37. The method of claim 36, wherein the homologous recombination DNA repair defect is defined by the presence of a BRCA1 mutation.

38. The method of claim 36, wherein the homologous recombination DNA repair defect is defined by a negative score in a RAD51 foci formation assay.

\* \* \* \* \*

UNITED STATES PATENT AND TRADEMARK OFFICE
CERTIFICATE OF CORRECTION

PATENT NO. : 11,795,225 B2  
APPLICATION NO. : 17/471723  
DATED : October 24, 2023  
INVENTOR(S) : Kinneer et al.

Page 1 of 3

It is certified that error appears in the above-identified patent and that said Letters Patent is hereby corrected as shown below:

In the Claims

In Claim 9, please delete structure SG3249:

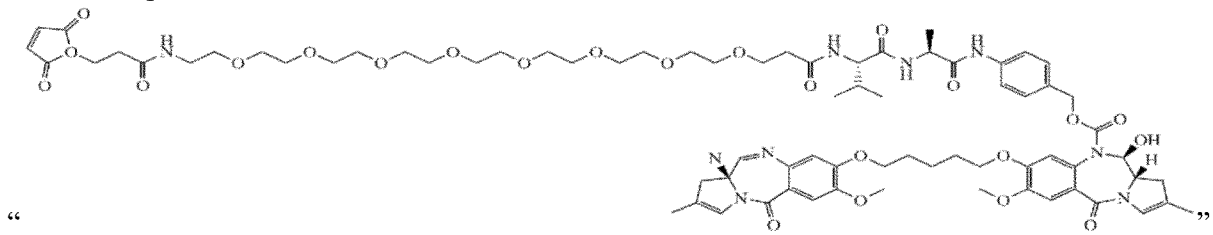

"

And replace it with:

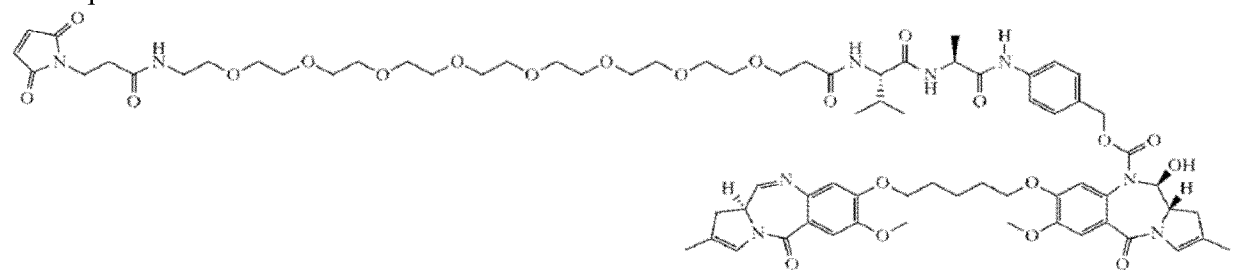

Signed and Sealed this  
Sixteenth Day of July, 2024

Katherine Kelly Vidal  
*Director of the United States Patent and Trademark Office*

CERTIFICATE OF CORRECTION (continued)
U.S. Pat. No. 11,795,225 B2

Page 2 of 3

In Claim 10, please delete structure SG3932:

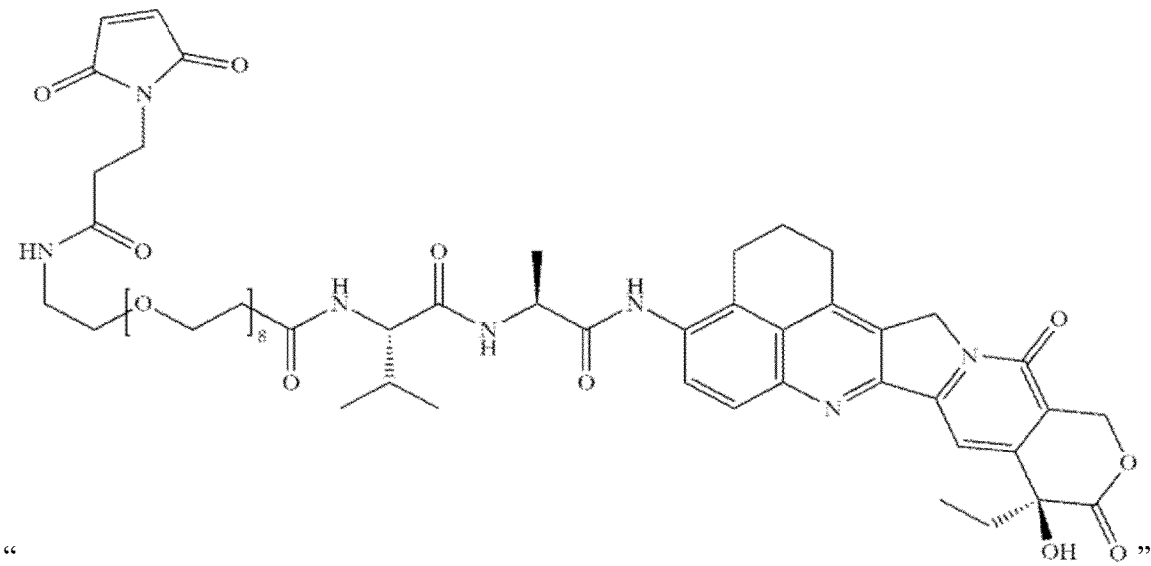

"

And replace it with:

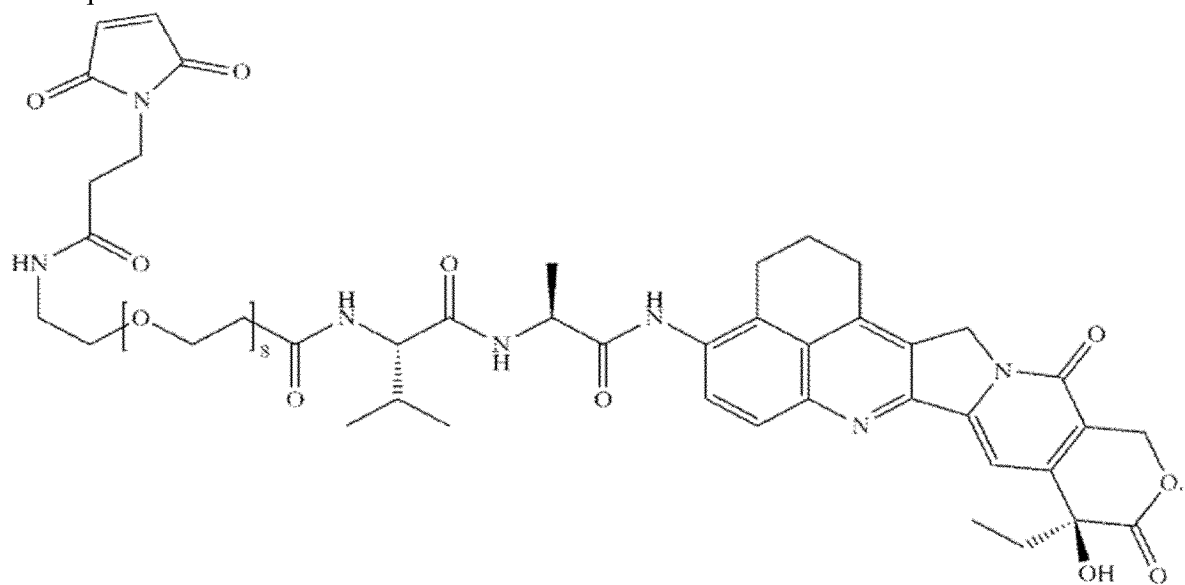

In Claim 10, please delete structure SG4057:

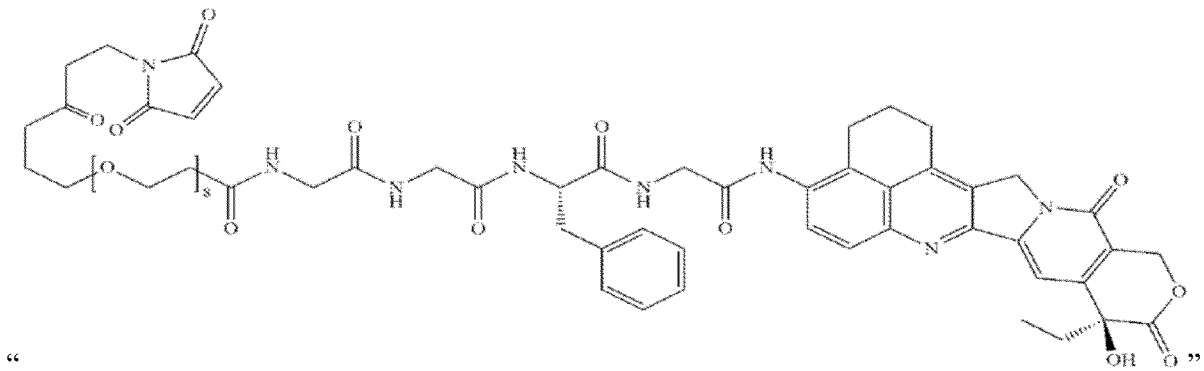

"

CERTIFICATE OF CORRECTION (continued)
U.S. Pat. No. 11,795,225 B2

And replace it with:

SEQUENCE LISTING

```
<160> NUMBER OF SEQ ID NOS: 55

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Gly Tyr Tyr Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Glu Ile Asn His Ser Gly Ser Thr Asn Tyr Asn Pro Ser Leu Lys Ser
1               5                   10                  15
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Asn Leu Tyr Asn Trp Asn Leu Asp Ser
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Ala Ser Gln Gly Ile Arg Asn Asp Leu Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Val Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Leu Gln His Asn Ser Tyr Pro Arg Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Gly Tyr Tyr Trp Asn
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Glu Ile Asn His Ser Gly Ser Thr Ser Tyr Asn Pro Ser Leu Lys Ser
1               5                   10                  15
```

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Val Leu Tyr Asn Trp Asn Val Asp Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Arg Ala Ser Gln Asp Ile Arg Asn Asp Val Gly
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Ala Ala Ser Arg Leu Gln Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Leu Gln His Asn Ser Tyr Pro Arg Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Ser Gly Gly Tyr Tyr Trp Ser
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic

<400> SEQUENCE: 14

Asn Ile Tyr Tyr Ser Gly Ser Thr Tyr Tyr Asn Pro Ser Leu Lys Ser
1               5                   10                  15

```
<210> SEQ ID NO 15
<211> LENGTH: 20
<212> TYPE: PRT
<213> ORGANISM: Artificial Sequence
<220> FEATURE:
<223> OTHER INFORMATION: Synthetic

<400> SEQUENCE: 15

Glu Lys Ala Leu Ala Thr Val Thr Pro Ser Gly Tyr Glu Asn Tyr Tyr
1               5                   10                  15

Thr Val Asp Val
            20

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Trp Ala Ser Gln Gly Ile Ser Ser Tyr Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Ala Ala Ser Thr Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln His Leu Asn Ser Tyr Pro Leu Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Ser Gly Gly Tyr Tyr Trp Ser
1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

Asn Ile Tyr Tyr Ser Gly Ser Thr Tyr Tyr Asn Pro Ser Leu Lys Ser
1               5                   10                  15
```

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Glu Lys Ala Leu Ala Ser Val Ile Pro Ser Gly Tyr Glu Asn Tyr Tyr
1               5                   10                  15

Val Val Asp Val
            20

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Trp Ala Ser Gln Gly Ile Ala Gly Tyr Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Ala Ala Ser Thr Leu Gln Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Gln His Leu Asn Ser Tyr Pro Leu Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Asp Tyr Tyr Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic

<400> SEQUENCE: 26

```
Tyr Ile Ser Ser Ser Gly Ser Thr Ile Tyr Tyr Thr Asp Ser Val Lys
1               5                   10                  15

Gly
```

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

```
Asp Gly Val Gly Phe Asp Tyr
1               5
```

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

```
Arg Ala Ser Gln Ser Val Ser Ser Ser Tyr Leu Ala
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

```
Ala Ala Ser Ser Arg Ala Thr
1               5
```

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

```
Gln Gln Tyr Gly Ser Ser Pro Leu Tyr Thr
1               5                   10
```

<210> SEQ ID NO 31
<211> LENGTH: 117
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60
```

```
Ser Arg Val Thr Ile Leu Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Leu Tyr Asn Trp Asn Leu Asp Ser Trp Gly Gln Gly Thr Leu
            100                 105                 110

Val Thr Val Ser Ser
            115

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Arg Ala Pro Lys Arg Leu Ile
             35                  40                  45

Tyr Val Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Thr Phe Gly Gln Gly Thr Lys Val Glu Ile Lys
            100                 105

<210> SEQ ID NO 33
<211> LENGTH: 117
<212> TYPE: PRT
<213> ORGANISM: Artificial Sequence
<220> FEATURE:
<223> OTHER INFORMATION: Synthetic

<400> SEQUENCE: 33

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Asn Trp Ile Arg Gln Pro Pro Gly Lys Gly Leu Glu Trp Ile
             35                  40                  45

Gly Glu Ile Asn His Ser Gly Ser Thr Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Leu Tyr Asn Trp Asn Val Asp Ser Trp Gly Gln Gly Thr Leu
            100                 105                 110

Val Thr Val Ser Ser
            115

<210> SEQ ID NO 34
```

```
<211> LENGTH: 107
<212> TYPE: PRT
<213> ORGANISM: Artificial Sequence
<220> FEATURE:
<223> OTHER INFORMATION: Synthetic

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Val Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 35
<211> LENGTH: 130
<212> TYPE: PRT
<213> ORGANISM: Artificial Sequence
<220> FEATURE:
<223> OTHER INFORMATION: Synthetic

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Thr Glu Lys Ala Leu Ala Thr Val Thr Pro Ser Gly Tyr Glu
            100                 105                 110

Asn Tyr Tyr Thr Val Asp Val Trp Gly Gln Gly Thr Thr Val Thr Val
        115                 120                 125

Ser Ser
    130

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Gln Leu Thr Gln Ser Pro Ser Phe Leu Ser Ala Ser Val Gly
1               5                   10                  15
```

```
Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Leu Asn Ser Tyr Pro Leu
                85                  90                  95

Thr Phe Gly Gly Gly Thr Lys Val Glu Ile Lys
                100                 105
```

<210> SEQ ID NO 37
<211> LENGTH: 130
<212> TYPE: PRT
<213> ORGANISM: Artificial Sequence
<220> FEATURE:
<223> OTHER INFORMATION: Synthetic

<400> SEQUENCE: 37

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Lys Ala Leu Ala Ser Val Ile Pro Ser Gly Tyr Glu
                100                 105                 110

Asn Tyr Tyr Val Val Asp Val Trp Gly Gln Gly Thr Thr Val Thr Val
            115                 120                 125

Ser Ser
    130
```

<210> SEQ ID NO 38
<211> LENGTH: 107
<212> TYPE: PRT
<213> ORGANISM: Artificial Sequence
<220> FEATURE:
<223> OTHER INFORMATION: Synthetic

<400> SEQUENCE: 38

```
Asp Ile Gln Leu Thr Gln Ser Pro Ser Phe Leu Ser Ala Ser Val Gly
1               5                   10                  15

Gly Arg Val Thr Ile Thr Cys Trp Ala Ser Gln Gly Ile Ala Gly Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Gln His Leu Asn Ser Tyr Pro Leu
                85                  90                  95

Thr Phe Gly Gly Gly Thr Lys Val Glu Ile Lys
            100                 105

<210> SEQ ID NO 39
<211> LENGTH: 116
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Glu Ser Gly Gly Val Leu Val Lys Pro Gly Gly
1               5                   10                  15

Ser Leu Arg Leu Ser Cys Ala Ala Ser Gly Phe Thr Leu Ser Asp Tyr
            20                  25                  30

Tyr Met Ser Trp Ile Arg Gln Ala Pro Gly Met Gly Leu Glu Trp Val
        35                  40                  45

Ser Tyr Ile Ser Ser Ser Gly Ser Thr Ile Tyr Tyr Thr Asp Ser Val
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Gly Phe Asp Tyr Trp Gly Gln Gly Thr Leu Val
            100                 105                 110

Thr Val Ser Ser
        115

<210> SEQ ID NO 40
<211> LENGTH: 109
<212> TYPE: PRT
<213> ORGANISM: Artificial Sequence
<220> FEATURE:
<223> OTHER INFORMATION: Synthetic

<400> SEQUENCE: 40

Glu Ile Val Leu Thr Gln Ser Pro Gly Thr Leu Ser Leu Phe Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ser Pro Arg Leu Leu
        35                  40                  45

Ile Tyr Ala Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Tyr Thr Phe Gly Gln Gly Thr Lys Leu Glu Ile Lys
            100                 105

<210> SEQ ID NO 41
<211> LENGTH: 331
<212> TYPE: PRT
<213> ORGANISM: Artificial Sequence
<220> FEATURE:
<223> OTHER INFORMATION: Synthetic -continued

```
<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Cys Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 43
<211> LENGTH: 117
<212> TYPE: PRT
<213> ORGANISM: Artificial Sequence
<220> FEATURE:
<223> OTHER INFORMATION: Synthetic

<400> SEQUENCE: 43

Gln Val Gln Leu Gln Gln Trp Gly Ala Gly Leu Leu Lys Pro Ser Glu
 1               5                  10                  15

Thr Leu Ser Leu Thr Cys Thr Val Tyr Gly Gly Ser Phe Ser Gly Tyr
            20                  25                  30

Tyr Trp Asn Trp Ile Arg Gln Pro Pro Gly Arg Gly Leu Glu Trp Ile
            35                  40                  45

Gly Glu Ile Asn His Ser Gly Ser Thr Ser Tyr Asn Pro Ser Leu Lys
 50                  55                  60

Ser Arg Ile Thr Ile Ser Ile Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
            100                 105                 110

Val Thr Val Ser Ser
        115

<210> SEQ ID NO 44
<211> LENGTH: 214
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Val Gly Trp Tyr Gln Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 117
<212> TYPE: PRT
<213> ORGANISM: Artificial Sequence
<220> FEATURE:
<223> OTHER INFORMATION: Synthetic

<400> SEQUENCE: 45

Gln Val Gln Leu Gln Gln Trp Gly Ala Gly Leu Leu Lys Pro Ser Glu
1               5                   10                  15

Thr Leu Ser Leu Ala Cys Thr Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: Synthetic

<400> SEQUENCE: 46

Gln Val Gln Leu Gln Gln Trp Gly Ala Gly Leu Leu Lys Pro Ser Glu
1               5                   10                  15

Thr Leu Ser Leu Ala Cys Thr Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Tyr His Ser Gly Ser Thr Ser Tyr Asn Pro Ser Leu Lys
```

```
                50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
                100                 105                 110

Val Thr Val Ser Ser
            115

<210> SEQ ID NO 47
<211> LENGTH: 117
<212> TYPE: PRT
<213> ORGANISM: Artificial Sequence
<220> FEATURE:
<223> OTHER INFORMATION: Synthetic

<400> SEQUENCE: 47

Gln Val Gln Leu Gln Gln Trp Gly Ala Gly Leu Leu Lys Pro Ser Glu
 1               5                  10                  15

Thr Leu Ser Leu Ala Cys Thr Val Tyr Gly Gly Ser Phe Ser Gly Tyr
                20                  25                  30

Tyr Trp Asn Trp Ile Arg Gln Pro Pro Gly Lys Gly Leu Glu Trp Ile
            35                  40                  45

Gly Glu Ile Gln His Ser Gly Ser Thr Ser Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
                100                 105                 110

Val Thr Val Ser Ser
            115

<210> SEQ ID NO 48
<211> LENGTH: 448
<212> TYPE: PRT
<213> ORGANISM: Artificial Sequence
<220> FEATURE:
<223> OTHER INFORMATION: Synthetic

<400> SEQUENCE: 48

Gln Val Gln Leu Gln Gln Trp Gly Ala Gly Leu Leu Lys Pro Ser Glu
 1               5                  10                  15

Thr Leu Ser Leu Ala Cys Thr Val Tyr Gly Gly Ser Phe Ser Gly Tyr
                20                  25                  30

Tyr Trp Asn Trp Ile Arg Gln Pro Pro Gly Lys Gly Leu Glu Trp Ile
            35                  40                  45

Gly Glu Ile Asn His Ser Gly Ser Thr Ser Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
                100                 105                 110
```

-continued

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Leu Leu Gly Gly Pro Ser Cys
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 49
<211> LENGTH: 448
<212> TYPE: PRT
<213> ORGANISM: Artificial Sequence
<220> FEATURE:
<223> OTHER INFORMATION: Synthetic

<400> SEQUENCE: 49

Gln Val Gln Leu Gln Gln Trp Gly Ala Gly Leu Leu Lys Pro Ser Glu
1               5                   10                  15

Thr Leu Ser Leu Ala Cys Thr Val Tyr Gly Gly Ser Phe Ser Gly Tyr
            20                  25                  30

```
Tyr Trp Asn Trp Ile Arg Gln Pro Gly Lys Gly Leu Glu Trp Ile
         35                  40                  45

Gly Glu Ile Tyr His Ser Gly Ser Thr Ser Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Leu Tyr Asn Trp Asn Val Asp Ser Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
     130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Arg Val Glu Pro Lys Ser Cys Asp Lys Thr His
     210                 215                 220

Thr Cys Pro Pro Cys Pro Ala Pro Glu Leu Leu Gly Gly Pro Ser Cys
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
     290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Glu Glu Met Thr Lys Asn Gln Val Ser Leu Thr Cys
         355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430

Leu His Asn His Tyr Thr Gln Lys Ser Leu Ser Leu Ser Pro Gly Lys
         435                 440                 445
```

<210> SEQ ID NO 50
<211> LENGTH: 448
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Gln Gln Trp Gly Ala Gly Leu Leu Lys Pro Ser Glu
1               5                   10                  15

Thr Leu Ser Leu Ala Cys Thr Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Gln His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Cys
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

```
            370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 51
<211> LENGTH: 447
<212> TYPE: PRT
<213> ORGANISM: Artificial Sequence
<220> FEATURE:
<223> OTHER INFORMATION: Synthetic

<400> SEQUENCE: 51

Gln Val Gln Leu Gln Gln Trp Gly Ala Gly Leu Leu Lys Pro Ser Glu
1               5                   10                  15

Thr Leu Ser Leu Ala Cys Thr Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Leu Tyr Asn Trp Asn Val Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
            290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 52
<211> LENGTH: 331
<212> TYPE: PRT
<213> ORGANISM: Artificial Sequence
<220> FEATURE:
<223> OTHER INFORMATION: Synthetic

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Cys Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
```

```
        210                 215                 220
Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 53
<211> LENGTH: 858
<212> TYPE: DNA
<213> ORGANISM: Homo sapiens

<400> SEQUENCE: 53
gccaccatgg cttccctggg gcagatcctc ttctggagca taattagcat catcattatt      60
ctggctggag caattgcact catcattggc tttggtattt cagggagaca ctccatcaca     120
gtcactactg tcgcctcagc tgggaacatt ggggaggatg gaatcctgag ctgcactttt     180
gaacctgaca tcaaactttc tgatatcgtg atacaatggc tgaaggaagg tgttttaggc     240
ttggtccatg agttcaaaga aggcaaagat gagctgtcgg agcaggatga aatgttcaga     300
ggccggacag cagtgtttgc tgatcaagtg atagttggca atgcctcttt gcggctgaaa     360
aacgtgcaac tcacagatgc tggcacctac aaatgttata tcatcacttc taaaggcaag     420
gggaatgcta accttgagta taaaactgga gccttcagca tgccggaagt gaatgtggac     480
tataatgcca gctcagagac cttgcggtgt gaggctcccc gatggttccc ccagcccaca     540
gtggtctggg catcccaagt tgaccaggga gccaacttct cggaagtctc aataccagc     600 tttgagctga ctctgagaa tgtgaccatg aaggttgtgt ctgtgctcta caatgttacg     660
atcaacaaca catactcctg tatgattgaa atgacattg ccaaagcaac aggggatatc     720
aaagtgacag aatcggagat caaaaggcgg agtcacctac agctgctaaa ctcaaaggct     780
tctctgtgtg tctcttcttt ctttgccatc agctgggcac ttctgcctct cagcccttac     840
ctgatgctaa ataataa                                                    858

<210> SEQ ID NO 54
<211> LENGTH: 846
<212> TYPE: DNA
<213> ORGANISM: Homo sapiens

<400> SEQUENCE: 54
atggcttccc tggggcagat cctcttctgg agcataatta gcatcatcat tattctggct      60
ggagcaattg cactcatcat tggctttggt atttcaggga gacactccat cacagtcact     120
actgtcgcct cagctgggaa cattggggag gatggaatcc tgagctgcac ttttgaacct     180
gacatcaaac tttctgatat cgtgatacaa tggctgaagg aaggtgtttt aggcttggtc     240
catgagttca agaaggcaa agatgagctg tcggagcagg atgaaatgtt cagaggccgg     300
```

```
acagcagtgt tgctgatca agtgatagtt ggcaatgcct ctttgcggct gaaaaacgtg    360
caactcacag atgctggcac ctacaaatgt tatatcatca cttctaaagg caagggaat    420 gctaaccttg agtataaaac tggagccttc agcatgccgg aagtgaatgt ggactataat    480
gccagctcag agaccttgcg gtgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttctctg    780
tgtgtctctt ctttctttgc catcagctgg gcacttctgc ctctcagccc ttacctgatg    840
ctaaaa                                                                846

<210> SEQ ID NO 55
<211> LENGTH: 282
<212> TYPE: PRT
<213> ORGANISM: Homo sapiens

<400> SEQUENCE: 55

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240
```

```
Thr Glu Ser Glu Ile Lys Arg Arg Ser His Leu Gln Leu Leu Asn Ser
                245                 250                 255
Lys Ala Ser Leu Cys Val Ser Ser Phe Phe Ala Ile Ser Trp Ala Leu
                260                 265                 270
Leu Pro Leu Ser Pro Tyr Leu Met Leu Lys
                275                 280
```